(12) United States Patent
Liu et al.

(10) Patent No.: US 8,975,232 B2
(45) Date of Patent: Mar. 10, 2015

(54) MACROCYCLIC KINASE INHIBITORS AND USES THEREOF

(75) Inventors: David R. Liu, Lexington, MA (US); Ralph E. Kleiner, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/812,431

(22) PCT Filed: Jul. 29, 2011

(86) PCT No.: PCT/US2011/045966
§ 371 (c)(1),
(2), (4) Date: Mar. 26, 2013

(87) PCT Pub. No.: WO2012/016186
PCT Pub. Date: Feb. 2, 2012

(65) Prior Publication Data
US 2013/0178429 A1 Jul. 11, 2013

Related U.S. Application Data

(60) Provisional application No. 61/368,986, filed on Jul. 29, 2010.

(51) Int. Cl.
A61P 35/00 (2006.01)
C07K 5/02 (2006.01)
A61K 38/12 (2006.01)
C07K 5/107 (2006.01)

(52) U.S. Cl.
CPC . C07K 5/02 (2013.01); A61K 38/12 (2013.01); C07K 5/1016 (2013.01)
USPC ......... 514/19.2; 514/21.9; 530/317; 530/323; 530/330

(58) Field of Classification Search
None
See application file for complete search history.

(56) References Cited

U.S. PATENT DOCUMENTS

| | | | |
|---|---|---|---|
| 2002/0068301 | A1 | 6/2002 | Lai et al. |
| 2004/0067503 | A1 | 4/2004 | Tan et al. |
| 2006/0025566 | A1 | 2/2006 | Hoveyda et al. |
| 2008/0139456 | A1 | 6/2008 | Burke et al. |
| 2008/0242598 | A1 | 10/2008 | Fairlie et al. |
| 2010/0105601 | A2 | 4/2010 | Brady et al. |

FOREIGN PATENT DOCUMENTS

| | | | |
|---|---|---|---|
| WO | WO 2004/016767 | A2 | 2/2004 |
| WO | WO 2007/016441 | A1 | 2/2007 |
| WO | WO 2008/156701 | A2 | 12/2008 |
| WO | WO 2012/016186 | A1 | 2/2012 |
| WO | WO 2013/006451 | A2 | 1/2013 |

OTHER PUBLICATIONS

Bednarek, Maria A. et al; "Seletive, high affinity peptide antagonist of alpha melanotropin action at human melanocortin receptor 4: their synthesis and biological evaluation in vitro." J. Med. Chem. (2001) 44 p. 3665-3672.*
Tse, Brian N. et al; "Translation of dna into a library of 13000 synthetic small molecule macrocycles suitable for in vitro selection." J. Am. Chem. Soc. (2008) 130 p. 15611-15626.*
Tse, Brian N. et al; "Translation of dna into a library of 13000 synthetic small molecule macrocycles suitable for in vitro selection." J. Am. Chem. Soc. (2008) 130, supporting information.*
Liu, Tao et al; "Synthesis and screening of a cyclic peptide library: Discovery of small molecule ligands against human prolactin receptor." Bioorg. Med. Chem. Lett. (2009) 17 p. 1026-1033.*
Tse et al J. Am. Chem. Soc. (2008) 130 p. 15611-15626.*
International Search Report and Written Opinion for Application No. PCT/US2011/045966, mailed Dec. 16, 2011.
International Preliminary Report on Patentability for Application No. PCT/US2011/045966, mailed Feb. 7, 2013.
Adams et al., Phenix: building new software for automated crystallographic structure determination. Acta Crystallogr D Biol Crystallogr. Nov. 2002;58(Pt 11):1948-54. Epub Oct. 21, 2002.
Adrian et al., Allosteric inhibitors of Bcr-abl-dependent cell proliferation. Nat Chem Biol. Feb. 2006;2(2):95-102. Epub Jan. 15, 2006.
Ahren et al., The augmenting effect on insulin secretion by oral versus intravenous glucose is exaggerated by high-fat diet in mice. J Endocrinol. Apr. 2008;197(1):181-7.
Anderson et al., Discovery of selective aminothiazole aurora kinase inhibitors. ACS Chem Biol. Mar. 20, 2008;3(3):180-92. Epub Feb. 29, 2008.

(Continued)

*Primary Examiner* — James H Alstrum Acevedo
*Assistant Examiner* — Fred Reyolds
(74) *Attorney, Agent, or Firm* — Wolf, Greenfield & Sacks, P.C.; C. Hunter Baker; Robin A. Weatherhead

(57) ABSTRACT

The present invention provides macrocyclic compounds of Formula (I): pharmaceutically acceptable salts thereof; and pharmaceutical compositions thereof, wherein $R_1$, $R_2$, $R_3$, $R_4$, $R^E$, $R^F$, $R^G$, $R^H$, $R^I$, f, g, h, n, and m are as defined herein. The present invention further provides methods of synthesizing these macrocyclic compounds, and methods of their use and treatment. Certain aspects of the present invention relate to modulation of kinase activity, and in the treatment of kinase-associated diseases or disorders.

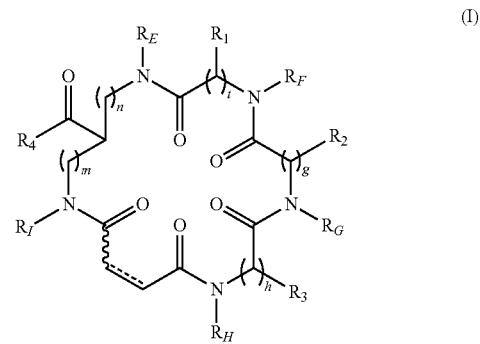

(I)

16 Claims, 67 Drawing Sheets

(56) References Cited

OTHER PUBLICATIONS

Azam et al., Activation of tyrosine kinases by mutation of the gatekeeper threonine. Nat Struct Mol Biol. Oct. 2008;15(10):1109-18. Epub Sep. 14, 2008.

Azam et al., Activity of dual SRC-ABL inhibitors highlights the role of BCR/ABL kinase dynamics in drug resistance. Proc Natl Acad Sci U S A. Jun. 13, 2006;103(24):9244-9. Epub Jun. 5, 2006.

Barker et al., Characterization of pp60c-src tyrosine kinase activities using a continuous assay: autoactivation of the enzyme is an intermolecular autophosphorylation process. Biochemistry. Nov. 14, 1995;34(45):14843-51.

Barnard et al., In vitro inhibition of Ras-Raf association by short peptides. Biochem Biophys Res Commun. Jun. 9, 1998;247(1):176-80.

Barouch-Bentov et al, A conserved salt bridge in the G loop of multiple protein kinases is important for catalysis and for in vivo Lyn function. Mol Cell. Jan. 16, 2009;33(1):43-52.

Becker et al., Insulysin and pitrilysin: insulin-degrading enzymes of mammals and bacteria. Methods Enzymol. 1995;248:693-703.

Bentley et al., Accurate whole human genome sequencing using reversible terminator chemistry. Nature. Nov. 6, 2008;456(7218):53-9.

Berge et al., Pharmaceutical salts. J Pharm Sci. Jan. 1977;66(1):1-19.

Bikker et al., Kinase domain mutations in cancer: implications for small molecule drug design strategies. J Med Chem. Mar. 26, 2009;52(6):1493-509.

Bradner et al., A robust small-molecule microarray platform for screening cell lysates. Chem Biol. May 2006;13(5):493-504.

Brudno et al., An in vitro translation, selection and amplification system for peptide nucleic acids. Nat Chem Biol. Feb. 2010;6(2):148-55. Epub Dec. 27, 2009.

Calderone et al., Small-molecule diversification from iterated branching reaction pathways enabled by DNA-templated synthesis. Angew Chem Int Ed Engl. Dec. 1, 2005;44(45):7383-6.

Capdeville et al., Glivec (STI571, imatinib), a rationally developed, targeted anticancer drug. Nat Rev Drug Discov. Jul. 2002;1(7):493-502.

Cheetham et al., Crystal structure of aurora-2, an oncogenic serine/threonine kinase. J Biol Chem. Nov. 8, 2002;277(45):42419-22. Epub Sep. 16, 2002.

Chen et al., A biomolecule-compatible visible-light-induced azide reduction from a DNA-encoded reaction-discovery system. Nat Chem. Feb. 2011;3(2):146-53. Epub Jan. 9, 2011.

Chene et al., A small synthetic peptide, which inhibits the p53-hdm2 interaction, stimulates the p53 pathway in tumour cell lines. J Mol Biol. May 26, 2000;299(1):245-53.

Church, Genomes for all. Sci Am. Jan. 2006;294(1):46-54.

Clark et al., Design, synthesis and selection of DNA-encoded small-molecule libraries. Nat Chem Biol. Sep. 2009;5(9):647-54. Epub Aug. 2, 2009. Erratum in: Nat Chem Biol. Oct. 2009;5(10):772.

Coan et al., Stoichiometry and physical chemistry of promiscuous aggregate-based inhibitors. J Am Chem Soc. Jul. 23, 2008;130(29):9606-12. Epub Jun. 28, 2008.

Cohen, Protein kinases—the major drug targets of the twenty-first century? Nat Rev Drug Discov. Apr. 2002;1(4):309-15.

Cools et al., PKC412 overcomes resistance to imatinib in a murine model of FIP1L1-PDGFRα-induced myeloproliferative disease. Cancer Cell. May 2003;3(5):459-69.

Cowan-Jacob et al., The crystal structure of a c-Src complex in an active conformation suggests possible steps in c-Src activation. Structure. Jun. 2005;13(6):861-71.

Cronican et al., Potent delivery of functional proteins into Mammalian cells in vitro and in vivo using a supercharged protein. ACS Chem Biol. Aug. 20, 2010;5(8):747-52.

Cronican et al., Potent delivery of functional proteins into Mammalian cells in vitro and in vivo using a supercharged protein. ACS Chem Biol. Aug. 20, 2010;5(8):747-52. Supporting Information. 18 pages.

Das et al., 2-aminothiazole as a novel kinase inhibitor template. Structure-activity relationship studies toward the discovery of N-(2-chloro-6-methylphenyl)-2-[[6-[4-(2-hydroxyethyl)-1-piperazinyl)]-2-methyl-4-pyrimidinyl]amino)]-1,3-thiazole-5-carboxamide (dasatinib, BMS-354825) as a potent pan-Src kinase inhibitor. J Med Chem. Nov. 16, 2006;49(23):6819-32.

Dewey et al., New uridine derivatives for systematic evolution of RNA ligands by exponential enrichment. J. Am. Chem. Soc. Aug. 1995;117(32):8474-5.

Ditchfield et al., Aurora B couples chromosome alignment with anaphase by targeting BubR1, Mad2, and Cenp-E to kinetochores. J Cell Biol. Apr. 28, 2003;161(2):267-80.

Doyon et al., Highly sensitive in vitro selections for DNA-linked synthetic small molecules with protein binding affinity and specificity. J Am Chem Soc. Oct. 15, 2003;125(41):12372-3.

Driggers et al., The exploration of macrocycles for drug discovery—an underexploited structural class. Nat Rev Drug Discov. Jul. 2008;7(7):608-24.

Duckworth et al., Insulin degradation: progress and potential. Endocr Rev. Oct. 1998;19(5):608-24.

Dumelin et al., Selection of streptavidin binders from a DNA-encoded chemical library. Bioconjug Chem. Mar.-Apr. 2006;17(2):366-70.

Emsley et al., Coot: model-building tools for molecular graphics. Acta Crystallogr D Biol Crystallogr. Dec. 2004;60(Pt 12 Pt 1):2126-32. Epub Nov. 26, 2004.

Fancelli et al., Potent and selective Aurora inhibitors identified by the expansion of a novel scaffold for protein kinase inhibition. J Med Chem. Apr. 21, 2005;48(8):3080-4.

Farris et al., Insulin-degrading enzyme regulates the levels of insulin, amyloid beta-protein, and the beta-amyloid precursor protein intracellular domain in vivo. Proc Natl Acad Sci U S A. Apr. 1, 2003;100(7):4162-7. Epub Mar. 12, 2003.

Forster et al., Programming peptidomimetic syntheses by translating genetic codes designed de novo. Proc Natl Acad Sci U S A. May 27, 2003;100(11):6353-7. Epub May 16, 2003.

Fu et al., Roles of Aurora kinases in mitosis and tumorigenesis. Mol Cancer Res. Jan. 2007;5(1):1-10.

García-Echeverría et al., Discovery of potent antagonists of the interaction between human double minute 2 and tumor suppressor p53. J Med Chem. Aug. 24, 2000;43(17):3205-8.

Gartner et al. DNA-templated organic synthesis and selection of a library of macrocycles. Science. Sep. 10, 2004;305(5690):1601-5. Epub Aug. 19, 2004.

Gartner et al., Expanding the reaction scope of DNA-templated synthesis. Angew Chem Int Ed Engl. May 17, 2002;41(10):1796-800.

Gartner et al., Multistep small-molecule synthesis programmed by DNA templates. J Am Chem Soc. Sep. 4, 2002;124(35):10304-6.

Gartner et al., The generality of DNA-templated synthesis as a basis for evolving non-natural small molecules. J Am Chem Soc. Jul. 18, 2001;123(28):6961-3.

Gazit et al., Tyrphostins I: synthesis and biological activity of protein tyrosine kinase inhibitors. J Med Chem. Oct. 1989;32(10):2344-52.

Georghiou et al., Highly specific, bisubstrate-competitive Src inhibitors from DNA-templated macrocycles. Nat Chem Biol. Feb. 19, 2012;8(4):366-74.

Golas et al., SKI-606, a Src/Abl inhibitor with in vivo activity in colon tumor xenograft models. Cancer Res. Jun. 15, 2005;65(12):5358-64.

Hall, Advanced sequencing technologies and their wider impact in microbiology. J Exp Biol. May 2007;210(Pt 9):1518-25.

Halpin et al., DNA display I. Sequence-encoded routing of DNA populations. PLoS Biology. Jul. 2004; 2(7):1015-21.

Halpin et al., DNA display II. Genetic manipulation of combinatorial chemistry libraries for small-molecule evolution. PLoS Biology. Jul. 2004; 2(7):1022-30.

Halpin et al., DNA display III. Solid-phase organic synthesis on unprotected DNA. PLoS Biology. Jul. 2004; 2(7):1031-8.

Hanke et al., Discovery of a novel, potent, and Src family-selective tyrosine kinase inhibitor. Study of Lck- and FynT-dependent T cell activation. J Biol Chem. Jan. 12, 1996;271(2):695-701.

Hanks et al., Protein kinase catalytic domain sequence database: identification of conserved features of primary structure and classification of family members. Methods Enzymol. 1991;200:38-62.

(56) References Cited

OTHER PUBLICATIONS

Hanks et al., The eukaryotic protein kinase superfamily: kinase (catalytic) domain structure and classification. FASEB J. May 1995;9(8):576-96.

Hanks et al., The protein kinase family: conserved features and deduced phylogeny of the catalytic domains. Science. Jul. 1, 1988;241(4861):42-52.

Hansen et al., A yoctoliter-scale DNA reactor for small-molecule evolution. J Am Chem Soc. Jan. 28, 2009;131(3):1322-7.

Harrington et al., VX-680, a potent and selective small-molecule inhibitor of the Aurora kinases, suppresses tumor growth in vivo. Nat Med. Mar. 2004;10(3):262-7. Epub Feb. 22, 2004. Erratum in: Nat Med. Apr. 2007;13(4):511.

Heid et al., Real time quantitative PCR. Genome Res. Oct. 1996;6(10):986-94.

Higuchi et al., Simultaneous amplification and detection of specific DNA sequences. Biotechnology (N Y). Apr. 1992;10(4):413-7.

Hill et al., A chemical genetic method for generating bivalent inhibitors of protein kinases. J Am Chem Soc. May 20, 2009;131(19):6686-8.

Holmes et al., Vascular endothelial growth factor receptor-2: structure, function, intracellular signalling and therapeutic inhibition. Cell Signal. Oct. 2007;19(10):2003-12. Epub Jun. 12, 2007.

Horhota et al., Kinetic analysis of an efficient DNA-dependent TNA polymerase. J Am Chem Soc. May 25, 2005;127(20):7427-34.

Hruby et al., Synthesis of oligopeptide and peptidomimetic libraries. Curr Opin Chem Biol. Jun. 1997;1(1):114-9.

Hubbard, Crystal structure of the activated insulin receptor tyrosine kinase in complex with peptide substrate and ATP analog. EMBO J. Sep. 15, 1997;16(18):5572-81.

Irby et al., Activating SRC mutation in a subset of advanced human colon cancers. Nat Genet. Feb. 1999;21(2):187-90.

Johnson et al., Development of an internally quenched fluorescent substrate selective for endothelin-converting enzyme-1. Anal Biochem. Nov. 1, 2000;286(1):112-8.

Josephson et al., Ribosomal synthesis of unnatural peptides. J Am Chem Soc. Aug. 24, 2005; 127(33): 11727-35.

Joyce, Directed evolution of nucleic acid enzymes. Annu Rev Biochem. 2004;73:791-836.

Kanan et al., Reaction discovery enabled by DNA-templated synthesis and in vitro selection. Nature. Sep. 30, 2004;431(7008):545-9.

Kansy et al., Physicochemical high throughput screening: parallel artificial membrane permeation assay in the description of passive absorption processes. J Med Chem. Mar. 26, 1998;41(7):1007-10.

Karaman et al., A quantitative analysis of kinase inhibitor selectivity. Nat Biotechnol. Jan. 2008;26(1):127-32.

Kim et al., Peptidomics approach to elucidate the proteolytic regulation of bioactive peptides. Proc Natl Acad Sci U S A. May 29, 2012;109(22):8523-7. Epub May 14, 2012.

Kleiner et al., DNA-templated polymerization of side-chain-functionalized peptide nucleic acid aldehydes. J Am Chem Soc. Apr. 9, 2008;130(14):4646-59. Epub Mar. 15, 2008.

Kleiner et al., In vitro selection of a DNA-templated small-molecule library reveals a class of macrocyclic kinase inhibitors. J Am Chem Soc. Aug. 25, 2010;132(33):11779-91.

Kleiner et al., In vitro selection of a DNA-templated small-molecule library reveals a class of macrocyclic kinase inhibitors. J Am Chem Soc. Aug. 25, 2010;132(33):11779-91. Supporting Information. 36 pages.

Kleiner et al., Small-molecule discovery from DNA-encoded chemical libraries. Chem Soc Rev. Dec. 2011;40(12):5707-17. Epub Jun. 14, 2011.

Knight et al., Features of selective kinase inhibitors. Chem Biol. Jun. 2005;12(6):621-37.

Krishnamurty et al., Biochemical mechanisms of resistance to small-molecule protein kinase inhibitors. ACS Chem Biol. Jan. 15, 2010;5(1):121-38.

Kwon et al., Quantitative comparison of the relative cell permeability of cyclic and linear peptides. Chem Biol. Jun. 2007;14(6):671-7.

Lam et al., The "One-Bead-One-Compound" Combinatorial Library Method. Chem Rev. Apr. 1, 1997;97(2):411-448.

Latham et al., The application of a modified nucleotide in aptamer selection: novel thrombin aptamers containing 5-(1-pentynyl)-2'-deoxyuridine. Nucleic Acids Res. Jul. 25, 1994;22(14):2817-22.

Lee et al., Enhancing the catalytic repertoire of nucleic acids: a systematic study of linker length and rigidity. Nucleic Acids Res. Apr. 1, 2001;29(7):1565-73.

Leissring et al., Designed inhibitors of insulin-degrading enzyme regulate the catabolism and activity of insulin. PLoS One. May 7, 2010;5(5):e10504.

Leslie, Recent changes to the MOSFLM package for processing film and image plate data Joint CCP4 + ESF-EAMCB Newsletter on Protein Crystallography, 1992;26:27-33.

Levinson et al., A Src-like inactive conformation in the abl tyrosine kinase domain. PLoS Biol. May 2006;4(5):e144. Epub May 2, 2006.

Levitzki, Protein tyrosine kinase inhibitors as novel therapeutic agents. Pharmacol Ther. May-Jun. 1999;82(2-3):231-9.

Li et al., DNA-templated organic synthesis: nature's strategy for controlling chemical reactivity applied to synthetic molecules. Angew Chem Int Ed Engl. Sep. 20, 2004;43(37):4848-70.

Lin et al., Screening and selection methods for large-scale analysis of protein function. Angew Chem Int Ed Engl. Dec. 2, 2002;41(23):4402-25.

Livak et al., Oligonucleotides with fluorescent dyes at opposite ends provide a quenched probe system useful for detecting PCR product and nucleic acid hybridization. PCR Methods Appl. Jun. 1995;4(6):357-62.

Llauger-Bufi et al., Synthesis of novel fluorescent probes for the molecular chaperone Hsp90. Bioorg Med Chem Lett. Nov. 17, 2003;13(22):3975-8.

Löber et al., Palladium-catalyzed hydroamination of 1,3-dienes: a colorimetric assay and enantioselective additions. J Am Chem Soc. May 9, 2001;123(18):4366-7.

Lombardo et al., Discovery of N-(2-chloro-6-methyl-phenyl)-2-(6-(4-(2-hydroxyethyl)-piperazin-1-y1)-2-methylpyrimidin-4-ylamino)thiazole-5-carboxamide (BMS-354825), a dual Src/Abl kinase inhibitor with potent antitumor activity in preclinical assays. J Med Chem. Dec. 30, 2004;47(27):6658-61.

Manfredi et al., Antitumor activity of MLN8054, an orally active small-molecule inhibitor of Aurora A kinase. Proc Natl Acad Sci U S A. Mar. 6, 2007;104(10):4106-11. Epub Feb. 23, 2007.

Manning et al., The protein kinase complement of the human genome. Science. Dec. 6, 2002;298(5600):1912-34.

Maresso et al., Sortase as a target of anti-infective therapy. Pharmacol Rev. Mar. 2008;60(1):128-41.

Martens et al., PREPL: a putative novel oligopeptidase propelled into the limelight. Biol Chem. Jul. 2006;387(7):879-83.

Matulic-Adamic et al., Functionalized nucleoside 5'-triphosphates for in vitro selection of new catalytic ribonucleic acids. Bioorg Med Chem Lett. Jun. 5, 2000;10(11):1299-302.

McCoy et al., Likelihood-enhanced fast translation functions. Acta Crystallogr D Biol Crystallogr. Apr. 2005;61(Pt 4):458-64. Epub Mar. 24, 2005.

Melkko et al., Encoded self-assembling chemical libraries. Nat Biotechnol. May 2004;22(5):568-74. Epub Apr. 18, 2004.

Melkko et al., Isolation of high-affinity trypsin inhibitors from a DNA-encoded chemical library. Angew Chem Int Ed Engl. 2007;46(25):4671-4.

Minerva et al., Concordant association of insulin degrading enzyme gene (IDE) variants with IDE mRNA, Abeta, and Alzheimer's disease. PLoS One. Jan. 19, 2010;5(1):e8764.

Mirsky et al., The inactivation of insulin by tissue extracts; the distribution and properties of insulin inactivating extracts. Arch Biochem. Jan. 1949;20(1):1-9.

Mol et al., Structural basis for the autoinhibition and STI-571 inhibition of c-Kit tyrosine kinase. J Biol Chem. Jul. 23, 2004;279(30):31655-63. Epub Apr. 29, 2004.

Momiyama et al., Synthesis of acyclic alpha,beta-unsaturated ketones via Pd(II)-catalyzed intermolecular reaction of alkynamides and alkenes. J Am Chem Soc. Feb. 28, 2007;129(8):2230-1. Epub Feb. 6, 2007.

(56) References Cited

OTHER PUBLICATIONS

Musich et al, Synthesis of anthopleurine, the alarm pheromone from *Anthopleura elegantissima*. J. Am. Chem. Soc. Jul. 1987;100(15):4865-72.

Ohren et al., Structures of human MAP kinase kinase 1 (MEK1) and MEK2 describe novel noncompetitive kinase inhibition. Nat Struct Mol Biol. Dec. 2004;11(12):1192-7. Epub Nov. 14, 2004. Erratum in: Nat Struct Mol Biol. Mar. 2005;12(3):278.

Otwinowski et al., Processing of x-ray diffraction data collected in oscillation mode. Methods in Enzymology. 276 (Macromolecular Crystallography, part A):307-26, 1997.

Patick et al., Protease inhibitors as antiviral agents. Clin Microbiol Rev. Oct. 1998;11(4):614-27.

Perrin et al., Bridging the gap between proteins and nucleic acids: a metal-independent RNAseA mimic with two protein-like functionalities. J Am Chem Soc. Feb. 28, 2001;123(8):1556-63.

Pirrung, Spatially Addressable Combinatorial Libraries. Chem Rev. Apr. 1, 1997;97(2):473-488.

PubChem CID 46938796. Nov. 15, 2010. [Retrieved from the internet Dec. 2, 2011:http://pubchem.ncbi.nim.nih.gov/summary/summary.cgi?cid=46938796&loc=ec_rcs].

Roh et al., Overexpression of the oncogenic kinase Pim-1 leads to genomic instability. Cancer Res. Dec. 1, 2003;63(23):8079-84.

Rosenbaum et al., Efficient and sequence-specific DNA-templated polymerization of peptide nucleic acid aldehydes. J Am Chem Soc. Nov. 19, 2003;125(46):13924-5.

Rozenman et al., Development and initial application of a hybridization-independent, DNA-encoded reaction discovery system compatible with organic solvents. J Am Chem Soc. Dec. 5, 2007;129(48):14933-8. Epub Nov. 10, 2007.

Ruff et al., Enhanced functional potential of nucleic acid aptamer libraries patterned to increase secondary structure. J Am Chem Soc. Jul. 14, 2010;132(27):9453-64.

Ruff et al., Enhanced functional potential of nucleic acid aptamer libraries patterned to increase secondary structure. J Am Chem Soc. Jul. 14, 2010;132(27):9453-64. Supporting Information. 25 pages.

Sattler et al., Structure of Bcl-xL-Bak peptide complex: recognition between regulators of apoptosis. Science. Feb. 14, 1997;275(5302):983-6.

Scheuermann et al., DNA-encoded chemical libraries for the discovery of MMP-3 inhibitors. Bioconjug Chem. Mar. 2008;19(3):778-85. Epub Feb. 7, 2008.

Schindler et al., Structural mechanism for STI-571 inhibition of abelson tyrosine kinase. Science. Sep. 15, 2000;289(5486):1938-42.

Seeliger et al., c-Src binds to the cancer drug imatinib with an inactive Abl/c-Kit conformation and a distributed thermodynamic penalty. Structure. Mar. 2007;15(3):299-311.

Seeliger et al., Equally potent inhibition of c-Src and Abl by compounds that recognize inactive kinase conformations. Cancer Res. Mar. 15, 2009;69(6):2384-92. Epub Mar. 10, 2009.

Seeliger et al., High yield bacterial expression of active c-Abl and c-Src tyrosine kinases. Protein Sci. Dec. 2005;14(12):3135-9. Epub Oct. 31, 2005.

Shan et al., How does a drug molecule find its target binding site? J Am Chem Soc. Jun. 22, 2011;133(24):9181-3. Epub May 13, 2011.

Sharma et al., Targeting Akt3 signaling in malignant melanoma using isoselenocyanates. Clin Cancer Res. Mar. 1, 2009;15(5):1674-85. Epub Feb. 10, 2009.

Shen et al., Structures of human insulin-degrading enzyme reveal a new substrate recognition mechanism. Nature. Oct. 19, 2006;443(7113):870-4. Epub Oct. 11, 2006.

Shoichet, Interpreting steep dose-response curves in early inhibitor discovery. J Med Chem. Dec. 14, 2006;49(25):7274-7.

Sicheri et al., Crystal structure of the Src family tyrosine kinase Hck. Nature. Feb. 13, 1997;385(6617):602-9.

Snyder et al., Ordered multistep synthesis in a single solution directed by DNA templates. Angew Chem Int Ed Engl. Dec. 1, 2005;44(45):7379-82.

Songyang et al., Catalytic specificity of protein-tyrosine kinases is critical for selective signalling. Nature. Feb. 9, 1995;373(6514):536-9.

Songyang et al., Recognition and specificity in protein tyrosine kinase-mediated signalling. Trends Biochem Sci. Nov. 1995;20(11):470-5.

Stout et al., High-throughput structural biology in drug discovery: protein kinases. Curr Pharm Des. 2004;10(10):1069-82.

Sugimura et al., Mutation of the SRC gene in endometrial carcinoma. Jpn J Cancer Res. Apr. 2000;91(4):395-8.

Tan, Diversity-oriented synthesis: exploring the intersections between chemistry and biology. Nat Chem Biol. Jul. 2005;1(2):74-84.

Tatton et al., The Src-selective kinase inhibitor PP1 also inhibits Kit and Bcr-Abl tyrosine kinases. J Biol Chem. Feb. 14, 2003;278(7):4847-53. Epub Dec. 9, 2002.

Taylor et al., Investigating and Engineering Enzymes by Genetic Selection. Angew Chem Int Ed Engl. Sep. 17, 2001;40(18):3310-3335.

Thompson et al., Attenuation of androgen receptor-dependent transcription by the serine/threonine kinase Pim-1. Lab Invest. Sep. 2003;83(9):1301-9.

Tse et al., Translation of DNA into a library of 13,000 synthetic small-molecule macrocycles suitable for in vitro selection. J Am Chem Soc. Nov. 19, 2008;130(46):15611-26. Epub Oct. 29, 2008.

Walters et al., Designing screens: how to make your hits a hit. Nat Rev Drug Discov. Apr. 2003;2(4):259-66.

Wilson et al., In vitro Selection of Functional Nucleic Acids. Ann. Rev. Biochem., 1999; 68:611-48.

Wrenn et al., Synthetic ligands discovered by in vitro selection. J Am Chem Soc. Oct. 31, 2007;129(43):13137-43. Epub Oct. 6, 2007.

Xu et al., Crystal structures of c-Src reveal features of its autoinhibitory mechanism. Mol Cell. May 1999;3(5):629-38.

Xu et al., Three-dimensional structure of the tyrosine kinase c-Src. Nature. Feb. 13, 1997;385(6617):595-602.

Zhang et al., Targeting cancer with small molecule kinase inhibitors. Nat Rev Cancer. Jan. 2009;9(1):28-39.

International Search Report and Written Opinion for Application No. PCT/US2012/044977, mailed Dec. 6, 2012.

International Preliminary Report on Patentability for Application No. PCT/US2012/044977, mailed Jan. 16, 2014.

Genbank Submission; NIH/NCBI, Accession No. NP_001159418.1. McFall et al., May 25, 2014. 3 pages.

Genbank Submission; NIH/NCBI, Accession No. NP_004960.2. McFall et al., May 25, 2014. 4 pages.

Genbank Submission; NIH/NCBI, Accession No. NP_112419.2. Kim et al., Feb. 9, 2013. 3 pages.

Abdul-Hay et al., Deletion of insulin-degrading enzyme elicits antipodal, age-dependent effects on glucose and insulin tolerance. PLoS One. 2011;6(6):e20818. doi: 10.1371/journal.pone.0020818. Epub Jun. 9, 2011.

Abdul-Hay et al., Optimization of Peptide Hydroxamate Inhibitors of Insulin-Degrading Enzyme Reveals Marked Substrate-Selectivity. J Med Chem 2013;56(6):2246-2255. doi:10.1021/jm301280p. Epub Mar. 15, 2013.

Adams et al., Phenix: a comprehensive Python-based system for macromolecular structure solution. Acta Crystallogr D Biol Crystallogr. Feb. 2010;66(Pt 2):213-21. doi: 10.1107/S0907444909052925. Epub Jan. 22, 2010.

Andrikopoulos et al., Evaluating the glucose tolerance test in mice. Am J Physiol Endocrinol Metab. Dec. 2008;295(6):E1323-32. doi: 10.1152/ajpendo.90617.2008. Epub Sep. 23, 2008.

Authier et al., Proteolysis of glucagon within hepatic endosomes by membrane-associated cathepsins B and D. J Biol Chem. Jun, 30, 1995;270(26):15798-807.

Bartl et al., Disorder-specific effects of polymorphisms at opposing ends of the Insulin Degrading Enzyme gene. BMC Med Genet. Nov. 22, 2011;12:151. doi: 10.1186/1471-2350-12-151.

Bennett et al., Degradation of amylin by insulin-degrading enzyme. J Biol Chem. Nov. 24, 2000;275(47):36621-5.

Bennett et al., Degradation of relaxin family peptides by insulin-degrading enzyme. Ann N Y Acad Sci. Apr. 2009;1160:38-41. doi:10.1111/j.1749-6632.2008.03782.x.

(56) References Cited

OTHER PUBLICATIONS

Chudakov et al., Fluorescent proteins and their applications in imaging living cells and tissues. Physiol Rev. Jul. 2010;90(3):1103-63. doi: 10.1152/physrev.00038.2009.

Ciaccio et al., Somatostatin: a novel substrate and a modulator of insulin-degrading enzyme activity. J Mol Biol. Feb. 6, 2009;385(5):1556-67. doi:10.1016/j.jmb.2008.11.025. Epub Nov. 25, 2008.

Crowell et al., The effects of tegaserod, a 5-HT receptor agonist, on gastric emptying in a murine model of diabetes mellitus. Neurogastroenterol Motil. Oct. 2005;17(5):738-43.

Drucker, The biology of incretin hormones. Cell Metab. Mar. 2006;3(3):153-65.

Duckworth et al., Insulin and glucagon degradation by the same enzyme. Diabetes. Jun. 1974;23(6):536-43.

Fontés et al., Miniglucagon (MG)-generating endopeptidase, which processes glucagon into MG, is composed of N-arginine dibasic convertase and aminopeptidase B. Endocrinology. Feb. 2005;146(2):702-12. Epub Nov. 11, 2004.

Gedulin et al., Role of endogenous amylin in glucagon secretion and gastric emptying in rats demonstrated with the selective antagonist, AC187. Regul Pept. Dec. 10, 2006;137(3):121-7. Epub Aug. 17, 2006.

Gelling et al., Lower blood glucose, hyperglucagonemia, and pancreatic alpha cell hyperplasia in glucagon receptor knockout mice. Proc Natl Acad Sci U S A. Feb. 4, 2003;100(3):1438-43. Epub Jan. 24, 2003.

Gu et al., Quantitative trait loci near the insulin-degrading enzyme (IDE) gene contribute to variation in plasma insulin levels. Diabetes. Aug. 2004;53(8):2137-42.

Guo et al., Molecular basis for the recognition and cleavages of IGF-II, TGF-alpha, and amylin by human insulin-degrading enzyme. J Mol Biol. Jan. 15, 2010;395(2):430-43. doi:10.1016/j.jmb.2009.10.072. Epub Nov. 5, 2009.

Hamel et al., Identification of the cleavage sites of transforming growth factor alpha by insulin-degrading enzymes. Biochim Biophys Acta. Apr. 4, 1997;1338(2):207-14.

Hollander et al., Effect of pramlintide on weight in overweight and obese insulin-treated type 2 diabetes patients. Obes Res. Apr. 2004;12(4):661-8.

Karamohamed et al., Polymorphisms in the insulin-degrading enzyme gene are associated with type 2 diabetes in men from the NHLBI Framingham Heart Study. Diabetes. Jun. 2003;52(6):1562-7.

Knight et al, Chemical genetics: where genetics and pharmacology meet. Cell. Feb. 9, 2007;128(3):425-30.

Kolterman et al., Reduction of postprandial hyperglycemia in subjects with IDDM by intravenous infusion of AC137, a human amylin analogue. Diabetes Care. Aug. 1995;18(8):1179-82.

Kurochkin et al., Alzheimer's beta-amyloid peptide specifically interacts with and is degraded by insulin degrading enzyme. FEBS Lett. May 23, 1994;345(1):33-7.

Lang et al., DOCK 6: combining techniques to model RNA-small molecule complexes. RNA. Jun. 2009;15(6):1219-30. doi: 10.1261/rna.1563609. Epub Apr. 15, 2009.

Lee et al., Metabolic manifestations of insulin deficiency do not occur without glucagon action. Proc Natl Acad Sci U S A. Sep. 11, 2012;109(37):14972-6. doi: 10.1073/pnas.1205983109. Epub Aug. 13, 2012.

Llovera et al., The catalytic domain of insulin-degrading enzyme forms a denaturant-resistant complex with amyloid beta peptide: implications for Alzheimer disease pathogenesis. J Biol Chem. Jun. 20, 2008;283(25):17039-48. doi: 10.1074/jbc.M706316200. Epub Apr. 14, 2008.

Malito et al., Molecular bases for the recognition of short peptide substrates and cysteine-directed modifications of human insulin-degrading enzyme. Biochemistry. Dec. 2, 2008;47(48):12822-34. doi: 10.1021/bi801192h.

Manolopoulou et al., Molecular basis of catalytic chamber-assisted unfolding and cleavage of human insulin by human insulin-degrading enzyme. J Biol Chem. May 22, 2009;284(21):14177-88. doi:10.1074/jbc.M900068200. Epub Mar. 25, 2009.

McCoy et al., Phaser crystallographic software. J Appl Crystallogr. Aug. 1, 2007;40(Pt 4):658-674. Epub Jul. 13, 2007.

Miller et al., Amyloid-beta peptide levels in brain are inversely correlated with insulysin activity levels in vivo. Proc Natl Acad Sci U S A. May 13, 2003;100(10):6221-6. Epub May 5, 2003.

Mirsky et al, Effect of insulinase-inhibitor on hypoglycemic action of insulin. Science. Sep. 23, 1955;122(3169):559-60.

Misbin et al., Inhibition of insulin degradation by insulin-like growth factors. Endocrinology. Oct. 1983;113(4):1525-7.

Müller et al., Atrial natriuretic peptide (ANP) is a high-affinity substrate for rat insulin-degrading enzyme. Eur J Biochem. Dec. 5, 1991;202(2):285-92.

Owicki., Fluorescence polarization and anisotropy in high throughput screening: perspectives and primer. J Biomol Screen. Oct. 2000;5(5):297-306. Review.

Parker et al., The regulation of *Acinetobacter* sp. alpha-oxoglutarate dehydrogenase complex. Biochem J. Nov. 1972;130(1):39P.

Qiu et al., Insulin-degrading enzyme regulates extracellular levels of amyloid beta-protein by degradation. J Biol Chem. Dec. 4, 1998;273(49):32730-8.

Riddle et al., Emerging therapies mimicking the effects of amylin and glucagon-like peptide 1. Diabetes Care. Feb. 2006;29(2):435-49. Review.

Riediger et al., The anorectic hormone amylin contributes to feeding-related changes of neuronal activity in key structures of the gut-brain axis. Am J Physiol Regul Integr Comp Physiol. Jan. 2004;286(1):R114-22. Epub Sep. 4, 2003.

Sadry et al., Emerging combinatorial hormone therapies for the treatment of obesity and T2DM. Nat Rev Endocrinol. Jul. 2013;9(7):425-33. doi:10.1038/nrendo.2013.47. Epub Mar. 12, 2013.

Safavi et al., Identification of gamma-endorphin-generating enzyme as insulin-degrading enzyme. Biochemistry. Nov. 12, 1996;35(45):14318-25.

Saghatelian et al., Activity-based probes for the proteomic profiling of metalloproteases. Proc Natl Acad Sci U S A. Jul. 6, 2004;101(27):10000-5. Epub Jun. 25, 2004.

Schmitz et al., Amylin agonists: a novel approach in the treatment of diabetes. Diabetes. Dec. 2004;53 Suppl 3:S233-8.

Stella et al., Cyclodextrins. Toxicol Pathol. Jan. 2008;36(1):30-42. doi: 10.1177/0192623307310945.

Trebbien et al., Neutral endopeptidase 24.11 is important for the degradation of both endogenous and exogenous glucagon in anesthetized pigs. Am J Physiol Endocrinol Metab. Sep. 2004;287(3):E431-8. Epub May 4, 2004.

Unger et al., Glucagonocentric restructuring of diabetes: a pathophysiologic and therapeutic makeover. J Clin Invest. Jan. 3, 2012;122(1):4-12. doi: 10.1172/JCI60016. Epub Jan. 3, 2012. Review.

Vonrhein et al., Data processing and analysis with the autoPROC toolbox. Acta Crystallogr D Biol Crystallogr. Apr. 2011;67(Pt 4):293-302. doi: 10.1107/S0907444911007773. Epub Mar. 18, 2011.

Winzell et al., The high-fat diet-fed mouse: a model for studying mechanisms and treatment of impaired glucose tolerance and type 2 diabetes. Diabetes. Dec. 2004;53 Suppl 3:S215-9.

Workman et al., Probing the probes: fitness factors for small molecule tools. Chem Biol. Jun. 25, 2010;17(6):561-77. doi: 10.1016/j.chembiol.2010.05.013.

Zhang et al., In vitro degradation of insulin-like peptide 3 by insulin-degrading enzyme. Protein J. Feb. 2010;29(2):93-8. doi:10.1007/s10930-009-9226-8.

\* cited by examiner

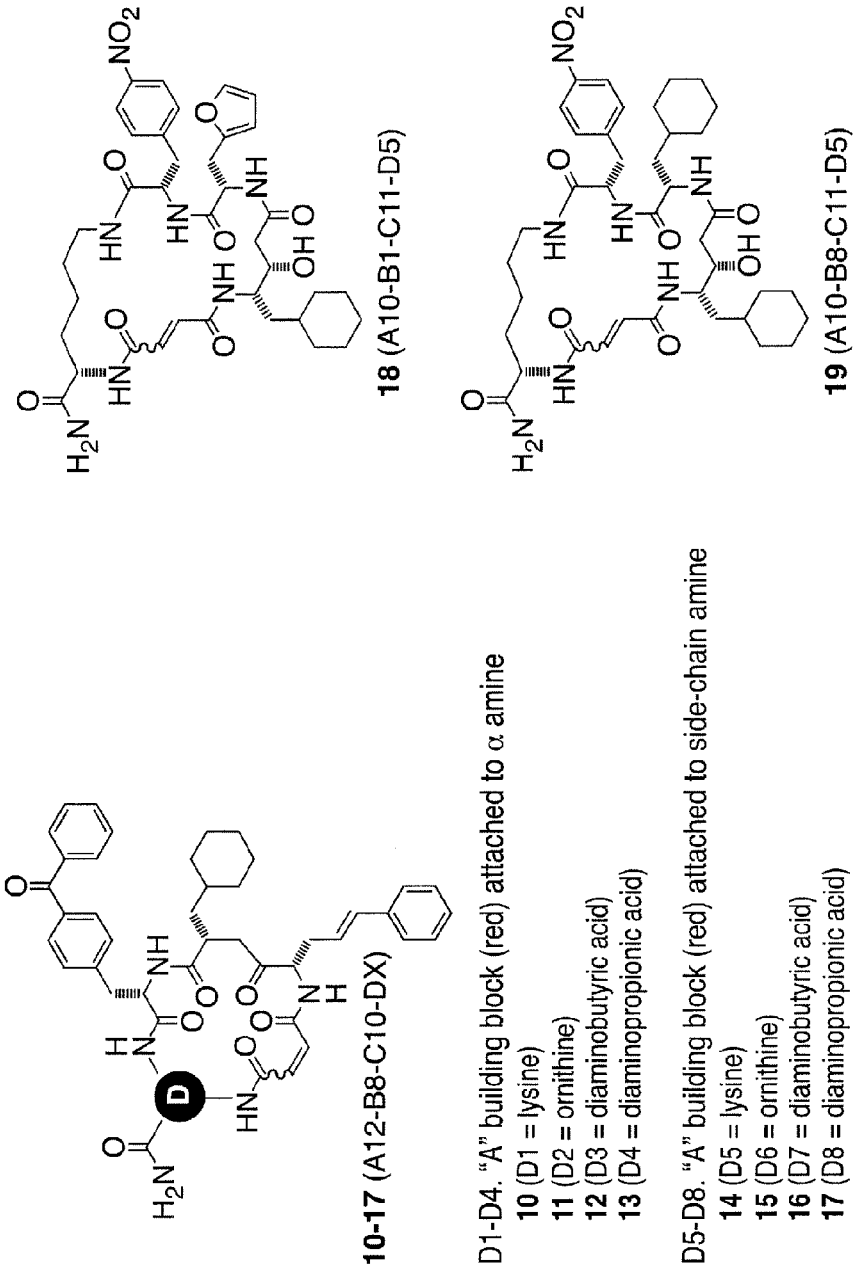
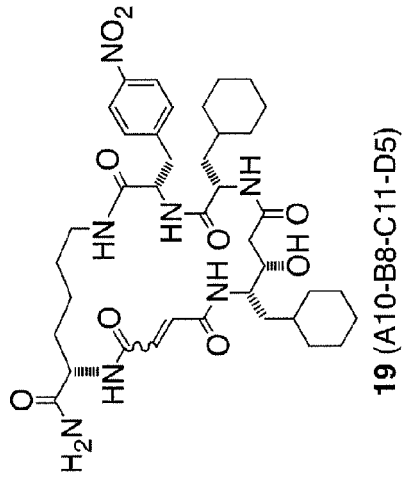
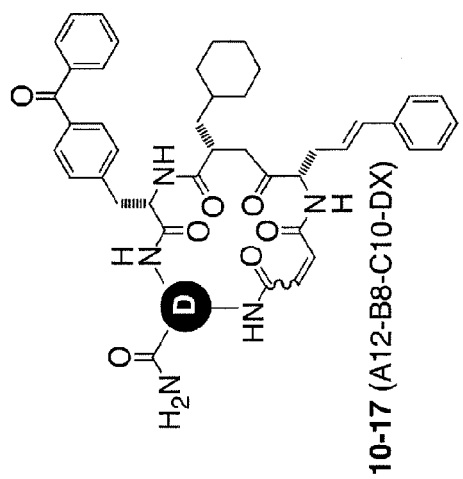
Fig. 6-3

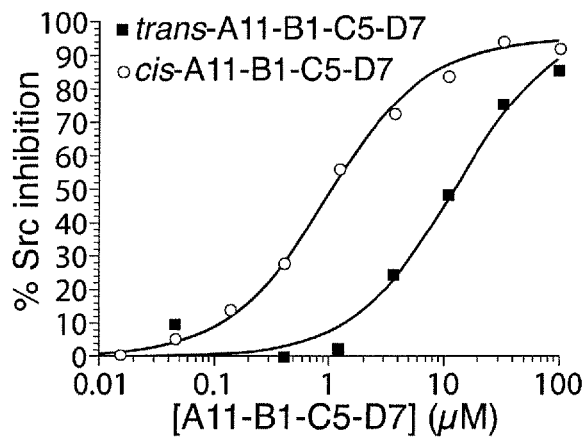
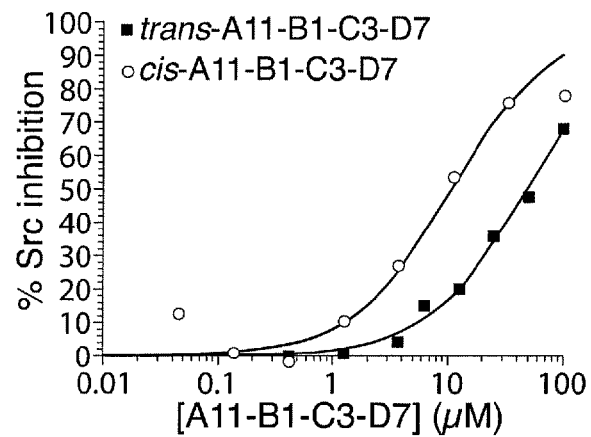
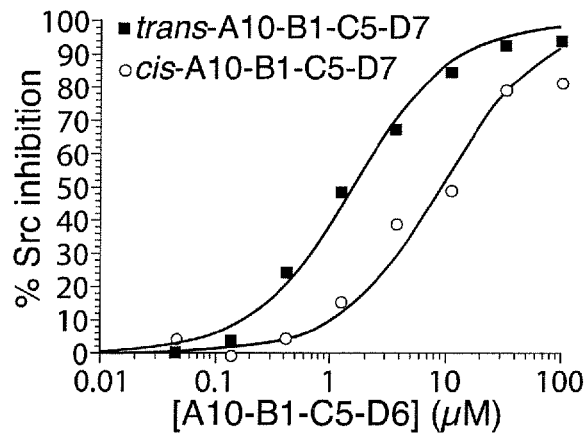
Fig. 8-1 linear A10-B1-C5-D6
IC$_{50}$ > 100 μM linear A11-B1-C5-D7
IC$_{50}$ > 100 μM

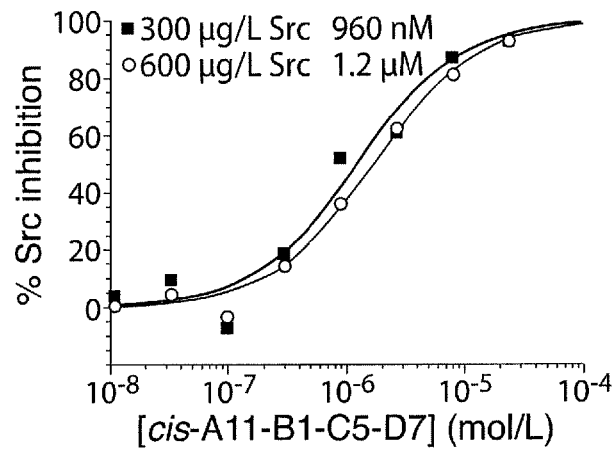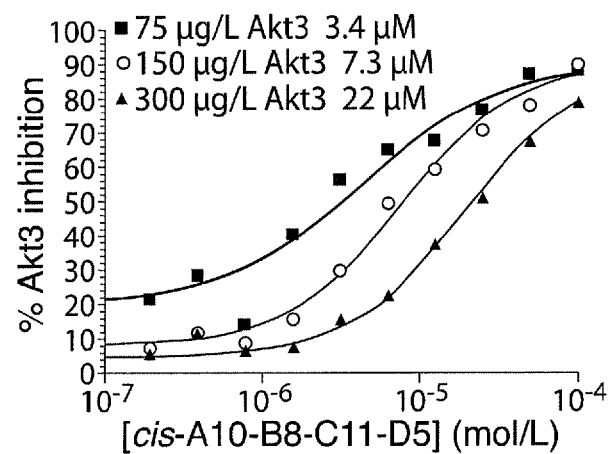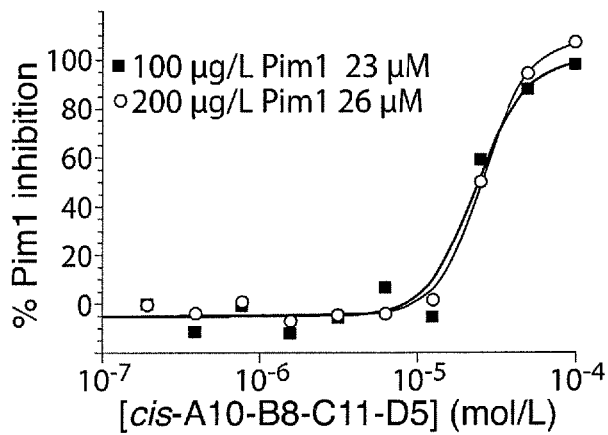
Fig. 17-1

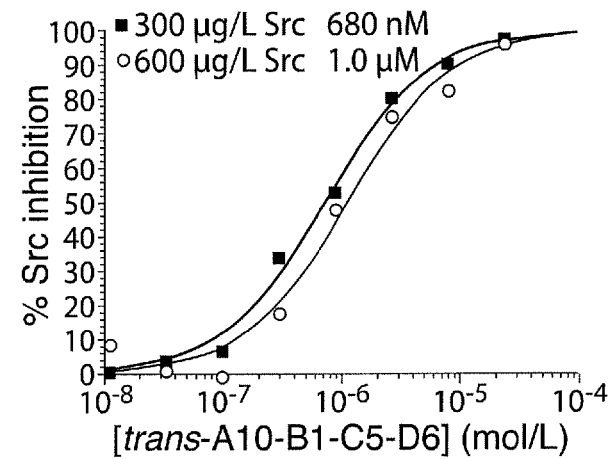
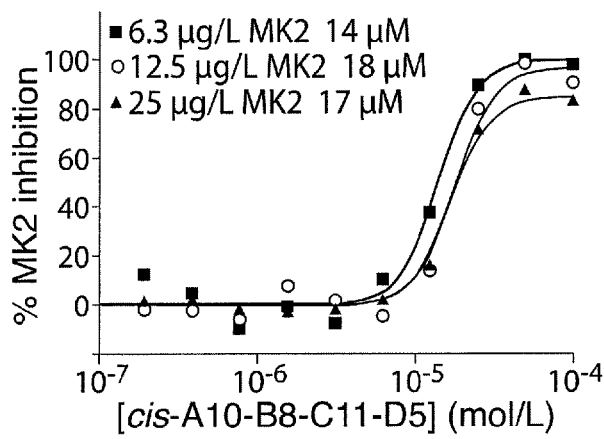
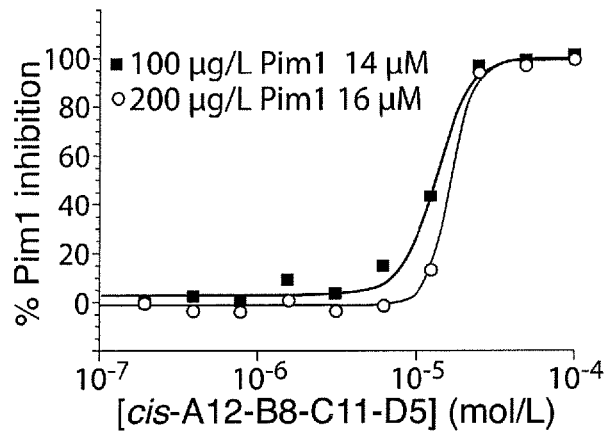
Fig. 17-2

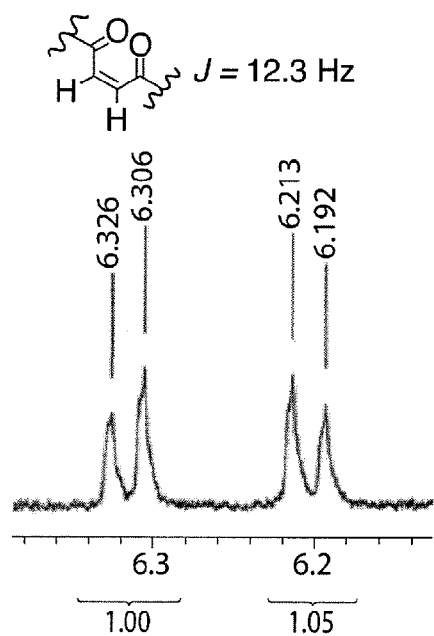
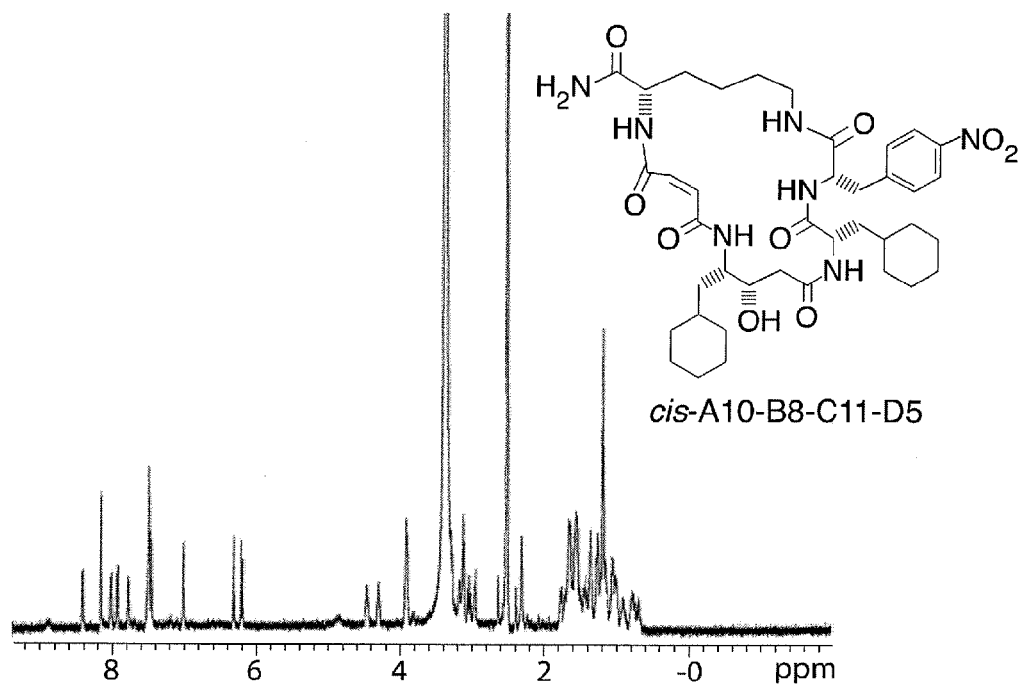
Fig. 18-20

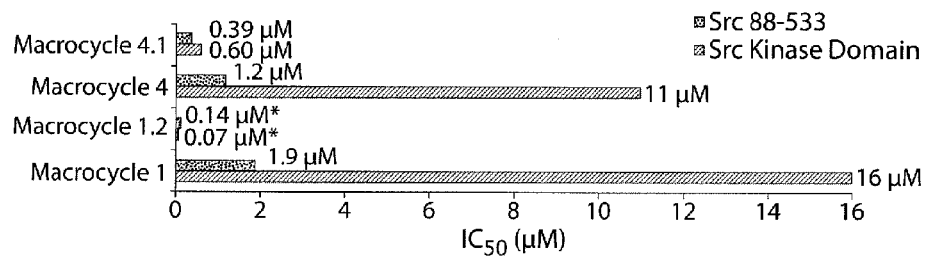
Fig. 20A
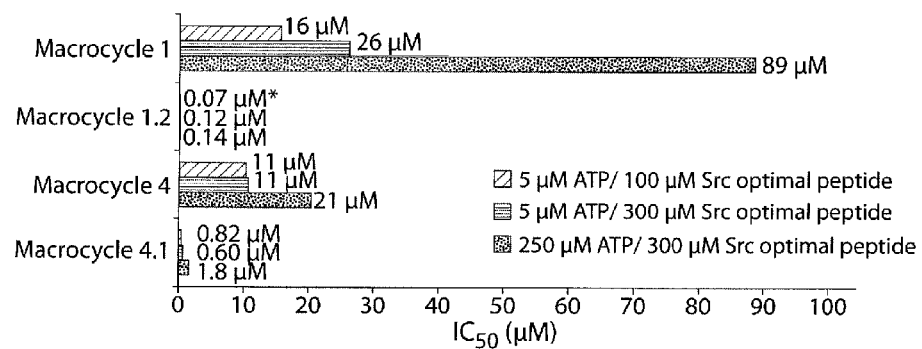
Fig. 20B
Fig. 20C

US 8,975,232 B2

MACROCYCLIC KINASE INHIBITORS AND USES THEREOF

RELATED APPLICATIONS

This application is a national stage filing under 35 U.S.C. §371 of international PCT application, PCT/US2011/045966, filed Jul. 29, 2011, which claims priority under 35 U.S.C. §119(e) to U.S. provisional patent application, U.S. Ser. No. 61/368,986, filed Jul. 29, 2010, the entire contents of each of which are hereby incorporated by reference.

GOVERNMENT SUPPORT

This invention was made with U.S. Government support under grant R01 GM065865 awarded by the National Institutes of Health (NIH). The U.S. Government has certain rights in the invention.

BACKGROUND

The discovery of small molecules capable of selectively modulating the activity of biological targets remains a central challenge of chemistry and chemical biology. Such small molecules are commonly discovered through combinatorial[1,2] or diversity-oriented[3] synthesis and high-throughput screening[4] (HTS). In contrast, functional molecules emerge in nature through iterated cycles of translation, selection, and amplification with mutation.[5-8] While scientists have applied components of biological evolution to generate DNA, RNA, and protein molecules with tailor-made catalytic or binding properties, this approach has traditionally been restricted to molecules whose structures are compatible with biosynthetic machinery.[9-16] DNA-templated organic synthesis was recently developed as a method for translating DNA sequences into synthetic small molecules[17-25] (see also published PCT application, WO 2004/016767) and synthetic polymers[26-28] that can be subjected to in vitro selection for desired properties.[17,20,23,28,29] Several related approaches to generate and evaluate DNA-encoded small-molecule libraries have also been used successfully in academic[30-37] and industrial settings.[38,39]

Macrocycles are particularly attractive candidates for the discovery of biologically active small molecules because their rigid scaffolds can decrease the entropic cost of target binding and limit access to non-binding conformations, resulting in higher affinity and greater binding specificity than their corresponding linear counterparts.[40] In addition, macrocyclic peptide-like structures can offer advantages for applications in cell culture and in vivo over their linear analogs since they can possess higher bioavailability, membrane permeability, and resistance to in vivo degradation.[40] While synthesizing macrocyclic structures, especially in a library format, can be challenging,[41,42] features of DNA-templated synthesis including compatibility with aqueous solvents, extremely low (nM) reactant concentrations, and the ability of base pairing to hold together relevant reactants at high effective molarities can promote efficient macrocylization.

SUMMARY OF THE INVENTION

DNA-templated organic synthesis enables the translation of DNA sequences into synthetic small-molecule libraries suitable for in vitro selection. Previously, model in vitro selection of a pilot library of 65 macrocycles was described[20]. Subsequent advances in DNA template design and DNA-templated synthesis methods enabled the preparation and characterization of a larger 13,824-membered DNA-templated macrocycle library.[24] Here the discovery of small molecules that modulate the activity of kinase enzymes through the in vitro selection of this DNA-templated small-molecule macrocycle library against 36 biomedically relevant protein targets is reported. Some of these protein targets are kinases-enzymes that phosphorylate their substrate, for example, their specific target protein in the case of protein kinases. The human genome contains about 500 protein kinase genes and dysregulation of kinase activity has been implicated in numerous diseases. Accordingly, compounds modulating the activity of specific kinases, for example, the kinases described herein, are useful for clinical as well as basic research applications.

DNA encoding selection survivors was amplified by PCR and identified by DNA sequencing. Macrocycles corresponding to DNA sequences enriched upon selection against several protein kinases were synthesized on a multi-milligram scale. In vitro assays revealed that these macrocycles inhibit (or activate) the kinases against which they were selected with $IC_{50}$ values as low as approximately 680 nM. A family of macrocycles enriched upon selection against Src kinase was characterized in depth, and inhibition was shown to be highly dependent on the identity of macrocycle building blocks as well as on backbone conformation (see, e.g., FIGS. 5 and 8-11). Two macrocycles in this family exhibited unusually strong Src inhibition selectivity even among kinases closely related to Src. One macrocycle was found to activate, rather than inhibit, its target kinase, VEGFR2. These results establish the use of DNA-templated synthesis and in vitro selection to discover novel small molecules that modulate enzyme activities, and also reveal a new molecular scaffold for selective ATP-competitive kinase inhibitors.

The Src kinase inhibitors discovered through this approach are believed to represent the first examples of synthetic peptidic macrocycles that inhibit protein kinase activity in an ATP-competitive manner. Some of the Src-inhibiting macrocycles exhibited unusual selectivity for Src when screened against a representative panel of human protein kinases. Further, some of the Src-inhibiting macrocylces described herein inhibit mutant forms of kinases, for example, mutant forms of Src kinase (e.g., Src kinase having a gatekeeper residue mutation, e.g., a Thr338Ile mutation). Macrocycles that activate VEGFR2 kinase and that inhibit Akt3, MAPKAPK2, p38α, and Pim1 kinases were also discovered. These results reveal two novel and synthetically versatile scaffolds for the selective inhibition of Src-family protein kinases.

Some aspects of this invention relate to compounds that bind and modulate the activity of kinases. In some embodiments, macrocyclic compounds are provided that modulate the activity of a kinase. For example, in some embodiments, kinase-inhibitory compounds are provided and in other embodiments, kinase-activating compounds are provided. In some embodiments, macrocyclic compounds that inhibit Src, Akt3, MAPKAPK2, p38α, and/or Pim1 kinases are provided. In some embodiments, compounds that activate VEGFR2 kinase are provided.

In certain embodiments, a compound that binds and modulates the activity of a kinase as provided herein is of Formula (I):

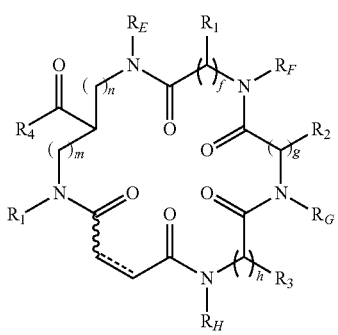

(I)

or a pharmaceutically acceptable salt thereof;
wherein:
  n is 0 or an integer between 1-4, inclusive;
  m is 0 an integer between 1-4, inclusive;
  f is an integer between 1-3, inclusive;
  g is an integer between 1-3, inclusive;
  h is an integer between 1-3, inclusive;
  ═══ is a single or double C—C bond, wherein when ═══ is a double C—C bond, then ∿∿ indicates that the adjacent C—C double bond is in a cis or trans configuration;
  each instance of $R_1$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_A$; —$N(R_A)_2$; —$SR_A$; ═O; —CN; —$NO_2$; —SCN; —$SOR_A$; or —$SO_2R_A$; wherein each occurrence of $R_A$ is independently hydrogen; a protecting group; substituted or unsubstituted aliphatic; substituted or unsubstituted heteroaliphatic; acyl; substituted or unsubstituted aryl; or substituted or unsubstituted heteroaryl;
  each instance of $R_2$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_B$; —$N(R_B)_2$; —$SR_B$; ═O; —CN; —$NO_2$; —SCN; —$SOR_B$; or —$SO_2R_B$; wherein each occurrence of $R_B$ independently hydrogen; a protecting group; substituted or unsubstituted aliphatic; substituted or unsubstituted heteroaliphatic; acyl; substituted or unsubstituted aryl; or substituted or unsubstituted heteroaryl;
  each instance of $R_3$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_C$; —$N(R_C)_2$; —$SR_C$; ═O; —CN; —$NO_2$; —SCN; —$SOR_C$; or —$SO_2R_C$; wherein each occurrence of $R_C$ is independently hydrogen; a protecting group; substituted or unsubstituted aliphatic; substituted or unsubstituted heteroaliphatic; acyl; substituted or unsubstituted aryl; or substituted or unsubstituted heteroaryl;
  $R_4$ is substituted or unsubstituted aliphatic; substituted or unsubstituted heteroaliphatic; substituted or unsubstituted aryl; substituted or unsubstituted heteroaryl; —$N(R_D)_2$; —$OR_D$; or —$SR_D$; wherein each occurrence of $R_D$ is independently hydrogen; a protecting group; substituted or unsubstituted aliphatic; substituted or unsubstituted heteroaliphatic; acyl; substituted or unsubstituted aryl; or substituted or unsubstituted heteroaryl; or two $R_D$ groups are joined to form a substituted or unsubstituted heterocyclic group; optionally wherein $R^4$ further comprises a label, resin, or therapeutic agent attached thereto; and
  each instance of $R_E$, $R_F$, $R_G$, $R_H$, and $R_I$ is independently hydrogen; acyl; a nitrogen protecting group; substituted or unsubstituted aliphatic; substituted or unsubstituted heteroaliphatic; substituted or unsubstituted aryl; substituted or unsubstituted heteroaryl; substitute or unsubstituted hydroxyl; substituted or unsubstituted thiol; substituted or unsubstituted amino; or halogen; optionally wherein an $R_1$ group and $R^F$ are joined to form a substituted or unsubstituted heterocyclic ring; an $R_2$ group and $R^G$ are joined to form a substituted or unsubstituted heterocyclic ring; and/or an $R_3$ group and $R^H$ are joined to form a substituted or unsubstituted heterocyclic ring.

Some aspects of this invention relate to compositions comprising any of the kinase-modulating compounds provided herein. In some embodiments, compositions of the kinase-modulating macrocyclic compounds are provided. In some embodiments, the provided compositions are pharmaceutical compositions, for example, compositions for clinical use in humans.

Other aspects of this invention relate to methods of synthesizing a kinase-modulating compound as provided herein. In some embodiments, methods of synthesizing kinase-modulatory macrocyclic compounds via DNA-encoded addition synthesis are provided. In other embodiments, synthesis methods that do not rely on DNA encoded synthesis are provided. In some embodiments, synthetic methods including multiple Fmoc synthesis cycles to generate a peptidic macrocyclization precursor from individual building blocks are provided. In some embodiments, the building blocks are amino acids or amino-acid like compounds. In some embodiments, the synthetic methods include cyclization of a macrocyclization precursor, for example, by Wittig cyclization. In certain embodiments, synthetic methods provided herein are solid-phase synthetic methods.

Some aspects of this invention relate to methods of using a compound provided herein to modulate the activity of a kinase. In some embodiments, methods that include contacting the kinase with a compound as provided herein are provided to modulate the activity of a specific kinase. In some embodiments, the kinase is a clinically relevant kinase, for example, a Src, Akt3, MAPKAPK2, p38α, Pim1, or VEGFR2 kinase. In some embodiments, the kinase is inhibited or activated by administering to a subject exhibiting an aberrant (e.g., an increased or constitutive) activity of the kinase an effective amount of a compound as provided herein. In some embodiments, the subject is diagnosed with a disease or disorder associated with aberrant kinase activity, for example, with a proliferative disorder, including, but not limited to benign neoplasm, malignant neoplasm, or cancer associated with increased Src, Akt3, MAPKAP2, p38, or Pim1 activity, or with metabolic syndrome, diabetes, insulin resistance, a neurodegenerative disorder, osteoporosis, inflammatory disease, or an autoimmune disorder.

Other advantages, features, and uses of the invention will become apparent from the following detailed description of non-limiting embodiments of the invention when considered in conjunction with the accompanying drawings. All publications, patents, patent applications, database entries, and other references cited herein are incorporated in their entirety by reference into this application.

DEFINITIONS

Chemical Definitions

Figure 1:
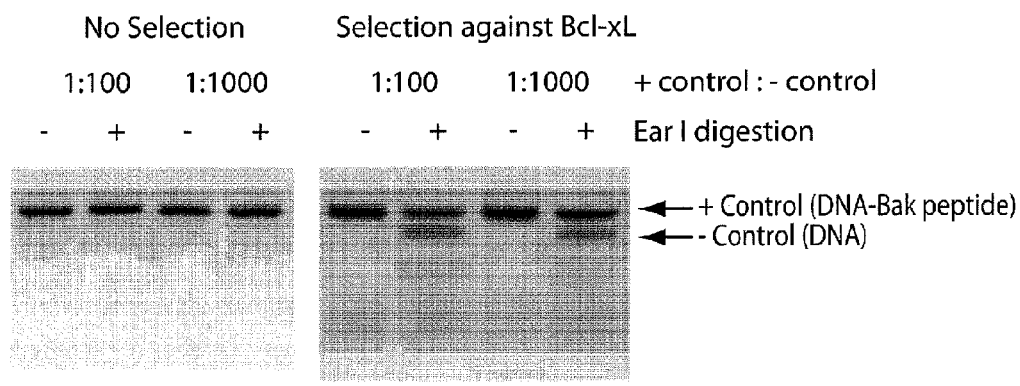
FIG. 1. Restriction endonuclease digestion to reveal enrichment of BAK peptide-linked DNA after selection for binding to immobilized GST-BcL-xL, followed by PCR amplification of eluted molecules.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGrawHill, NY, 1962); Wilen, *Tables of Resolving Agents and Optical Resolutions* p. 268 (E. L. Eliel, Ed., Univ. of Notre Dame Press, Notre Dame, Ind. 1972).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, includes both saturated and unsaturated, straight chain (i.e., unbranched), branched, acyclic, and cyclic (i.e., carbocyclic) hydrocarbons, which are optionally substituted with one or more functional groups. It is understood from the above description that the term "aliphatic," whether preceded by the terms substituted or unsubstituted, and unless otherwise specified, encompasses "cyclic or acyclic" and "branched or unbranched" groups. As will be appreciated by one of ordinary skill in the art, "aliphatic" is intended herein to include, but is not limited to, alkyl, alkenyl, alkynyl, and carbocyclyl (cycloalkyl, cycloalkenyl, and cycloalkynyl) moieties. In certain embodiments, as used herein, "aliphatic" is used to indicate those aliphatic groups (cyclic, acyclic, substituted, unsubstituted, branched or unbranched) having 1-20 carbon atoms. Unless otherwise specified, each instance of an aliphatic group is independently unsubstituted or substituted with one or more substituents, as valency permits, and which results in a stable compound. Exemplary substituents are further described herein.

The term "alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tertbutyl ($C_4$), secbutyl ($C_4$), isobutyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$), and the like, which may bear one or more substituents. Additional examples of alkyl groups include n-heptyl ($C_7$), n-octyl ($C_8$) and the like, which may bear one or more substitutents. Unless otherwise specified, each instance of an alkyl group is independently unsubstituted or substituted with one or more substituents, as valency permits, and which results in a stable compound. Exemplary substituents are further described herein.

The term "perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

The term "alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like, which may bear one or more substituents. Examples of $C_{2-6}$ alkenyl groups include the aforementioned $C_{2-4}$ alkenyl groups as well as pentenyl ($C_5$), pentadienyl ($C_5$), hexenyl ($C_6$), and the like, which may bear one or more substituents. Additional examples of alkenyl include heptenyl ($C_7$), octenyl ($C_8$), octatrienyl ($C_8$), and the like, which may bear one or more substituents. Unless otherwise specified, each instance of an alkenyl group is independently unsubstituted or substituted with one or more substituents, as valency permits, and which results in a stable compound. Exemplary substituents are further described herein.

The term "alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like, which may bear one or more substituents. Examples of $C_{2-6}$ alkenyl groups include the aforementioned $C_{2-4}$ alkynyl groups as well as pentynyl ($C_5$), hexynyl ($C_6$), and the like, which may bear one or more substituents. Additional examples of alkynyl include heptynyl ($C_7$), octynyl ($C_8$), and the like, which may bear one or more substituents. Unless otherwise specified, each instance of an alkynyl group is independently unsubstituted or substituted with one or more substituents, as valency permits, and which results in a stable compound. Exemplary substituents are further described herein.

The term "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted or substituted with one or more substituents, as valency permits, and which results in a stable compound. Exemplary substituents are further described herein.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted or substituted with one or more substituents, as valency permits, and which results in a stable compound. Exemplary substituents are further described herein.

The term "heteroaliphatic," as used herein, refers to an aliphatic moiety, as defined herein, which includes both saturated and unsaturated, nonaromatic, straight chain (i.e., unbranched), branched, acyclic or cyclic (i.e., heterocyclic) groups which are optionally substituted with one or more substituents, and which contain one or more oxygen, sulfur, nitrogen, phosphorus, or silicon atoms, e.g., in place of carbon atoms. It is understood from the above description that the term "heteroaliphatic," whether preceded by the terms substituted or unsubstituted, and unless otherwise specified, encompasses "cyclic or acyclic" and "branched or unbranched" groups. It is also understood, similar to aliphatic, that "heteroaliphatic" is intended to encompass heteroalkyl, heteroalkenyl, heteroalkynyl, and heterocyclic (heterocycloalkyl, heterocycloalkenyl, and heterocycloalkynyl) moieties. The terms "heteroalkyl," "heteroalkenyl," and "heteroalkynyl" are defined similarly, i.e., respectively refer to an alkyl, alkenyl, and alkynyl group, as defined herein, which are optionally substituted with one or more substituents, and which contain one or more oxygen, sulfur, nitrogen, phosphorus, or silicon atoms, e.g., in place of carbon atoms. Unless otherwise specified, each instance of a heteroaliphatic group is independently unsubstituted or substituted with one or more substituents, as valency permits, and which results in a stable compound. Exemplary substituents are further described herein.

The term "heterocyclic," "heterocycles," or "heterocyclyl," as used herein, refers to a cyclic heteroaliphatic group. A heterocyclic group refers to a nonaromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to four heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. In the instance of ring fusion, it is understood that "heterocyclyl" refers to a ring system wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of a heterocyclyl group is independently unsubstituted or substituted with one or more substituents, as valency permits, and which results in a stable compound. Exemplary substituents are further described herein.

In some embodiments, a heterocyclyl group is a 5- to 10-membered non-aromatic ring system having ring carbon atoms and 1-4 ring heteroatoms, wherein each heteroatom is independently selected from nitrogen, oxygen, and sulfur ("5- to 10-membered heterocyclyl"). In some embodiments, a heterocyclyl group is a 5- to 8-membered non-aromatic ring system having ring carbon atoms and 1-4 ring heteroatoms, wherein each heteroatom is independently selected from nitrogen, oxygen, and sulfur ("5- to 8-membered heterocyclyl"). In some embodiments, a heterocyclyl group is a 5- to 6-membered non-aromatic ring system having ring carbon atoms and 1-4 ring heteroatoms, wherein each heteroatom is independently selected from nitrogen, oxygen, and sulfur ("5- to 6-membered heterocyclyl"). In some embodiments, the 5-6 membered heterocyclyl has 1-3 ring heteroatoms selected from nitrogen, oxygen, and sulfur. In some embodiments, the 5- to 6-membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted or substituted with one or more substituents, as valency permits, and which results in a stable compound. Exemplary substituents are further described herein.

The term "heteroaryl" refers to a radical of a 5-10 membered monocyclic or bicyclic 4n+2 aromatic ring system (e.g., having 6 or 10 it electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Unless otherwise specified, each instance of a heteroaryl group is independently unsubstituted or substituted with one or more substituents, as valency permits, and which results in a stable compound. Exemplary substituents are further described herein.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

The term "acyl," as used herein, refers to a group having the general formula $-C(=O)R^{X5}$, $-C(=O)OR^{X5}$, $-C(=O)SR^{X5}$, $-C(=O)N(R^{X6})_2$, $-C(=NR^{X6})R^{X1}$, $-C(=NR^{X6})OR^{X5}$, $-C(=NR^{X6})SR^{X5}$, $-C(=NR^{X6})N(R^{X6})_2$, $-C(=S)R^{X5}$, $-C(=S)OR^{X5}$, $-C(=S)SR^{X5}$, and $-C(=S)N(R^{X6})_2$, wherein each occurrence of $R^{X5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{X6}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{X6}$ groups are joined to form an substituted or unsubstituted heterocyclic ring.

The term "oxo," as used herein, refers to a group of the formula (=O). The term "thiooxo," as used herein, refers to a group of the formula (=S).

Aliphatic (alkyl, alkenyl, alkynyl, carbocyclyl), heteroaliphatic (heteroalkyl, heteroalkenyl, heteroalkynyl, heterocyclyl), aryl, and heteroaryl groups, as defined herein, are optionally substituted. "Optionally substituted" refers to a group which may be substituted or unsubstituted. In general, the term "substituted" means that at least one hydrogen present on a group (e.g., a carbon or nitrogen atom) is replaced with a permissible substituent, e.g., a substituent which upon substitution results in a stable moiety or compound, e.g., a compound which does not spontaneously undergo transformation such as by rearrangement, cyclization, elimination, or other reaction, and preferably possess stability sufficient to allow manufacture, and which maintains its integrity for a sufficient period of time to be useful for the purposes detailed herein. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms may have hydrogen substituents and/or any substituent as described herein which satisfy the valencies of the heteroatom and results in the formation of a stable moiety.

Exemplary substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, and combinations thereof, e.g., aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). Other exemplary substitutents are further described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$alkyl), —OC(=O)(C$_{1-6}$alkyl), —OCO$_2$(C$_{1-6}$ alkyl), —C(=O)NH$_2$, —C(=O)N(C$_{1-6}$alkyl)$_2$, —OC(=O)NH(C$_{1-6}$alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$-alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-4}$ alkyl)$_3$, —OSi(C$_{1-6}$alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$-alkyl, —SC(=S)SC$_{1-6}$ alkyl, —P(=O)$_2$(C$_{1-6}$alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

As used herein, the term "unsubstituted hydroxyl" or "unsubstituted hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein. In the case wherein "substituted hydroxyl" is a ligand L$_1$ or L$_2$, "substituted hydroxyl" also refers to the group (R$^{aa}$)$_2$O, wherein R$^{aa}$ is as defined herein.

As used herein, the term "unsubstituted thiol" or "unsubstituted thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term "unsubstituted amino" or "amino" refers to the group —NH$_2$. The term "substituted amino," by extension, refers to a monosubstituted, disubstituted, or trisubstituted amino group.

As used herein, the term "monosubstituted amino" refers to an amino group wherein the nitrogen atom directly attached to the parent molecule is substituted with one hydrogen and one group other than hydrogen. Exemplary monosubstituted amino groups include, but are not limited to, —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen. Exemplary disubstituted amino groups include, but are not limited to, —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups. Exemplary trisubstituted amino groups include, but are not limited to, —N(R$^{bb}$)$_3$ and —N(R$^{bb}$)$_3$$^+$X$^-$, wherein R$^{bb}$ and X$^-$ are as defined herein.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{cc}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

The term "protecting group" as used herein, refers to a chemical modification of a functional group of a compound that prevents the functional group to take part in an undesired chemical reaction. Protecting groups play an important role in multi-step organic compound synthesis, and suitable protecting groups for various functional groups and chemical environments are well known in the art. Examples of protecting groups are nitrogen protecting groups, oxygen protecting groups, sulfur protecting groups, and carboxylic acid protecting groups are described in more detail herein.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)

$R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., $-C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., $-C(=O)OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., $-S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pmc), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

A "carboxylic acid protecting group" or "protected carboxylic acid," as used herein, are well known in the art and include those described in detail in Greene (1999). Examples of protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

These and other exemplary substituents and protecting groups are described in more detail in the Detailed Description, Examples, and claims. The invention is not intended to be limited in any manner by the above exemplary listing of substituents and protecting groups.

Other Definitions

As used herein, the term "pharmaceutically acceptable salt" refers to those salts which are, within the scope of sound medical judgment, suitable for use in contact with the tissues of humans and lower animals without undue toxicity, irritation, immunological response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female at any stage of development. A non-human animal may be a transgenic animal.

The terms "administer," "administering," or "administration," as used herein refers to implanting, absorbing, ingesting, injecting, or inhaling a substance, for example, a compound as described herein.

As used herein the term "inhibit" or "inhibition" in the context of enzymes, for example, in the context of kinases, refers to a reduction in the level of kinase activity. In some embodiments, the term refers to a reduction of the level of kinase activity to a level that is statistically significantly lower than an initial level, which may, for example, be a baseline level of kinase activity.

As used herein, the term "activate" or "activation" in the context of enzymes, for example, in the context of kinases, refers to an increase in the level of kinase activity. In some embodiments, the term refers to an increase of the level of kinase activity to a level that is statistically significantly higher than an initial level, which may, for example, be a baseline level of kinase activity.

As used herein, the terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The terms "effective amount" and "therapeutically effective amount," as used herein, refer to the amount or concentration of an inventive compound, that, when administered to a subject, is effective to at least partially treat a condition from which the subject is suffering. In some embodiments, an effective amount of a kinase inhibitor is an amount the administration of which results in inhibition of at least about 50%, at least about 60%, at least about 70%, at least about 75%, at least about 80%, at least about 90%, at least about 95%, at least about 98%, at least about 99%, at least about 99.5%, or about 100% of target kinase activity as compared to a baseline level, for example, a level of target kinase activity in the absence of the inhibitor. In some embodiments, an effective amount of a kinase activator is an amount the administration of which results in an increase of target kinase activity of at least about 2-fold, at least about 3-fold, at least about 4-fold, at least about 5-fold, at least about 7.5-fold, at least about 10-fold, at least about 20-fold, at least about 50-fold, at least about 75-fold, at least about 100-fold, at least about 200-fold, or at least about 500-fold as compared to a baseline level of target kinase activity, for example, a level in the absence of the activator.

As used herein, the term "kinase-associated disease or disorder" refers to, but is not limited to diseases and disorders in which there is abnormal kinase activity. As used herein, the term "kinase activity" refers to the enzymatic activity of a kinase, for example to the phosphotransferase activity of a kinase. Abnormal kinase activity may, in some embodiments, be determined to be an abnormal level of kinase activity. In some embodiments, abnormal kinase activity may be dysregulated kinase activity, for example, constitutive activity of a kinase that is normally regulated. An abnormal level of kinase activity may be a level that is higher than a normal level or may be a level that is lower than a normal level, wherein a "normal" level is, in some embodiments, the level in a cell, tissue, or subject that is not characterized by or that does not have a disease or disorder associated with aberrant kinase activity. For example, a normal activity of Src kinase in a tissue, for example, colonic tissue, is, in some embodiments, the average level of Src kinase activity that can be detected in subjects with healthy colonic tissue, for example, in subjects that do not manifest any clinical symptoms or any clinical symptoms associated with a colonic tissue dysfunction. In some embodiments, a kinase-associated disease or disorder is characterized by a higher-than-normal level of a specific kinase activity, a suitable therapeutic intervention, in some embodiments, may be the administration of an effective amount of an inhibitor of the respective kinase. Similarly, if a kinase-associated disease or disorder is characterized by a lower-than-normal level of a specific kinase activity, a suitable therapeutic intervention, in some embodiments, may be the administration of an effective amount of an activator of the respective kinase. Examples of kinase-activity-associated diseases and disorders include, but are not limited to proliferative diseases, benign neoplasms, cancer, inflammatory diseases, autoimmune diseases, developmental defects, neurodegenerative disorders (e.g., Alzheimer's disease); metabolic syndrome, diabetes mellitus, and insulin resistance.

The term "cancer" as used herein refers to an uncontrolled growth of cells. In some embodiments, a cancer is an uncontrolled growth that interferes with the normal functioning of the bodily organs and systems. Cancers which migrate from their original location and seed vital organs can eventually lead to the death of the subject through the functional deterioration of the affected organs. Some exemplary subtypes of cancers are sarcoma, carcinoma, and hematopoietic cancers. The term "carcinoma" refers to a malignant cancer originating from epithelial cells and includes adenocarcinoma and squamous cell carcinoma. The term "sarcoma" refers to a cancer of the connective or supportive tissue and includes osteosarcoma, chondrosarcoma and gastrointestinal stromal tumors. The term "hematopoietic cancer", refers to a cancer of the blood cell lineages, such as leukemia. Hematopoietic cancers are able to outcompete the normal hematopoietic compartments in a subject, thereby leading to hematopoietic failure (e.g., in the form of anemia, thrombocytopenia and neutropenia) and can ultimately cause death. A person of ordinary skill in the art will appreciate that other classifications of cancers are known and will be able to classify a cancer according to the known classification schemes.

As used herein, the term "resin" refers to a resin useful for solid phase synthesis. Solid phase synthesis is a well-known synthetic technique; see generally, Atherton, E., Sheppard, R. C. *Solid Phase Peptide Synthesis: A Practical Approach*, IRL Press, Oxford, England, 1989, and Stewart J. M., Young, J. D. *Solid Phase Peptide Synthesis*, 2nd edition, Pierce Chemical Company, Rockford, 1984, the entire contents of each of which are hereby incorporated herein by reference.

As used herein, a "therapeutic agent" refers to any substance used as a medicine for treatment, prevention, delay, reduction or amelioration of a disease, condition, or disorder, and refers to a substance that is useful for therapy, including prophylactic and therapeutic treatment.

As used herein, a "label" refers to a moiety that has at least one element, isotope, or functional group incorporated into the moiety which enables detection of the compound to which the label is attached. In general, a label can fall into any one (or more) of five classes: a) a label which contains isotopic moieties, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{69}$Yb, and $^{186}$Re; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label FITC); d) a label which has one or more photoaffinity moieties; and e) a label which has a ligand moiety with one or more known binding partners (such as biotin-streptavidin, FK506-FKBP, etc.). Any of these type of labels as described above may also be referred to as "diagnostic agents" as defined herein.

In certain embodiments, such as in the identification of a biological target, label comprises a radioactive isotope, preferably an isotope which emits detectable particles, such as β particles. In certain embodiments, the label comprises one or more photoaffinity moieties for the direct elucidation of intermolecular interactions in biological systems. A variety of known photophores can be employed, most relying on photoconversion of diazo compounds, azides, or diazirines to nitrenes or carbenes (see, Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid. In certain embodiments, the label comprises one or more fluorescent moieties. In certain embodiments, the label is the fluorescent label FITC. In certain embodiments, the label comprises a ligand moiety with one or more known binding partners. In certain embodiments, the label comprises the ligand moiety biotin.

In certain embodiments, the label is an imaging agent. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F. Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and *Handbook of Fluorescent Probes and Research Products*, Molecular Probes, 9$^{th}$ edition, 2002).

DETAILED DESCRIPTION OF CERTAIN EMBODIMENTS

Some aspects of the invention provide macrocyclic compounds that bind and/or modulate the activity of specific kinases. In some embodiments, a macrocyclic compound is provided that modulates the activity of a kinase it binds. In some embodiments, a macrocyclic compound is provided that inhibits the activity of a kinase. In some embodiments, a macrocyclic compound is provided that activates a specific kinase. In some embodiments, a macrocyclic compound is provided that selectively inhibits Src, Akt3, AMPK, ERBB4, MK2, p38α, MKK6, and/or Pim1. In some embodiments, a macrocyclic compound is provided that activates VEGFR2.

In some embodiments, a macrocyclic compound is provided that specifically binds and inhibits a Src kinase. Src kinases are a family of proto-oncogenic tyrosine kinases. The human c-Src gene is similar to the v-Src gene of Rous Sarcoma Virus (RSV). Without wishing to be bound by theory, it is believed that c-Src may play a role in the regulation of embryonic development and cell growth. In normal cells, Src activity is regulated, at least in part, by phosphorylation. Without wishing to be bound by theory, it is believed that phosphorylation of a specific C-terminal residue inhibits Src activity. Mutations resulting in truncation of the Src protein, e.g., a loss of the C-terminal phosphorylation site, can lead to aberrant activity of the Src kinase, which, in turn, is thought to be causally associated with increased cell proliferation and survival, and, thus, with the formation of various cancers. In humans, two c-Src transcript variants have been described. Src protein and nucleotide sequences are well known to those of skill in the art and can be retrieved from publicly available databases (e.g., the NCBI and Ensemble databases at www.ncbi.nlm,nih.gov or www.ensembl.org, respectively). Representative sequences for Src are provided below:

```
>gi|38202215|ref|NM_005417.3| Homo sapiens v-src sarcoma (Schmidt-
Ruppin A-2) viral oncogene homolog (avian) (SRC), transcript variant 1, mRNA
                                                        (SEQ ID NO: 1)
CAAACAAGTGCGGCCATTTCACCAGCCCAGGCTGGCTTCTGCTGTTGACTGGCTG

TGGCACCTCAAGCAGCCCCTTTCCCCTCTAGCCTCAGTTTATCACCGCAAGAGCT

ACCATTCATCTAGCACAACCTGACCATCCTCACACTGGTCAGTTCCAACCTTCCC

AGGAATCTTCTGTGGCCATGTTCACTCCGGTTTTACAGAACAGAGAACAGAAGCT

CAGAGAAGTGAAGCAACTTGCCCAGCTATGAGAGACAGAGCCAGGATTTGAAAC

CAGATGAGGACGCTGAGGCCCAGAGAGGGAAAGCCACTTGCCTAGGGACACAC

AGCGGGGAGAGGTGGAGCAGGGCCTCTATTTCGAGACCCCTGACTCCACACCTG

GTGTTTGTGCCAAGACCCCAGGCTGCCTCCCAGGTCCTCTGGGACAGCCCCTGCC

TTCTACCAGGACCATGGGTAGCAACAAGAGCAAGCCCAAGGATGCCAGCCAGCG

GCGCCGCAGCCTGGAGCCCGCCGAGAACGTGCACGGCGCTGGCGGGGCGCTTT

CCCCGCCTCGCAGACCCCAGCAAGCCAGCCTCGGCCGACGGCCACCGCGGCCC

CAGCGCGGCCTTCGCCCCCGCGGCCGCCGAGCCCAAGCTGTTCGGAGGCTTCAA

CTCCTCGGACACCGTCACCTCCCCGCAGAGGGCGGGCCCGCTGGCCGGTGGAGT

GACCACCTTTGTGGCCCTCTATGACTATGAGTCTAGGACGGAGACAGACCTGTCC

TTCAAGAAAGGCGAGCGGCTCCAGATTGTCAACAACACAGAGGGAGACTGGTGG

CTGGCCCACTCGCTCAGCACAGGACAGACAGGCTACATCCCCAGCAACTACGTG

GCGCCCTCCGACTCCATCCAGGCTGAGGAGTGGTATTTTGGCAAGATCACCAGAC

GGGAGTCAGAGCGGTTACTGCTCAATGCAGAGAACCCGAGAGGGACCTTCCTCG

TGCGAGAAAGTGAGACCACGAAAGGTGCCTACTGCCTCTCAGTGTCTGACTTCGA

CAACGCCAAGGGCCTCAACGTGAAGCACTACAAGATCCGCAAGCTGGACAGCGG

CGGCTTCTACATCACCTCCCGCACCCAGTTCAACAGCCTGCAGCAGCTGGTGGCC

TACTACTCCAAACACGCCGATGGCCTGTGCCACCGCCTCACCACCGTGTGCCCCA

CGTCCAAGCCGCAGACTCAGGGCCTGGCCAAGGATGCCTGGGAGATCCCTCGGG

AGTCGCTGCGGCTGGAGGTCAAGCTGGGCCAGGGCTGCTTTGGCGAGGTGTGGA

TGGGGACCTGGAACGGTACCACCAGGGTGGCCATCAAAACCCTGAAGCCTGGCA

CGATGTCTCCAGAGGCCTTCCTGCAGGAGGCCCAGGTCATGAAGAAGCTGAGGC

ATGAGAAGCTGGTGCAGTTGTATGCTGTGGTTTCAGAGGAGCCCATTTACATCGT

CACGGAGTACATGAGCAAGGGGAGTTTGCTGGACTTTCTCAAGGGGGAGACAGG

CAAGTACCTGCGGCTGCCTCAGCTGGTGGACATGGCTGCTCAGATCGCCTCAGGC

ATGGCGTACGTGGAGCGGATGAACTACGTCCACCGGGACCTTCGTGCAGCCAAC

ATCCTGGTGGGAGAGAACCTGGTGTGCAAAGTGGCCGACTTTGGGCTGGCTCGG

CTCATTGAAGACAATGAGTACACGGCGCGGCAAGGTGCCAAATTCCCCATCAAG

TGGACGGCTCCAGAAGCTGCCCTCTATGGCCGCTTCACCATCAAGTCGGACGTGT
```

-continued

```
GGTCCTTCGGGATCCTGCTGACTGAGCTCACCACAAAGGGACGGGTGCCCTACCC

TGGGATGGTGAACCGCGAGGTGCTGGACCAGGTGGAGCGGGGCTACCGGATGCC

CTGCCCGCCGGAGTGTCCCGAGTCCCTGCACGACCTCATGTGCCAGTGCTGGCGG

AAGGAGCCTGAGGAGCGGCCCACCTTCGAGTACCTGCAGGCCTTCCTGGAGGAC

TACTTCACGTCCACCGAG

CCCCAGTACCAGCCCGGGGAGAACCTCTAGGCACAGGCGGGCCCAGACCGGCTT

CTCGGCTTGGATCCTGGGCTGGGTGGCCCCTGTCTCGGGGCTTGCCCCACTCTGC

CTGCCTGCTGTTGGTCCTCTCTCTGTGGGGCTGAATTGCCAGGGGCGAGGCCCTT

CCTCTTTGGTGGCATGGAAGGGGCTTCTGGACCTAGGGTGGCCTGAGAGGGCGG

TGGGTATGCGAGACCAGCACGGTGACTCTGTCCAGCTCCCGCTGTGGCCGCACGC

CTCTCCCTGCACTCCCTCCTGGAGCTCTGTGGGTCTCTGGAAGAGGAACCAGGAG

AAGGGCTGGGGCCGGGGCTGAGGGTGCCCTTTTCCAGCCTCAGCCTACTCCGCTC

ACTGAACTCCTTCCCCACTTCTGTGCCACCCCCGGTCTATGTCGAGAGCTGGCCA

AAGAGCCTTTCCAAAGAGGAGCGATGGGCCCCTGGCCCCGCCTGCCTGCCACCC

TGCCCCTTGCCATCCATTCTGGAAACACCTGTAGGCAGAGGCTGCCGAGACAGA

CCCTCTGCCGCTGCTTCCAGGCTGGGCAGCACAAGGCCTTGCCTGGCCTGATGAT

GGTGGGTGGGTGGGATGAGTACCCCCTCAAACCCTGCCCTCCTTAGACCTGAGGG

ACCCTTCGAGATCATCACTTCCTTGCCCCCATTTCACCCATGGGGAGACAGTTGA

GAGCGGGGATGTGACATGCCCAAGGCCACGGAGCAGTTCAGAGTGGAGGCGGG

CTTGGAACCCGGTGCTCCCTCTGTCATCCTCAGGAACCAACAATTCGTCGGAGGC

ATCATGGAAAGACTGGGACAGCCCAGGAAACAAGGGGTCTGAGGATGCATTCGA

GATGGCAGATTCCCACTGCCGCTGCCCGCTCAGCCCAGCTGTTGGGAACAGCATG

GAGGCAGATGTGGGGCTGAGCTGGGGAATCAGGGTAAAAGGTGCAGGTGTGGA

GAGAGAGGCTTCAATCGGCTTGTGGGTGATGTTTGACCTTCAGAGCCAGCCGGCT

ATGAAAGGGAGCGAGCCCCTCGGCTCTGGAGGCAATCAAGCAGACATAGAAGA

GCCAAGAGTCCAGGAGGCCCTGGTCCTGGCCTCCTTCCCCGTACTTTGTCCCGTG

GCATTTCAATTCCTGGCCCTGTTCTCCTCCCCAAGTCGGCACCCTTTAACTCATGA

GGAGGGAAAAGAGTGCCTAAGCGGGGGTGAAAGAGGACGTGTTACCCACTGCC

ATGCACCAGGACTGGCTGTGTAACCTTGGGTGGCCCCTGCTGTCTCTCTGGGCTG

CAGAGTCTGCCCCACATGTGGCCATGGCCTCTGCAACTGCTCAGCTCTGGTCCAG

GCCCTGTGGCAGGACACACATGGTGAGCCTAGCCCTGGGACATCAGGAGACTGG

GCTCTGGCTCTGTTCGGCCTTTGGGTGTGTGGTGGATTCTCCCTGGGCCTCAG

TGTGCCCATCTGTAAAGGGGCAGCTGACAGTTTGTGGCATCTTGCCAAGGGTCCC

TGTGTGTGTGTATGTGTGTGCATGTGTGCGTGTCTCCATGTGCGTCCATATTTAAC

ATGTAAAAATGTCCCCCCCGCTCCGTCCCCCAAACATGTTGTACATTTCACCATG

GCCCCCTCATCATAGCAATAACATTCCCACTGCCAGGGGTTCTTGAGCCAGCCAG

GCCCTGCCAGTGGGAAGGAGGCCAAGCAGTGCCTGCCTATGAAATTTCAACTTT

TCCTTTCATACGTCTTTATTACCCAAGTCTTCTCCCGTCCATTCCAGTCAAATCTG

GGCTCACTCACCCCAGCGAGCTCTCAAATCCCTCTCCAACTGCCTAAGGCCCTTT

GTGTAAGGTGTCTTAATACTGTCCTTTTTTTTTTTAACAGTGTTTTGTAGATTTC

AGATGACTATGCAGAGGCCTGGGGACCCCTGGCTCTGGGCCGGGCCTGGGGCT
```

-continued

CCGAAATTCCAAGGCCCAGACTTGCGGGGGGTGGGGGGGTATCCAGAATTGGTT

GTAAATACTTTGCATATTGTCTGATTAAACACAAACAGACCTCAGAAAAAAAAA

AAAAAAAAAAAAAAAAAAAAAAAAAAAAAAAAAAAAAAA.

>gi|38202216|ref|NM_198291.1| Homo sapiens v-src sarcoma (Schmidt-
Ruppin A-2) viral oncogene homolog (avian) (SRC), transcript variant 2, mRNA (SEQ ID NO: 2)

GCCGGAGCGGCCAGGCCGCCGTCTGCCCGTCCCGCTGGACGTCCCGCGGTCCGC

CCTCCCGTGCGTCCGTCTGCCGGTGAGCCCGCCCGCCCGCCGGCCCAGAACAGA

GAACAGAAGCTCAGAGAAGTGAAGCAACTTGCCCAGCTATGAGAGACAGAGCC

AGGATTTGAAACCAGATGAGGACGCTGAGGCCCAGAGAGGGAAAGCCACTTGCC

TAGGGACACACAGCGGGGAGAGGTGGAGCAGGGCCTCTATTTCGAGACCCCTGA

CTCCACACCTGGTGTTTGTGCCAAGACCCCAGGCTGCCTCCCAGGTCCTCTGGGA

CAGCCCCTGCCTTCTACCAGGACCATGGGTAGCAACAAGAGCAAGCCCAAGGAT

GCCAGCCAGCGGCGCCGCAGCCTGGAGCCCGCCGAGAACGTGCACGGCGCTGGC

GGGGGCGCTTTCCCCGCCTCGCAGACCCCAGCAAGCCAGCCTCGGCCGACGGC

CACCGCGGCCCCAGCGCGGCCTTCGCCCCCGCGGCCGCCGAGCCCAAGCTGTTC

GGAGGCTTCAACTCCTCGGACACCGTCACCTCCCCGCAGAGGGCGGGCCCGCTG

GCCGGTGGAGTGACCACCTTTGTGGCCCTCTATGACTATGAGTCTAGGACGGAGA

CAGACCTGTCCTTCAAGAAAGGCGAGCGGCTCCAGATTGTCAACAACACAGAGG

GAGACTGGTGGCTGGCCCACTCGCTCAGCACAGGACAGACAGGCTACATCCCCA

GCAACTACGTGGCGCCCTCCGACTCCATCCAGGCTGAGGAGTGGTATTTTGGCAA

GATCACCAGACGGGAGTCAGAGCGGTTACTGCTCAATGCAGAGAACCCCGAGAGG

GACCTTCCTCGTGCGAGAAAGTGAGACCACGAAAGGTGCCTACTGCCTCTCAGTG

TCTGACTTCGACAACGCCAAGGGCCTCAACGTGAAGCACTACAAGATCCGCAAG

CTGGACAGCGGCGGCTTCTACATCACCTCCCGCACCCAGTTCAACAGCCTGCAGC

AGCTGGTGGCCTACTACTCCAAACACGCCGATGGCCTGTGCCACCGCCTCACCAC

CGTGTGCCCCACGTCCAAGCCGCAGACTCAGGGCCTGGCCAAGGATGCCTGGGA

GATCCCTCGGGAGTCGCTGCGGCTGGAGGTCAAGCTGGGCCAGGGCTGCTTTGG

CGAGGTGTGGATGGGGACCTGGAACGGTACCACCAGGGTGGCCATCAAAACCCT

GAAGCCTGGCACGATGTCTCCAGAGGCCTTCCTGCAGGAGGCCCAGGTCATGAA

GAAGCTGAGGCATGAGAAGCTGGTGCAGTTGTATGCTGTGGTTTCAGAGGAGCC

CATTTACATCGTCACGGAGTACATGAGCAAGGGGAGTTTGCTGGACTTTCTCAAG

GGGGAGACAGGCAAGTACCTGCGGCTGCCTCAGCTGGTGGACATGGCTGCTCAG

ATCGCCTCAGGCATGGCGTACGTGGAGCGGATGAACTACGTCCACCGGGACCTT

CGTGCAGCCAACATCCTGGTGGGAGAGAACCTGGTGTGCAAAGTGGCCGACTTT

GGGCTGGCTCGGCTCATTGAAGACAATGAGTACACGGCGCGGCAAGGTGCCAAA

TTCCCCATCAAGTGGACGGCTCCAGAAGCTGCCCTCTATGGCCGCTTCACCATCA

AGTCGGACGTGTGGTCCTTCGGGATCCTGCTGACTGAGCTCACCACAAAGGGAC

GGGTGCCCTACCCTGGGATGGTGAACCGCGAGGTGCTGGACCAGGTGGAGCGGG

GCTACCGGATGCCCTGCCCGCCGGAGTGTCCCGAGTCCCTGCACGACCTCATGTG

CCAGTGCTGGCGGAAGGAGCCTGAGGAGCGGCCCACCTTCGAGTACCTGCAGGC

CTTCCTGGAGGACTACTTCACGTCCACCGAGCCCCAGTACCAGCCCGGGGAGAA

-continued

```
CCTCTAGGCACAGGCGGGCCCAGACCGGCTTCTCGGCTTGGATCCTGGGCTGGGT

GGCCCCTGTCTCGGGGCTTGCCCCACTCTGCCTGCCTGCTGTTGGTCCTCTCTCTG

TGGGGCTGAATTGCCAGGGGCGAGGCCCTTCCTCTTTGGTGGCATGGAAGGGGCT

TCTGGACCTAGGGTGGCCTGAGAGGGCGGTGGGTATGCGAGACCAGCACGGTGA

CTCTGTCCAGCTCCCGCTGTGGCCGCACGCCTCTCCCTGCACTCCCTCCTGGAGCT

CTGTGGGTCTCTGGAAGAGGAACCAGGAGAAGGGCTGGGGCCGGGGCTGAGGGT

GCCCTTTTCCAGCCTCAGCCTACTCCGCTCACTGAACTCCTTCCCCACTTCTGTGC

CACCCCCGGTCTATGTCGAGAGCTGGCCAAAGAGCCTTTCCAAAGAGGAGCGAT

GGGCCCCTGGCCCCGCCTGCCTGCCACCCTGCCCCTTGCCATCCATTCTGGAAAC

ACCTGTAGGCAGAGGCTGCCGAGACAGACCCTCTGCCGCTGCTTCCAGGCTGGG

CAGCACAAGGCCTTGCCTGGCCTGATGATGGTGGGTGGGTGGGATGAGTACCCC

CTCAAACCCTGCCCTCCTTAGACCTGAGGGACCCTTCGAGATCATCACTTCCTTG

CCCCCATTTCACCCATGGGGAGACAGTTGAGAGCGGGGATGTGACATGCCCAAG

GCCACGGAGCAGTTCAGAGTGGAGGCGGGCTTGGAACCCGGTGCTCCCTCTGTC

ATCCTCAGGAACCAACAATTCGTCGGAGGCATCATGGAAAGACTGGGACAGCCC

AGGAAACAAGGGGTCTGAGGATGCATTCGAGATGGCAGATTCCCACTGCCGCTG

CCCGCTCAGCCCAGCTGTTGGGAACAGCATGGAGGCAGATGTGGGGCTGAGCTG

GGGAATCAGGGTAAAAGGTGCAGGTGTGGAGAGAGAGGCTTCAATCGGCTTGTG

GGTGATGTTTGACCTTCAGAGCCAGCCGGCTATGAAAGGGAGCGAGCCCCTCGG

CTCTGGAGGCAATCAAGCAGACATAGAAGAGCCAAGAGTCCAGGAGGCCCTGGT

CCTGGCCTCCTTCCCCGTACTTTGTCCCGTGGCATTTCAATTCCTGGCCCTGTTCT

CCTCCCCAAGTCGGCACCCTTTAACTCATGAGGAGGGAAAAGAGTGCCTAAGCG

GGGGTGAAAGAGGACGTGTTACCCACTGCCATGCACCAGGACTGGCTGTGTAAC

CTTGGGTGGCCCCTGCTGTCTCTCTGGGCTGCAGAGTCTGCCCCACATGTGGCCA

TGGCCTCTGCAACTGCTCAGCTCTGGTCCAGGCCCTGTGGCAGGACACACATGGT

GAGCCTAGCCCTGGGACATCAGGAGACTGGGCTCTGGCTCTGTTCGGCCTTTGGG

TGTGTGGTGGATTCTCCCTGGGCCTCAGTGTGCCCATCTGTAAAGGGGCAGCTGA

CAGTTTGTGGCATCTTGCCAAGGGTCCCTGTGTGTGTGTATGTGTGTGCATGTGTG

CGTGTCTCCATGTGCGTCCATATTTAACATGTAAAAATGTCCCCCCCGCTCCGTCC

CCCAAACATGTTGTACATTTCACCATGGCCCCCTCATCATAGCAATAACATTCCC

ACTGCCAGGGGTTCTTGAGCCAGCCAGGCCCTGCCAGTGGGGAAGGAGGCCAAG

CAGTGCCTGCCTATGAAATTTCAACTTTTCCTTTCATACGTCTTTATTACCCAAGT

CTTCTCCCGTCCATTCCAGTCAAATCTGGGCTCACTCACCCCAGCGAGCTCTCAA

ATCCCTCTCCAACTGCCTAAGGCCCTTTGTGTAAGGTGTCTTAATACTGTCCTTTT

TTTTTTTTAACAGTGTTTTGTAGATTTCAGATGACTATGCAGAGGCCTGGGGGAC

CCCTGGCTCTGGGCCGGGCCTGGGGCTCCGAAATTCCAAGGCCCAGACTTGCGG

GGGGTGGGGGGGTATCCAGAATTGGTTGTAAATACTTTGCATATTGTCTGATTAA

ACACAAACAGACCTCAGAAAAAAAAAAAAAAAAAAAAAAAAAAAAAAAAAA

AAAAAAAAAAAA.
```

```
>gi|4885609|ref|NP_005408.1| proto-oncogene tyrosine-protein kinase Src
[Homo sapiens] (See also NP_938033.1)
                                                      (SEQ ID NO: 3)
MGSNKSKPKDASQRRRSLEPAENVHGAGGGAFPASQTPSKPASADGHRGPSAAFAP

AAAEPKLFGGFNSSDTVTSPQRAGPLAGGVTTFVALYDYESRTETDLSFKKGERLQI

VNNTEGDWWLAHSLSTGQTGYIPSNYVAPSDSIQAEEWYFGKITRRESERLLLNAEN

PRGTFLVRESETTKGAYCLSVSDFDNAKGLNVKHYKIRKLDSGGFYITSRTQFNSLQ

QLVAYYSKHADGLCHRLTTVCPTSKPQTQGLAKDAWEIPRESLRLEVKLGQGCFGE

VWMGTWNGTTRVAIKTLKPGTMSPEAFLQEAQVMKKLRHEKLVQLYAVVSEEPIYI

VTEYMSKGSLLDFLKGETGKYLRLPQLVDMAAQIASGMAYVERMNYVHRDLRAA

NILVGENLVCKVADFGLARLIEDNEYTARQGAKFPIKWTAPEAALYGRFTIKSDVWS

FGILLTELTTKGRVPYPGMVNREVLDQVERGYRMPCPPECPESLHDLMCQCWRKEP

EERPTFEYLQAFLEDYFTSTEPQYQPGENL.
```

The underlined residue, threonine 341 in the representative sequence above, is referred to herein as the "gatekeeper residue" or "gatekeeper threonine". Depending on the numbering scheme, the gatekeeper residue may be assigned a different residue number. Those of skill in the art will, however, be able to ascertain the gatekeeper residue, e.g, the gatekeeper threonine of src, for example, by identifying the residue that is homologous with the T341 in the above described sequence, or with a gatekeeper residue or residue position described in the art. The src kinase gatekeeper threonine is also often referred to as threonine 338, Thr338, or T338, and the terms "T338" and "T341," as used in connection with src kinase herein, both refer to the gatekeeper threonine residue of src kinase. Mutations of the gatekeeper residue, for example, T338I or T341I mutations in src kinases, typically results in resistance of the mutated kinase to kinase inhibitors. Since aberrant src kinase activation can lead to disease, e.g., certain types of cancer, as described in more detail elsewhere herein, a gatekeeper mutation can hamper the treatment of such a disease with a src kinase inhibitor. Gatekeeper residues and gatekeeper residue mutations in kinases, for example, in src kinases, are well known in the art (see, e.g., FIG. 1a and related text in Azam et al., Nat Struct Mol. Biol. 2008 October; 15(10): 1109-1118, the entire contents of which are incorporated herein by reference).

Mutated forms, for example, truncated forms of Src kinases have been described and sequences related to such mutated forms are well known in the art. In some instances, mutation, for example, truncation of a Src kinase can lead to aberrant activity, for example increased or constitutive activity of the kinase. Such aberrant Src kinase activity has been linked to various forms of cancer. For example, a truncated, activated form of Src has been found in colon cancers and in sarcomas (e.g., Sugimura M, Kobayashi K, Sagae S, Nishioka Y, Ishioka S, Terasawa K, Tokino T, Kudo R. *Mutation of the SRC gene in endometrial carcinoma*. Jpn J Cancer Res. 2000 April; 91(4):395-8; Irby R B, Mao W, Coppola D, Kang J, Loubeau J M, Trudeau W, Karl R, Fujita D J, Jove R, Yeatman T J. *Activating SRC mutation in a subset of advanced human colon cancers*. Nat. Genet. 1999 February; 21(2):187-90; all references incorporated herein by reference). Further, it has been reported that Src expression and Src kinase activity are frequently increased in a wide array of cancers, including tumors from breast, colon, pancreas, lung, ovary, and CNS (e.g., Irby R B, Mao W, Coppola D, Kang J, Loubeau J M, Trudeau W, Karl R, Fujita D J, Jove R, Yeatman T J. *Activating SRC mutation in a subset of advanced human colon cancers*. Nat. Genet. 1999 February; 21(2): 187-90; incorporated herein by reference). Accordingly, inhibition of Src kinase activity is desirable in certain clinical scenarios characterized by aberrant Src kinase activity, for example, but not limited to cancers exhibiting constitutive or increased Src expression or expressing mutated (e.g., truncated) forms of a Src kinase.

In some embodiments, compounds are provided that bind Akt3, MAPKAPK2, Pim1, or VEGFR2. In some embodiments, compounds are provided that inhibit Akt3, MAPKAPK2, Pim1, and p38α-MAPKAPK2. In some embodiments, compounds are provided that activate VEGFR2. In some embodiments, a compound provided herein modulates (e.g., inhibits or activates) the activity of a clinically relevant target kinase, for example, of a Abll, ACK, ACTR2B, Akt1, Akt2, ALK, ALK1, ALK2, ALK4, ANKK1, ANPα, ANPβ, ARG, ATM, ATR, AurA, AurB, Ax1, BARK1, Bcr, BMPR1A, BMPR1B, BMPR2, BRAF, BRD4, BRK, BTK, BUB1, BUBR1, CAMK26, CDC2, CDK2, CDK4, CDK5, CDK6, CDK9, CDKL5, CHK1, CHK2, CK1δ, CK1α, CK1ε, CK2α1, CK2α2, COT/TPL2, CTK/MATK, CYGD, CYGF, DAPK1, DCAMKL1, DMPK1, DNAPK, DYRK1A, eEF2K, EGFR, Eph, family, EphA1, EphA2, EphA3, EphB2, EphB4, Erk5, FAK, FER, FES, FGFR1, FGFR2, FGFR3, FGFR4, FGR, FLT1, FLT3, FLT4, FMS, Fyn, GRK4, GSK3, HER2, HER3, HER4, HGK, HIPK1, HIPK2, IGF1R, IKKα, IKKβ, IKKε, ILK, INSR, IRAK2, IRAK4, ITK, Jak1, Jak2, Jak3, JNK1, JNK3, KDR, Kit, LATS1, LATS2, LCK, LIMK1, LKB1, LRRK2, LTK, LYN, MASTL, MEK1, MEK2, MELK, Mer, Met, MISR2, MKK3, MKK4, MLK4, skMLCK, smMLCK, Mst4, mTOR, MusK, MYO3A, NEK1, NEK2, NEK8, p38, p70S6K, PAK3, PAK4, PDGFRα, PDGFRβ, PEK, PHKγ2, Pim-1, Pim-2, Pim-3, PINK1, PKACα, PKC, PKCα, PKCβ, PKCγ, PKCδ, PKCε, PKCη, PKCθ, PKR, PLK1, PRKX, PRKY, PYK2, Raf1, Ret, RHOK, RNAseL, ROCK1, ROCK2, RON, ROR2, ROS, RSK2, SGK1, SRC, Syk, TGFβR1, TGFβR2, Tie2, TITIN, TrkA, TrkB, TrkC, Tyk2, TYRO3, Wnk1, Wnk4, Yes, or Zap-70 kinase.

In some embodiments, a compound provided herein that inhibits or activates a kinase is useful for clinical applications, for example, for the inhibition or activation of a kinase implicated in a human disease or condition. In some embodiments, a compound provided herein that inhibits or activates a kinase is useful for basic research applications, for example, for characterizing a kinase, and/or for studying the role or function of a target kinase in a molecular pathway, a cell, a tissue, or an organism.

Akt 3 is a member of the AKT, also called PKB, serine/threonine protein kinase family. AKT kinases are known to be regulators of cell signaling in response to insulin and growth factors. They are involved in a wide variety of biological processes including cell proliferation, differentiation, apoptosis, tumorigenesis, as well as glycogen synthesis and glucose uptake. Akt3 has been shown to be stimulated by platelet-derived growth factor (PDGF), insulin, and insulin-like growth factor 1 (IGF1). Alternatively splice transcript variants encoding distinct isoforms have been described. Increased Akt3 activity has been reported in various cancers, including melanomas (e.g., Sharma et al., *Targeting Akt3 signaling in malignant melanoma using isoelenocyanates*, Clinical Cancer Research, 2009, 15:1647, incorporated herein by reference). Representative AKT3 sequences are given below:

```
>gi|32307164|ref|NM_005465.3| Homo sapiens v-akt murine thymoma viral
oncogene homolog 3 (protein kinase B, gamma) (AKT3), transcript variant 1, mRNA
                                                             (SEQ ID NO: 4)
GCAGCAGCAGAGAATCCAAACCCTAAAGCTGATATCACAAAGTACCATTTCTCC

AAGTTGGGGGCTCAGAGGGGAGTCATCATGAGCGATGTTACCATTGTGAAAGAA

GGTTGGGTTCAGAAGAGGGGAGAATATATAAAAAACTGGAGGCCAAGATACTT

CCTTTTGAAGACAGATGGCTCATTCATAGGATATAAAGAGAAACCTCAAGATGT

GGATTTACCTTATCCCCTCAACAACTTTTCAGTGGCAAAATGCCAGTTAATGAAA

ACAGAACGACCAAAGCCAAACACATTTATAATCAGATGTCTCCAGTGGACTACT

GTTATAGAGAACATTTCATGTAGATACTCCAGAGGAAAGGGAAGAATGGAC

AGAAGCTATCCAGGCTGTAGCAGACAGACTGCAGAGGCAAGAAGAGGAGAGAA

TGAATTGTAGTCCAACTTCACAAATTGATAATATAGGAGAGGAAGAGATGGATG

CCTCTACAACCCATCATAAAAGAAAGACAATGAATGATTTTGACTATTTGAAAC

TACTAGGTAAAGGCACTTTTGGGAAAGTTATTTTGGTTCGAGAGAAGGCAAGTG

GAAAATACTATGCTATGAAGATTCTGAAGAAAGAAGTCATTATTGCAAAGGATG

AAGTGGCACACACTCTAACTGAAAGCAGAGTATTAAAGAACACTAGACATCCCT

TTTTAACATCCTTGAAATATTCCTTCCAGACAAAAGACCGTTTGTGTTTTGTGAT

GGAATATGTTAATGGGGCGAGCTGTTTTTCCATTTGTCGAGAGAGCGGGTGTTC

TCTGAGGACCGCACACGTTTCTATGGTGCAGAAATTGTCTCTGCCTTGGACTATC

TACATTCCGGAAAGATTGTGTACCGTGATCTCAAGTTGGAGAATCTAATGCTGG

ACAAAGATGGCCACATAAAAATTACAGATTTTGGACTTTGCAAAGAAGGGATCA

CAGATGCAGCCACCATGAAGACATTCTGTGGCACTCCAGAATATCTGGCACCAG

AGGTGTTAGAAGATAATGACTATGGCCGAGCAGTAGACTGGTGGGGCCTAGGG

GTTGTCATGTATGAAATGATGTGTGGGAGGTTACCTTTCTACAACCAGGACCATG

AGAAACTTTTTGAATTAATATTAATGGAAGACATTAAATTTCCTCGAACACTCTC

TTCAGATGCAAAATCATTGCTTTCAGGGCTCTTGATAAAGGATCCAAATAAACG

CCTTGGTGGAGGACCAGATGATGCAAAAGAAATTATGAGACACAGTTTCTTCTC

TGGAGTAAACTGGCAAGATGTATATGATAAAAAGCTTGTACCTCCTTTTAAACCT

CAAGTAACATCTGAGACAGATACTAGATATTTTGATGAAGAATTTACAGCTCAG

ACTATTACAATAACACCACCTGAAAAATATGATGAGGATGGTATGGACTGCATG

GACAATGAGAGGCGGCCGCATTTCCCTCAATTTTCCTACTCTGCAAGTGGACGA

GAATAAGTCTCTTTCATTCTGCTACTTCACTGTCATCTTCAATTTATTACTGAAAA

TGATTCCTGGACATCACCAGTCCTAGCTCTTACACATAGCAGGGGCACCTTCCGA

CATCCCAGACCAGCCAAGGGTCCTCACCCCTCGCCACCTTTCACCCTCATGAAAA

CACACATACACGCAAATACACTCCAGTTTTTGTTTTTGCATGAAATTGTATCTCA

GTCTAAGGTCTCATGCTGTTGCTGCTACTGTCTTACTATTATAGCAACTTTAAGA
```

```
AGTAATTTTCCAACCTTTGGAAGTCATGAGCCCACCATTGTTCATTTGTGCACCA
ATTATCATCTTTTGATCTTTTAGTTTTTCCCTCAGTGAAGGCTAAATGAGATACAC
TGATTCTAGGTACATTTTTTAACTTTCTAGAAGAGAAAAACTAACTAGACTAAGA
AGATTTAGTTTATAAATTCAGAACAAGCAATTGTGGAAGGGTGGTGGCGTGCAT
ATGTAAAGCACATCAGATCCGTGCGTGAAGTAGGCATATATCACTAAGCTGTGG
CTGGAATTGATTAGGAAGCATTTGGTAGAAGGACTGAACAACTGTTGGGATATA
TATATATATATATAATTTTTTTTTTTAAATTCCTGGTGGATACTGTAGAAGAAGC
CCATATCACATGTGGATGTCGAGACTTCACGGGCAATCATGAGCAAGTGAACAC
TGTTCTACCAAGAACTGAAGGCATATGCACAGTCAAGGTCACTTAAAGGGTCTT
ATGAAACAATTTGAGCCAGAGAGCATCTTTCCCCTGTGCTTGGAAACCTTTTTC
CTTCTTGACATTTATCACCTCTGATGGCTGAAGAATGTAGACAGGTATAATGATA
CTGCTTTTCACCAAAATTTCTACACCAAGGTAAACAGGTGTTTGCCTTATTTAAT
TTTTTACTTTCAGTTCTACGTGAATTAGCTTTTTCTCAGATGTTGAAACTTTGAAT
GTCCTTTTATGATTTTGTTTATATTGCAGTAGTATTTATTTTTTAGTGATGAGAAT
TGTATGTCATGTTAGCAAACGCAGCTCCAACTTATATAAAATAGACTTACTGCAG
TTACTTTTGACCCATGTGCAAGGATTGTACACGCTGATGAGAATCATGCACTTTT
TCTCCTCTGTTAAAAAAAATGATAAGGCTCTGAAATGGAATATATTGGTTAGAA
TTTGGCTTTGGGAGAAGAGATGCTGCCATTTAACCCCTTGGTACTGAAAATGAG
AAAATCCCCAACTATGCATGCCAAGGGGTTAATGAAACAAATAGCTGTTGACGT
TTGCTCATTTAAGAATTTGAAACGTTATGATGACCTGGCAACAAAAAGTAATGA
AGAAAATTGAGACCTGAGTGAAGATAAGAAATGATCTTTACGTGGCAAAATGA
ACACATCTTGAGTATTTAGGAAATGGGCAGTGAAGGCTAAGAACCTGGTGTGTT
TCTTGGGATCATGGTACATTTATCACTGAATTAAGCCATCAGGGAAAAAACAAC
AAAAAAAGAGAACACCTCCAGCTTTTCTTTTTCTGTATATACTCATGTCCCCCAG
ATTCCAACATTTCTCACTGAAAGGGGGCATGTATGCAAACCTCATCTTTCTCCTT
CATTAATGATGATCTTCAGATTAAACCCTTTGGTGCTAGGAGCTGACAATTTCCA
AAGCAGCCTGTGAAGTCCTAGGGGCTGGGGGCCACTCTTGCGGCAAGCAGAAG
GCCATCCTACTCCGCGGAGTGATCATGGAAATGTATTTTAGTTAAACTCTGACAG
CTCCCAAACGGAAGACTACAGCATGACGTAGTATTATGATTGCATTGTATGAAA
GAGCAAGTGACTTTCTAAGTAGGATGAATCATATTCATATGCAGATGTCTTAGCC
TCTTGACGCTGGAAGTGTGGATTTATAGCTATGAAACCACTGCTGGCAGTGGGT
GGGCCACTGGGACTGACGGGGGTTAAAGGGCATTTTACTAAGGCAGCTAAGACA
TATTCAGACATCAACGTTATCCTTCTTTTTCATATTTCTACCTGAGTGAAG.
```

>gi|32307162|ref|NM_181690.1| Homo sapiens v-akt murine thymoma viral
oncogene homolog 3 (protein kinase B, gamma) (AKT3), transcript variant 2, mRNA
(SEQ ID NO: 5)

```
GCAGCAGCAGAGAATCCAAACCCTAAAGCTGATATCACAAAGTACCATTTCTCC
AAGTTGGGGGCTCAGAGGGGAGTCATCATGAGCGATGTTACCATTGTGAAAGAA
GGTTGGGTTCAGAAGAGGGGAGAATATATAAAAAACTGGAGGCCAAGATACTT
CCTTTTGAAGACAGATGGCTCATTCATAGGATATAAAGAGAAACCTCAAGATGT
GGATTTACCTTATCCCCTCAACAACTTTTCAGTGGCAAAATGCCAGTTAATGAAA
ACAGAACGACCAAAGCCAAACACATTTATAATCAGATGTCTCCAGTGGACTACT
```

```
GTTATAGAGAGAACATTTCATGTAGATACTCCAGAGGAAAGGGAAGAATGGAC

AGAAGCTATCCAGGCTGTAGCAGACAGACTGCAGAGGCAAGAAGAGGAGAGAA

TGAATTGTAGTCCAACTTCACAAATTGATAATATAGGAGAGGAAGAGATGGATG

CCTCTACAACCCATCATAAAAGAAAGACAATGAATGATTTTGACTATTTGAAAC

TACTAGGTAAAGGCACTTTTGGGAAAGTTATTTTGGTTCGAGAGAAGGCAAGTG

GAAAATACTATGCTATGAAGATTCTGAAGAAAGAAGTCATTATTGCAAAGGATG

AAGTGGCACACACTCTAACTGAAAGCAGAGTATTAAAGAACACTAGACATCCCT

TTTTAACATCCTTGAAATATTCCTTCCAGACAAAAGACCGTTTGTGTTTTGTGAT

GGAATATGTTAATGGGGGCGAGCTGTTTTTCCATTTGTCGAGAGAGCGGGTGTTC

TCTGAGGACCGCACACGTTTCTATGGTGCAGAAATTGTCTCTGCCTTGGACTATC

TACATTCCGGAAAGATTGTGTACCGTGATCTCAAGTTGGAGAATCTAATGCTGG

ACAAAGATGGCCACATAAAAATTACAGATTTTGGACTTTGCAAAGAAGGGATCA

CAGATGCAGCCACCATGAAGACATTCTGTGGCACTCCAGAATATCTGGCACCAG

AGGTGTTAGAAGATAATGACTATGGCCGAGCAGTAGACTGGTGGGGCCTAGGG

GTTGTCATGTATGAAATGATGTGTGGGAGGTTACCTTTCTACAACCAGGACCATG

AGAAACTTTTTGAATTAATATTAATGGAAGACATTAAATTTCCTCGAACACTCTC

TTCAGATGCAAAATCATTGCTTTCAGGGCTCTTGATAAAGGATCCAAATAAACG

CCTTGGTGGAGGACCAGATGATGCAAAAGAAATTATGAGACACAGTTTCTTCTC

TGGAGTAAACTGGCAAGATGTATATGATAAAAAGCTTGTACCTCCTTTTAAACCT

CAAGTAACATCTGAGACAGATACTAGATATTTTGATGAAGAATTTACAGCTCAG

ACTATTACAATAACACCACCTGAAAAATGTCAGCAATCAGATTGTGGCATGCTG

GGTAACTGGAAAAAATAATAAAAATCGGCTTCCTACAGCCAGCAGCACAGTCAC

CCATGGAACTGTTGGCTTTGGATTAAATGTGGAATTGAACGACTACCCAGAAGT

GTTCTGGAAAGAAGCGAGATGTGTGGCCTGCCTCACCGTCCTCACCCATCAAAA

GCACCAGCAGGCACGTTAACTCGAATTCTCACAAGGAAAAGGCCATTAAAGCTC

AAGGTGCATTTCAAACTCCAGGCTAC.
```

>gi|4885549|ref|NP_005456.1| RAC-gamma serine/threonine-protein kinase
isoform 1 [Homo sapiens]

(SEQ ID NO: 6)

```
MSDVTIVKEGWVQKRGEYIKNWRPRYFLLKTDGSFIGYKEKPQDVDLPYPLNNFSV

AKCQLMKTERPKPNTFIIRCLQWTTVIERTFHVDTPEEREEWTEAIQAVADRLQRQE

EERMNCSPTSQIDNIGEEEMDASTTHHKRKTMNDFDYLKLLGKGTFGKVILVREKA

SGKYYAMKILKKEVIIAKDEVAHTLTESRVLKNTRHPFLTSLKYSFQTKDRLCFVME

YVNGGELFFHLSRERVFSEDRTRFYGAEIVSALDYLHSGKIVYRDLKLENLMLDKD

GHIKITDFGLCKEGITDAATMKTFCGTPEYLAPEVLEDNDYGRAVDWWGLGVVMY

EMMCGRLPFYNQDHEKLFELILMEDIKFPRTLSSDAKSLLSGLLIKDPNKRLGGGPD

DAKEIMRHSFFSGVNWQDVYDKKLVPPFKPQVTSETDTRYFDEEFTAQTITITPPEK

YDEDGMDCMDNERRPHFPQFSYSASGRE.
```

>gi|32307163|ref|NP_859029.1| RAC-gamma serine/threonine-protein kinase
isoform 2 [Homo sapiens]

(SEQ ID NO: 7)

```
MSDVTIVKEGWVQKRGEYIKNWRPRYFLLKTDGSFIGYKEKPQDVDLPYPLNNFSV

AKCQLMKTERPKPNTFIIRCLQWTTVIERTFHVDTPEEREEWTEAIQAVADRLQRQE
```

-continued

```
EERMNCSPTSQIDNIGEEEMDASTTHHKRKTMNDFDYLKLLGKGTFGKVILVREKA

SGKYYAMKILKKEVIIAKDEVAHTLTESRVLKNTRHPFLTSLKYSFQTKDRLCFVME

YVNGGELFFHLSRERVFSEDRTRFYGAEIVSALDYLHSGKIVYRDLKLENLMLDKD

GHIKITDFGLCKEGITDAATMKTFCGTPEYLAPEVLEDNDYGRAVDWWGLGVVMY

EMMCGRLPFYNQDHEKLFELILMEDIKFPRTLSSDAKSLLSGLLIKDPNKRLGGGPD

DAKEIMRHSFFSGVNWQDVYDKKLVPPFKPQVTSETDTRYFDEEFTAQTITITPPEKC

QQSDCGMLGNWKK.
```

MAPKAP2 is a member of the serine/threonine protein kinase family. MAPKAP2 is regulated through direct phosphorylation by p38 MAP kinase. In conjunction with p38 MAP kinase, MAPKAP2 has been reported to be involved in many cellular processes including stress and inflammatory responses, nuclear export, gene expression regulation and cell proliferation. Two transcript variants encoding two different isoforms have been reported. Representative sequences are given below:

```
>gi|32481207|ref|NM_004759.3| Homo sapiens mitogen-activated protein
kinase-activated protein kinase 2 (MAPKAPK2), transcript variant 1, mRNA
                                                          (SEQ ID NO: 8)
GCGGCCGCTTCCCCCCGGCCGGGCCCCGCCGCCCCGCGGTCCCCAGAGCGCCA

GGCCCCCGGGGGGAGGGAGGGAGGGCGCCGGGCCGGTGGGAGCCAGCGGCGCG

CGGTGGGACCCACGGAGCCCCGCGACCCGCCGAGCCTGGAGCCGGGCCGGGTC

GGGGAAGCCGGCTCCAGCCCGGAGCGAACTTCGCAGCCCGTCGGGGGGCGGCG

GGGAGGGGGCCCGGAGCCGGAGGAGGGGCGGCCGCGGGCACCCCCGCCTGTG

CCCCGGCGTCCCCGGGCACCATGCTGTCCAACTCCCAGGGCCAGAGCCCGCCGG

TGCCGTTCCCCGCCCCGGCCCCGCCGCCGCAGCCCCCCACCCCTGCCCTGCCGCA

CCCCCCGGCGCAGCCGCCGCCGCCGCCCCCGCAGCAGTTCCCGCAGTTCCACGT

CAAGTCCGGCCTGCAGATCAAGAAGAACGCCATCATCGATGACTACAAGGTCAC

CAGCCAGGTCCTGGGGCTGGGCATCAACGGCAAAGTTTTGCAGATCTTCAACAA

GAGGACCCAGGAGAAATTCGCCCTCAAAATGCTTCAGGACTGCCCCAAGGCCCG

CAGGGAGGTGGAGCTGCACTGGCGGGCCTCCCAGTGCCCGCACATCGTACGGAT

CGTGGATGTGTACGAGAATCTGTACGCAGGGAGGAAGTGCCTGCTGATTGTCAT

GGAATGTTTGGACGGTGGAGAACTCTTTAGCCGAATCCAGGATCGAGGAGACCA

GGCATTCACAGAAAGAGAAGCATCCGAAATCATGAAGAGCATCGGTGAGGCCA

TCCAGTATCTGCATTCAATCAACATTGCCCATCGGGATGTCAAGCCTGAGAATCT

CTTATACACCTCCAAAAGGCCCAACGCCATCCTGAAACTCACTGACTTTGGCTTT

GCCAAGGAAACCACCAGCCACAACTCTTTGACCACTCCTTGTTATACACCGTACT

ATGTGGCTCCAGAAGTGCTGGGTCCAGAGAAGTATGACAAGTCCTGTGACATGT

GGTCCCTGGGTGTCATCATGTACATCCTGCTGTGTGGGTATCCCCCCTTCTACTC

CAACCACGGCCTTGCCATCTCTCCGGGCATGAAGACTCGCATCCGAATGGGCCA

GTATGAATTTCCCAACCCAGAATGGTCAGAAGTATCAGAGGAAGTGAAGATGCT

CATTCGGAATCTGCTGAAAACAGAGCCCACCCAGAGAATGACCATCACCGAGTT

TATGAACCACCCTTGGATCATGCAATCAACAAAGGTCCCTCAAACCCCACTGCA

CACCAGCCGGGTCCTGAAGGAGGACAAGGAGCGGTGGGAGGATGTCAAGGGGT

GTCTTCATGACAAGAACAGCGACCAGGCCACTTGGCTGACCAGGTTGTGAGCAG

AGGATTCTGTGTTCCTGTCCAAACTCAGTGCTGTTTCTTAGAATCCTTTTATTCCC

TGGGTCTCTAATGGGACCTTAAAGACCATCTGGTATCATCTTCTCATTTTGCAGA
```

-continued

```
AGAGAAACTGAGGCCCAGAGGCGGAGGGCAGTCTGCTCAAGGTCACGCAGCTG
GTGACTGGTTGGGGCAGACCGGACCCAGGTTTCCTGACTCCTGGCCCAAGTCTCT
TCCTCCTATCCTGCGGGATCACTGGGGGGCTCTCAGGGAACAGCAGCAGTGCCA
TAGCCAGGCTCTCTGCTGCCCAGCGCTGGGGTGAGGCTGCCGTTGTCAGCGTGG
ACCACTAACCAGCCCGTCTTCTCTCTCTGCTCCCACCCCTGCCGCCCTCACCCTG
CCCTTGTTGTCTCTGTCTCTCACGTCTCTCTTCTGCTGTCTCTCCTACCTGTCTTCT
GGCTCTCTCTGTACCCTTCCTGGTGCTGCCGTGCCCCCAGGAGGAGATGACCAGT
GCCTTGGCCACAATGCGCGTTGACTACGAGCAGATCAAGATAAAAAAGATTGAA
GATGCATCCAACCCTCTGCTGCTGAAGAGGCGGAAGAAAGCTCGGGCCCTGGAG
GCTGCGGCTCTGGCCCACTGAGCCACCGCGCCCTCCTGCCCACGGGAGGACAAG
CAATAACTCTCTACAGGAATATATTTTTTAAACGAAGAGACAGAACTGTCCACA
TCTGCCTCCTCTCCTCCTCAGCTGCATGGAGCCTGGAACTGCATCAGTGACTGAA
TTCTGCCTTGGTTCTGGCCACCCCAGAGTGGGAGAGGCTGGGAGGTTGGGAGGC
TGTGGAGAGAAGTGAGCAAGGTGCTCTTGAACCTGTGCTCATTTTGCAATTTTAT
CAGTAATTTGACTTAGAGTTTTTACGAAACCTCTTTTGTTGTCCTTGCCCCACTCC
TCTCCACCAGACGCCTTCCTCTCTGGATACTGCAAAGGCTTGTGGTTTGTTAGAG
GGTATTTGTGGAAACTGTCATAGGGATTGTCCCTGTGTTGTCCCATCTGCCCTCC
CTGTTTCTCCACAACAGCCTGGGGTTGTCCCCGCTGGCTCACGCGTTCTGGGAGC
TCAAGGCCACCTTGGAGGAGGATGCCACGCACTTCCTCTCTCGGAGCCCTCAGA
CATCTCCAGTGTGCCAGACAAATAGGAGTGAGTGTATGTGTGTGTGTGTGTGT
GTGTGTGCACACGTGTGTATGAGTGCGCAGATCTGTGCCTGGGATCGTGCATTTG
AGGGGCCAGGGGCAGGCAGGGCTGCAGAGGGAGACGGCCCTGCTGGGGCTTAG
GAACCTTCTCCCTTCTTGGGTCTGCCCTGCCCATACTGAGCCTGCCAAAGTGCCT
GGGAAGCCCACCCAGATTCTGAAACAGGCCCTCTGTGGCCTGTCTCTATTAGCTG
GGTTCCGGGAGGCAGAGAGGAGTGACCGGGCACTGGCACTGCGATCAGGAAGA
CTGGACCCCCAGCCCCAGGGCCCCCCTCCCCCCACTTAGTGCTGGTCCTAGGTC
CTCTGAGGCACTCATCTACTGAATGACCTCTCTACTTCCCCTTCTTGCCATTATTA
ACCCATTTTTGTTTATTTTCCTTAAATTTTTAGCCATTTCTCCATGGGCCACCGCC
CAGCTCATGTAGGTGAGCCTGGGCAGCTTCTGTTGGCAGAGCTTTTGCATTTCCT
GTGTTTGTCCTGGGTTCTGGGGCATCAGCCAGCTACCCCTTGTGGGCAAAGGCA
GGGCCACTTTTGAAGTCTTCCCTCAGATTTCCATTGTGTGGCCTGGTGGGTCAGG
GGGAGTCTTTGCACCAAAGATGTCCTGACTTTGCCCCCTTGCCCATCAGCCATTT
GCCATCACCCCAAACAACTCAGCTTCGGGGCCGGTGAGGGGAGGGCCTCCCCC
AGCACAGATGAGGAGCAGCTGGGGTAGGCTGTCTGTGCCATGGCCCCCCACTCC
CCCTTCCCTTGGAGGGAGAGGTGGCAGGAATACTTCACCTTTCCTCTCCCTCAGG
GGCAGGTGGTGGAGGGGCGCCCAGGGTCGTCTTTGTGTATGGGGAAGGCGCTG
GGTGCCTGCAGCGCCTCCCTTGTCTCAGATGGTGTGTCCAGCACTCGATTGTTGT
AAACTGTTGTTTTGTATGAGCGAAATTGTCTTTACTAAACAGATTTAATAGTTAA
AAAAAAAAAAAAAAAA.
```

-continued

>gi|32481208|ref|NM_032960.2| *Homo sapiens* mitogen-activated protein
kinase-activated protein kinase 2 (MAPKAPK2), transcript variant 2, mRNA
(SEQ ID NO: 9)

```
GCGGCCGCTTCCCCCCGGCCGGGCCCCCGCCGCCCCGCGGTCCCCAGAGCGCCA

GGCCCCCGGGGGAGGGAGGGAGGGCGCCGGGCCGGTGGGAGCCAGCGGCGCG

CGGTGGGACCCACGGAGCCCCGCGACCCGCCGAGCCTGGAGCCGGGCCGGGTC

GGGGAAGCCGGCTCCAGCCCGGAGCGAACTTCGCAGCCCGTCGGGGGCGGCG

GGGAGGGGGCCCGGAGCCGGAGGAGGGGGCGGCCGCGGGCACCCCCGCCTGTG

CCCCGGCGTCCCCGGGCACCATGCTGTCCAACTCCCAGGGCCAGAGCCCGCCGG

TGCCGTTCCCCGCCCCGGCCCCGCCGCCGCAGCCCCCCACCCCTGCCCTGCCGCA

CCCCCCGGCGCAGCCGCCGCCGCCGCCCCCGCAGCAGTTCCCGCAGTTCCACGT

CAAGTCCGGCCTGCAGATCAAGAAGAACGCCATCATCGATGACTACAAGGTCAC

CAGCCAGGTCCTGGGGCTGGGCATCAACGGCAAAGTTTTGCAGATCTTCAACAA

GAGGACCCAGGAGAAATTCGCCCTCAAAATGCTTCAGGACTGCCCCAAGGCCCG

CAGGGAGGTGGAGCTGCACTGGCGGGCCTCCCAGTGCCCGCACATCGTACGGAT

CGTGGATGTGTACGAGAATCTGTACGCAGGGAGGAAGTGCCTGCTGATTGTCAT

GGAATGTTTGGACGGTGGAGAACTCTTTAGCCGAATCCAGGATCGAGGAGACCA

GGCATTCACAGAAAGAGAAGCATCCGAAATCATGAAGAGCATCGGTGAGGCCA

TCCAGTATCTGCATTCAATCAACATTGCCCATCGGGATGTCAAGCCTGAGAATCT

CTTATACACCTCCAAAAGGCCCAACGCCATCCTGAAACTCACTGACTTTGGCTTT

GCCAAGGAAACCACCAGCCACAACTCTTTGACCACTCCTTGTTATACACCGTACT

ATGTGGCTCCAGAAGTGCTGGGTCCAGAGAAGTATGACAAGTCCTGTGACATGT

GGTCCCTGGGTGTCATCATGTACATTCTGCTGTGTGGGTATCCCCCCTTCTACTCC

AACCACGGCCTTGCCATCTCTCCGGGCATGAAGACTCGCATCCGAATGGGCCAG

TATGAATTTCCCAACCCAGAATGGTCAGAAGTATCAGAGGAAGTGAAGATGCTC

ATTCGGAATCTGCTGAAAACAGAGCCCACCCAGAGAATGACCATCACCGAGTTT

ATGAACCACCCTTGGATCATGCAATCAACAAAGGTCCCTCAAACCCCACTGCAC

ACCAGCCGGGTCCTGAAGGAGGACAAGGAGCGGTGGGAGGATGTCAAGGAGGA

GATGACCAGTGCCTTGGCCACAATGCGCGTTGACTACGAGCAGATCAAGATAAA

AAAGATTGAAGATGCATCCAACCCTCTGCTGCTGAAGAGGCGGAAGAAAGCTCG

GGCCCTGGAGGCTGCGGCTCTGGCCCACTGAGCCACCGCGCCCTCCTGCCCACG

GGAGGACAAGCAATAACTCTCTACAGGAATATATTTTTTAAACGAAGAGACAGA

ACTGTCCACATCTGCCTCCTCTCCTCCTCAGCTGCATGGAGCCTGGAACTGCATC

AGTGACTGAATTCTGCCTTGGTTCTGGCCACCCCAGAGTGGGAGAGGCTGGGAG

GTTGGGAGGCTGTGGAGAGAAGTGAGCAAGGTGCTCTTGAACCTGTGCTCATTT

TGCAATTTTATCAGTAATTTGACTTAGAGTTTTTACGAAACCTCTTTTGTTGTCCT

TGCCCCACTCCTCTCCACCAGACGCCTTCCTCTCTGGATACTGCAAAGGCTTGTG

GTTTGTTAGAGGGTATTTGTGGAAACTGTCATAGGGATTGTCCCTGTGTTGTCCC

ATCTGCCCTCCCTGTTTCTCCACAACAGCCTGGGGTTGTCCCCGCTGGCTCACGC

GTTCTGGGAGCTCAAGGCCACCTTGGAGGAGGATGCCACGCACTTCCTCTCTCG
```

-continued

```
GAGCCCTCAGACATCTCCAGTGTGCCAGACAAATAGGAGTGAGTGTATGTGTGT

GTGTGTGTGTGTGTGTGCACACGTGTGTATGAGTGCGCAGATCTGTGCCTGGG

ATCGTGCATTTGAGGGGCCAGGGGCAGGCAGGGCTGCAGAGGGAGACGGCCCT

GCTGGGGCTTAGGAACCTTCTCCCTTCTTGGGTCTGCCCTGCCCATACTGAGCCT

GCCAAAGTGCCTGGGAAGCCCACCCAGATTCTGAAACAGGCCCTCTGTGGCCTG

TCTCTATTAGCTGGGTTCCGGGAGGCAGAGAGGAGTGACCGGGCACTGGCACTG

CGATCAGGAAGACTGGACCCCCAGCCCCCAGGGCCCCCCTCCCCCCACTTAGTG

CTGGTCCTAGGTCCTCTGAGGCACTCATCTACTGAATGACCTCTCTACTTCCCCTT

CTTGCCATTATTAACCCATTTTTGTTTATTTTCCTTAAATTTTTAGCCATTTCTCCA

TGGGCCACCGCCCAGCTCATGTAGGTGAGCCTGGGCAGCTTCTGTTGGCAGAGC

TTTTGCATTTCCTGTGTTTGTCCTGGGTTCTGGGGCATCAGCCAGCTACCCCTTGT

GGGCAAAGGCAGGGCCACTTTTGAAGTCTTCCCTCAGATTTCCATTGTGTGGCCT

GGTGGGTCAGGGGGAGTCTTTGCACCAAAGATGTCCTGACTTTGCCCCCTTGCCC

ATCAGCCATTTGCCATCACCCCAAACAACTCAGCTTCGGGGCCGGTGAGGGGAG

GGGCCTCCCCCAGCACAGATGAGGAGCAGCTGGGGTAGGCTGTCTGTGCCATGG

CCCCCCACTCCCCCTTCCCTTGGAGGGAGAGGTGGCAGGAATACTTCACCTTTCC

TCTCCCTCAGGGGCAGGTGGTGGAGGGGCGCCCAGGGTCGTCTTTGTGTATGGG

GGAAGGCGCTGGGTGCCTGCAGCGCCTCCCTTGTCTCAGATGGTGTGTCCAGCA

CTCGATTGTTGTAAACTGTTGTTTTGTATGAGCGAAATTGTCTTTACTAAACAGA

TTTAATAGTTAAAAAAAAAAAAAAAAAAA.
```

>gi|10863901|ref|NP_004750.1| MAP kinase-activated protein kinase 2 isoform 1 [Homo sapiens]

(SEQ ID NO: 10)

```
MLSNSQGQSPPVPFPAPAPPPQPPTPALPHPPAQPPPPPPQQFPQFHVKSGLQIKKNAII

DDYKVTSQVLGLGINGKVLQIFNKRTQEKFALKMLQDCPKARREVELHWRASQCP

HIVRIVDVYENLYAGRKCLLIVMECLDGGELFSRIQDRGDQAFTEREASEIMKSIGEA

IQYLHSINIAHRDVKPENLLYTSKRPNAILKLTDFGFAKETTSHNSLTTPCYTPYYVA

PEVLGPEKYDKSCDMWSLGVIMYILLCGYPPFYSNHGLAISPGMKTRIRMGQYEFPN

PEWSEVSEEVKMLIRNLLKTEPTQRMTITEFMNHPWIMQSTKVPQTPLHTSRVLKED

KERWEDVKGCLHDKNSDQATWLTRL.
```

>gi|32481209|ref|NP_116584.2| MAP kinase-activated protein kinase 2 isoform 2 [Homo sapiens]

(SEQ ID NO: 11)

```
MLSNSQGQSPPVPFPAPAPPPQPPTPALPHPPAQPPPPPPQQFPQFHVKSGLQIKKNAII

DDYKVTSQVLGLGINGKVLQIFNKRTQEKFALKMLQDCPKARREVELHWRASQCP

HIVRIVDVYENLYAGRKCLLIVMECLDGGELFSRIQDRGDQAFTEREASEIMKSIGEA

IQYLHSINIAHRDVKPENLLYTSKRPNAILKLTDFGFAKETTSHNSLTTPCYTPYYVA

PEVLGPEKYDKSCDMWSLGVIMYILLCGYPPFYSNHGLAISPGMKTRIRMGQYEFPN

PEWSEVSEEVKMLIRNLLKTEPTQRMTITEFMNHPWIMQSTKVPQTPLHTSRVLKED

KERWEDVKEEMTSALATMRVDYEQIKIKKIEDASNPLLLKRRKKARALEAAALAH.
```

Pim1 is a proto-oncogenic kinase that is believed to be regulated by the Jak/Stat pathway. Representative Pim1 sequences are given below:

>gi|208431772|ref|NM_002648.3| *Homo sapiens* pim-1 oncogene (PIM1), mRNA (SEQ ID NO: 12)

```
CCCTTTACTCCTGGCTGCGGGGCGAGCCGGGCGTCTGCTGCAGCGGCCGCGGTGG
CTGAGGAGGCCCGAGAGGAGTCGGTGGCAGCGGCGGCGGCGGGACCGGCAGCA
GCAGCAGCAGCAGCAGCAGCAACCACTAGCCTCCTGCCCCGCGGCGCTGCC
GCACGAGCCCCACGAGCCGCTCACCCCGCCGTTCTCAGCGCTGCCCGACCCCGCT
GGCGCGCCCTCCCGCCGCCAGTCCCGGCAGCGCCCTCAGTTGTCCTCCGACTCGC
CCTCGGCCTTCCGCGCCAGCCGCAGCCACAGCCGCAACGCCACCCGCAGCCACA
GCCACAGCCACAGCCCCAGGCATAGCCTTCGGCACAGCCCCGGCTCCGGCTCCT
GCGGCAGCTCCTCTGGGCACCGTCCCTGCGCCGACATCCTGGAGGTTGGGATGCT
CTTGTCCAAAATCAACTCGCTTGCCCACCTGCGCGCCGCGCCCTGCAACGACCTG
CACGCCACCAAGCTGGCGCCCGGCAAGGAGAAGGAGCCCCTGGAGTCGCAGTAC
CAGGTGGGCCCGCTACTGGGCAGCGGCGGCTTCGGCTCGGTCTACTCAGGCATCC
GCGTCTCCGACAACTTGCCGGTGGCCATCAAACACGTGGAGAAGGACCGGATTT
CCGACTGGGGAGAGCTGCCTAATGGCACTCGAGTGCCCATGGAAGTGGTCCTGC
TGAAGAAGGTGAGCTCGGGTTTCTCCGGCGTCATTAGGCTCCTGGACTGGTTCGA
GAGGCCCGACAGTTTCGTCCTGATCCTGGAGAGGCCCGAGCCGGTGCAAGATCT
CTTCGACTTCATCACGGAAAGGGGAGCCCTGCAAGAGGAGCTGGCCCGCAGCTT
CTTCTGGCAGGTGCTGGAGGCCGTGCGGCACTGCCACAACTGCGGGGTGCTCCAC
CGCGACATCAAGGACGAAAACATCCTTATCGACCTCAATCGCGGCGAGCTCAAG
CTCATCGACTTCGGGTCGGGGCGCTGCTCAAGGACACCGTCTACACGGACTTCG
ATGGGACCCGAGTGTATAGCCCTCCAGAGTGGATCCGCTACCATCGCTACCATGG
CAGGTCGGCGGCAGTCTGGTCCCTGGGGATCCTGCTGTATGATATGGTGTGTGGA
GATATTCCTTTCGAGCATGACGAAGAGATCATCAGGGGCCAGGTTTTCTTCAGGC
AGAGGGTCTCTTCAGAATGTCAGCATCTCATTAGATGGTGCTTGGCCCTGAGACC
ATCAGATAGGCCAACCTTCGAAGAAATCCAGAACCATCCATGGATGCAAGATGT
TCTCCTGCCCCAGGAAACTGCTGAGATCCACCTCCACAGCCTGTCGCCGGGGCCC
AGCAAATAGCAGCCTTTCTGGCAGGTCCTCCCCTCTCTTGTCAGATGCCCGAGGG
AGGGGAAGCTTCTGTCTCCAGCTTCCCGAGTACCAGTGACACGTCTCGCCAAGCA
GGACAGTGCTTGATACAGGAACAACATTTACAACTCATTCCAGATCCCAGGCCCC
TGGAGGCTGCCTCCCAACAGTGGGGAAGAGTGACTCTCCAGGGGTCCTAGGCCT
CAACTCCTCCCATAGATACTCTCTTCTTCTCATAGGTGTCCAGCATTGCTGGACTC
TGAAATATCCCGGGGGTGGGGGGTGGGGGTGGGTCAGAACCCTGCCATGGAACT
GTTTCCTTCATCATGAGTTCTGCTGAATGCCGCGATGGGTCAGGTAGGGGGGAAA
CAGGTTGGGATGGGATAGGACTAGCACCATTTTAAGTCCCTGTCACCTCTTCCGA
CTCTTTCTGAGTGCCTTCTGTGGGGACTCCGGCTGTGCTGGGAGAAATACTTGAA
CTTGCCTCTTTTACCTGCTGCTTCTCCAAAAATCTGCCTGGGTTTTGTTCCCTATTT
TTCTCTCCTGTCCTCCCTCACCCCCTCCTTCATATGAAAGGTGCCATGGAAGAGGC
TACAGGGCCAAACGCTGAGCCACCTGCCCTTTTTTCTGCCTCCTTTAGTAAAACTC
```

-continued

```
CGAGTGAACTGGTCTTCCTTTTTGGTTTTTACTTAACTGTTTCAAAGCCAAGACCT

CACACACACAAAAAATGCACAAACAATGCAATCAACAGAAAAGCTGTAAATGTG

TGTACAGTTGGCATGGTAGTATACAAAAAGATTGTAGTGGATCTAATTTTTAAGA

AATTTTGCCTTTAAGTTATTTTACCTGTTTTTGTTTCTTGTTTTGAAAGATGCGCAT

TCTAACCTGGAGGTCAATGTTATGTATTTATTTATTTATTTATTTGGTTCCCTTCCT

ATTCCAAGCTTCCATAGCTGCTGCCCTAGTTTTCTTTCCTCCTTTCCTCCTCTGACT

TGGGGACCTTTTGGGGGAGGGCTGCGACGCTTGCTCTGTTTGTGGGGTGACGGGA

CTCAGGCGGGACAGTGCTGCAGCTCCCTGGCTTCTGTGGGGCCCCTCACCTACTT

ACCCAGGTGGGTCCCGGCTCTGTGGGTGATGGGGAGGGGCATTGCTGACTGTGT

ATATAGGATAATTATGAAAAGCAGTTCTGGATGGTGTGCCTTCCAGATCCTCTCT

GGGGCTGTGTTTTGAGCAGCAGGTAGCCTGCTGGTTTTATCTGAGTGAAATACTG

TACAGGGGAATAAAAGAGATCTTATTTTTTTTTTATACTTGGCGTTTTTTGAATA

AAAACCTTTTGTCTTAAAAAAAAAAAAAAAAAAAAAAAAAAAAAAAAAAAAAA

AAAAAA.

>gi|4505811|ref|NP_002639.1| proto-oncogene serine/threonine-protein kinase
pim-1 [Homo sapiens]
                                                            (SEQ ID NO: 13)
MLLSKINSLAHLRAAPCNDLHATKLAPGKEKEPLESQYQVGPLLGSGGFGSVYSGIR

VSDNLPVAIKHVEKDRISDWGELPNGTRVPMEVVLLKKVSSGFSGVIRLLDWFERPD

SFVLILERPEPVQDLFDFITERGALQEELARSFFWQVLEAVRHCHNCGVLHRDIKDEN

ILIDLNRGELKLIDFGSGALLKDTVYTDFDGTRVYSPPEWIRYHRYHGRSAAVWSLGI

LLYDMVCGDIPFEHDEEIIRGQVFFRQRVSSECQHLIRWCLALRPSDRPTFEEIQNHPW

MQDVLLPQETAEIHLHSLSPGPSK.
```

Without wishing to be bound by any particular theory, Pim1 expression has been reported to be increased in certain prostate cancers where it may lead to genomic instability (e.g., Roh M, Gary B, Song C, Said-Al-Naief N, Tousson A, Kraft A, Eltoum I E, Abdulkadir S A, *Overexpression of the oncogenic kinase Pim-1 leads to genomic instability.* Cancer Res. 2003 Dec. 1; 63(23):8079-84; incorporated herein by reference) and reduce androgen receptor-dependent transcription (e.g., Thompson J, Peltola K J, Koskinen P J, Jänne O A, Palvimo J J. *Attenuation of androgen receptor-dependent transcription by the serine/threonine kinase Pim-1.* Lab Invest. 2003 September; 83(9):1301-9; incorporated herein by reference). Pim1 expression level has been reported to carry prognostic value. Increased Pim1 activity or expression has also been observed in hematopoietic malignancies and in diffuse large-cell lymphomas. T cell lymphomas have been reported in Pim-1 overexpressing mice and can be induced by viral insertions at the Pim-1 locus.

VEGFR2 is a tyrosine kinase, also known as kinase insert domain receptor (KDR), a type III receptor tyrosine kinase or CD309 (cluster of differentiation 309). Aberrant VEGFR2 activity is implicated in numerous diseases (e.g., Holmes K, Roberts O L, Thomas A M, Cross M J. *Vascular endothelial growth factor receptor-2: structure, function, intracellular signaling and therapeutic inhibition.* Cell Signal. 2007 October; 19(10):2003-12; incorporated herein by reference). The activation of VEGFR2 is envisioned as a clinically useful means to heal, for example, bone and tissue. Further, the activation of VEGFR2 is expected to be a useful research tool to study, for example, the effects of VEGFR2 upregulation in the cell (e.g., to better characterize the molecular details of cancer). Representative sequences of VEGFR2 are given below.

```
>gi|195546779|ref|NM_002253.2| Homo sapiens kinase insert domain receptor
(a type III receptor tyrosine kinase) (KDR), mRNA
                                                            (SEQ ID NO: 14)
ACTGAGTCCCGGGACCCCGGGAGAGCGGTCAATGTGTGGTCGCTGCGTTTCCTCT

GCCTGCGCCGGGCATCACTTGCGCGCCGCAGAAAGTCCGTCTGGCAGCCTGGAT

ATCCTCTCCTACCGGCACCCGCAGACGCCCCTGCAGCCGCGGTCGGCGCCCGGGC

TCCCTAGCCCTGTGCGCTCAACTGTCCTGCGCTGCGGGGTGCCGCGAGTTCCACC

TCCGCGCCTCCTTCTCTAGACAGGCGCTGGGAGAAAGAACCGGCTCCCGAGTTCT
```

-continued

```
GGGCATTTCGCCCGGCTCGAGGTGCAGGATGCAGAGCAAGGTGCTGCTGGCCGT

CGCCCTGTGGCTCTGCGTGGAGACCCGGGCCGCCTCTGTGGGTTTGCCTAGTGTT

TCTCTTGATCTGCCCAGGCTCAGCATACAAAAAGACATACTTACAATTAAGGCTA

ATACAACTCTTCAAATTACTTGCAGGGGACAGAGGGACTTGGACTGGCTTTGGCC

CAATAATCAGAGTGGCAGTGAGCAAAGGGTGGAGGTGACTGAGTGCAGCGATGG

CCTCTTCTGTAAGACACTCACAATTCCAAAAGTGATCGGAAATGACACTGGAGCC

TACAAGTGCTTCTACCGGGAAACTGACTTGGCCTCGGTCATTTATGTCTATGTTCA

AGATTACAGATCTCCATTTATTGCTTCTGTTAGTGACCAACATGGAGTCGTGTAC

ATTACTGAGAACAAAAACAAAACTGTGGTGATTCCATGTCTCGGGTCCATTTCAA

ATCTCAACGTGTCACTTTGTGCAAGATACCCAGAAAAGAGATTTGTTCCTGATGG

TAACAGAATTTCCTGGGACAGCAAGAAGGGCTTTACTATTCCCAGCTACATGATC

AGCTATGCTGGCATGGTCTTCTGTGAAGCAAAAATTAATGATGAAAGTTACCAGT

CTATTATGTACATAGTTGTCGTTGTAGGGTATAGGATTTATGATGTGGTTCTGAGT

CCGTCTCATGGAATTGAACTATCTGTTGGAGAAAAGCTTGTCTTAAATTGTACAG

CAAGAACTGAACTAAATGTGGGGATTGACTTCAACTGGGAATACCCTTCTTCGAA

GCATCAGCATAAGAAACTTGTAAACCGAGACCTAAAAACCCAGTCTGGGAGTGA

GATGAAGAAATTTTTGAGCACCTTAACTATAGATGGTGTAACCCGGAGTGACCA

AGGATTGTACACCTGTGCAGCATCCAGTGGGCTGATGACCAAGAAGAACAGCAC

ATTTGTCAGGGTCCATGAAAAACCTTTTGTTGCTTTTGGAAGTGGCATGGAATCT

CTGGTGGAAGCCACGGTGGGGAGCGTGTCAGAATCCCTGCGAAGTACCTTGGT

TACCCACCCCCAGAAATAAAATGGTATAAAAATGGAATACCCCTTGAGTCCAAT

CACACAATTAAAGCGGGGCATGTACTGACGATTATGGAAGTGAGTGAAAGAGAC

ACAGGAAATTACACTGTCATCCTTACCAATCCCATTTCAAAGGAGAAGCAGAGC

CATGTGGTCTCTCTGGTTGTGTATGTCCCACCCCAGATTGGTGAGAAATCTCTAAT

CTCTCCTGTGGATTCCTACCAGTACGGCACCACTCAAACGCTGACATGTACGGTC

TATGCCATTCCTCCCCCGCATCACATCCACTGGTATTGGCAGTTGGAGGAAGAGT

GCGCCAACGAGCCCAGCCAAGCTGTCTCAGTGACAAACCCATACCCTTGTGAAG

AATGGAGAAGTGTGGAGGACTTCCAGGGAGGAAATAAAATTGAAGTTAATAAAA

ATCAATTTGCTCTAATTGAAGGAAAAAACAAAACTGTAAGTACCCTTGTTATCCA

AGCGGCAAATGTGTCAGCTTTGTACAAATGTGAAGCGGTCAACAAAGTCGGGAG

AGGAGAGAGGGTGATCTCCTTCCACGTGACCAGGGGTCCTGAAATTACTTTGCAA

CCTGACATGCAGCCCACTGAGCAGGAGAGCGTGTCTTTGTGGTGCACTGCAGAC

AGATCTACGTTTGAGAACCTCACATGGTACAAGCTTGGCCCACAGCCTCTGCCAA

TCCATGTGGGAGAGTTGCCCACACCTGTTTGCAAGAACTTGGATACTCTTTGGAA

ATTGAATGCCACCATGTTCTCTAATAGCACAAATGACATTTTGATCATGGAGCTT

AAGAATGCATCCTTGCAGGACCAAGGAGACTATGTCTGCCTTGCTCAAGACAGG

AAGACCAAGAAAAGACATTGCGTGGTCAGGCAGCTCACAGTCCTAGAGCGTGTG

GCACCCACGATCACAGGAAACCTGGAGAATCAGACGACAAGTATTGGGGAAAGC

ATCGAAGTCTCATGCACGGCATCTGGGAATCCCCCTCCACAGATCATGTGGTTTA

AAGATAATGAGACCCTTGTAGAAGACTCAGGCATTGTATTGAAGGATGGGAACC

GGAACCTCACTATCCGCAGAGTGAGGAAGGAGGACGAAGGCCTCTACACCTGCC
```

```
AGGCATGCAGTGTTCTTGGCTGTGCAAAAGTGGAGGCATTTTTCATAATAGAAGG

TGCCCAGGAAAAGACGAACTTGGAAATCATTATTCTAGTAGGCACGGCGGTGAT

TGCCATGTTCTTCTGGCTACTTCTTGTCATCATCCTACGGACCGTTAAGCGGGCCA

ATGGAGGGGAACTGAAGACAGGCTACTTGTCCATCGTCATGGATCCAGATGAAC

TCCCATTGGATGAACATTGTGAACGACTGCCTTATGATGCCAGCAAATGGGAATT

CCCCAGAGACCGGCTGAAGCTAGGTAAGCCTCTTGGCCGTGGTGCCTTTGGCCAA

GTGATTGAAGCAGATGCCTTTGGAATTGACAAGACAGCAACTTGCAGGACAGTA

GCAGTCAAAATGTTGAAAGAAGGAGCAACACACAGTGAGCATCGAGCTCTCATG

TCTGAACTCAAGATCCTCATTCATATTGGTCACCATCTCAATGTGGTCAACCTTCT

AGGTGCCTGTACCAAGCCAGGAGGGCCACTCATGGTGATTGTGGAATTCTGCAA

ATTTGGAAACCTGTCCACTTACCTGAGGAGCAAGAGAAATGAATTTGTCCCCTAC

AAGACCAAAGGGGCACGATTCCGTCAAGGGAAAGACTACGTTGGAGCAATCCCT

GTGGATCTGAAACGGCGCTTGGACAGCATCACCAGTAGCCAGAGCTCAGCCAGC

TCTGGATTTGTGGAGGAGAAGTCCCTCAGTGATGTAGAAGAAGAGGAAGCTCCT

GAAGATCTGTATAAGGACTTCCTGACCTTGGAGCATCTCATCTGTTACAGCTTCC

AAGTGGCTAAGGGCATGGAGTTCTTGGCATCGCGAAAGTGTATCCACAGGGACC

TGGCGGCACGAAATATCCTCTTATCGGAGAAGAACGTGGTTAAAATCTGTGACTT

TGGCTTGGCCCGGGATATTTATAAAGATCCAGATTATGTCAGAAAAGGAGATGCT

CGCCTCCCTTTGAAATGGATGGCCCCAGAAACAATTTTTGACAGAGTGTACACAA

TCCAGAGTGACGTCTGGTCTTTTGGTGTTTTGCTGTGGGAAATATTTTCCTTAGGT

GCTTCTCCATATCCTGGGGTAAAGATTGATGAAGAATTTTGTAGGCGATTGAAAG

AAGGAACTAGAATGAGGGCCCCTGATTATACTACACCAGAAATGTACCAGACCA

TGCTGGACTGCTGGCACGGGGAGCCCAGTCAGAGACCCACGTTTTCAGAGTTGGT

GGAACATTTGGGAAATCTCTTGCAAGCTAATGCTCAGCAGGATGGCAAAGACTA

CATTGTTCTTCCGATATCAGAGACTTTGAGCATGGAAGAGGATTCTGGACTCTCT

CTGCCTACCTCACCTGTTTCCTGTATGGAGGAGGAGGAAGTATGTGACCCCAAAT

TCCATTATGACAACACAGCAGGAATCAGTCAGTATCTGCAGAACAGTAAGCGAA

AGAGCCGGCCTGTGAGTGTAAAAACATTTGAAGATATCCCGTTAGAAGAACCAG

AAGTAAAAGTAATCCCAGATGACAACCAGACGGACAGTGGTATGGTTCTTGCCT

CAGAAGAGCTGAAAACTTTGGAAGACAGAACCAAATTATCTCCATCTTTTGGTGG

AATGGTGCCCAGCAAAAGCAGGGAGTCTGTGGCATCTGAAGGCTCAAACCAGAC

AAGCGGCTACCAGTCCGGATATCACTCCGATGACACAGACACCACCGTGTACTCC

AGTGAGGAAGCAGAACTTTTAAAGCTGATAGAGATTGGAGTGCAAACCGGTAGC

ACAGCCCAGATTCTCCAGCCTGACTCGGGGACCACACTGAGCTCTCCTCCTGTTT

AAAAGGAAGCATCCACACCCCCAACTCCTGGACATCACATGAGAGGTGCTGCTC

AGATTTTCAAGTGTTGTTCTTTCCACCAGCAGGAAGTAGCCGCATTTGATTTTCAT

TTCGACAACAGAAAAAGGACCTCGGACTGCAGGGAGCCAGTCTTCTAGGCATAT

CCTGGAAGAGGCTTGTGACCCAAGAATGTGTCTGTGTCTTCTCCCAGTGTTGACC

TGATCCTCTTTTTCATTCATTTAAAAAGCATTTATCATGCCCCCTGCTGCGGGTCT

CACCATGGGTTTAGAACAAAGACGTTCAAGAAATGGCCCCATCCTCAAAGAAGT
```

```
-continued
AGCAGTACCTGGGGAGCTGACACTTCTGTAAAACTAGAAGATAAACCAGGCAAT

GTAAGTGTTCGAGGTGTTGAAGATGGGAAGGATTTGCAGGGCTGAGTCTATCCA

AGAGGCTTTGTTTAGGACGTGGGTCCCAAGCCAAGCCTTAAGTGTGGAATTCGGA

TTGATAGAAAGGAAGACTAACGTTACCTTGCTTTGGAGAGTACTGGAGCCTGCA

AATGCATTGTGTTTGCTCTGGTGGAGGTGGGCATGGGGTCTGTTCTGAAATGTAA

AGGGTTCAGACGGGGTTTCTGGTTTTAGAAGGTTGCGTGTTCTTCGAGTTGGGCT

AAAGTAGAGTTCGTTGTGCTGTTTCTGACTCCTAATGAGAGTTCCTTCCAGACCG

TTACGTGTCTCCTGGCCAAGCCCCAGGAAGGAAATGATGCAGCTCTGGCTCCTTG

TCTCCCAGGCTGATCCTTTATTCAGAATACCACAAAGAAAGGACATTCAGCTCAA

GGCTCCCTGCCGTGTTGAAGAGTTCTGACTGCACAAACCAGCTTCTGGTTTCTTCT

GGAATGAATACCCTCATATCTGTCCTGATGTGATATGTCTGAGACTGAATGCGGG

AGGTTCAATGTGAAGCTGTGTGTGGTGTCAAAGTTTCAGGAAGGATTTTACCCTT

TTGTTCTTCCCCCTGTCCCCAACCCACTCTCACCCCGCAACCCATCAGTATTTTAG

TTATTTGGCCTCTACTCCAGTAAACCTGATTGGGTTTGTTCACTCTCTGAATGATT

ATTAGCCAGACTTCAAAATTATTTTATAGCCCAAATTATAACATCTATTGTATTAT

TTAGACTTTTAACATATAGAGCTATTTCTACTGATTTTTGCCCTTGTTCTGTCCTTT

TTTTCAAAAAGAAAATGTGTTTTTTGTTTGGTACCATAGTGTGAAATGCTGGGA

ACAATGACTATAAGACATGCTATGGCACATATATTTATAGTCTGTTTATGTAGAA

ACAAATGTAATATATTAAAGCCTTATATATAATGAACTTTGTACTATTCACATTTT

GTATCAGTATTATGTAGCATAACAAAGGTCATAATGCTTTCAGCAATTGATGTCA

TTTTATTAAAGAACATTGAAAAACTTGAAGGAATCCCTTTGCAAGGTTGCATTAC

TGTACCCATCATTTCTAAAATGGAAGAGGGGGTGGCTGGGCACAGTGGCCGACA

CCTAAAAACCCAGCACTTTGGGGGGCCAAGGTGGGAGGATCGCTTGAGCCCAGG

AGTTCAAGACCAGTCTGGCCAACATGGTCAGATTCCATCTCAAAGAAAAAAGGT

AAAAATAAAATAAAATGGAGAAGAAGGAATCAGA.
```

>gi|11321597|ref|NP_002244.1| vascular endothelial growth factor receptor 2 precursor [Homo sapiens]

(SEQ ID NO: 15)

```
MQSKVLLAVALWLCVETRAASVGLPSVSLDLPRLSIQKDILTIKANTTLQITCRGQRD

LDWLWPNNQSGSEQRVEVTECSDGLFCKTLTIPKVIGNDTGAYKCFYRETDLASVIY

VYVQDYRSPFIASVSDQHGVVYITENKNKTVVIPCLGSISNLNVSLCARYPEKRFVPD

GNRISWDSKKGFTIPSYMISYAGMVFCEAKINDESYQSIMYIVVVVGYRIYDVVLSPS

HGIELSVGEKLVLNCTARTELNVGIDFNWEYPSSKHQHKKLVNRDLKTQSGSEMKK

FLSTLTIDGVTRSDQGLYTCAASSGLMTKKNSTFVRVHEKPFVAFGSGMESLVEATV

GERVRIPAKYLGYPPPEIKWYKNGIPLESNHTIKAGHVLTIMEVSERDTGNYTVILTNP

ISKEKQSHVVSLVVYVPPQIGEKSLISPVDSYQYGTTQTLTCTVYAIPPPHHIHWYWQ

LEEECANEPSQAVSVTNPYPCEEWRSVEDFQGGNKIEVNKNQFALIEGKNKTVSTLVI

QAANVSALYKCEAVNKVGRGERVISFHVTRGPEITLQPDMQPTEQESVSLWCTADRS

TFENLTWYKLGPQPLPIHVGELPTPVCKNLDTLWKLNATMFSNSTNDILIMELKNAS

LQDQGDYVCLAQDRKTKKRHCVVRQLTVLERVAPTITGNLENQTTSIGESIEVSCTA

SGNPPPQIMWFKDNETLVEDSGIVLKDGNRNLTIRRVRKEDEGLYTCQACSVLGCAK

VEAFFIIEGAQEKTNLEIIILVGTAVIAMFFWLLLVIILRTVKRANGGELKTGYLSIVMD
```

```
-continued
PDELPLDEHCERLPYDASKWEFPRDRLKLGKPLGRGAFGQVIEADAFGIDKTATCRT

VAVKMLKEGATHSEHRALMSELKILIHIGHHLNVVNLLGACTKPGGPLMVIVEFCKF

GNLSTYLRSKRNEFVPYKTKGARFRQGKDYVGAIPVDLKRRLDSITSSQSSASSGFVE

EKSLSDVEEEEAPEDLYKDFLTLEHLICYSFQVAKGMEFLASRKCIHRDLAARNILLS

EKNVVKICDFGLARDIYKDPDYVRKGDARLPLKWMAPETIFDRVYTIQSDVWSFGV

LLWEIFSLGASPYPGVKIDEEFCRRLKEGTRMRAPDYTTPEMYQTMLDCWHGEPSQR

PTFSELVEHLGNLLQANAQQDGKDYIVLPISETLSMEEDSGLSLPTSPVSCMEEEEVC

DPKFHYDNTAGISQYLQNSKRKSRPVSVKTFEDIPLEEPEVKVIPDDNQTDSGMVLAS

EELKTLEDRTKLSPSFGGMVPSKSRESVASEGSNQTSGYQSGYHSDDTDTTVYSSEE

AELLKLIEIGVQTGSTAQILQPDSGTTLSSPPV.
```

Compounds

Macrocyclic compounds that modulate kinase activity are described herein. In certain embodiments, compounds of the present invention include inhibitors of Src, Akt3, MAPKAP2, AMPK, ERBB4, MK2, p38α, MKK6, or Pim1, and activators of VEGFR2. In certain embodiments, the compounds have an $IC_{50}$ of less than approximately 100 µM, e.g., less than approximately 10 µM, e.g., less than approximately 1 µM, e.g., less than approximately 0.1 µM, or e.g., less than approximately 0.01 µM. In some embodiments, the inventive compounds may be useful in the treatment of a variety of diseases as described in more detail elsewhere herein. In certain embodiments, the compounds are useful in the treatment of proliferative diseases, for example, in the treatment of certain cancers or benign neoplasms. In some embodiments, the inventive compounds are useful in the treatment of metabolic syndrome, diabetes and complications thereof, and insulin resistance. Certain compounds are also useful in treating neurological diseases, such as neurodegenerative diseases. In certain embodiments, the compounds are useful in treating autoimmune diseases or inflammatory diseases.

Certain compounds provided herein are useful for the inhibition of kinases, for example, Src kinases, that comprise a gatekeeper mutation, for example, a src kinase T338I or T341I mutation, or a kinase having a homologous gatekeeper mutation. The targeted inhibition of protein tyrosine kinases is an effective therapeutic regimen for the treatment of various neoplastic and malignant diseases, for example, chronic myeloid leukemia (CML) and several solid tumors. Inhibitors employed for such therapies include, for example, GLEEVEC™, IRESSA™, TARCEVA™, and IMATINIB™. Some small-molecule kinase inhibitors exploit a conserved threonine residue within the ATP binding site of the targeted kinase for binding specificity, which controls access of the inhibitors to a hydrophobic pocket deep in the active site that is not contacted by ATP. Accordingly, this threonine residue is often referred to as a gatekeeper residue. Substitution of the gatekeeper threonine residue with an amino acid comprising a bulky side chains can lead to resistance to ATP-competitive kinase inhibitors. See Azam et al., Nat Struct Mol. Biol. 2008 October; 15(10): 1109-1118, the entire contents of which are incorporated herein by reference. In some embodiments, a kinase inhibitor is provided that inhibits the activity of a kinase comprising a gatekeeper mutation, for example, of a src kinase comprising a T338I or T341I mutation. For example, macrocycle trans-A10-B1-C5-D6 inhibits both wild-type src kinase and src kinase comprising a gatekeeper mutation, e.g., a T338I or T341I mutation. Further exemplary macrocycle src kinase inhibitors that inhibit both wild-type src kinase and src kinase comprising a gatekeeper residue mutation include, but are not limited to macrocycles A10-Phe-C5-D6, [4-Me-Phe]-Phe-C5-D6, [4-Cl-Phe]-Phe-C5-D6, [4-Br-Phe]-Phe-C5-D6, [4-CF$_3$-Phe]-Phe-C5-D6, [4-CONH$_2$-Phe]-Phe-C5-D6, [4-CN-Phe]-Phe-C5-D6, A10-Phe-Cha-D6, [4-Me-Phe]-Phe-Cha-D6, [4-Cl-Phe]-Cha-D6, [4-Br-Phe]-Phe-Cha-D6, [4-CF$_3$-Phe]-Phe-Cha-D6, [4-CONH$_2$-Phe]-Phe-Cha-D6, [4-CN-Phe]-Phe-Cha-D6, A10-[4-F-Phe]-Cha-D6, [4-Me-Phe]-[4-F-Phe]-Cha-D6, [4-Cl-Phe]-[4-F-Phe]-Cha-D6, [4-Br-Phe]-[4-F-Phe]-Cha-D6, [4-CF$_3$-Phe]-[4-F-Phe]-Cha-D6, [4-CONH$_2$-Phe]-[4-F-Phe]-Cha-D6, and [4-CN-Phe]-[4-F-Phe]-Cha-D6, where Phe is phenylalanine, Cha is cyclohexylalanine, 4-Me-Phe is 4-methyl-phenylalanine, 4-F-Phe is 4-fluoro-phenylalanine, etc. (A-B-C-D nomenclature as illustrated in e.g., FIGS. 5 and 19). In some embodiments, the exemplary macrocycle src kinase inhibitors that inhibit both wild-type src kinase and src kinase comprising a gatekeeper residue mutation are in trans-configuration.

In some embodiments, a macrocyclic kinase-modulating compound as described herein is provided, that comprises a tag. In some embodiments, the tag is a fluorescent tag, for example, a fluorescent molecule, or moiety, that is conjugated, for example, covalently via a linker, to the macrocycle. In some embodiments, the fluorescent tag is a fluorescent protein tag, for example, a GFP tag, a YFP tag, an RFP tag, a BFP tag, or a tag comprising an enhanced fluorescent protein, such as eGFP. Other fluorescent proteins and protein tags are well known to those of skill in the art. In some embodiments, the tag is a cyane dye, or CyDye tag, for example, a Cy3 or C5 tag. In some embodiments, the tag is a fluorescein tag, for example, a fluorescein tag conjugated to the macrocycle structure via a linker as described in FIG. 21A. Additional suitable fluorescent tags are known to those of skill in the art and the invention is not limited in this respect. In some embodiments, the tag comprises a binding agent. In some embodiments, the binding agent is an antibody or an antigen-binding antibody fragment, a nanobody, an ScFv, an aptamer, or an adnectin. Other binding agents are known to those of skill in the art and the invention is not limited in this respect. In some embodiments, the binding agent specifically binds an antigen, for example, an antigen immobilized on a solid surface, or a cellular antigen, e.g., a cell-surface antigen. In some embodiments, the tag comprising a binding agent specifically binds to a particular cell or cell type, for example, to a tumor cell. In some embodiments, the binding agent binds to a particular cell-surface antigen of a specific cell type, for example, a tumor cell type. In some embodiments, such binding-agent-tagged macrocycles target a specific site characterised by expressing the antigen bound by the binding agent, for example, after administration to a subject harboring such a target site, e.g., a solid tumor, such as a tumor expressing an aberrant level of src kinase, which allows for the creation of high concentrations of the macrocycle at the target site. Antigens useful for targeting specific cells, cell types, or tissues, for example, malignant cells, cell types, or tissues, are well known to those of skill in the art and the invention is not limited in this respect.

In some embodiments, a compound that binds and modulates the activity of a kinase, as provided herein, is of Formula (I):

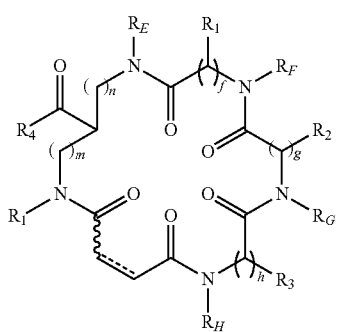

(I)

or a pharmaceutically acceptable salt thereof;
or a pharmaceutically acceptable salt thereof;
wherein:
n is 0 or an integer between 1-4, inclusive;
m is 0 an integer between 1-4, inclusive;
f is an integer between 1-3, inclusive;
g is an integer between 1-3, inclusive;
h is an integer between 1-3, inclusive;
⋯ is a single or double C—C bond, wherein when ⋯ is a double C—C bond, then ∿ indicates that the adjacent C—C double bond is in a cis or trans configuration;

each instance of $R_1$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_A$; —$N(R_A)_2$; —$SR_A$; =O; —CN; —$NO_2$; —SCN; —$SOR_A$; or —$SO_2R_A$; wherein each occurrence of $R_A$ is independently hydrogen; a protecting group; substituted or unsubstituted aliphatic; substituted or unsubstituted heteroaliphatic; acyl; substituted or unsubstituted aryl; or substituted or unsubstituted heteroaryl;

each instance of $R_2$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_B$; —$N(R_B)_2$; —$SR_B$; =O; —CN; —$NO_2$; —SCN; —$SOR_B$; or —$SO_2R_B$; wherein each occurrence of $R_B$ independently hydrogen; a protecting group; substituted or unsubstituted aliphatic; substituted or unsubstituted heteroaliphatic; acyl; substituted or unsubstituted aryl; or substituted or unsubstituted heteroaryl;

each instance of $R_3$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_C$; —$N(R_C)_2$; —$SR_C$; =O; —CN; —$NO_2$; —SCN; —$SOR_C$; or —$SO_2R_C$; wherein each occurrence of $R_C$ is independently hydrogen; a protecting group; substituted or unsubstituted aliphatic; substituted or unsubstituted heteroaliphatic; acyl; substituted or unsubstituted aryl; or substituted or unsubstituted heteroaryl;

$R_4$ is substituted or unsubstituted aliphatic; substituted or unsubstituted heteroaliphatic; substituted or unsubstituted aryl; substituted or unsubstituted heteroaryl; —$N(R_D)_2$; —$OR_D$; or —$SR_D$; wherein each occurrence of $R_D$ is independently hydrogen; a protecting group; substituted or unsubstituted aliphatic; substituted or unsubstituted heteroaliphatic; acyl; substituted or unsubstituted aryl; or substituted or unsubstituted heteroaryl; or two $R_D$ groups are joined to form a substituted or unsubstituted heterocyclic group; optionally wherein $R^4$ further comprises a label, resin, or therapeutic agent attached thereto; and each instance of $R_E$, $R_F$, $R_G$, $R_H$, and $R_I$ is independently hydrogen; acyl; a nitrogen protecting group; substituted or unsubstituted aliphatic; substituted or unsubstituted heteroaliphatic; substituted or unsubstituted aryl; substituted or unsubstituted heteroaryl; substitute or unsubstituted hydroxyl; substituted or unsubstituted thiol; substituted or unsubstituted amino; or halogen; optionally wherein an $R_1$ group and $R^F$ are joined to form a substituted or unsubstituted heterocyclic ring; an $R_2$ group and $R^G$ are joined to form a substituted or unsubstituted heterocyclic ring; and/or an $R_3$ group and $R^H$ are joined to form a substituted or unsubstituted heterocyclic ring.

Embodiments of $R_1$

As generally defined above, each instance of $R_1$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_A$; —$N(R_A)_2$; —$SR_A$; =O; —CN; —$NO_2$; —SCN; —$SOR_A$; or —$SO_2R_A$; wherein each occurrence of $R_A$ is independently hydrogen; a protecting group; substituted or unsubstituted aliphatic; substituted or unsubstituted heteroaliphatic; acyl; substituted or unsubstituted aryl; or substituted or unsubstituted heteroaryl.

In certain embodiments, $R_1$ is hydrogen. In certain embodiments, $R_1$ is halogen, i.e., —F, —Cl, —Br, or —I. In certain embodiments, $R_1$ is —$OR_A$. In certain embodiments, $R_1$ is —$N(R_A)_2$. In certain embodiments, $R_1$ is —$SR_A$. In certain embodiments, $R_1$ is =O. In certain embodiments, $R_1$ is —CN. In certain embodiments, $R_1$ is —$NO_2$. In certain embodiments, $R_1$ is —SCN. In certain embodiments, $R_1$ is —$SOR_A$. In certain embodiments, $R_1$ is —$SO_2R_A$.

In certain embodiments, $R_1$ is acyl. For example, in certain embodiments, $R^1$ is acyl selected from the group consisting of —C(=O)$R^{45}$, —C(=O)O$R^{45}$, —C(=O)S$R^{45}$, —C(=O)N($R^{46}$)$_2$, —C(=N$R^{46}$)$R^{45}$, —C(=N$R^{46}$)O$R^{45}$, —C(=N$R^{46}$)S$R^{45}$, —C(=N$R^{46}$)N($R^{46}$)$_2$, —C(=S)$R^{45}$, —C(=S)O$R^{45}$, —C(=S)S$R^{45}$, and —C(=S)N($R^{46}$)$_2$, wherein each occurrence of $R^{45}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{46}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{46}$ groups are joined to form an substituted or unsubstituted heterocyclic ring.

In certain embodiments, $R_1$ is substituted or unsubstituted aryl, e.g., phenyl, napthyl. In certain embodiments, $R_1$ is substituted or unsubstituted phenyl. In certain embodiments, $R_1$ is substituted phenyl, e.g., a monosubstituted, disubstituted, or trisubstituted phenyl.

In certain embodiments, $R_1$ is substituted or unsubstituted heteroaryl, e.g., a substituted or unsubstituted 5- to 6-membered heteroaryl. In certain embodiments, $R_1$ is a substituted or unsubstituted 5-membered heteroaryl, e.g., pyrrolyl, furanyl, thiophenyl, imidazolyl, pyrazolyl, oxazolyl, isoxazolyl, thiazolyl, isothiazolyl, triazolyl, oxadiazolyl, thiadiazolyl, or tetrazolyl. In certain embodiments, $R_1$ is a substituted or unsubstituted 6-membered heteroaryl, e.g., pyridinyl, pyridazinyl, pyrimidinyl, pyrazinyl, triazinyl, or tetrazinyl.

In certain embodiments, $R_1$ is substituted or unsubstituted aliphatic. In certain embodiments, $R_1$ is a substituted or unsubstituted aliphatic group comprising 1 to 10 carbon atoms ("$C_{1-10}$aliphatic"). In certain embodiments, $R_1$ is substituted or unsubstituted aliphatic group comprising 1 to 8 carbon atoms ("$C_{1-8}$aliphatic"). In certain embodiments, $R_1$ is a substituted or unsubstituted aliphatic group comprising 1 to 6 carbon atoms ("$C_{1-6}$aliphatic"). In certain embodiments, $R_1$ is a substituted or unsubstituted aliphatic group comprising 1 to 4 carbon atoms ("$C_{1-4}$aliphatic"). In certain embodiments, $R_1$ is a substituted or unsubstituted aliphatic group comprising 1 to 3 carbon atoms ("$C_{1-3}$aliphatic"). In certain embodiments, $R_1$ is a substituted or unsubstituted aliphatic group comprising 1 carbon atom ("$C_1$aliphatic"). In certain embodiments, $R_1$ is a substituted or unsubstituted aliphatic group comprising 2 carbon atoms ("$C_2$aliphatic"). In certain embodiments, $R_1$ is a substituted or unsubstituted aliphatic group comprising 3 carbon atoms ("$C_3$aliphatic"). In any of the above embodiments, $R_1$ is an acyclic aliphatic group. In any of the above embodiments, $R_1$ is an acyclic and substituted aliphatic group. In any of the above embodiments, the aliphatic group is an alkyl, alkenyl, or alkynyl group.

In certain embodiments, $R_1$ is substituted or unsubstituted alkyl. In certain embodiments, $R_1$ is unsubstituted alkyl. In certain embodiments, $R_1$ is substituted alkyl. In certain embodiments, $R_1$ is substituted $C_{1-10}$alkyl. In certain embodiments, $R_1$ is substituted $C_{1-8}$alkyl. In certain embodiments, $R_1$ is substituted $C_{1-6}$alkyl. In certain embodiments, $R_1$ is substituted $C_{1-5}$alkyl. In certain embodiments, $R_1$ is substituted $C_{1-4}$alkyl. In certain embodiments, $R_1$ is substituted $C_{1-3}$alkyl. In certain embodiments, $R_1$ is substituted $C_{1-2}$alkyl. In certain embodiments, $R_1$ is substituted $C_{2-4}$alkyl. In certain embodiments, $R_1$ is substituted $C_1$alkyl. In certain embodiments, $R_1$ is substituted $C_2$alkyl. In certain embodiments, $R_1$ is substituted $C_3$alkyl. In certain embodiments, $R_1$ is substituted $C_4$alkyl.

In certain embodiments, $R_1$ is substituted or unsubstituted alkenyl. In certain embodiments, $R_1$ is unsubstituted alkenyl. In certain embodiments, $R_1$ is substituted alkenyl. In certain embodiments, $R_1$ is substituted $C_{2-10}$alkenyl. In certain embodiments, $R_1$ is substituted $C_{2-8}$alkenyl. In certain embodiments, $R_1$ is substituted $C_{2-6}$alkenyl. In certain embodiments, $R_1$ is substituted $C_{2-5}$alkenyl. In certain embodiments, $R_1$ is substituted $C_{2-4}$alkenyl. In certain embodiments, $R_1$ is substituted $C_{2-3}$alkenyl. In certain embodiments, $R_1$ is substituted $C_1$alkenyl. In certain embodiments, $R_1$ is substituted $C_2$alkenyl. In certain embodiments, $R_1$ is substituted $C_3$alkenyl. In certain embodiments, $R_1$ is substituted $C_4$alkenyl.

In certain embodiments, $R_1$ is substituted or unsubstituted heteroaliphatic. In certain embodiments, $R_1$ is substituted or unsubstituted heteroaliphatic group comprising 1 to 10 carbon atoms and 1 to 3 heteroatoms independently selected from oxygen, nitrogen, and sulfur ("$C_{1-10}$heteroaliphatic"). In certain embodiments, the heteroaliphatic group comprises 1 heteroatom selected from oxygen, nitrogen, and sulfur. In certain embodiments, the heteroaliphatic group comprises 2 heteroatoms independently selected from oxygen, nitrogen, and sulfur. In certain embodiments, the heteroaliphatic group comprises 3 heteroatoms independently selected from oxygen, nitrogen, and sulfur. In certain embodiments, $R_1$ is a substituted or unsubstituted heteroaliphatic group comprising 1 to 8 carbon atoms and 1-3 heteroatoms selected from oxygen, nitrogen, and sulfur ("$C_{1-8}$heteroaliphatic"). In certain embodiments, $R_1$ is a substituted or unsubstituted heteroaliphatic group comprising 1 to 6 carbon atoms and 1-2 heteroatoms selected from oxygen, nitrogen, and sulfur ("$C_{1-6}$heteroaliphatic"). In certain embodiments, $R_1$ is a substituted or unsubstituted heteroaliphatic group comprising 1 to 4 carbon atoms and 1-2 heteroatoms selected from oxygen, nitrogen, and sulfur ("$C_{1-4}$heteroaliphatic"). In certain embodiments, $R_1$ is a substituted or unsubstituted heteroaliphatic group comprising 1 to 3 carbon atoms and 1 heteroatom selected from oxygen, nitrogen, and sulfur ("$C_{1-3}$heteroaliphatic"). In certain embodiments, $R_1$ is a substituted or unsubstituted heteroaliphatic group comprising 1 carbon atom and 1 heteroatom selected from oxygen, nitrogen, and sulfur ("$C_1$heteroaliphatic"). In certain embodiments, $R_1$ is a substituted or unsubstituted heteroaliphatic group comprising 2 carbon atoms and 1 heteroatom selected from oxygen, nitrogen, and sulfur ("$C_2$heteroaliphatic"). In certain embodiments, $R_1$ is a substituted or unsubstituted heteroaliphatic group comprising 3 carbon atoms and 1 heteroatom selected from oxygen, nitrogen, and sulfur ("$C_3$heteroaliphatic"). In any of the above embodiments, $R_1$ is an acyclic heteroaliphatic group. In any of the above embodiments, $R_1$ is an acyclic and substituted heteroaliphatic group. In any of the above embodiments, the heteroaliphatic group is an heteroalkyl, heteroalkenyl, or heteroalkynyl group.

In certain embodiments, $R_1$ is substituted or unsubstituted heteroalkyl comprising 10 carbon atoms and 1-3 heteroatoms selected from oxygen, nitrogen, and sulfur ("substituted $C_{1-10}$heteroalkyl"). In certain embodiments, the heteroalkyl group comprises 1 heteroatom selected from oxygen, nitrogen, and sulfur. In certain embodiments, the heteroalkyl group comprises 2 heteroatoms independently selected from oxygen, nitrogen, and sulfur. In certain embodiments, the heteroalkyl group comprises 3 heteroatoms independently selected from oxygen, nitrogen, and sulfur. In certain embodiments, $R_1$ is a substituted heteroalkyl comprising 1-8 carbon atoms and 1-3 heteroatoms selected from oxygen, nitrogen, and sulfur ("substituted $C_{1-6}$heteroalkyl"). In certain embodiments, $R_1$ is a substituted heteroalkyl comprising 1-6 carbon atoms and 1-2 heteroatoms selected from oxygen, nitrogen, and sulfur ("substituted $C_{1-6}$heteroalkyl"). In certain embodiments, $R_1$ is a substituted heteroalkyl comprising 1-4 carbon atoms and 1-2 heteroatoms selected from oxygen, nitrogen, and sulfur ("substituted $C_{1-4}$heteroalkyl"). In certain embodiments, $R_1$ is a substituted heteroalkyl comprising 1-3 carbon atoms and 1 heteroatom selected from oxygen, nitrogen, and sulfur ("substituted $C_{1-3}$heteroalkyl"). In certain embodiments, $R_1$ is a substituted heteroalkyl comprising 1-2 carbon atoms and 1 heteroatom selected from oxygen, nitrogen, and sulfur ("substituted $C_{1-2}$heteroalkyl"). In certain embodiments, $R_1$ is a substituted heteroalkyl comprising 1 carbon atom and 1 heteroatom selected from oxygen, nitrogen, and sulfur ("substituted $C_1$heteroalkyl"). In certain embodiments, $R_1$ is a substituted heteroalkyl comprising 2 carbon atoms and 1 heteroatom selected from oxygen, nitrogen, and sulfur ("substituted $C_2$heteroalkyl"). In certain embodiments, $R_1$ is a substituted heteroalkyl comprising 3 carbon atoms and 1 heteroatom selected from oxygen, nitrogen, and sulfur ("substituted $C_3$heteroalkyl"). In certain embodiments, $R_1$ is a substituted heteroalkyl comprising 4 carbon atoms and 1-2 heteroatoms selected from oxygen, nitrogen, and sulfur ("substituted $C_4$heteroalkyl").

As generally understood from the above, in certain embodiments, $R_1$ is a group selected from aliphatic, heteroaliphatic, aryl, or heteroaryl which may be unsubstituted or substituted with one or more substituents. Exemplary $R_1$ group substituents, collectively referred to herein as "$R^4$," include, but are not limited to, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{41}$, $-N(R^{42})_2$, $-SR^{41}$, $-C(=O)R^{41}$, $-C(=O)OR^{41}$, $-C(=O)SR^{41}$, $-C(=O)N(R^{42})_2$, $-OC(=O)R^{41}$, $-OC(=O)OR^{41}$, $-OC(=O)SR^{41}$, $-OC(=O)N(R^{42})_2$, $-NR^{42}C(=O)R^{42}$, $-NR^{42}C(=O)OR^{41}$, $-NR^{42}C(=O)SR^{41}$, $-NR^{42}C(=O)N(R^{42})_2$, $-SC(=O)R^{41}$, $-SC(=O)OR^{41}$, $-SC(=O)SR^{41}$, $-SC(=O)N(R^{42})_2$, $-C(=NR^{42})R^{41}$, $-C(=NR^{42})OR^{41}$, $-C(=NR^{42})SR^{41}$, $-C(=NR^{42})N(R^{42})_2$, $-OC(=NR^{42})R^{41}$, $-OC(=NR^{42})OR^{41}$, $-OC(=NR^{42})SR^{41}$, $-OC(=NR^{42})N(R^{42})_2$, $-NR^{42}C(=NR^{42})R^{42}$, $-NR^{42}C(=NR^{42})OR^{41}$, $-NR^{42}C(=NR^{42})SR^{41}$, $-NR^{42}C(=NR^{42})N(R)_2$, $-SC(=NR^{42})R^{41}$, $-SC(=NR^{42})OR^{41}$, $-SC(=NR^{42})SR^{41}$, $-SC(=NR^{42})N(R^{42})_2$, $-C(=S)R^{41}$, $-C(=S)OR^{41}$, $-C(=S)SR^{41}$, $-C(=S)N(R^{42})_2$, $-OC(=S)R^{41}$, $-OC(=S)OR^{41}$, $-OC(=S)SR^{41}$, $-OC(=S)N(R^{42})_2$, $-NR^{42}C(=S)R^{42}$, $-NR^{42}C(=S)OR^{41}$, $-NR^{42}C(=S)SR^{41}$, $-NR^{42}C(=S)N(R^{42})_2$, $-SC(=S)R^{41}$, $-SC(=S)OR^{41}$, $-SC(=S)SR^{41}$, $-SC(=S)N(R^{42})_2$, $-S(=O)R^{41}$, $-SO_2R^{41}$, $-NR^{42}SO_2R^{41}$, $-SO_2N(R^{42})_2$, $-N_3$, $-CN$, $-SCN$, and $-NO_2$, wherein each occurrence of $R^{41}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{42}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{42}$ groups are joined to form an substituted or unsubstituted heterocyclic ring.

In certain embodiments, $R_1$ is aliphatic, as defined above and herein, substituted by one or more $R^4$ substituents, as provided above, e.g., 1, 2, 3, or 4 substituents. In certain embodiments, $R_1$ is alkyl, as defined above and herein, substituted by one or more $R^4$ substituents, as provided above, e.g., 1, 2, 3, or 4 substituents. In certain embodiments, $R_1$ is a $C_{1-4}$alkyl substituted by one or more $R^4$ substituents, as provided above, e.g., 1, 2, 3, or 4 substituents. In certain embodiments, $R_1$ is a $C_{2-4}$alkenyl substituted by one or more $R^4$ substituents, as provided above, e.g., 1, 2, 3, or 4 substituents.

For example, in certain embodiments, $R_1$ is aliphatic substituted by an optionally substituted aryl or optionally substituted heteroaryl group, e.g., an optionally substituted phenyl group or optionally substituted 5- to 6-membered heteroaryl group.

In certain embodiments, $R_1$ is aliphatic substituted by an optionally substituted aryl group ("optionally substituted arylaliphatic"). In certain embodiments, the aryl group is an optionally substituted phenyl ("optionally substituted phenylaliphatic"). In certain embodiments, the aryl group is unsubstituted. However, in certain embodiments, the aryl group is substituted. For example, in certain embodiments, the aryl group is a monosubstituted phenyl ring, e.g., substituted at the ortho, meta, or para position of the phenyl ring relative to the point of attachment. In certain embodiments, the aryl group is a disubstituted phenyl ring, e.g., substituted at the 1,2-, the 1,3-, the 1,4-, the 2,3-, the 3,4-, or the 2,4-positions of the phenyl ring relative to the point of attachment. In certain embodiments, the aryl group is a trisubstituted phenyl ring, e.g., substituted at the 1,2,3-, the 1,2,4-, or the 2,3,4-, positions of the phenyl ring relative to the point of attachment. In certain embodiments, the aryl group is a tetrasubstituted phenyl ring. In any of the above embodiments, the aliphatic group is selected from alkyl, alkenyl, or alkynyl. In certain embodiments, the aliphatic group is alkyl. For example, in certain embodiments, $R_1$ is alkyl substituted by an optionally substituted aryl group ("optionally substituted arylalkyl"), e.g., an optionally substituted phenyl group ("optionally substituted phenylalkyl"). In certain embodiments, $R_1$ is a $C_{1-4}$alkyl substituted by an optionally substituted aryl group, e.g., an optionally substituted phenyl group. In certain embodiments, $R_1$ is a $C_1$alkyl substituted by an optionally substituted aryl group, e.g., an optionally substituted phenyl group In certain embodiments, the aliphatic group is alkenyl. For example, in certain embodiments, $R_1$ is a $C_{2-4}$alkenyl substituted by an optionally substituted aryl group ("optionally substituted arylalkenyl"), e.g., an optionally substituted phenyl group ("optionally substituted phenylalkenyl"). In certain embodiments, $R_1$ is a $C_2$alkenyl substituted by an optionally substituted aryl group, e.g., an optionally substituted phenyl group. In certain embodiments, $R_1$ is a $C_3$alkenyl substituted by an optionally substituted aryl group, e.g., an optionally substituted phenyl group.

In certain embodiments, $R_1$ is aliphatic substituted by an optionally substituted 5- to 6-membered heteroaryl group, e.g., a substituted or unsubstituted 5-membered heteroaryl, e.g., pyrrolyl, furanyl, thiophenyl, imidazolyl, pyrazolyl, oxazolyl, isoxazolyl, thiazolyl, isothiazolyl, triazolyl, oxadiazolyl, thiadiazolyl, or tetrazolyl, or a substituted or unsubstituted 6-membered heteroaryl, e.g., pyridinyl, pyridazinyl, pyrimidinyl, pyrazinyl, triazinyl, or tetrazinyl. In certain embodiments, the heteroaryl group is a substituted 5- to 6-membered heteroaryl ("substituted 5- to 6-membered heteroarylaliphatic"). In any of the above embodiments, the aliphatic group is selected from alkyl, alkenyl, or alkynyl. In certain embodiments, the aliphatic group is alkyl. For example, in certain embodiments, $R_1$ is alkyl substituted by a substituted by an optionally substituted heteroaryl group ("optionally substituted heteroarylalkyl"), e.g., an optionally substituted 5- to 6-membered heteroaryl group ("optionally substituted 5- to 6-membered heteroarylalkyl"). In certain embodiments, $R_1$ is a $C_{1-4}$alkyl substituted by an optionally substituted heteroaryl group, e.g., an optionally substituted 5- to 6-membered heteroaryl group. In certain embodiments, $R_1$ is a $C_1$alkyl substituted by an optionally substituted heteroaryl group, e.g., an optionally substituted 5- to 6-membered heteroaryl group. In certain embodiments, $R_1$ is a $C_{2-4}$alkenyl substituted by an optionally substituted heteroaryl group, e.g., an optionally substituted 5- to 6-membered heteroaryl group. In certain embodiments, $R_1$ is a $C_2$alkenyl substituted by an optionally substituted heteroaryl group, e.g., an optionally substituted 5- to 6-membered heteroaryl group. In certain embodiments, $R_1$ is a $C_3$alkenyl substituted by an optionally substituted heteroaryl group, e.g., an optionally substituted 5- to 6-membered heteroaryl group. In any of the above embodiments, the heteroaryl group is substituted. However, in any of the above embodiments, the heteroaryl group is unsubstituted.

In certain embodiments, $R_1$ is aliphatic substituted by a substituted or unsubstituted carbocyclyl ("optionally substituted carbocyclyl") or a substituted or unsubstituted heterocyclyl ("optionally substituted heterocyclyl"), e.g., optionally substituted $C_{3-8}$carbocyclyl or optionally substituted 5- to 8-membered heterocyclyl.

For example, in certain embodiments, $R_1$ is aliphatic substituted by an optionally substituted 5- to 8-membered heterocyclyl comprising 1 to 3 heteroatoms selected from oxygen, nitrogen, and sulfur. In certain embodiments, $R_1$ is aliphatic substituted by an optionally substituted 8-membered heterocyclyl comprising 1 to 3 heteroatoms selected from oxygen, nitrogen, and sulfur, e.g., azocanyl, oxecanyl, or thiocanyl. In certain embodiments, $R_1$ is aliphatic substituted by an optionally substituted 7-membered heterocyclyl comprising 1 to 3 heteroatoms selected from oxygen, nitrogen, and sulfur, e.g., azepanyl, oxepanyl, or thiepanyl. In certain embodiments, $R_1$ is aliphatic substituted by an optionally substituted 6-membered heterocyclyl comprising 1 to 3 heteroatoms selected from oxygen, nitrogen, and sulfur, e.g., piperazinyl, morpholinyl, dithianyl, dioxanyl, triazinanyl, and 6,6-bicycles such as tetrahydroquinolinyl and tetrahydroisoquinolinyl. In certain embodiments, $R_1$ is aliphatic substituted by an optionally substituted 5-membered heterocyclyl comprising 1 to 3 heteroatoms selected from oxygen, nitrogen, and sulfur, e.g., tetrahydrofuranyl, dihydrofuranyl, tetrahydrothiophenyl, dihydrothiophenyl, pyrrolidinyl, dihydropyrrolyl, pyrrolyl-2,5-dione, dioxolanyl, oxasulfuranyl, disulfuranyl, oxazolidin-2-one, triazolinyl, oxadiazolinyl, thiadiazolinyl, and 5,6-bicycles such as indolinyl, isoindolinyl, dihydrobenzofuranyl, dihydrobenzothienyl, and benzoxazolinonyl. In any of the above embodiments, the heterocyclyl contains 1 heteroatom. In any of the above embodiments, the heterocyclyl contains 2 heteroatoms. In any of the above embodiments, the heterocyclyl contains 3 heteroatoms. In any of the above embodiments, the aliphatic group is selected from alkyl, alkenyl, or alkynyl. In certain embodiments, the aliphatic group is alkyl. For example, in certain embodiments, $R_1$ is alkyl substituted by a substituted by an optionally substituted heterocyclyl group ("optionally substituted heterocyclylalkyl"), e.g., an optionally substituted 5- to 8-membered heterocyclyl comprising 1 to 3 heteroatoms selected from oxygen, nitrogen, and sulfur. In certain embodiments, $R_1$ is a $C_{1-4}$alkyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_1$ is a $C_1$alkyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_1$ is a $C_{2-4}$alkenyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_1$ is a $C_2$alkenyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_1$ is a $C_3$alkenyl substituted by an optionally substituted heterocyclyl group, e.g., an optionally substituted 5- to 8-membered heterocyclyl comprising 1 to 3 heteroatoms selected from oxygen, nitrogen, and sulfur. In any of the above embodiments, the heterocyclyl group is not substituted. However, in any of the above embodiments, the heterocyclyl group is substituted.

In certain embodiments, $R_1$ is aliphatic substituted by an optionally substituted $C_{3-7}$carbocyclyl. In certain embodiments, $R_1$ is aliphatic substituted by an optionally substituted $C_{3-6}$carbocyclyl. In certain embodiments, $R_1$ is aliphatic substituted by an optionally substituted $C_{3-5}$carbocyclyl. In certain embodiments, $R_1$ is aliphatic substituted by an optionally substituted $C_{3-4}$carbocyclyl. In certain embodiments, $R_1$ is aliphatic substituted by an optionally substituted $C_{4-6}$carbocyclyl. In certain embodiments, $R_1$ is aliphatic substituted by an optionally substituted $C_3$carbocyclyl, e.g., optionally substituted cyclopropyl or optionally substituted cyclopropenyl. In certain embodiments, $R_1$ is aliphatic substituted by an optionally substituted $C_4$carbocyclyl, e.g., optionally substituted cyclobutyl or optionally substituted cyclobutenyl. In certain embodiments, $R_1$ is aliphatic substituted by an optionally substituted $C_5$carbocyclyl, e.g., optionally substituted cyclopentyl or optionally substituted cyclopentenyl. In certain embodiments, $R_1$ is aliphatic substituted by an optionally substituted $C_6$carbocyclyl, e.g., optionally substituted cyclohexyl, optionally substituted cyclohexenyl, or optionally substituted cyclohexadienyl. In certain embodiments, $R_1$ is aliphatic substituted by an optionally substituted $C_7$carbocyclyl, e.g., optionally substituted cycloheptyl, optionally substituted cycloheptenyl, optionally substituted cycloheptadienyl, or optionally substituted cycloheptatrienyl. In any of the above embodiments, the aliphatic group is selected from alkyl, alkenyl, or alkynyl. In certain embodiments, the aliphatic group is alkyl. For example, in certain embodiments, $R_1$ is alkyl substituted by a substituted by an optionally substituted carbocyclyl group ("optionally substituted carbocyclylalkyl"), e.g., an optionally substituted $C_{3-7}$carbocyclyl group. In certain embodiments, $R_1$ is a $C_{1-4}$alkyl substituted by an optionally substituted carbocyclyl group, e.g., an optionally substituted $C_{3-7}$-carbocyclyl. In certain embodiments, $R_1$ is a $C_1$alkyl substituted by an optionally substituted carbocyclyl group, e.g., an optionally substituted $C_{3-7}$carbocyclyl. In certain embodiments, $R_1$ is a $C_{2-4}$alkenyl substituted by an optionally substituted carbocyclyl group, e.g., an optionally substituted $C_{3-7}$carbocyclyl. In certain embodiments, $R_1$ is a $C_2$alkenyl substituted by an optionally substituted carbocyclyl group, e.g., an optionally substituted $C_{3-7}$carbocyclyl. In certain embodiments, $R_1$ is a $C_3$alkenyl substituted by an optionally substituted carbocyclyl group, e.g., an optionally substituted $C_{3-7}$carbocyclyl. In any of the above embodiments, the carbocyclyl group is not substituted. However, in any of the above embodiments, the carbocyclyl group is substituted.

As understood from the above, the carbocyclyl, heterocyclyl, aryl, and/or heteroaryl substituents present on the $R_1$ aliphatic group may be unsubstituted or substituted with one or more substituents. Such substituents, collectively referred to herein as "$R^{AA}$" include, but are not limited to, halogen, substituted or unsubstituted alkyl (e.g., perhaloalkyl), substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A3}$, —$N(R^{A4})_2$, —$SR^{A3}$, —$C(=O)R^{A3}$, —$C(=O)OR^{A3}$, —$C(=O)SR^{A3}$, —$C(=O)N(R^{A4})_2$, —$OC(=O)R^{A3}$, —$OC(=O)OR^{A3}$, —$OC(=O)SR^{A3}$, —$OC(=O)N(R^{A4})_2$, —$NR^{A4}C(=O)R^{A4}$, —$NR^{A4}C(=O)OR^{A3}$, —$NR^{A4}C(=O)SR^{A3}$, —$NR^{A4}C(=O)N(R^{A4})_2$, —$SC(=O)R^{A3}$, —$SC(=O)OR^{A3}$, —$SC(=O)SR^{A3}$, —$SC(=O)N(R^{A4})_2$, —$C(=NR^{A4})R^{A3}$, —$C(=NR^{A4})OR^{A3}$, —$C(=NR^{A4})SR^{A3}$, —$C(=NR^{A4})$ N(R$^{A4}$)$_2$, —OC(=NR$^{A4}$)R$^{A3}$, —OC(=NR$^{A4}$)OR$^{A3}$, —OC(=NR$^{A4}$)SR$^{A3}$, —OC(=NR$^{A4}$)N(R$^{A4}$)$_2$, —NR$^{A4}$C(=NR$^{A4}$)R$^{A2}$, —NR$^{A4}$C(=NR$^{A4}$)OR$^{A3}$, —NR$^{A4}$C(=NR$^{A4}$)SR$^{A3}$, —NR$^{A4}$C(=NR$^{A4}$)N(R$^{A4}$)$_2$, —SC(=NR$^{A4}$)R$^{A3}$, —SC(=NR$^{A4}$)OR$^{A3}$, —SC(=NR$^{A4}$)SR$^{A3}$, —SC(=NR$^{A4}$)N(R$^{A4}$)$_2$, —C(=S)R$^{A3}$, —C(=S)OR$^{A3}$, —C(=S)SR$^{A3}$, —C(=S)N(R$^{A4}$)$_2$, —OC(=S)R$^{A3}$, —OC(=S)OR$^{A3}$, —OC(=S)SR$^{A3}$, —OC(=S)N(R$^{A4}$)$_2$, —NR$^{A4}$C(=S)R$^{A4}$, —NR$^{A4}$C(=S)OR$^{A3}$, —NR$^{A4}$C(=S)SR$^{A3}$, —NR$^{A4}$C(=S)N(R$^{A4}$)$_2$, —SC(=S)R$^{A3}$, —SC(=S)OR$^{A3}$, —SC(=S)SR$^{A3}$, —SC(=S)N(R$^{A4}$)$_2$, —S(=O)R$^{A3}$, —SO$_2$R$^{A3}$, —NR$^{A4}$SO$_2$R$^{A3}$, —SO$_2$N(R$^{A4}$)$_2$, —N$_3$, —CN, —SCN, and —NO$_2$, wherein each occurrence of R$^{A3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of R$^{A4}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two R$^{A4}$ groups are joined to form an substituted or unsubstituted heterocyclic ring.

In certain embodiments, at least one R$^{AA}$ substituent (e.g., 1, 2, 3, or 4 R$^{AA}$ substituents) is an electron-withdrawing group, e.g., a substituent which pulls electron density away from the parent molecule (e.g., a ring system) and/or stabilizes anions or electron rich structures. Exemplary electron-withdrawing substituents include, but are not limited to, halogen, perhaloalkyl, —C(=O)R$^{A3}$, —C(=O)OR$^{A3}$, —C(=O)SR$^{A3}$, —C(=O)N(R$^{A4}$)$_2$, —OC(=O)R$^{A3}$, —OC(=O)OR$^{A3}$, —OC(=O)SR$^{A3}$, —OC(=O)N(R$^{A4}$)$_2$, —NR$^{A4}$C(=O)R$^{A4}$, —NR$^{A4}$C(=O)OR$^{A3}$, —NR$^{A4}$C(=O)SR$^{A3}$, —NR$^{A4}$C(=O)N(R$^{A4}$)$_2$, —SC(=O)R$^{A3}$, —SC(=O)OR$^{A3}$, —SC(=O)SR$^{A3}$, —SC(=O)N(R$^{A4}$)$_2$, —C(=NR$^{A4}$)R$^{A3}$, —C(=NR$^{A4}$)OR$^{A3}$, —C(=NR$^{A4}$)SR$^{A3}$, —C(=NR$^{A4}$)N(R$^{A4}$)$_2$, —OC(=NR$^{A4}$)R$^{A3}$, —OC(=NR$^{A4}$)OR$^{A3}$, —OC(=NR$^{A4}$)SR$^{A3}$, —OC(=NR$^{A4}$)N(R$^{A4}$)$_2$, —NR$^{A4}$C(=NR$^{A4}$)R$^{A2}$, —NR$^{A4}$C(=NR$^{A4}$)OR$^{A3}$, —NR$^{A4}$C(=NR$^{A4}$)SR$^{A3}$, —NR$^{A4}$C(=NR$^{A4}$)N(R$^{A4}$)$_2$, —SC(=NR$^{A4}$)R$^{A3}$, —SC(=NR$^{A4}$)OR$^{A3}$, —SC(=NR$^{A4}$)SR$^{A3}$, —SC(=NR$^{A4}$)N(R$^{A4}$)$_2$, —C(=S)R$^{A3}$, —C(=S)OR$^{A3}$, —C(=S)SR$^{A3}$, —C(=S)N(R$^{A4}$)$_2$, —OC(=S)R$^{A3}$, —OC(=S)OR$^{A3}$, —OC(=S)SR$^{A3}$, —OC(=S)N(R$^{A4}$)$_2$, —NR$^{A4}$C(=S)R$^{A4}$, —NR$^{A4}$C(=S)OR$^{A3}$, —NR$^{A4}$C(=S)SR$^{A3}$, —NR$^{A4}$C(=S)N(R$^{A4}$)$_2$, —SC(=S)R$^{A3}$, —SC(=S)OR$^{A3}$, —SC(=S)SR$^{A3}$, —SC(=S)N(R$^{A4}$)$_2$, —S(=O)R$^{A3}$, —SO$_2$R$^{A3}$, —NR$^{A4}$SO$_2$R$^{A3}$, —SO$_2$N(R$^{A4}$)$_2$, —CN, —SCN, and —NO$_2$, wherein R$^{A3}$ and R$^{A4}$ are as defined herein.

In certain embodiments, at least one R$^{AA}$ substituent is an electron withdrawing group selected from the group consisting of halogen (e.g., —Br, —Cl), perhaloalkyl (e.g., —CF$_3$), —C(=O)N(R$^{A2}$)$_2$ (e.g., —C(=O)NH$_2$)—CN, —SCN, and —NO$_2$. In certain embodiments, at least one R$^{AA}$ substituent is an electron withdrawing group selected from the group consisting of halogen (e.g., —Br, —Cl), perhaloalkyl (e.g., —CF$_3$), —C(=O)N(R$^{A2}$)$_2$ (e.g., —C(=O)NH$_2$), or —CN. In certain embodiments, at least one R$^{AA}$ substituent is the electron withdrawing group —CN. In certain embodiments, at least one R$^{AA}$ substituent is the electron withdrawing group —NO$_2$. However, in certain embodiments, —NO$_2$ as an aryl group substituent is specifically excluded.

However, in certain embodiments, at least one R$^{AA}$ substituent (e.g., 1, 2, 3, or 4 R$^{AA}$ substituents) is an electron-donating group, e.g., a substituent which donates electron density toward the parent molecule (e.g., a ring system) and/or stabilizes cations or electron poor structures. Exemplary electron-donating substituents include, but are not limited to, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A3}$, —N(R$^{A4}$)$_2$, —SR$^{A3}$, wherein R$^{A3}$ and R$^{A4}$ are as defined herein.

Specific combinations of groups comprising R$_1$ are further contemplated.

In certain embodiments, R$_1$ is an optionally substituted arylalkyl group of the formula:

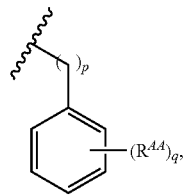

wherein:
p is an integer between 1 and 6, inclusive;
q is 0 or an integer between 1 and 5, inclusive; and
each instance of R$^{AA}$ is independently as defined above and herein.

In some embodiments, p is 1. In some embodiments, p is 2. In some embodiments, p is 3. In some embodiments, p is 4. In some embodiments, p is 5. In some embodiments, p is 6. In certain embodiments, q is 0. In certain embodiments, q is 1. In certain embodiments, q is 2. In certain embodiments, q is 3. In certain embodiments, q is 4. In certain embodiments, q is 5. In certain embodiments, wherein q is an integer between 1 and 5, inclusive, R$_1$ is a substituted arylalkyl group.

In certain embodiments, wherein q is 1, and R$^{AA}$ is located in the ortho position relative to the point of attachment, R$_1$ is a monosubstituted arylalkyl group of the formula:

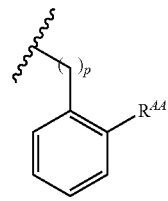

wherein p and R$^{AA}$ are as defined herein.

In certain embodiments, wherein q is 1, and R$^{AA}$ is located in the meta position relative to the point of attachment, R$_1$ is a monosubstituted arylalkyl group of the formula:

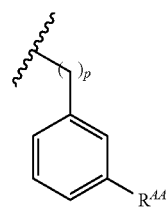

wherein p and R$^{AA}$ are as defined herein.

In certain embodiments, wherein q is 1, and $R^{AA}$ is located in the para position relative to the point of attachment, $R_1$ is a monosubstituted arylalkyl group of the formula:

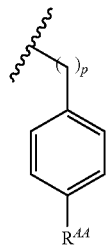

wherein p and $R^{AA}$ are as defined herein.

In certain embodiments, wherein q is 2, $R_1$ is a disubstituted arylalkyl group of the formula:

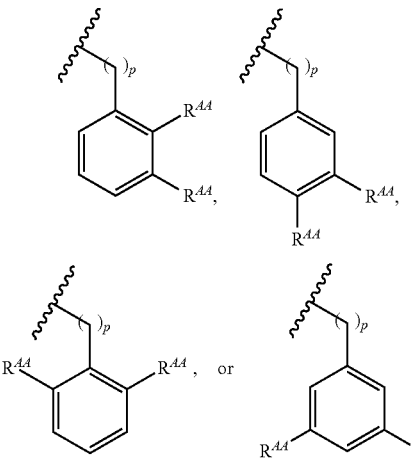

wherein p and $R^{AA}$ are as defined herein.

In certain embodiments, wherein q is 3, $R_1$ is a trisubstituted arylalkyl group of the formula:

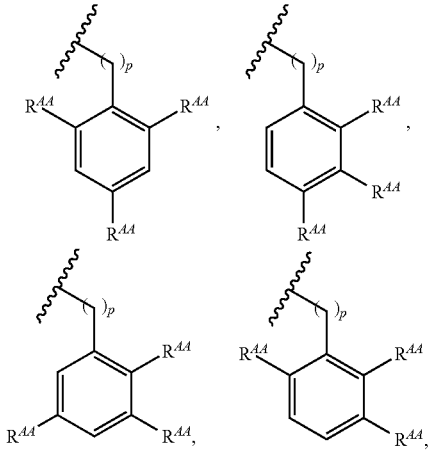

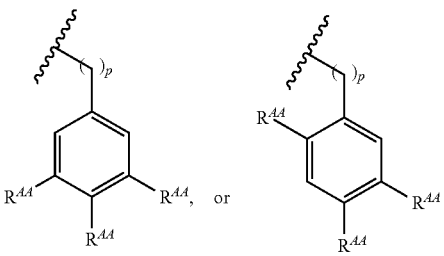

wherein p and $R^{AA}$ are as defined herein.

In certain embodiments, wherein q is 4, $R_1$ is a tetrasubstituted arylalkyl group of the formula:

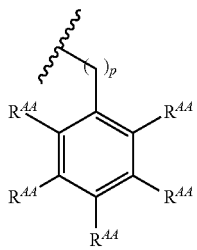

wherein p and $R^{AA}$ are as defined herein.

Exemplary substituted arylalkyl $R_1$ groups include, but are not limited to,

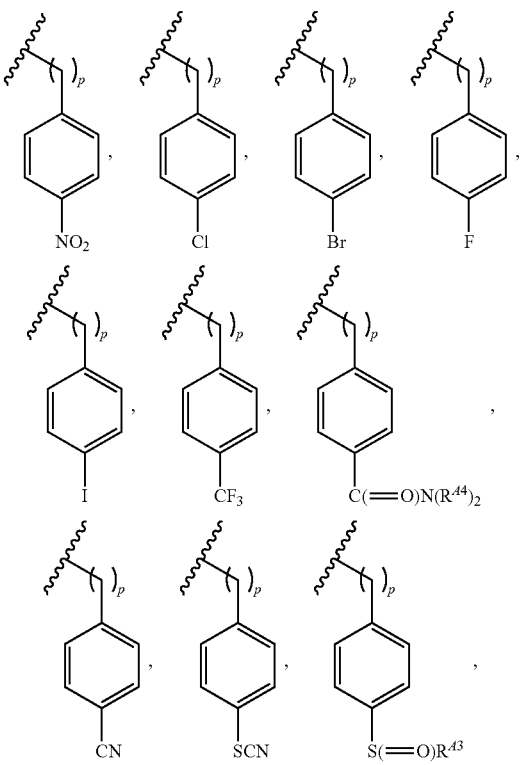

-continued

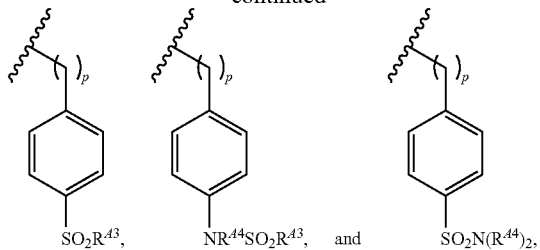

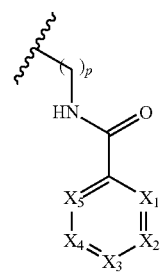

wherein $R^{43}$, $R^{44}$, and p is as defined herein. In some embodiments, p is 1. In some embodiments, p is 2. In some embodiments, p is 3. In some embodiments, p is 4. In some embodiments, p is 5. In some embodiments, p is 6.

In certain embodiments, $R_1$ is aliphatic substituted by —$NR^{A2}C(=O)R^{A2}$, —$NR^{A2}C(=O)OR^{A1}$, —$NR^{A2}C(=O)SR^{A1}$, or —$NR^{A2}C(=O)N(R^{A2})_2$, wherein each occurrence of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{A2}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{A2}$ groups are joined to form an substituted or unsubstituted heterocyclic ring. In certain embodiments, $R_1$ is aliphatic substituted by —$NR^{A2}C(=O)R^{A2}$. In certain embodiments, $R_1$ is aliphatic substituted by —$NHC(=O)R^{A2}$, wherein $R^{A2}$ is substituted or unsubstituted aryl (e.g., optionally substituted phenyl) or substituted or unsubstituted heteroaryl (e.g., optionally substituted 5- to 6-membered heteroaryl). In certain embodiments, $R_1$ is aliphatic substituted by —$NHC(=O)R^{A2}$, wherein $R^{A2}$ is substituted or unsubstituted aryl (e.g., substituted or unsubstituted phenyl). In certain embodiments, $R_1$ is aliphatic substituted by —$NHC(=O)R^{A2}$, wherein $R^{A2}$ is substituted or unsubstituted heteroaryl (e.g., substituted or unsubstituted 5- to 6-membered heteroaryl). In certain embodiments, $R_1$ is aliphatic substituted by —$NHC(=O)R^{A2}$, wherein $R^{A2}$ is substituted or unsubstituted 5-membered heteroaryl, e.g., pyrrolyl, furanyl, thiophenyl, imidazolyl, pyrazolyl, oxazolyl, isoxazolyl, thiazolyl, isothiazolyl, triazolyl, oxadiazolyl, thiadiazolyl, and tetrazolyl. In certain embodiments, $R_1$ is aliphatic substituted by —$NHC(=O)R^{A2}$, wherein $R^{A2}$ is substituted or unsubstituted 6-membered heteroaryl, e.g., pyridinyl, pyridazinyl, pyrimidinyl, pyrazinyl, triazinyl, and tetrazinyl. In certain embodiments, $R_1$ is aliphatic substituted by —$NHC(=O)R^{A2}$, wherein $R^{A2}$ is substituted or unsubstituted pyridinyl. In certain embodiments, $R_1$ is aliphatic substituted by —$NHC(=O)R^{A2}$, wherein $R^{A2}$ is substituted or unsubstituted pyrazinyl.

In certain embodiments, wherein $R_1$ is alkyl substituted by —$NR^{A2}C(=O)R^{A2}$, $R_1$ is a group the formula:

wherein:

p is an integer between 1 and 6, inclusive;

each instance of $X^1$, $X^2$, $X^3$, $X^4$, and $X^5$ is independently selected from N, CH, or $CR^{AA}$; and each instance of $R^{AA}$ is independently as defined above and herein.

In certain embodiments, each instance of $X^1$, $X^2$, $X^3$, $X^4$, and $X^5$ is independently selected from CH or $CR^{AA}$.

In certain embodiments, $X^1$ is N and $X^2$, $X^3$, $X^4$, and $X^5$ are independently selected from CH or $CR^{AA}$. In certain embodiments, $X^2$ is N and $X^5$, $X^3$, $X^4$, and $X^5$ are independently selected from CH or $CR^{AA}$. In certain embodiments, $X^3$ is N and $X^1$, $X^2$, $X^4$, and $X^5$ are independently selected from CH or $CR^{AA}$.

In certain embodiments, $X^1$ and $X^3$ are N and $X^2$, $X^4$, and $X^5$ are independently selected from CH or $CR^{AA}$. In certain embodiments, $X^2$ and $X^4$ are N and $X^1$, $X^3$, and $X^5$ are independently selected from CH or $CR^{AA}$. In certain embodiments, $X^1$ and $X^2$ are N and $X^3$, $X^4$, and $X^5$ are independently selected from CH or $CR^{AA}$. In certain embodiments, $X^3$ and $X^4$ are N and $X^1$, $X^2$, and $X^5$ are independently selected from CH or $CR^{AA}$.

In certain embodiments, $X^1$, $X^3$, and $X^5$ are N and $X^2$ and $X^4$ are independently selected from CH or $CR^{AA}$.

In certain embodiments, wherein $R_1$ is aliphatic substituted by —$NR^{A2}C(=O)R^{A2}$, $R_1$ is a group the formula:

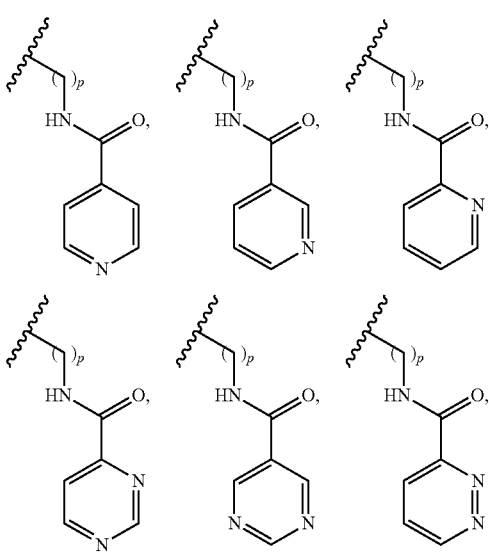

-continued

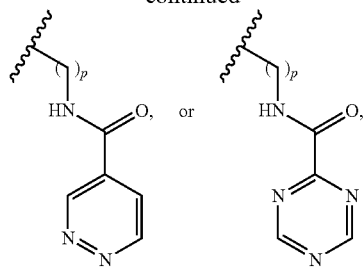

wherein p is as defined herein. In some embodiments, p is 1. In some embodiments, p is 2. In some embodiments, p is 3. In some embodiments, p is 4. In some embodiments, p is 5. In some embodiments, p is 6.

In certain embodiments, $R_1$ is aliphatic substituted by —S(=O)$R^{A1}$, —SO$_2$$R^{A1}$, —N$R^{A2}$SO$_2$$R^{A1}$, or —SO$_2$N($R^{A2}$)$_2$, wherein each occurrence of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{A2}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{A2}$ groups are joined to form an substituted or unsubstituted heterocyclic ring. In certain embodiments, $R_1$ is aliphatic substituted by —SO$_2$$R^{A1}$, wherein $R^{A1}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl ("sulfonyl-substituted aliphatic"). In certain embodiments, $R_1$ is aliphatic substituted by —SO$_2$$R^{A1}$, wherein $R^{A1}$ is substituted or unsubstituted alkyl, substituted or unsubstituted alkenyl, substituted or unsubstituted alkynyl. In certain embodiments, $R_1$ is aliphatic substituted by —SO$_2$$R^{A1}$, wherein $R^{A1}$ is substituted or unsubstituted alkyl (e.g., —CH$_3$, "methyl-sulfonyl-substituted aliphatic"). In certain embodiments, $R_1$ is alkyl substituted by —SO$_2$$R^{A1}$, wherein $R^{A1}$ is substituted or unsubstituted alkyl (e.g., —CH$_3$).

In certain embodiments, wherein $R_1$ is aliphatic substituted by —S(=O)$R^{A1}$, $R^1$ is a group of the formula:

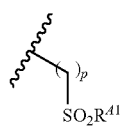

wherein p is an integer between 1 and 6, inclusive, and $R^{A1}$ is as defined above and herein. In some embodiments, p is 1. In some embodiments, p is 2. In some embodiments, p is 3. In some embodiments, p is 4. In some embodiments, p is 5. In some embodiments, p is 6. In certain embodiments, $R^{A1}$ is substituted or unsubstituted alkyl (e.g., —CH$_3$).

Embodiments of $R_2$

As generally defined above, each instance of $R_2$ is independently hydrogen; halogen; substituted or unsubstituted aliphatic; substituted or unsubstituted heteroaliphatic; substituted or unsubstituted aryl; substituted or unsubstituted heteroaryl; acyl; —O$R_B$; —N($R_B$)$_2$; —S$R_B$; =O; —CN; —NO$_2$; —SCN; —SO$R_B$; or —SO$_2$$R_B$; wherein each occurrence of $R_B$ independently is hydrogen; a protecting group; substituted or unsubstituted aliphatic; substituted or unsubstituted heteroaliphatic; acyl; substituted or unsubstituted aryl; or substituted or unsubstituted heteroaryl.

In certain embodiments, $R_2$ is hydrogen. In certain embodiments, $R_2$ is halogen, i.e., —F, —Cl, —Br, or —I. In certain embodiments, $R_2$ is —O$R_B$. In certain embodiments, $R_2$ is —N($R_B$)$_2$. In certain embodiments, $R_2$ is —S$R_B$. In certain embodiments, $R_2$ is =O. In certain embodiments, $R_2$ is —CN. In certain embodiments, $R_2$ is —NO$_2$. In certain embodiments, $R_2$ is —SCN. In certain embodiments, $R_2$ is —SO$R_B$. In certain embodiments, $R_2$ is —SO$_2$$R_B$.

In certain embodiments, $R_2$ is acyl. For example, in certain embodiments, $R_2$ is acyl selected from the group consisting of —C(=O)$R^{B5}$, —C(=O)O$R^{B5}$, —C(=O)S$R^{B5}$, —C(=O)N($R^{B6}$)$_2$, —C(=N$R^{B6}$)$R^{B5}$, —C(=N$R^{B6}$)O$R^{B5}$, —C(=N$R^{B6}$)S$R^{B5}$, —C(=N$R^{B6}$)N($R^{B6}$)$_2$, —C(=S)$R^{B5}$, —C(=S)O$R^{B5}$, —C(=S)S$R^{B5}$, and —C(=S)N($R^{B6}$)$_2$, wherein each occurrence of $R^{B5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{B6}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{B6}$ groups are joined to form an substituted or unsubstituted heterocyclic ring.

In certain embodiments, $R_2$ is substituted or unsubstituted aryl, e.g., phenyl, napthyl. In certain embodiments, $R_2$ is substituted or unsubstituted phenyl. In certain embodiments, $R_2$ is substituted phenyl, e.g., a monosubstituted, disubstituted, or trisubstituted phenyl.

In certain embodiments, $R_2$ is substituted or unsubstituted heteroaryl, e.g., a substituted or unsubstituted 5- to 6-membered heteroaryl. In certain embodiments, $R_2$ is a substituted or unsubstituted 5-membered heteroaryl, e.g., pyrrolyl, furanyl, thiophenyl, imidazolyl, pyrazolyl, oxazolyl, isoxazolyl, thiazolyl, isothiazolyl, triazolyl, oxadiazolyl, thiadiazolyl, or tetrazolyl. In certain embodiments, $R_2$ is a substituted or unsubstituted 6-membered heteroaryl, e.g., pyridinyl, pyridazinyl, pyrimidinyl, pyrazinyl, triazinyl, or tetrazinyl.

In certain embodiments, $R_2$ is substituted or unsubstituted aliphatic. In certain embodiments, $R_2$ is a substituted or unsubstituted aliphatic group comprising 1 to 10 carbon atoms ("$C_{1-10}$aliphatic"). In certain embodiments, $R_2$ is substituted or unsubstituted aliphatic group comprising 1 to 8 carbon atoms ("$C_{1-8}$aliphatic"). In certain embodiments, $R_2$ is a substituted or unsubstituted aliphatic group comprising 1 to 6 carbon atoms ("$C_{1-6}$aliphatic"). In certain embodiments, $R_2$ is a substituted or unsubstituted aliphatic group comprising 1 to 4 carbon atoms ("$C_{1-4}$aliphatic"). In certain embodiments, $R_2$ is a substituted or unsubstituted aliphatic group comprising 1 to 3 carbon atoms ("$C_{1-3}$aliphatic"). In certain embodiments, $R_2$ is a substituted or unsubstituted aliphatic group comprising 1 carbon atom ("$C_1$aliphatic"). In certain embodiments, $R_2$ is a substituted or unsubstituted aliphatic group comprising 2 carbon atoms ("$C_2$aliphatic"). In certain embodiments, $R_2$ is a substituted or unsubstituted aliphatic group comprising 3 carbon atoms ("$C_3$aliphatic"). In any of the above embodiments, $R_2$ is an acyclic aliphatic group. In any of the above embodiments, $R_2$ is an acyclic and substituted aliphatic group. In any of the above embodiments, the aliphatic group is an alkyl, alkenyl, or alkynyl group.

In certain embodiments, $R_2$ is substituted or unsubstituted alkyl. In certain embodiments, $R_2$ is unsubstituted alkyl. In certain embodiments, $R_2$ is substituted alkyl. In certain embodiments, $R_2$ is substituted $C_{1-10}$alkyl. In certain embodiments, $R_2$ is substituted $C_{1-8}$alkyl. In certain embodiments, $R_2$ is substituted $C_{1-6}$alkyl. In certain embodiments, $R_2$ is substituted $C_{1-5}$alkyl. In certain embodiments, $R_2$ is substituted $C_{1-4}$alkyl. In certain embodiments, $R_2$ is substituted $C_{1-3}$alkyl. In certain embodiments, $R_2$ is substituted $C_{1-2}$alkyl. In certain embodiments, $R_2$ is substituted $C_{2-4}$alkyl. In certain embodiments, $R_2$ is substituted $C_1$alkyl. In certain embodiments, $R_2$ is substituted $C_2$alkyl. In certain embodiments, $R_2$ is substituted $C_3$alkyl. In certain embodiments, $R_2$ is substituted $C_4$alkyl.

In certain embodiments, $R_2$ is substituted or unsubstituted alkenyl. In certain embodiments, $R_2$ is unsubstituted alkenyl. In certain embodiments, $R_2$ is substituted alkenyl. In certain embodiments, $R_2$ is substituted $C_{2-10}$alkenyl. In certain embodiments, $R_2$ is substituted $C_{2-8}$alkenyl. In certain embodiments, $R_2$ is substituted $C_{2-6}$alkenyl. In certain embodiments, $R_2$ is substituted $C_{2-5}$alkenyl. In certain embodiments, $R_2$ is substituted $C_{2-4}$alkenyl. In certain embodiments, $R_2$ is substituted $C_{2-3}$alkenyl. In certain embodiments, $R_2$ is substituted $C_1$alkenyl. In certain embodiments, $R_2$ is substituted $C_2$alkenyl. In certain embodiments, $R_2$ is substituted $C_3$alkenyl. In certain embodiments, $R_2$ is substituted $C_4$alkenyl.

In certain embodiments, $R_2$ is substituted or unsubstituted heteroaliphatic. In certain embodiments, $R_2$ is substituted or unsubstituted heteroaliphatic group comprising 1 to 10 carbon atoms and 1 to 3 heteroatoms independently selected from oxygen, nitrogen, and sulfur ("$C_{1-10}$heteroaliphatic"). In certain embodiments, the heteroaliphatic group comprises 1 heteroatom selected from oxygen, nitrogen, and sulfur. In certain embodiments, the heteroaliphatic group comprises 2 heteroatoms independently selected from oxygen, nitrogen, and sulfur. In certain embodiments, the heteroaliphatic group comprises 3 heteroatoms independently selected from oxygen, nitrogen, and sulfur. In certain embodiments, $R_2$ is a substituted or unsubstituted heteroaliphatic group comprising 1 to 8 carbon atoms and 1-3 heteroatoms selected from oxygen, nitrogen, and sulfur ("$C_{1-8}$heteroaliphatic"). In certain embodiments, $R_2$ is a substituted or unsubstituted heteroaliphatic group comprising 1 to 6 carbon atoms and 1-2 heteroatoms selected from oxygen, nitrogen, and sulfur ("$C_{1-6}$heteroaliphatic"). In certain embodiments, $R_2$ is a substituted or unsubstituted heteroaliphatic group comprising 1 to 4 carbon atoms and 1-2 heteroatoms selected from oxygen, nitrogen, and sulfur ("$C_{1-4}$heteroaliphatic"). In certain embodiments, $R_2$ is a substituted or unsubstituted heteroaliphatic group comprising 1 to 3 carbon atoms and 1 heteroatom selected from oxygen, nitrogen, and sulfur ("$C_{1-3}$heteroaliphatic"). In certain embodiments, $R_2$ is a substituted or unsubstituted heteroaliphatic group comprising 1 carbon atom and 1 heteroatom selected from oxygen, nitrogen, and sulfur ("$C_1$heteroaliphatic"). In certain embodiments, $R_2$ is a substituted or unsubstituted heteroaliphatic group comprising 2 carbon atoms and 1 heteroatom selected from oxygen, nitrogen, and sulfur ("$C_2$heteroaliphatic"). In certain embodiments, $R_2$ is a substituted or unsubstituted heteroaliphatic group comprising 3 carbon atoms and 1 heteroatom selected from oxygen, nitrogen, and sulfur ("$C_3$heteroaliphatic"). In any of the above embodiments, $R_2$ is an acyclic heteroaliphatic group. In any of the above embodiments, $R_2$ is an acyclic and substituted heteroaliphatic group. In any of the above embodiments, the heteroaliphatic group is an heteroalkyl, heteroalkenyl, or heteroalkynyl group.

In certain embodiments, $R_2$ is substituted or unsubstituted heteroalkyl comprising 10 carbon atoms and 1-3 heteroatoms selected from oxygen, nitrogen, and sulfur ("substituted $C_{1-10}$heteroalkyl"). In certain embodiments, the heteroalkyl group comprises 1 heteroatom selected from oxygen, nitrogen, and sulfur. In certain embodiments, the heteroalkyl group comprises 2 heteroatoms independently selected from oxygen, nitrogen, and sulfur. In certain embodiments, the heteroalkyl group comprises 3 heteroatoms independently selected from oxygen, nitrogen, and sulfur. In certain embodiments, $R_2$ is a substituted heteroalkyl comprising 1-8 carbon atoms and 1-3 heteroatoms selected from oxygen, nitrogen, and sulfur ("substituted $C_{1-6}$heteroalkyl"). In certain embodiments, $R_2$ is a substituted heteroalkyl comprising 1-6 carbon atoms and 1-2 heteroatoms selected from oxygen, nitrogen, and sulfur ("substituted $C_{1-6}$heteroalkyl"). In certain embodiments, $R_2$ is a substituted heteroalkyl comprising 1-4 carbon atoms and 1-2 heteroatoms selected from oxygen, nitrogen, and sulfur ("substituted $C_{1-4}$heteroalkyl"). In certain embodiments, $R_2$ is a substituted heteroalkyl comprising 1-3 carbon atoms and 1 heteroatom selected from oxygen, nitrogen, and sulfur ("substituted $C_{1-3}$heteroalkyl"). In certain embodiments, $R_2$ is a substituted heteroalkyl comprising 1-2 carbon atoms and 1 heteroatom selected from oxygen, nitrogen, and sulfur ("substituted $C_{1-2}$heteroalkyl"). In certain embodiments, $R_2$ is a substituted heteroalkyl comprising 1 carbon atom and 1 heteroatom selected from oxygen, nitrogen, and sulfur ("substituted $C_1$heteroalkyl"). In certain embodiments, $R_2$ is a substituted heteroalkyl comprising 2 carbon atoms and 1 heteroatom selected from oxygen, nitrogen, and sulfur ("substituted $C_2$heteroalkyl"). In certain embodiments, $R_2$ is a substituted heteroalkyl comprising 3 carbon atoms and 1 heteroatom selected from oxygen, nitrogen, and sulfur ("substituted $C_3$heteroalkyl"). In certain embodiments, $R_2$ is a substituted heteroalkyl comprising 4 carbon atoms and 1-2 heteroatoms selected from oxygen, nitrogen, and sulfur ("substituted $C_4$heteroalkyl").

As generally understood from the above, in certain embodiments, $R_2$ is a group selected from aliphatic, heteroaliphatic, aryl, or heteroaryl which may be unsubstituted or substituted with one or more substituents. Exemplary $R_2$ group substituents, collectively referred to as "$R^B$", include, but are not limited to, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B1}$, —$N(R^{B2})_2$, —$SR^{B1}$, —$C(=O)R^{B1}$, —$C(=O)OR^{B1}$, —$C(=O)SR^{B1}$, —$C(=O)N(R^{B2})_2$, —$OC(=O)R^{B1}$, —$OC(=O)OR^{B1}$, —$OC(=O)SR^{B1}$, —$OC(=O)N(R^{B2})_2$, —$NR^{B2}C(=O)R^{B2}$, —$NR^{B2}C(=O)OR^{B1}$, —$NR^{B2}C(=O)SR^{B1}$, —$NR^{B2}C(=O)N(R^{B2})_2$, —$SC(=O)R^{B1}$, —$SC(=O)OR^{B1}$, —$SC(=O)SR^{B1}$, —$SC(=O)N(R^{B2})_2$, —$C(=NR^{B2})R^{B1}$, —$C(=NR^{B2})OR^{B1}$, —$C(=NR^{B2})SR^{B1}$, —$C(=NR^{B2})N(R^{B2})_2$, —$OC(=NR^{B2})R^{B1}$, —$OC(=NR^{B2})OR^{B1}$, —$OC(=NR^{B2})SR^{B1}$, —$OC(=NR^{B2})N(R^{B2})_2$, —$NR^{B2}C(=NR^{B2})R^{B2}$, —$NR^{B2}C(=NR^{B2})OR^{B1}$, —$NR^{B2}C(=NR^{B2})SR^{B1}$, —$NR^{B2}C(=NR^{B2})N(R^{B2})_2$, —$SC(=NR^{B2})R^{B1}$, —$SC(=NR^{B2})OR^{B1}$, —$SC(=NR^{B2})SR^{B1}$, —$SC(=NR^{B2})N(R^{B2})_2$, —$C(=S)R^{B1}$, —$C(=S)OR^{B1}$, —$C(=S)SR^{B1}$, —$C(=S)N(R^{B2})_2$, —$OC(=S)R^{B1}$, —$OC (=S)OR$^{B1}$, —OC(=S)SR$^{B1}$, —OC(=S)N(R$^{B2}$)$_2$, —NR$^{B2}$C(=S)R$^{B2}$, —NR$^{B2}$C(=S)OR$^{B1}$, —NR$^{B2}$C(=S)SR$^{B1}$, —NR$^{B2}$C(=S)N(R$^{B2}$)$_2$, —SC(=S)R$^{B1}$, —SC(=S)OR$^{B1}$, —SC(=S)SR$^{B1}$, —SC(=S)N(R$^{B2}$)$_2$, —S(=O)R$^{B1}$, —SO$_2$R$^{B1}$, —NR$^{B2}$SO$_2$R$^{B1}$, —SO$_2$N(R$^{B2}$)$_2$, —N$_3$, —CN, —SCN, and —NO$_2$, wherein each occurrence of R$^{B1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of R$^{B2}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two R$^{B2}$ groups are joined to form an substituted or unsubstituted heterocyclic ring.

In certain embodiments, R$_2$ is aliphatic, as defined above and herein, substituted by one or more R$^B$ substituents, as provided above, e.g., 1, 2, 3, or 4 substituents. In certain embodiments, R$_2$ is alkyl, as defined above and herein, substituted by one or more R$^B$ substituents, as provided above, e.g., 1, 2, 3, or 4 substituents. In certain embodiments, R$_2$ is a C$_{1-4}$alkyl substituted by one or more R$^B$ substituents, as provided above, e.g., 1, 2, 3, or 4 substituents. In certain embodiments, R$_2$ is a C$_{2-4}$alkenyl substituted by one or more R$^B$ substituents, as provided above, e.g., 1, 2, 3, or 4 substituents.

For example, in certain embodiments, R$_2$ is aliphatic substituted by an optionally substituted aryl or optionally substituted heteroaryl group, e.g., an optionally substituted phenyl group or optionally substituted 5- to 6-membered heteroaryl group.

In certain embodiments, R$_2$ is aliphatic substituted by an optionally substituted aryl group ("optionally substituted arylaliphatic"). In certain embodiments, the aryl group is an optionally substituted phenyl ("optionally substituted phenylaliphatic"). In certain embodiments, the aryl group is unsubstituted. However, in certain embodiments, the aryl group is substituted. For example, in certain embodiments, the aryl group is a monosubstituted phenyl ring, e.g., substituted at the ortho, meta, or para position of the phenyl ring relative to the point of attachment. In certain embodiments, the aryl group is a disubstituted phenyl ring, e.g., substituted at the 1,2-, the 1,3-, the 1,4-, the 2,3-, the 3,4-, or the 2,4-positions of the phenyl ring relative to the point of attachment. In certain embodiments, the aryl group is a trisubstituted phenyl ring, e.g., substituted at the 1,2,3-, the 1,2,4-, or the 2,3,4-, positions of the phenyl ring relative to the point of attachment. In certain embodiments, the aryl group is a tetrasubstituted phenyl ring. In any of the above embodiments, the aliphatic group is selected from alkyl, alkenyl, or alkynyl. In certain embodiments, the aliphatic group is alkyl. For example, in certain embodiments, R$_2$ is alkyl substituted by an optionally substituted aryl group ("optionally substituted arylalkyl"), e.g., an optionally substituted phenyl group ("optionally substituted phenylalkyl"). In certain embodiments, R$_2$ is a C$_{1-4}$alkyl substituted by an optionally substituted aryl group, e.g., an optionally substituted phenyl group. In certain embodiments, R$_2$ is a C$_1$alkyl substituted by an optionally substituted aryl group, e.g., an optionally substituted phenyl group. In certain embodiments, the aliphatic group is alkenyl. For example, in certain embodiments, R$_2$ is a C$_{2-4}$alkenyl substituted by an optionally substituted aryl group ("optionally substituted arylalkenyl"), e.g., an optionally substituted phenyl group ("optionally substituted phenylalkenyl"). In certain embodiments, R$_2$ is a C$_2$alkenyl substituted by an optionally substituted aryl group, e.g., an optionally substituted phenyl group. In certain embodiments, R$_2$ is a C$_3$alkenyl substituted by an optionally substituted aryl group, e.g., an optionally substituted phenyl group.

In certain embodiments, R$_2$ is aliphatic substituted by an optionally substituted 5- to 6-membered heteroaryl group, e.g., a substituted or unsubstituted 5-membered heteroaryl, e.g., pyrrolyl, furanyl, thiophenyl, imidazolyl, pyrazolyl, oxazolyl, isoxazolyl, thiazolyl, isothiazolyl, triazolyl, oxadiazolyl, thiadiazolyl, or tetrazolyl, or a substituted or unsubstituted 6-membered heteroaryl, e.g., pyridinyl, pyridazinyl, pyrimidinyl, pyrazinyl, triazinyl, or tetrazinyl. In certain embodiments, the heteroaryl group is a substituted 5- to 6-membered heteroaryl ("substituted 5- to 6-membered heteroarylaliphatic"). In any of the above embodiments, the aliphatic group is selected from alkyl, alkenyl, or alkynyl. In certain embodiments, the aliphatic group is alkyl. For example, in certain embodiments, R$_2$ is alkyl substituted by a substituted by an optionally substituted heteroaryl group ("optionally substituted heteroarylalkyl"), e.g., an optionally substituted 5- to 6-membered heteroaryl group ("optionally substituted 5- to 6-membered heteroarylalkyl"). In certain embodiments, R$_2$ is a C$_{1-4}$alkyl substituted by an optionally substituted heteroaryl group, e.g., an optionally substituted 5- to 6-membered heteroaryl group. In certain embodiments, R$_2$ is a C$_1$alkyl substituted by an optionally substituted heteroaryl group, e.g., an optionally substituted 5- to 6-membered heteroaryl group. In certain embodiments, R$_2$ is a C$_{2-4}$alkenyl substituted by an optionally substituted heteroaryl group, e.g., an optionally substituted 5- to 6-membered heteroaryl group. In certain embodiments, R$_2$ is a C$_2$alkenyl substituted by an optionally substituted heteroaryl group, e.g., an optionally substituted 5- to 6-membered heteroaryl group. In certain embodiments, R$_2$ is a C$_3$alkenyl substituted by an optionally substituted heteroaryl group, e.g., an optionally substituted 5- to 6-membered heteroaryl group. In any of the above embodiments, the heteroaryl group is substituted. However, in any of the above embodiments, the heteroaryl group is unsubstituted.

In certain embodiments, R$_2$ is aliphatic substituted by a substituted or unsubstituted carbocyclyl ("optionally substituted carbocylcyl") or a substituted or unsubstituted heterocyclyl ("optionally substituted heterocyclyl"), e.g., optionally substituted C$_{3-8}$carbocyclyl or optionally substituted 5- to 8-membered heterocyclyl.

For example, in certain embodiments, R$_2$ is aliphatic substituted by an optionally substituted 5- to 8-membered heterocyclyl comprising 1 to 3 heteroatoms selected from oxygen, nitrogen, and sulfur. In certain embodiments, R$_2$ is aliphatic substituted by an optionally substituted 8-membered heterocyclyl comprising 1 to 3 heteroatoms selected from oxygen, nitrogen, and sulfur, e.g., azocanyl, oxecanyl, or thiocanyl. In certain embodiments, R$_2$ is aliphatic substituted by an optionally substituted 7-membered heterocyclyl comprising 1 to 3 heteroatoms selected from oxygen, nitrogen, and sulfur, e.g., azepanyl, oxepanyl, or thiepanyl. In certain embodiments, R$_2$ is aliphatic substituted by an optionally substituted 6-membered heterocyclyl comprising 1 to 3 heteroatoms selected from oxygen, nitrogen, and sulfur, e.g., piperazinyl, morpholinyl, dithianyl, dioxanyl, triazinanyl, and 6,6-bicycles such as tetrahydroquinolinyl and tetrahydroisoquinolinyl. In certain embodiments, R$_2$ is aliphatic substituted by an optionally substituted 5-membered heterocyclyl comprising 1 to 3 heteroatoms selected from oxygen, nitrogen, and sulfur, e.g., tetrahydrofuranyl, dihydrofuranyl, tetrahydrothiophenyl, dihydrothiophenyl, pyrrolidinyl, dihydropyrrolyl, pyrrolyl-2,5-dione, dioxolanyl, oxasulfuranyl, disulfuranyl, oxazolidin-2-one, triazolinyl, oxadiazolinyl, thiadiazolinyl, and 5,6-bicycles such as indolinyl, isoindolinyl, dihydrobenzofuranyl, dihydrobenzothienyl, and benzoxazolinonyl. In any of the above embodiments, the heterocyclyl contains 1 heteroatom. In any of the above embodiments, the heterocyclyl contains 2 heteroatoms. In any of the above embodiments, the heterocyclyl contains 3 heteroatoms. In any of the above embodiments, the aliphatic group is selected from alkyl, alkenyl, or alkynyl. In certain embodiments, the aliphatic group is alkyl. For example, in certain embodiments, $R_2$ is alkyl substituted by a substituted by an optionally substituted heterocyclyl group ("optionally substituted heterocyclylalkyl"), e.g., an optionally substituted 5- to 8-membered heterocyclyl comprising 1 to 3 heteroatoms selected from oxygen, nitrogen, and sulfur. In certain embodiments, $R_2$ is a $C_{1-4}$alkyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_2$ is a $C_1$alkyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_2$ is a $C_{2-4}$alkenyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_2$ is a $C_2$alkenyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_2$ is a $C_3$alkenyl substituted by an optionally substituted heterocyclyl group, e.g., an optionally substituted 5- to 8-membered heterocyclyl comprising 1 to 3 heteroatoms selected from oxygen, nitrogen, and sulfur. In any of the above embodiments, the heterocyclyl group is not substituted. However, in any of the above embodiments, the heterocyclyl group is substituted.

In certain embodiments, $R_2$ is aliphatic substituted by an optionally substituted $C_{3-7}$carbocyclyl. In certain embodiments, $R_2$ is aliphatic substituted by an optionally substituted $C_{3-6}$carbocyclyl. In certain embodiments, $R_2$ is aliphatic substituted by an optionally substituted $C_{3-5}$carbocyclyl. In certain embodiments, $R_2$ is aliphatic substituted by an optionally substituted $C_{3-4}$carbocyclyl. In certain embodiments, $R_2$ is aliphatic substituted by an optionally substituted $C_{4-6}$carbocyclyl. In certain embodiments, $R_2$ is aliphatic substituted by an optionally substituted $C_3$carbocyclyl, e.g., optionally substituted cyclopropyl or optionally substituted cyclopropenyl. In certain embodiments, $R_2$ is aliphatic substituted by an optionally substituted $C_4$carbocyclyl, e.g., optionally substituted cyclobutyl or optionally substituted cyclobutenyl. In certain embodiments, $R_2$ is aliphatic substituted by an optionally substituted $C_5$carbocyclyl, e.g., optionally substituted cyclopentyl or optionally substituted cyclopentenyl. In certain embodiments, $R_2$ is aliphatic substituted by an optionally substituted $C_6$carbocyclyl, e.g., optionally substituted cyclohexyl, optionally substituted cyclohexenyl, or optionally substituted cyclohexadienyl. In certain embodiments, $R_1$ is aliphatic substituted by an optionally substituted $C_7$carbocyclyl, e.g., optionally substituted cycloheptyl, optionally substituted cycloheptenyl, optionally substituted cycloheptadienyl, or optionally substituted cycloheptatrienyl. In any of the above embodiments, the aliphatic group is selected from alkyl, alkenyl, or alkynyl. In any of the above embodiments, the aliphatic group is alkyl. For example, in certain embodiments, $R_2$ is alkyl substituted by a substituted by an optionally substituted carbocyclyl group ("optionally substituted carbocyclylalkyl"), e.g., an optionally substituted $C_{3-7}$carbocyclyl group. In certain embodiments, $R_2$ is a $C_{1-4}$alkyl substituted by an optionally substituted carbocyclyl group, e.g., an optionally substituted $C_{3-7}$carbocyclyl. In certain embodiments, $R_2$ is a $C_1$alkyl substituted by an optionally substituted carbocyclyl group, e.g., an optionally substituted $C_{3-7}$carbocyclyl. In certain embodiments, $R_2$ is a $C_{2-4}$alkenyl substituted by an optionally substituted carbocyclyl group, e.g., an optionally substituted $C_{3-7}$carbocyclyl. In certain embodiments, $R_2$ is a $C_2$alkenyl substituted by an optionally substituted carbocyclyl group, e.g., an optionally substituted $C_{3-7}$carbocyclyl. In certain embodiments, $R_2$ is a $C_3$alkenyl substituted by an optionally substituted carbocyclyl group, e.g., an optionally substituted $C_{3-7}$carbocyclyl. In any of the above embodiments, the carbocyclyl group is not substituted. However, in any of the above embodiments, the carbocyclyl group is substituted.

As understood from the above, the carbocyclyl, heterocyclyl, aryl, and/or heteroaryl substituents present on the aliphatic group of $R_2$ may be unsubstituted or substituted with one or more substituents. Such substituents, collectively referred to herein as "$R^{BB}$", include, but are not limited to, halogen, substituted or unsubstituted alkyl (e.g., perhaloalkyl), substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B3}$, —$N(R^{B4})_2$, —$SR^{B3}$, —$C(=O)R^{B3}$, —$C(=O)OR^{B3}$, —$C(=O)SR^{B3}$, —$C(=O)N(R^{B4})_2$, —$OC(=O)R^{B3}$, —$OC(=O)OR^{B3}$, —$OC(=O)SR^{B3}$, —$OC(=O)N(R^{B4})_2$, —$NR^{B4}C(=O)R^{B4}$, —$NR^{B4}C(=O)OR^{B3}$, —$NR^{B4}C(=O)SR^{B3}$, —$NR^{B4}C(=O)N(R^{B4})_2$, —$SC(=O)R^{B3}$, —$SC(=O)OR^{B3}$, —$SC(=O)SR^{B3}$, —$SC(=O)N(R^{B4})_2$, —$C(=NR^{B4})R^{B3}$, —$C(=NR^{B4})OR^{B3}$, —$C(=NR^{B4})SR^{B3}$, —$C(=NR^{B4})N(R^{B4})_2$, —$OC(=NR^{B4})R^{B3}$, —$C(=NR^{B4})OR^{B3}$, —$OC(=NR^{B4})SR^{B3}$, —$OC(=NR^{B4})N(R^{B4})_2$, —$NR^{B4}C(=NR^{B4})R^{B2}$, —$NR^{B4}C(=NR^{B4})OR^{B3}$, —$NR^{B4}C(=NR^{B4})SR^{B3}$, —$NR^{B4}C(=NR^{B4})N(R^{B4})_2$, —$SC(=NR^{B4})R^{B3}$, —$SC(=NR^{B4})OR^{B3}$, —$SC(=NR^{B4})SR^{B3}$, —$SC(=NR^{B4})N(R^{B4})_2$, —$C(=S)R^{B3}$, —$C(=S)OR^{B3}$, —$C(=S)SR^{B3}$, —$C(=S)N(R^{B4})_2$, —$OC(=S)R^{B3}$, —$OC(=S)OR^{B3}$, —$OC(=S)SR^{B3}$, —$OC(=S)N(R^{B4})_2$, —$NR^{B4}C(=S)R^{B4}$, —$NR^{B4}C(=S)OR^{B3}$, —$NR^{B4}C(=S)SR^{B3}$, —$NR^{B4}C(=S)N(R^{B4})_2$, —$SC(=S)R^{B3}$, —$SC(=S)OR^{B3}$, —$SC(=S)SR^{B3}$, —$SC(=S)N(R^{B4})_2$, —$S(=O)R^{B3}$, —$SO_2R^{B3}$, —$NR^{B4}SO_2R^{B3}$, —$SO_2N(R^{B4})_2$, —$N_3$, —CN, —SCN, and —$NO_2$, wherein each occurrence of $R^{B3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{B4}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{B4}$ groups are joined to form an substituted or unsubstituted heterocyclic ring.

In certain embodiments, at least one $R^{BB}$ substituent (e.g., 1, 2, 3, or 4 $R^{BB}$ substituents) is an electron-withdrawing group, e.g., a substituent which pulls electron density away from the parent molecule (e.g., a ring system) and/or stabilizes anions or electron rich structures. Exemplary electron-withdrawing substituents include, but are not limited to, halogen, perhaloalkyl, —C(=O)R$^{B3}$, —C(=O)OR$^{B3}$, —C(=O)SR$^{B3}$, —C(=O)N(R$^{B4}$)$_2$, —OC(=O)R$^{B3}$, —OC(=O)OR$^{B3}$, —OC(=O)SR$^{B3}$, —OC(=O)N(R$^{B4}$)$_2$, —NR$^{B4}$C(=O)R$^{B4}$, —NR$^{B4}$C(=O)OR$^{B3}$, —NR C(=O)SR$^{B3}$, —NR$^{B4}$C(=O)N(R$^{B4}$)$_2$, —SC(=O)R$^{B3}$, —SC(=O)OR$^{B3}$, —SC(=O)SR$^{B3}$, —SC(=O)N(R$^{B4}$)$_2$, —C(=NR$^{B4}$)R$^{B3}$, —C(=NR$^{B4}$)OR$^{B3}$, —C(=NR$^{B4}$)SR$^{B3}$, —C(=NR$^{B4}$)N(R$^{B4}$)$_2$, —OC(=NR$^{B4}$)R$^{B4}$, —OC(=NR$^{B4}$)OR$^{B3}$, —OC(=NR$^{B4}$)SR$^{B3}$, —OC(=NR$^{B4}$)N(R$^{B4}$)$_2$, —NR$^{B4}$C(=NR$^{B4}$)R$^{B3}$, —NR$^{B4}$C(=NR$^{B4}$)OR$^{B3}$, —NR$^{B4}$C(=NR$^{B4}$)SR$^{B3}$, —NR$^{B4}$C(=NR$^{B4}$)N(R$^{B4}$)$_2$, —SC(=NR$^{B4}$)R$^{B3}$, —SC(=NR$^{B4}$)OR$^{B3}$, —SC(=NR$^{B4}$)SR$^{B3}$, —SC(=NR$^{B4}$)N(R$^{B4}$)$_2$, —C(=S)R$^{B3}$, —C(=S)OR$^{B3}$, —C(=S)SR$^{B3}$, —C(=S)N(R$^{B4}$)$_2$, —OC(=S)R$^{B3}$, —OC(=S)OR$^{B3}$, —OC(=S)SR$^{B3}$, —OC(=S)N(R$^{B4}$)$_2$, —NR$^{B4}$C(=S)R$^{B4}$, —NR$^{B4}$C(=S)OR$^{B3}$, —NR$^{B4}$C(=S)SR$^{B3}$, —NR$^{B4}$C(=S)N(R$^{B4}$)$_2$, —SC(=S)R$^{B3}$, —SC(=S)OR$^{B3}$, —SC(=S)SR$^{B3}$, —SC(=S)N(R$^{B4}$)$_2$, —S(=O)R$^{B3}$, —SO$_2$R$^{B3}$, —NR$^{B4}$SO$_2$R$^{B3}$, —SO$_2$N(R$^{B4}$)$_2$, —CN, —SCN, and —NO$_2$, wherein R$^{B3}$ and R$^{B4}$ are as defined herein. In certain embodiments, at least one R$^{BB}$ group is halogen, e.g., —F, —Br, —I, or —Cl.

However, in certain embodiments, at least one R$^{BB}$ substituent (e.g., 1, 2, 3, or 4 R$^{BB}$ substituents) is an electron-donating group, e.g., a substituent which donates electron density toward the parent molecule (e.g., a ring system) and/or stabilizes cations or electron poor structures. Exemplary electron-donating substituents include, but are not limited to, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B3}$, —N(R$^{B4}$)$_2$, —SR$^{B3}$.

Specific combinations of groups comprising R$_2$ are further contemplated.

In certain embodiments, R$_2$ is an optionally substituted arylalkyl group of the formula:

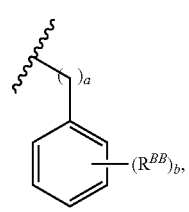

wherein:
a is an integer between 1 and 6, inclusive;
b is 0 or an integer between 1 and 5, inclusive; and
each instance of R$^{BB}$ is independently as defined herein.

In some embodiments, a is 1. In some embodiments, a is 2. In some embodiments, a is 3. In some embodiments, a is 4. In some embodiments, a is 5. In some embodiments, a is 6. In certain embodiments, b is 0. In certain embodiments, b is 1. In certain embodiments, b is 2. In certain embodiments, b is 3. In certain embodiments, b is 4. In certain embodiments, b is 5. In certain embodiments, a is 1 and b is 0.

In certain embodiments, wherein b is 1, and R$^{BB}$ is located in the ortho position relative to the point of attachment, R$_2$ is a monosubstituted arylalkyl group of the formula:

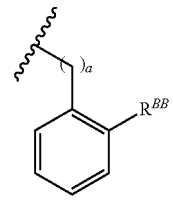

wherein a and R$^{BB}$ are as defined herein.

In certain embodiments, wherein b is 1, and R$^{BB}$ is located in the meta position relative to the point of attachment, R$_2$ is a monosubstituted arylalkyl group of the formula:

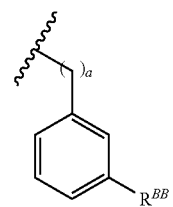

wherein a and R$^{BB}$ are as defined herein.

In certain embodiments, wherein b is 1, and R$^{BB}$ is located in the para position relative to the point of attachment, R$_2$ is a monosubstituted arylalkyl group of the formula:

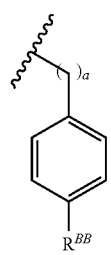

wherein a and R$^{BB}$ are as defined herein.

In certain embodiments, wherein a is 2, R$_2$ is a disubstituted arylalkyl group of the formula:

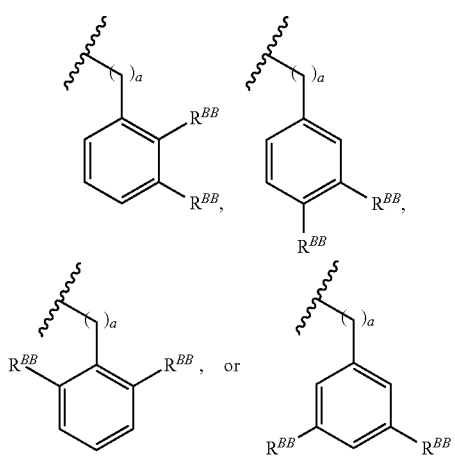

wherein a and R$^{BB}$ are as defined herein.

In certain embodiments, wherein b is 3, R$_2$ is a trisubstituted arylalkyl group of the formula:

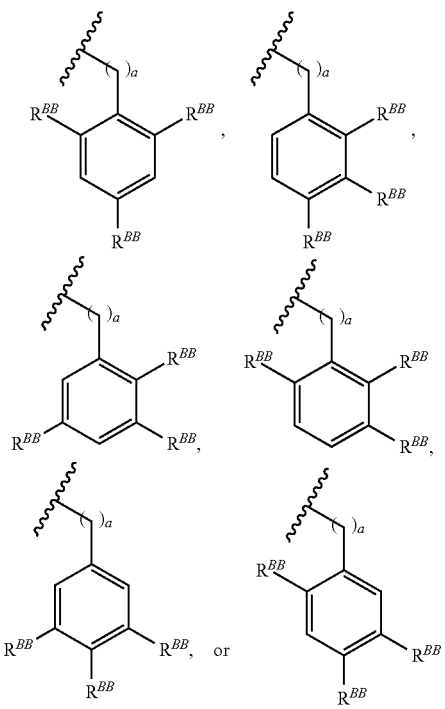

wherein a and $R^{BB}$ are as defined herein.

In certain embodiments, wherein b is 4, $R_2$ is a tetrasubstituted arylalkyl group of the formula:

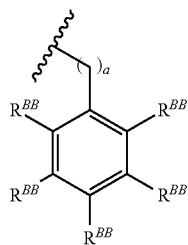

wherein a and $R^{BB}$ are as defined herein.

Exemplary substituted arylalkyl $R_2$ groups include, but are not limited to,

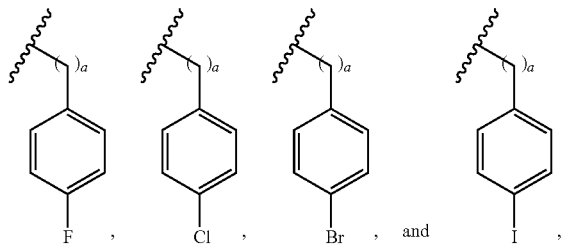

wherein a is as defined herein. In some embodiments, a is 1. In some embodiments, a is 2. In some embodiments, a is 3. In some embodiments, a is 4. In some embodiments, a is 5. In some embodiments, a is 6.

In certain embodiments, $R_2$ is alkyl substituted by an optionally substituted 5-membered heteroaryl group, e.g., an optionally substituted pyrrolyl, furanyl, thiophenyl, imidazolyl, pyrazolyl, oxazolyl, isoxazolyl, thiazolyl, isothiazolyl, triazolyl, oxadiazolyl, thiadiazolyl, or tetrazolyl group. In certain embodiments, $R_2$ is alkyl substituted by an optionally substituted pyrrolyl, optionally substituted furanyl, or optionally substituted thiophenyl. In certain embodiments, $R_2$ is alkyl substituted by an optionally substituted pyrrolyl (e.g., 2-pyrrolyl, 3-pyrrolyl). In certain embodiments, $R_2$ is alkyl substituted by an optionally substituted furanyl (e.g., 2-furanyl, 3-furanyl), i.e., $R_2$ is a "furanylalkyl" group (e.g., 2-furanylalkyl, 3-furanylalkyl). In certain embodiments, $R_2$ is alkyl substituted by an optionally substituted thiophenyl (e.g., 2-thiophenyl, 3-thiophenyl).

In certain embodiments, wherein $R_2$ is alkyl substituted with an optionally substituted 5-membered heteroaryl ring, $R_2$ is a group of the formula:

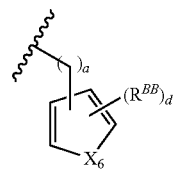

wherein:
a is an integer between 1 and 6, inclusive;
d is 0, 1, or 2; and
$X_6$ is O, S, NH, or $NR^{BB}$; wherein $R^{BB}$ is as defined above and herein.

In some embodiments, a is 1. In some embodiments, a is 2. In some embodiments, a is 3. In some embodiments, a is 4. In some embodiments, a is 5. In some embodiments, a is 6. In certain embodiments, d is 0. In certain embodiments, d is 1. In certain embodiments, d is 2. In certain embodiments, $X_6$ is O. In certain embodiments, $X_6$ is S. In certain embodiments, $X_6$ is NH or $NR^{BB}$. In certain embodiments, $X_6$ is NH. In certain embodiments, $X_6$ is $NR^{BB}$ In certain embodiments, wherein $R_2$ is alkyl substituted with an optionally substituted 5-membered heteroaryl ring, $R_2$ is a group of the formula:

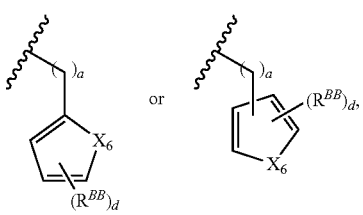

wherein a, d, $X_6$, and $R^{BB}$ are as defined herein. In certain embodiments, $X_6$ is O. In certain embodiments, $X_6$ is S. In certain embodiments, $X_6$ is NH or $NR^{BB}$. In certain embodiments, d is 0. In certain embodiments, a is 1.

In certain embodiments, wherein $R_2$ is alkyl substituted with an optionally substituted 5-membered heteroaryl ring, $R_2$ is a group of the formula:

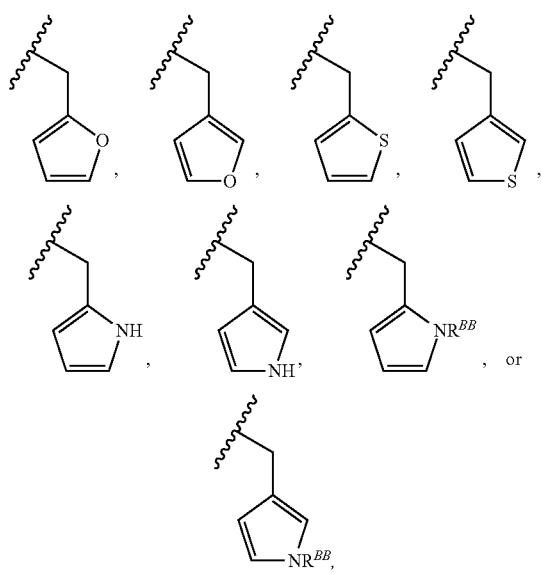

wherein $R^{BB}$ is as defined herein.

However, in some embodiments, $R_2$ is not:

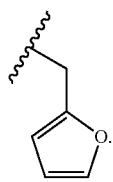 [SMILES: *Cc1ccco1]

In certain embodiments, $R_2$ is alkyl substituted by an optionally substituted $C_{3-7}$carbocyclyl group, e.g., an optionally substituted cyclopropyl, cyclopropenyl, cyclobutyl, cyclobutenyl, cyclopentyl, cyclopentenyl, cyclohexyl, cyclohexenyl, cyclohexadienyl, cycloheptyl, cycloheptenyl, cycloheptadienyl, or cycloheptatrienyl group. In certain embodiments, $R_2$ is alkyl substituted by an saturated carbocyclyl group, e.g., an optionally substituted cyclopropyl, cyclobutyl, cyclopentyl, cyclohexyl, or cycloheptyl group. In certain embodiments, $R_2$ is alkyl substituted by an optionally substituted cyclopropyl group ("optionally substituted cyclopropylalkyl"). In certain embodiments, $R_2$ is alkyl substituted by an optionally substituted cyclobutyl group ("optionally substituted cyclobutylalkyl"). In certain embodiments, $R_2$ is alkyl substituted by an optionally substituted cyclopentyl group ("optionally substituted cyclopentylalkyl"). In certain embodiments, $R_2$ is alkyl substituted by an optionally substituted cyclohexyl group ("optionally substituted cyclohexylalkyl"). In certain embodiments, $R_2$ is alkyl substituted by an optionally substituted cycloheptyl group ("optionally substituted cycloheptylalkyl").

In certain embodiments, wherein $R_2$ is alkyl substituted with an optionally substituted carbocyclyl ring, $R_2$ is a group of the formula:

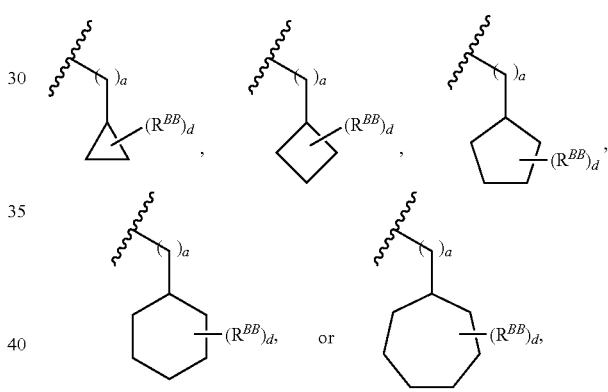

wherein:
a is an integer between 1 and 6, inclusive;
d is 0, 1, or 2;
e is 0 or an integer between 1 and 4, inclusive; and
$R^{BB}$ is as defined above and herein.

In some embodiments, a is 1. In some embodiments, a is 2. In some embodiments, a is 3. In some embodiments, a is 4. In some embodiments, a is 5. In some embodiments, a is 6. In certain embodiments, d is 0. In certain embodiments, d is 1. In certain embodiments, d is 2. In certain embodiments, e is 0. In certain embodiments, e is 1. In certain embodiments, e is 2. In certain embodiments, e is 3. In certain embodiments, e is 4.

In certain embodiments, wherein $R_2$ is alkyl substituted with an optionally substituted carbocyclyl ring, $R_2$ is a group of the formula:

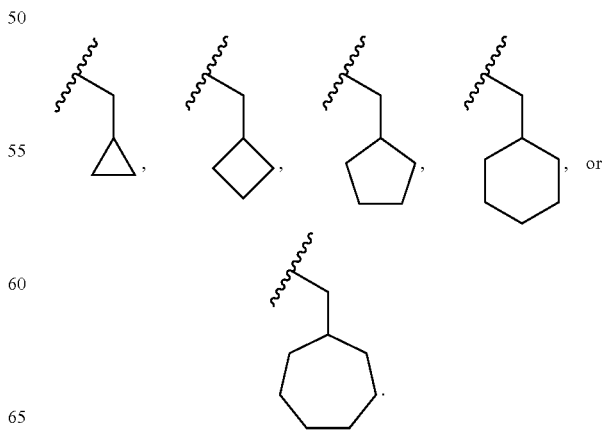

wherein a, d, and $R^{BB}$ is as defined herein. In certain embodiments, a is 1. In certain embodiments, d is 0.

In certain embodiments, wherein $R_2$ is alkyl substituted with an optionally substituted carbocyclyl ring, $R_2$ is a group of the formula:

However, in some embodiments, $R_2$ is not:

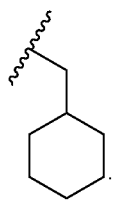

Embodiments of $R_3$

As generally defined above, each instance of $R_3$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_C$; —$N(R_C)_2$; —$SR_C$; =O; —CN; —$NO_2$; —SCN; —$SOR_C$; or —$SO_2R_C$; wherein each occurrence of $R_C$ is independently hydrogen; a protecting group; substituted or unsubstituted aliphatic; substituted or unsubstituted heteroaliphatic; acyl; substituted or unsubstituted aryl; or substituted or unsubstituted heteroaryl.

In certain embodiments, $R_3$ is hydrogen. In certain embodiments, $R_3$ is halogen, i.e., —F, —Cl, —Br, or —I. In certain embodiments, $R_3$ is —$OR_C$. In certain embodiments, $R_3$ is —$N(R_C)_2$. In certain embodiments, $R_3$ is —$SR_C$. In certain embodiments, $R_3$ is =O. In certain embodiments, $R_3$ is —CN. In certain embodiments, $R_3$ is —$NO_2$. In certain embodiments, $R_3$ is —SCN. In certain embodiments, $R_3$ is —$SOR_C$. In certain embodiments, $R_3$ is —$SO_2R_C$.

In certain embodiments, $R_3$ is acyl. For example, in certain embodiments, $R_3$ is acyl selected from the group consisting of —C(=O)$R^{C5}$, —C(=O)$OR^{C5}$, —C(=O)$SR^{C5}$, —C(=O)N($R^{C6}$)$_2$, —C(=N$R^{C6}$)$R^{C5}$, —C(=N$R^{C6}$)$OR^{C5}$, —C(=N$R^{C6}$)$SR^{C5}$, —C(=N$R^{C6}$)N($R^{C6}$)$_2$, —C(=S)$R^{C5}$, —C(=S)$OR^{C5}$, —C(=S)$SR^{C5}$, and —C(=S)N($R^{C6}$)$_2$, wherein each occurrence of $R^{C5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{C6}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{C6}$ groups are joined to form an substituted or unsubstituted heterocyclic ring.

In certain embodiments, $R_3$ is substituted or unsubstituted aryl, e.g., phenyl, napthyl. In certain embodiments, $R_3$ is substituted or unsubstituted phenyl. In certain embodiments, $R_3$ is substituted phenyl, e.g., a monosubstituted, disubstituted, or trisubstituted phenyl.

In certain embodiments, $R_3$ is substituted or unsubstituted heteroaryl, e.g., a substituted or unsubstituted 5- to 6-membered heteroaryl. In certain embodiments, $R_2$ is a substituted or unsubstituted 5-membered heteroaryl, e.g., pyrrolyl, furanyl, thiophenyl, imidazolyl, pyrazolyl, oxazolyl, isoxazolyl, thiazolyl, isothiazolyl, triazolyl, oxadiazolyl, thiadiazolyl, or tetrazolyl. In certain embodiments, $R_3$ is a substituted or unsubstituted 6-membered heteroaryl, e.g., pyridinyl, pyridazinyl, pyrimidinyl, pyrazinyl, triazinyl, or tetrazinyl.

In certain embodiments, $R_3$ is substituted or unsubstituted aliphatic. In certain embodiments, $R_3$ is a substituted or unsubstituted aliphatic group comprising 1 to 10 carbon atoms ("$C_{1-10}$aliphatic"). In certain embodiments, $R_3$ is substituted or unsubstituted aliphatic group comprising 1 to 8 carbon atoms ("$C_{1-8}$aliphatic"). In certain embodiments, $R_3$ is a substituted or unsubstituted aliphatic group comprising 1 to 6 carbon atoms ("$C_{1-6}$aliphatic"). In certain embodiments, $R_3$ is a substituted or unsubstituted aliphatic group comprising 1 to 4 carbon atoms ("$C_{1-4}$aliphatic"). In certain embodiments, $R_3$ is a substituted or unsubstituted aliphatic group comprising 1 to 3 carbon atoms ("$C_{1-3}$aliphatic"). In certain embodiments, $R_3$ is a substituted or unsubstituted aliphatic group comprising 1 carbon atom ("$C_1$aliphatic"). In certain embodiments, $R_3$ is a substituted or unsubstituted aliphatic group comprising 2 carbon atoms ("$C_2$aliphatic"). In certain embodiments, $R_3$ is a substituted or unsubstituted aliphatic group comprising 3 carbon atoms ("$C_3$aliphatic"). In any of the above embodiments, $R_3$ is an acyclic aliphatic group. In any of the above embodiments, $R_3$ is an acyclic and substituted aliphatic group. In any of the above embodiments, the aliphatic group is an alkyl, alkenyl, or alkynyl group.

In certain embodiments, $R_3$ is substituted or unsubstituted alkyl. In certain embodiments, $R_3$ is unsubstituted alkyl. In certain embodiments, $R_2$ is substituted alkyl. In certain embodiments, $R_3$ is substituted $C_{1-10}$alkyl. In certain embodiments, $R_3$ is substituted $C_{1-8}$alkyl. In certain embodiments, $R_3$ is substituted $C_{1-6}$alkyl. In certain embodiments, $R_3$ is substituted $C_{1-5}$alkyl. In certain embodiments, $R_3$ is substituted $C_{1-4}$alkyl. In certain embodiments, $R_3$ is substituted $C_{1-3}$alkyl. In certain embodiments, $R_3$ is substituted $C_{1-2}$alkyl. In certain embodiments, $R_3$ is substituted $C_{2-4}$alkyl. In certain embodiments, $R_2$ is substituted $C_1$alkyl. In certain embodiments, $R_3$ is substituted $C_2$alkyl. In certain embodiments, $R_3$ is substituted $C_3$alkyl. In certain embodiments, $R_3$ is substituted $C_4$alkyl.

In certain embodiments, $R_3$ is substituted or unsubstituted alkenyl. In certain embodiments, $R_3$ is unsubstituted alkenyl. In certain embodiments, $R_3$ is substituted alkenyl. In certain embodiments, $R_3$ is substituted $C_{2-10}$alkenyl. In certain embodiments, $R_3$ is substituted $C_{2-8}$alkenyl. In certain embodiments, $R_3$ is substituted $C_{2-6}$alkenyl. In certain embodiments, $R_3$ is substituted $C_{2-5}$alkenyl. In certain embodiments, $R_3$ is substituted $C_{2-4}$alkenyl. In certain embodiments, $R_3$ is substituted $C_{2-3}$alkenyl. In certain embodiments, $R_3$ is substituted $C_1$alkenyl. In certain embodiments, $R_3$ is substituted $C_2$alkenyl. In certain embodiments, $R_3$ is substituted $C_3$alkenyl. In certain embodiments, $R_3$ is substituted $C_4$alkenyl.

In certain embodiments, $R_3$ is substituted or unsubstituted heteroaliphatic. In certain embodiments, $R_3$ is substituted or unsubstituted heteroaliphatic group comprising 1 to 10 carbon atoms and 1 to 3 heteroatoms independently selected from oxygen, nitrogen, and sulfur ("$C_{1-10}$heteroaliphatic"). In certain embodiments, the heteroaliphatic group comprises 1 heteroatom selected from oxygen, nitrogen, and sulfur. In certain embodiments, the heteroaliphatic group comprises 2 heteroatoms independently selected from oxygen, nitrogen, and sulfur. In certain embodiments, the heteroaliphatic group comprises 3 heteroatoms independently selected from oxygen, nitrogen, and sulfur. In certain embodiments, $R_3$ is a substituted or unsubstituted heteroaliphatic group comprising 1 to 8 carbon atoms and 1-3 heteroatoms selected from oxygen, nitrogen, and sulfur ("$C_{1-8}$heteroaliphatic"). In certain embodiments, $R_3$ is a substituted or unsubstituted heteroaliphatic group comprising 1 to 6 carbon atoms and 1-2 heteroatoms selected from oxygen, nitrogen, and sulfur ("$C_{1-6}$heteroaliphatic"). In certain embodiments, $R_3$ is a substituted or unsubstituted heteroaliphatic group comprising 1 to 4 carbon atoms and 1-2 heteroatoms selected from oxygen, nitrogen, and sulfur ("$C_{1-4}$heteroaliphatic"). In certain embodiments, $R_3$ is a substituted or unsubstituted heteroaliphatic group comprising 1 to 3 carbon atoms and 1 heteroatom selected from oxygen, nitrogen, and sulfur ("$C_{1-3}$ heteroaliphatic"). In certain embodiments, $R_3$ is a substituted or unsubstituted heteroaliphatic group comprising 1 carbon atom and 1 heteroatom selected from oxygen, nitrogen, and sulfur ("$C_1$heteroaliphatic"). In certain embodiments, $R_3$ is a substituted or unsubstituted heteroaliphatic group comprising 2 carbon atoms and 1 heteroatom selected from oxygen, nitrogen, and sulfur ("$C_2$heteroaliphatic"). In certain embodiments, $R_3$ is a substituted or unsubstituted heteroaliphatic group comprising 3 carbon atoms and 1 heteroatom selected from oxygen, nitrogen, and sulfur ("$C_3$heteroaliphatic"). In any of the above embodiments, $R_3$ is an acyclic heteroaliphatic group. In any of the above embodiments, $R_3$ is an acyclic and substituted heteroaliphatic group. In any of the above embodiments, the heteroaliphatic group is an heteroalkyl, heteroalkenyl, or heteroalkynyl group.

In certain embodiments, $R_3$ is substituted or unsubstituted heteroalkyl comprising 10 carbon atoms and 1-3 heteroatoms selected from oxygen, nitrogen, and sulfur ("substituted $C_{1-10}$heteroalkyl"). In certain embodiments, the heteroalkyl group comprises 1 heteroatom selected from oxygen, nitrogen, and sulfur. In certain embodiments, the heteroalkyl group comprises 2 heteroatoms independently selected from oxygen, nitrogen, and sulfur. In certain embodiments, the heteroalkyl group comprises 3 heteroatoms independently selected from oxygen, nitrogen, and sulfur. In certain embodiments, $R_3$ is a substituted heteroalkyl comprising 1-8 carbon atoms and 1-3 heteroatoms selected from oxygen, nitrogen, and sulfur ("substituted $C_{1-8}$heteroalkyl"). In certain embodiments, $R_3$ is a substituted heteroalkyl comprising 1-6 carbon atoms and 1-2 heteroatoms selected from oxygen, nitrogen, and sulfur ("substituted $C_{1-6}$heteroalkyl"). In certain embodiments, $R_3$ is a substituted heteroalkyl comprising 1-4 carbon atoms and 1-2 heteroatoms selected from oxygen, nitrogen, and sulfur ("substituted $C_{1-4}$heteroalkyl"). In certain embodiments, $R_3$ is a substituted heteroalkyl comprising 1-3 carbon atoms and 1 heteroatom selected from oxygen, nitrogen, and sulfur ("substituted $C_{1-3}$heteroalkyl"). In certain embodiments, $R_3$ is a substituted heteroalkyl comprising 1-2 carbon atoms and 1 heteroatom selected from oxygen, nitrogen, and sulfur ("substituted $C_{1-2}$heteroalkyl"). In certain embodiments, $R_3$ is a substituted heteroalkyl comprising 1 carbon atom and 1 heteroatom selected from oxygen, nitrogen, and sulfur ("substituted $C_1$heteroalkyl"). In certain embodiments, $R_3$ is a substituted heteroalkyl comprising 2 carbon atoms and 1 heteroatom selected from oxygen, nitrogen, and sulfur ("substituted $C_2$heteroalkyl"). In certain embodiments, $R_3$ is a substituted heteroalkyl comprising 3 carbon atoms and 1 heteroatom selected from oxygen, nitrogen, and sulfur ("substituted $C_3$heteroalkyl"). In certain embodiments, $R_3$ is a substituted heteroalkyl comprising 4 carbon atoms and 1-2 heteroatoms selected from oxygen, nitrogen, and sulfur ("substituted $C_4$heteroalkyl").

As generally understood from the above, in certain embodiments, $R_3$ is a group selected from aliphatic, heteroaliphatic, aryl, or heteroaryl which may be unsubstituted or substituted with one or more substituents. Exemplary $R_3$ group substituents, collectively referred to as "$R^C$", include, but are not limited to, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{C1}$, —$N(R^{C2})_2$, —$SR^{C1}$, —$C(=O)R^{C1}$, —$C(=O)OR^{C1}$, —$C(=O)SR^{C1}$, —$C(=O)N(R^{C2})_2$, —$OC(=O)R^{C1}$, —$OC(=O)OR^{C1}$, —$OC(=O)SR^{C1}$, —$OC(=O)N(R^{C2})_2$, —$NR^{C2}C(=O)R^{C2}$, —$NR^{C2}C(=O)OR^{C1}$, —$NR^{C2}C(=O)SR^{C1}$, —$NR^{C2}C(=O)N(R^{C2})_2$, —$SC(=O)R^{C1}$, —$SC(=O)OR^{C1}$, —$SC(=O)SR^{C1}$, —$SC(=O)N(R^{C2})_2$, —$C(=NR^{C2})R^{C1}$, —$C(=NR^{C2})OR^{C1}$, —$C(=NR^{C2})SR^{C1}$, —$C(=NR^{C2})N(R^{C2})_2$, —$OC(=NR^{C2})R^{C1}$, —$OC(=NR^{C2})OR^{C1}$, —$OC(=NR^{C2})SR^{C1}$, —$OC(=NR^{C2})N(R^{C2})_2$, —$NR^{C2}C(=NR^{C2})R^{C2}$, —$NR^{C2}C(=NR^{C2})OR^{C1}$, —$NR^{C2}C(=NR^{C2})SR^{C1}$, —$NR^{C2}C(=NR^{C2})N(R^{C2})_2$, —$SC(=NR^{C2})R^{C1}$, —$SC(=NR^{C2})OR^{C1}$, —$SC(=NR^{C2})SR^{C1}$, —$SC(=NR^{C2})N(R^{C2})_2$, —$C(=S)R^{C1}$, —$C(=S)OR^{C1}$, —$C(=S)SR^{C1}$, —$C(=S)N(R^{C2})_2$, —$OC(=S)R^{C1}$, —$OC(=S)OR^{C1}$, —$OC(=S)SR^{C1}$, —$OC(=S)N(R^{C2})_2$, —$NR^{C2}C(=S)R^{C2}$, —$NR^{C2}C(=S)OR^{C1}$, —$NR^{C2}C(=S)SR^{C1}$, —$NR^{C2}C(=S)N(R^{C2})_2$, —$SC(=S)R^{C1}$, —$SC(=S)OR^{C1}$, —$SC(=S)SR^{C1}$, —$SC(=S)N(R^{C2})_2$, —$S(=O)R^{C1}$, —$SO_2R^{C1}$, —$NR^{C2}SO_2R^{C1}$, —$SO_2N(R^{C2})_2$, —$N_3$, —$CN$, —$SCN$, and —$NO_2$, wherein each occurrence of $R^{C1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{C2}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{C2}$ groups are joined to form an substituted or unsubstituted heterocyclic ring.

In certain embodiments, $R_3$ is aliphatic, as defined above and herein, substituted by one or more $R^C$ substituents, as provided above, e.g., 1, 2, 3, or 4 substituents. In certain embodiments, $R_3$ is alkyl, as defined above and herein, substituted by one or more $R^C$ substituents, as provided above, e.g., 1, 2, 3, or 4 substituents. In certain embodiments, $R_3$ is a $C_{1-4}$alkyl substituted by one or more $R^C$ substituents, as provided above, e.g., 1, 2, 3, or 4 substituents. In certain embodiments, $R_3$ is a $C_{2-4}$alkenyl substituted by one or more $R^C$ substituents, as provided above, e.g., 1, 2, 3, or 4 substituents.

For example, in certain embodiments, $R_3$ is aliphatic substituted by an optionally substituted aryl or optionally substituted heteroaryl group, e.g., an optionally substituted phenyl group or optionally substituted 5- to 6-membered heteroaryl group.

In certain embodiments, $R_3$ is aliphatic substituted by an optionally substituted aryl group ("optionally substituted aryllaliphatic"). In certain embodiments, the aryl group is an optionally substituted phenyl ("optionally substituted phenyllaliphatic"). In certain embodiments, the aryl group is unsubstituted. However, in certain embodiments, the aryl group is substituted. For example, in certain embodiments, the aryl group is a monosubstituted phenyl ring, e.g., substituted at the ortho, meta, or para position of the phenyl ring relative to the point of attachment. In certain embodiments, the aryl group is a disubstituted phenyl ring, e.g., substituted at the 1,2-, the 1,3-, the 1,4-, the 2,3-, the 3,4-, or the 2,4-positions of the phenyl ring relative to the point of attachment. In certain embodiments, the aryl group is a trisubstituted phenyl ring, e.g., substituted at the 1,2,3-, the 1,2,4-, or the 2,3,4-, positions of the phenyl ring relative to the point of attachment. In certain embodiments, the aryl group is a tetrasubstituted phenyl ring. In any of the above embodiments, the aliphatic group is selected from alkyl, alkenyl, or alkynyl. In certain embodiments, the aliphatic group is alkyl. For example, in certain embodiments, $R_3$ is alkyl substituted by an optionally substituted aryl group ("optionally substituted arylalkyl"), e.g., an optionally substituted phenyl group ("optionally substituted phenylalkyl"). In certain embodiments, $R_3$ is a $C_{1-4}$alkyl substituted by an optionally substituted aryl group, e.g., an optionally substituted phenyl group. In certain embodiments, $R_3$ is a $C_1$alkyl substituted by an optionally substituted aryl group, e.g., an optionally substituted phenyl group. In certain embodiments, the aliphatic group is alkenyl. For example, in certain embodiments, $R_3$ is a $C_{2-4}$alkenyl substituted by an optionally substituted aryl group ("optionally substituted arylalkenyl"), e.g., an optionally substituted phenyl group ("optionally substituted phenylalkenyl"). In certain embodiments, $R_3$ is a $C_2$alkenyl substituted by an optionally substituted aryl group, e.g., an optionally substituted phenyl group. In certain embodiments, $R_3$ is a $C_3$alkenyl substituted by an optionally substituted aryl group, e.g., an optionally substituted phenyl group.

In certain embodiments, $R_3$ is aliphatic substituted by an optionally substituted 5- to 6-membered heteroaryl group, e.g., a substituted or unsubstituted 5-membered heteroaryl, e.g., pyrrolyl, furanyl, thiophenyl, imidazolyl, pyrazolyl, oxazolyl, isoxazolyl, thiazolyl, isothiazolyl, triazolyl, oxadiazolyl, thiadiazolyl, or tetrazolyl, or a substituted or unsubstituted 6-membered heteroaryl, e.g., pyridinyl, pyridazinyl, pyrimidinyl, pyrazinyl, triazinyl, or tetrazinyl. In certain embodiments, the heteroaryl group is a substituted 5- to 6-membered heteroaryl ("substituted 5- to 6-membered heteroarylaliphatic"). In any of the above embodiments, the aliphatic group is selected from alkyl, alkenyl, or alkynyl. In certain embodiments, the aliphatic group is alkyl. For example, in certain embodiments, $R_3$ is alkyl substituted by a substituted by an optionally substituted heteroaryl group ("optionally substituted heteroarylalkyl"), e.g., an optionally substituted 5- to 6-membered heteroaryl group ("optionally substituted 5- to 6-membered heteroarylalkyl"). In certain embodiments, $R_3$ is a $C_{1-4}$alkyl substituted by an optionally substituted heteroaryl group, e.g., an optionally substituted 5- to 6-membered heteroaryl group. In certain embodiments, $R_3$ is a $C_1$alkyl substituted by an optionally substituted heteroaryl group, e.g., an optionally substituted 5- to 6-membered heteroaryl group. In certain embodiments, $R_3$ is a $C_{2-4}$alkenyl substituted by an optionally substituted heteroaryl group, e.g., an optionally substituted 5- to 6-membered heteroaryl group. In certain embodiments, $R_3$ is a $C_2$alkenyl substituted by an optionally substituted heteroaryl group, e.g., an optionally substituted 5- to 6-membered heteroaryl group. In certain embodiments, $R_3$ is a $C_3$alkenyl substituted by an optionally substituted heteroaryl group, e.g., an optionally substituted 5- to 6-membered heteroaryl group. In any of the above embodiments, the heteroaryl group is substituted. However, in any of the above embodiments, the heteroaryl group is unsubstituted.

In certain embodiments, $R_3$ is aliphatic substituted by a substituted or unsubstituted carbocyclyl ("optionally substituted carbocylcyl") or a substituted or unsubstituted heterocyclyl ("optionally substituted heterocyclyl"), e.g., optionally substituted $C_{3-8}$carbocyclyl or optionally substituted 5- to 8-membered heterocyclyl.

For example, in certain embodiments, $R_3$ is aliphatic substituted by an optionally substituted 5- to 8-membered heterocyclyl comprising 1 to 3 heteroatoms selected from oxygen, nitrogen, and sulfur. In certain embodiments, $R_3$ is aliphatic substituted by an optionally substituted 8-membered heterocyclyl comprising 1 to 3 heteroatoms selected from oxygen, nitrogen, and sulfur, e.g., azocanyl, oxecanyl, or thiocanyl. In certain embodiments, $R_3$ is aliphatic substituted by an optionally substituted 7-membered heterocyclyl comprising 1 to 3 heteroatoms selected from oxygen, nitrogen, and sulfur, e.g., azepanyl, oxepanyl, or thiepanyl. In certain embodiments, $R_3$ is aliphatic substituted by an optionally substituted 6-membered heterocyclyl comprising 1 to 3 heteroatoms selected from oxygen, nitrogen, and sulfur, e.g., piperazinyl, morpholinyl, dithianyl, dioxanyl, triazinanyl, and 6,6-bicycles such as tetrahydroquinolinyl and tetrahydroisoquinolinyl. In certain embodiments, $R_3$ is aliphatic substituted by an optionally substituted 5-membered heterocyclyl comprising 1 to 3 heteroatoms selected from oxygen, nitrogen, and sulfur, e.g., tetrahydrofuranyl, dihydrofuranyl, tetrahydrothiophenyl, dihydrothiophenyl, pyrrolidinyl, dihydropyrrolyl, pyrrolyl-2,5-dione, dioxolanyl, oxasulfuranyl, disulfuranyl, oxazolidin-2-one, triazolinyl, oxadiazolinyl, thiadiazolinyl, and 5,6-bicycles such as indolinyl, isoindolinyl, dihydrobenzofuranyl, dihydrobenzothienyl, and benzoxazolinonyl. In any of the above embodiments, the heterocyclyl contains 1 heteroatom. In any of the above embodiments, the heterocyclyl contains 2 heteroatoms. In any of the above embodiments, the heterocyclyl contains 3 heteroatoms. In any of the above embodiments, the aliphatic group is selected from alkyl, alkenyl, or alkynyl. In certain embodiments, the aliphatic group is alkyl. For example, in certain embodiments, $R_3$ is alkyl substituted by a substituted by an optionally substituted heterocyclyl group ("optionally substituted heterocyclylalkyl"), e.g., an optionally substituted 5- to 8-membered heterocyclyl comprising 1 to 3 heteroatoms selected from oxygen, nitrogen, and sulfur. In certain embodiments, $R_3$ is a $C_{1-4}$alkyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_3$ is a $C_1$alkyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_3$ is a $C_{2-4}$alkenyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_3$ is a $C_2$alkenyl substituted by an optionally substituted heterocyclyl group, e.g., an optionally substituted 5- to 8-membered heterocyclyl comprising 1 to 3 heteroatoms selected from oxygen, nitrogen, and sulfur. In certain embodiments, $R_3$ is a $C_3$alkenyl substituted by an optionally substituted heterocyclyl group, e.g., an optionally substituted 5- to 8-membered heterocyclyl comprising 1 to 3 heteroatoms selected from oxygen, nitrogen, and sulfur. In any of the above embodiments, the heterocyclyl group is not substituted. However, in any of the above embodiments, the heterocyclyl group is substituted.

In certain embodiments, $R_3$ is aliphatic substituted by an optionally substituted $C_{3-7}$carbocyclyl. In certain embodiments, $R_3$ is aliphatic substituted by an optionally substituted $C_{3-6}$carbocyclyl. In certain embodiments, $R_3$ is aliphatic substituted by an optionally substituted $C_{3-5}$carbocyclyl. In certain embodiments, $R_3$ is aliphatic substituted by an optionally substituted $C_{3-4}$carbocyclyl. In certain embodiments, $R_3$ is aliphatic substituted by an optionally substituted $C_{4-6}$carbocyclyl. In certain embodiments, $R_3$ is aliphatic substituted by an optionally substituted $C_3$carbocyclyl, e.g., optionally substituted cyclopropyl or optionally substituted cyclopropenyl. In certain embodiments, $R_3$ is aliphatic substituted by an optionally substituted $C_4$carbocyclyl, e.g., optionally substituted cyclobutyl or optionally substituted cyclobutenyl. In certain embodiments, $R_3$ is aliphatic substituted by an optionally substituted $C_5$carbocyclyl, e.g., optionally substituted cyclopentyl or optionally substituted cyclopentenyl. In certain embodiments, $R_3$ is aliphatic substituted by an optionally substituted $C_6$carbocyclyl, e.g., optionally substituted cyclohexyl, optionally substituted cyclohexenyl, or optionally substituted cyclohexadienyl. In certain embodiments, $R_3$ is aliphatic substituted by an optionally substituted $C_7$carbocyclyl, e.g., optionally substituted cycloheptyl, optionally substituted cycloheptenyl, optionally substituted cycloheptadienyl, or optionally substituted cycloheptatrienyl. In any of the above embodiments, the aliphatic group is selected from alkyl, alkenyl, or alkynyl. In certain embodiments, the aliphatic group is alkyl. For example, in certain embodiments, $R_3$ is alkyl substituted by a substituted by an optionally substituted carbocyclyl group ("optionally substituted carbocyclylalkyl"), e.g., an optionally substituted $C_{3-7}$carbocyclyl group. In certain embodiments, $R_3$ is a $C_{1-4}$alkyl substituted by an optionally substituted carbocyclyl group, e.g., an optionally substituted $C_{3-7}$carbocyclyl. In certain embodiments, $R_3$ is a $C_1$alkyl substituted by an optionally substituted carbocyclyl group, e.g., an optionally substituted $C_{3-7}$carbocyclyl. In certain embodiments, $R_3$ is a $C_{2-4}$alkenyl substituted by an optionally substituted carbocyclyl group, e.g., an optionally substituted $C_{3-7}$carbocyclyl. In certain embodiments, $R_3$ is a $C_2$alkenyl substituted by an optionally substituted carbocyclyl group, e.g., an optionally substituted $C_{3-7}$carbocyclyl. In certain embodiments, $R_3$ is a $C_3$alkenyl substituted by an optionally substituted carbocyclyl group, e.g., an optionally substituted $C_{3-7}$carbocyclyl. In any of the above embodiments, the carbocyclyl group is not substituted. However, in any of the above embodiments, the carbocyclyl group is substituted.

As understood from the above, the carbocyclyl, heterocyclyl, aryl, and/or heteroaryl substituents present on the aliphatic group of $R_3$ may be unsubstituted or substituted with one or more substituents. Such substituents, collectively referred to herein as "$R^{CC}$", include, but are not limited to, halogen, substituted or unsubstituted alkyl (e.g., perhaloalkyl), substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{C3}$, —$N(R^{C4})_2$, —$SR^{C3}$, —$C(=O)R^{C3}$, —$C(=O)OR^{C3}$, —$C(=O)SR^{C3}$, —$C(=O)N(R^{C4})_2$, —$OC(=O)R^{C3}$, —$OC(=O)OR^{C3}$, —$OC(=O)SR^{C3}$, —$OC(=O)N(R^{C4})_2$, —$NR^{C4}C(=O)R^{C4}$, —$NR^{C4}C(=O)OR^{C3}$, —$NR^{C4}C(=O)SR^{C3}$, —$NR^{C4}C(=O)N(R^{C4})_2$, —$SC(=O)R^{C3}$, —$SC(=O)OR^{C3}$, —$SC(=O)SR^{C3}$, —$SC(=O)N(R^{C4})_2$, —$C(=NR^{C4})R^{C3}$, —$C(=NR^{C4})OR^{C3}$, —$C(=NR^{C4})SR^{C3}$, —$C(=NR^{C4})N(R^{C4})_2$, —$OC(=NR^{C4})R^{C3}$, —$OC(=NR^{C4})OR^{C3}$, —$OC(=NR^{C4})SR^{C3}$, —$OC(=NR^{C4})N(R^{C4})_2$, —$NR^{C4}C(=NR^{C4})R^{C2}$, —$NR^{C4}C(=NR^{C4})OR^{C3}$, —$NR^{C4}C(=NR^{C4})SR^{C3}$, —$NR^{C4}C(=NR^{C4})N(R^{C4})_2$, —$SC(=NR^{C4})R^{C3}$, —$SC(=NR^{C4})OR^{C3}$, —$SC(=NR^{C4})SR^{C3}$, —$SC(=NR^{C4})N(R^{C4})_2$, —$C(=S)R^{C3}$, —$C(=S)OR^{C3}$, —$C(=S)SR^{C3}$, —$C(=S)N(R^{C4})_2$, —$OC(=S)R^{C3}$, —$OC(=S)OR^{C3}$, —$OC(=S)SR^{C3}$, —$OC(=S)N(R^{C4})_2$, —$NR^{C4}C(=S)R^{C4}$, —$NR^{C4}C(=S)OR^{C3}$, —$NR^{C4}C(=S)SR^{C3}$, —$NR^{C4}C(=S)N(R^{C4})_2$, —$SC(=S)R^{C3}$, —$SC(=S)OR^{C3}$, —$SC(=S)SR^{C3}$, —$SC(=S)N(R^{C4})_2$, —$S(=O)R^{C}$, —$SO_2R^{C3}$, —$NR^{C4}SO_2R^{C3}$, —$SO_2N(R^{C4})_2$, —$N_3$, —CN, —SCN, and —$NO_2$, wherein each occurrence of $R^{C3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{C4}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{C4}$ groups are joined to form an substituted or unsubstituted heterocyclic ring.

In certain embodiments, at least one $R^{CC}$ substituent (e.g., 1, 2, 3, or 4 $R^{CC}$ substituents) is an electron-withdrawing group, e.g., a substituent which pulls electron density away from the parent molecule (e.g., a ring system) and/or stabilizes anions or electron rich structures. Exemplary electron-withdrawing substituents include, but are not limited to, halogen, perhaloalkyl, —$C(=O)R^{C3}$, —$C(=O)OR^{C3}$, —$C(=O)SR^{C3}$, —$C(=O)N(R^{C4})_2$, —$OC(=O)R^{C3}$, —$OC(=O)OR^{C3}$, —$OC(=O)SR^{C3}$, —$OC(=O)N(R^{C4})_2$, —$NR^{C4}C(=O)R^{C4}$, —$NR^{C4}C(=O)OR^{C3}$, —$NR^{C4}C(=O)SR^{C3}$, —$NR^{C4}C(=O)N(R^{C4})_2$, —$SC(=O)R^{C3}$, —$SC(=O)OR^{C3}$, —$SC(=O)SR^{C3}$, —$SC(=O)N(R^{C4})_2$, —$C(=NR^{C4})R^{C3}$, —$C(=NR^{C4})OR^{C3}$, —$C(=NR^{C4})SR^{C3}$, —$C(=NR^{C4})N(R^{C4})_2$, —$OC(=NR^{C4})R^{C3}$, —$OC(=NR^{C4})OR^{C3}$, —$OC(=NR^{C4})SR^{C3}$, —$OC(=NR^{C4})N(R^{C4})_2$, —$NR^{C4}C(=NR^{C4})R^{C4}$, —$NR^{C4}C(=NR^{C4})OR^{C3}$, —$NR^{C4}C(=NR^{C4})SR^{C3}$, —$NR^{C4}C(=NR^{C4})N(R^{C4})_2$, —$SC(=NR^{C4})R^{C3}$, —$SC(=NR^{C4})OR^{C3}$, —$SC(=NR^{C4})SR^{C3}$, —$SC(=NR^{C4})N(R^{C4})_2$, —$C(=S)R^{C3}$, —$C(=S)OR^{C3}$, —$C(=S)SR^{C3}$, —$C(=S)N(R^{C4})_2$, —$OC(=S)R^{C3}$, —$OC(=S)OR^{C3}$, —$OC(=S)SR^{C3}$, —$OC(=S)N(R^{C4})_2$, —$NR^{C4}C(=S)R^{C4}$, —$NR^{C4}C(=S)OR^{C3}$, —$NR^{C4}C(=S)SR^{C3}$, —$NR^{C4}C(=S)N(R^{C4})_2$, —$SC(=S)R^{C3}$, —$SC(=S)OR^{C3}$, —$SC(=S)SR^{C3}$, —$SC(=S)N(R^{C4})_2$, —$S(=O)R^{C3}$, —$SO_2R^{C3}$, —$NR^{C4}SO_2R^{C3}$, —$SO_2N(R^{C4})_2$, —CN, —SCN, and —$NO_2$, wherein $R^{C3}$ and $R^{C4}$ are as defined herein.

However, in certain embodiments, at least one $R^{CC}$ substituent (e.g., 1, 2, 3, or 4 $R^{BB}$ substituents) is an electron-donating group, e.g., a substituent which donates electron density toward the parent molecule (e.g., a ring system) and/or stabilizes cations or electron poor structures. Exemplary electron-donating substituents include, but are not limited to, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{C3}$, —$N(R^{C4})_2$, —$SR^{C3}$, wherein $R^{C3}$ and $R^{C4}$ are as defined herein.

Specific combinations of groups comprising $R_3$ are further contemplated.

In certain embodiments, $R_3$ is alkyl substituted by an optionally substituted $C_{3-7}$carbocyclyl group, e.g., an optionally substituted cyclopropyl, cyclopropenyl, cyclobutyl, cyclobutenyl, cyclopentyl, cyclopentenyl, cyclohexyl, cyclohexenyl, cyclohexadienyl, cycloheptyl, cycloheptenyl, cycloheptadienyl, or cycloheptatrienyl group. In certain embodiments, $R_3$ is alkyl substituted by an saturated carbocyclyl group, e.g., an optionally substituted cyclopropyl, cyclobutyl, cyclopentyl, cyclohexyl, or cycloheptyl group. In certain embodiments, $R_3$ is alkyl substituted by an optionally substituted cyclopropyl group ("optionally substituted cyclopropylalkyl"). In certain embodiments, $R_3$ is alkyl substituted by an optionally substituted cyclobutyl group ("optionally substituted cyclobutylalkyl"). In certain embodiments, $R_3$ is alkyl substituted by an optionally substituted cyclopentyl group ("optionally substituted cyclopentylalkyl"). In certain embodiments, $R_3$ is alkyl substituted by an optionally substituted cyclohexyl group ("optionally substituted cyclohexylalkyl"). In certain embodiments, $R_3$ is alkyl substituted by an optionally substituted cycloheptyl group ("optionally substituted cycloheptylalkyl").

In certain embodiments, wherein $R_3$ is alkyl substituted with an optionally substituted carbocyclyl ring, $R_3$ is a group of the formula:

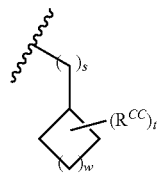

wherein:
s is an integer between 1 and 10, inclusive;
t is 0, 1, or 2;
w is 0 or an integer between 1 and 4, inclusive; and
each instance of $R^{BB}$ is independently as defined above and herein.

In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is an integer between 2 and 5, inclusive. In certain embodiments, t is 0. In certain embodiments, t is 1. In certain embodiments, t is 2. In certain embodiments, w is 0. In certain embodiments, w is 1. In certain embodiments, w is 2. In certain embodiments, w is 3. In certain embodiments, w is 4.

In certain embodiments, wherein $R_3$ is alkyl substituted with an optionally substituted carbocyclyl ring, $R_3$ is a group of the formula:

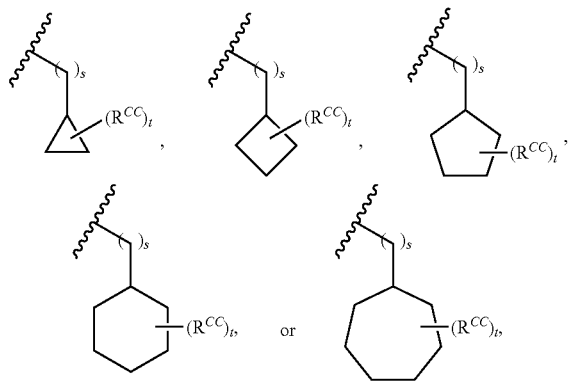

wherein s, t, and $R^{CC}$ is as defined herein. In certain embodiments, s is 1. In certain embodiments, t is 0.

In certain embodiments, wherein $R_3$ is alkyl substituted with an optionally substituted carbocyclyl ring, $R_3$ is a group of the formula:

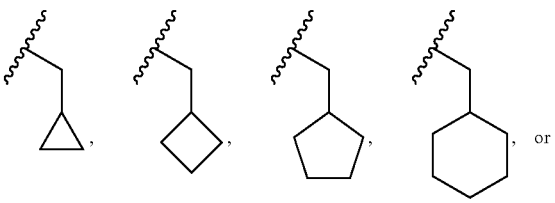

However, in some embodiments, $R_3$ is not:

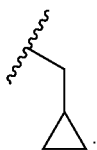 [SMILES: *CC1CC1]

In certain embodiments, $R_3$ is an optionally substituted arylalkyl group of the formula:

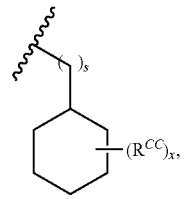

wherein:
s is an integer between 1 and 10, inclusive;
x is 0 or an integer between 1 and 5, inclusive; and
each instance of $R^{CC}$ is as defined herein.

In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is an integer between 2 and 5, inclusive. In certain embodiments, x is 0. In certain embodiments, x is 1. In certain embodiments, x is 2. In certain embodiments, x is 3. In certain embodiments, x is 4. In certain embodiments, x is 5. In certain embodiments, s is 1 and x is 0.

In certain embodiments, $R_3$ is an optionally substituted alkenyl group of the formula:

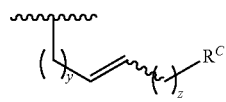

wherein:
y is 0 or an integer between 1 and 10, inclusive;
z is 0 or an integer between 1 and 4, inclusive;

provided that when z is >0 and $R^C$ is not hydrogen, the ⁓ indicates that the adjacent C—C double bond is in a cis or trans configuration; and $R^C$ is hydrogen or as defined herein.

In certain embodiments, y is 0. In certain embodiments, y is 1. In certain embodiments, y is 2. In certain embodiments, y is 3. In certain embodiments, y is 4. In certain embodiments, y is 5. In certain embodiments, y is 6. In certain embodiments, y is 7. In certain embodiments, y is 8. In certain embodiments, y is 9. In certain embodiments, y is 10. In certain embodiments, z is 0. In certain embodiments, z is 1. In certain embodiments, z is 2. In certain embodiments, z is 3. In certain embodiments, z is 4. In certain embodiments, wherein z is >0 and $R^C$ is not hydrogen, the ⁓ indicates that the adjacent C—C double bond is in a cis configuration. In certain embodiments, wherein z is >0 and $R^C$ is not hydrogen, the ⁓ indicates that the adjacent C—C double bond is in a trans configuration. In certain embodiments, $R^C$ is hydrogen. In certain embodiments, $R^C$ is optionally substituted aryl.

In certain embodiments of the above formula, wherein $R^C$ is optionally substituted aryl, $R_3$ is an optionally substituted alkenylaryl group of the formula:

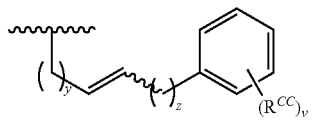

wherein y, z, and $R^{CC}$ are as defined herein, and v is 0 or an integer between 1 and 5, inclusive.

In certain embodiments, v is 0. In certain embodiments, v is 1. In certain embodiments, v is 2. In certain embodiments, v is 3. In certain embodiments, v is 4. In certain embodiments, v is 5.

In certain embodiments of the above formula, wherein $R^C$ is optionally substituted aryl, $R_3$ is an optionally substituted alkenylaryl group of the formula:

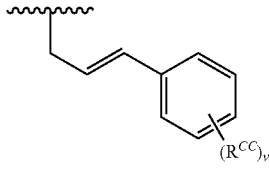

wherein y, z, v, and $R^{CC}$ are as defined herein.

In certain embodiments, $R_3$ is

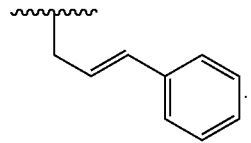 [SMILES: *C/C=C/c1ccccc1]

In certain embodiments, $R_3$ is

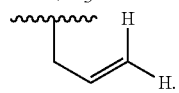

However, in certain embodiments, $R_3$ is not

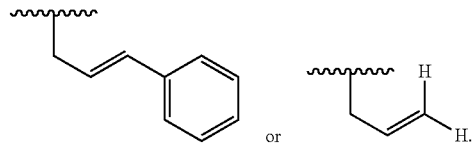

Other Embodiments

As generally defined above, $R_4$ is substituted or unsubstituted aliphatic; substituted or unsubstituted heteroaliphatic; substituted or unsubstituted aryl; substituted or unsubstituted heteroaryl; —N($R_D$)$_2$; —O$R_D$; or —S$R_D$; wherein each occurrence of $R_D$ is independently hydrogen; a protecting group; substituted or unsubstituted aliphatic; substituted or unsubstituted heteroaliphatic; acyl; substituted or unsubstituted aryl; or substituted or unsubstituted heteroaryl; or two $R_D$ groups are joined to form a substituted or unsubstituted heterocyclic group; optionally wherein $R^4$ further comprises a label, resin, or therapeutic agent attached thereto.

In certain embodiments, $R_4$ is substituted or unsubstituted aliphatic.

In certain embodiments, $R_4$ is substituted or unsubstituted heteroaliphatic.

In certain embodiments, $R_4$ is substituted or unsubstituted aryl.

In certain embodiments, $R_4$ is substituted or unsubstituted heteroaryl.

In certain embodiments, $R_4$ is —N($R_D$)$_2$. In certain embodiments, $R_4$ is —NH($R_D$). In certain embodiments, $R_4$ is —NH$_2$. In certain embodiments, $R_D$ is hydrogen or substituted or unsubstituted alkyl, e.g., $C_{1-6}$ alkyl. In certain embodiments, $R_D$ is hydrogen or substituted or unsubstituted $C_{1-3}$alkyl, e.g., hydrogen, methyl, ethyl, n-propyl, or isopropyl.

In certain embodiments, $R_4$ is —O$R_D$. In certain embodiments, $R_4$ is —OH. In certain embodiments, $R_D$ is hydrogen or substituted or unsubstituted alkyl, e.g., $C_{1-6}$alkyl. In certain embodiments, $R_D$ is hydrogen or substituted or unsubstituted $C_{1-3}$ alkyl, e.g., hydrogen, methyl, ethyl, n-propyl, or isopropyl.

In certain embodiments, $R_4$ is —S$R_D$. In certain embodiments, $R_4$ is —SH. In certain embodiments, $R_D$ is hydrogen or substituted or unsubstituted alkyl, e.g., $C_{1-6}$alkyl. In certain embodiments, $R_D$ is hydrogen or substituted or unsubstituted $C_{1-3}$ alkyl, e.g., hydrogen, methyl, ethyl, n-propyl, or isopropyl.

It is understood from the above that in certain embodiments, $R_4$ is comprises a label, resin, or therapeutic agent attached thereto, e.g., (i) the label, resin, or therapeutic agent is directly attached to the macrocycle via a bond; (ii) the label, resin, or therapeutic agent is attached to an $R_4$ group, e.g., a substituted aliphatic, substituted heteroaliphatic, substituted aryl, or substituted heteroaryl wherein the substituent covalently or non-covalently attached thereto is a resin, a label, or a therapeutic agent; (iii) the label, resin, or therapeutic agent is attached an $R^D$ group, wherein $R^D$ is substituted aliphatic, substituted heteroaliphatic, substituted aryl, or substituted heteroaryl wherein the substituent covalently or non-covalently attached thereto is a resin, a label, or a therapeutic agent; or (iv) $R^D$ is a label, resin, or therapeutic agent. In certain embodiments, at least one $R^D$ is a label, resin, or therapeutic agent. In certain embodiments, the substituent is a resin. In certain embodiments, the substituent is a label. In certain embodiments, the substituent is a therapeutic agent. In certain embodiments, the therapeutic agent is a small molecule, i.e., having a molecular weight under 800 g/mol, under 700 g/mol, under 600 g/mol, under 500 g/mol, under 400 g/mol, under 300 g/mol, under 200 g/mol, under 100 g/mol, under 50 g/mol, under 40 g/mol, under 30 g/mol, under 20 g/mol, or under 15 g/mol, e.g., between 15 g/mol and 800 g/mol. In certain embodiments, the therapeutic agent is an anti-cancer agent.

As generally defined above, each occurrence of $R_E$, $R_F$, $R_G$, $R_H$, and $R_I$ is independently hydrogen; acyl; a nitrogen protecting group; substituted or unsubstituted aliphatic; substituted or unsubstituted heteroaliphatic; substituted or unsubstituted aryl; substituted or unsubstituted heteroaryl; substitute or unsubstituted hydroxyl; substituted or unsubstituted thiol; substituted or unsubstituted amino; or halogen; optionally wherein an $R_1$ group and $R^F$ are joined to form a substituted or unsubstituted heterocyclic ring; an $R_2$ group and $R^G$ are joined to form a substituted or unsubstituted heterocyclic ring; and/or an $R_3$ group and $R^H$ are joined to form a substituted or unsubstituted heterocyclic ring.

In certain embodiments, each occurrence of $R_E$, $R_F$, $R_G$, $R_H$, and $R_I$ is independently hydrogen, a nitrogen protecting group, or substituted or unsubstituted aliphatic. In certain embodiments, each occurrence of $R_E$, $R_F$, $R_G$, $R_H$, and $R_I$ is independently hydrogen, a nitrogen protecting group, or substituted or unsubstituted alkyl. In certain embodiments, each occurrence of $R_E$, $R_F$, $R_G$, $R_H$, and $R_I$ is independently hydrogen or alkyl (e.g., —$CH_3$). In certain embodiments, each occurrence of $R_E$, $R_F$, $R_G$, $R_H$, and $R_I$ is independently hydrogen.

In certain embodiments, an $R_1$ group and $R^F$ are joined to form a substituted or unsubstituted heterocyclic ring; e.g., an optionally substituted proline ring.

In certain embodiments, an $R_2$ group and $R^G$ are joined to form a substituted or unsubstituted heterocyclic ring, e.g., an optionally substituted proline ring.

In certain embodiments, an $R_3$ group and $R^H$ are joined to form a substituted or unsubstituted heterocyclic ring; e.g., an optionally substituted proline ring.

As generally defined above, n is 0 or an integer between 1-4, inclusive. In certain embodiments, n is an integer between 1-4, inclusive. In certain embodiments, n is an integer between 2-4, inclusive. In certain embodiments, n is an integer between 2-3, inclusive. In certain embodiments, n is an integer between 3-4, inclusive. In certain embodiments, n is 0. In certain embodiments, n is 1. In certain embodiments, n is 2. In certain embodiments, n is 3. In certain embodiments, n is 4.

As generally defined above, m is 0 or an integer between 1-4, inclusive. In certain embodiments, m is an integer between 1-4, inclusive. In certain embodiments, m is an integer between 2-4, inclusive. In certain embodiments, m is an integer between 2-3, inclusive. In certain embodiments, m is an integer between 3-4, inclusive. In certain embodiments, m is 0. In certain embodiments, m is 1. In certain embodiments, m is 2. In certain embodiments, m is 3. In certain embodiments, m is 4.

In certain embodiments, n+m≤4. In certain embodiments, n+m≤3. In certain embodiments, n+m≤2. In certain embodiments, n is an integer between 2-4, inclusive, and m is 0. In certain embodiments, n is 2, and m is 0. In certain embodiments, n is 3, and m is 0. In certain embodiments, n is 4, and m is 0.

As generally defined above, f is an integer between 1-3, inclusive. In certain embodiments, f is 1. In certain embodiments, f is 2. In certain embodiments, f is 3.

As generally defined above, g is an integer between 1-3, inclusive. In certain embodiments, g is 1. In certain embodiments, g is 2. In certain embodiments, g is 3.

As generally defined above, h is an integer between 1-3, inclusive. In certain embodiments, h is 1. In certain embodiments, h is 2. In certain embodiments, h is 3.

As generally defined above, ═══ represents a single or double C—C bond. In certain embodiments, ═══ represents a single C—C bond. In certain embodiments, ═══ represents a double C—C bond. Furthermore, as generally defined above, when ═══ represents a double C—C bond, ⌇⌇ indicates that the adjacent C—C double bond in a cis or trans configuration. In some embodiments, ⌇⌇ represents an adjacent C—C double bond in the cis configuration. In other embodiments, ⌇⌇ represents an adjacent C—C double bond in the trans configuration. ⌇⌇

Additional Embodiments of Formula (I)

Various embodiments of Formula (I) are further contemplated herein.

In certain embodiments of Formula (I), when f is 1, g is 1, h is 1, $R^E$, $R^F$, $R^G$, $R^H$, and $R^I$, are hydrogen, the compound is of Formula (I-a):

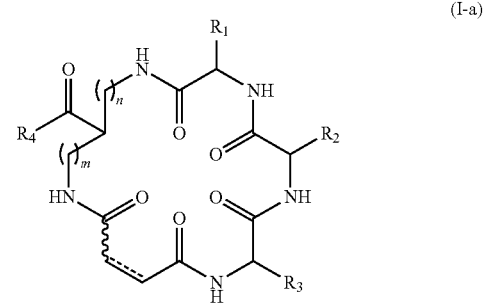

(I-a)

or a pharmaceutically acceptable salt thereof, wherein ═══, ⌇⌇, $R_1$, $R_2$, $R_3$, n, and m are as defined herein.

In certain embodiments of Formula (I-a), when $R_4$ is —$NH_2$, the compound is of Formula (I-b):

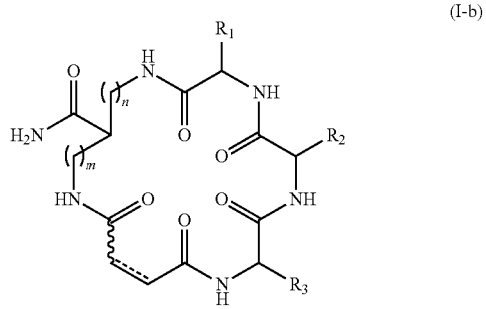

(I-b)

or a pharmaceutically acceptable salt thereof, wherein ⋯, ∼, $R_1$, $R_2$, $R_3$, n, and m are as defined herein.

In certain embodiments of Formula (I-b), the compound is of Formula (I-c):

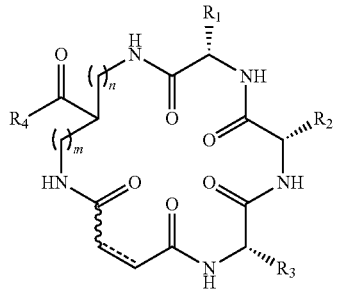

(I-c)

or a pharmaceutically acceptable salt thereof, wherein ⋯, ∼, $R_1$, $R_2$, $R_3$, $R_4$, n, and m are as defined herein.

In certain embodiments of Formula (I), when f is 1, g is 1, h is 1, and m is 0, provided is a compound of Formula (II):

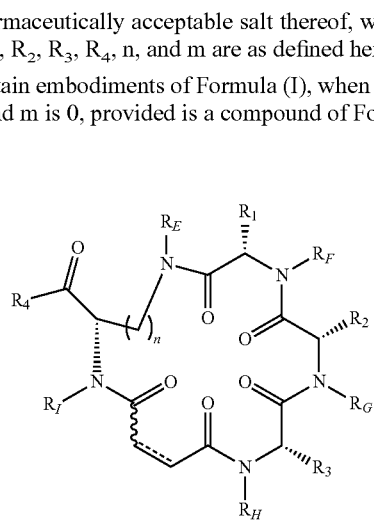

(II)

or a pharmaceutically acceptable salt thereof, wherein ⋯, ∼, $R_1$, $R_2$, $R_3$, $R_4$, $R^E$, $R^F$, $R^G$, $R^H$, $R^I$, n, and m are as defined herein.

In certain embodiments of Formula (II), when $R^E$, $R^F$, $R^G$, $R^H$, and $R^I$, are hydrogen, the compound is of Formula (II-a):

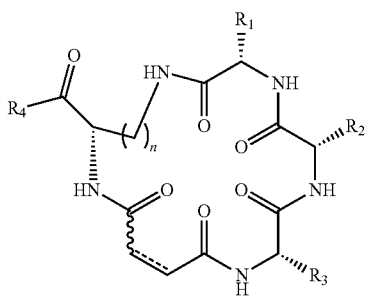

(II-a)

or a pharmaceutically acceptable salt thereof, wherein ⋯, ∼, $R_1$, $R_2$, $R_3$, $R_4$, n, and m are as defined herein.

In certain embodiments of Formula (II-a), when $R_4$ is —$NH_2$, the compound is of Formula (II-b):

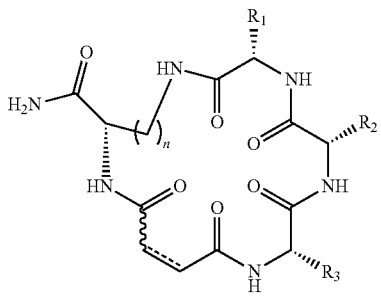

(II-b)

or a pharmaceutically acceptable salt thereof, wherein ⋯, ∼, $R_1$, $R_2$, $R_3$, n, and m are as defined herein.

In certain embodiments of Formula (I), when f is 1, g is 1, h is 1, and $R_1$ is an optionally substituted arylalkyl group, provided is a compound of Formula (III):

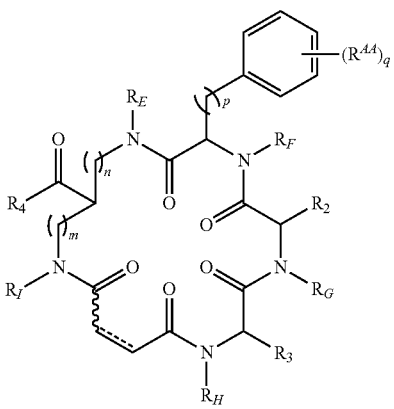

(III)

or a pharmaceutically acceptable salt thereof, wherein ⋯, ∼, $R^{AA}$, p, q, $R_2$, $R_3$, $R^E$, $R^F$, $R^G$, $R^H$, $R^I$, n, and m are as defined herein.

In certain embodiments of Formula (I), when f is 1, g is 1, h is 1, $R_1$ is an optionally substituted arylalkyl group and $R_2$ is an optionally substituted arylalkyl group, provided is a compound of Formula (IV):

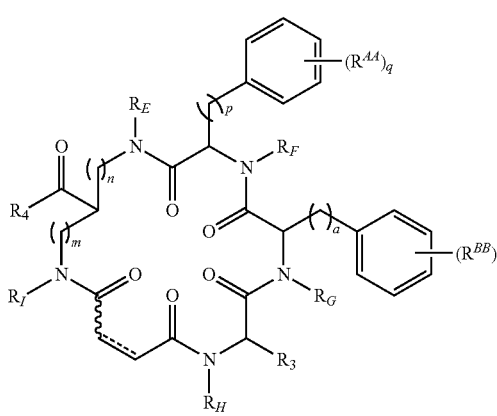

(IV)

or a pharmaceutically acceptable salt thereof, wherein ═, ⌇, $R^{AA}$, p, q, $R^{BB}$, a, b, $R_3$, $R^E$, $R^F$, $R^G$, $R^H$, $R^I$, n, and m are as defined herein.

In certain embodiments of Formula (I), when f is 1, g is 1, h is 1, $R_1$ is an optionally substituted arylalkyl group, and $R_3$ is an optionally substituted carbocyclyl group, provided is a compound of Formula (V):

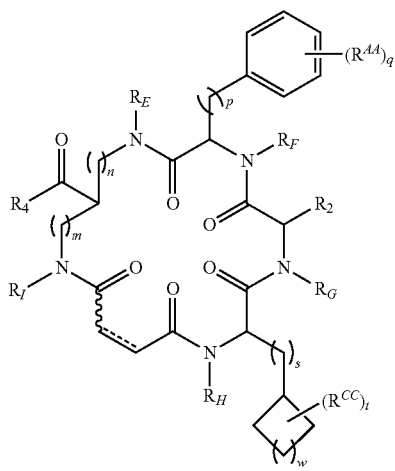

(V)

or a pharmaceutically acceptable salt thereof, wherein ═, ⌇, $R^{AA}$, p, q, $R_2$, $R^{CC}$, t, w, $R^E$, $R^F$, $R^G$, $R^H$, $R^I$, n, and m are as defined herein.

In certain embodiments of Formula (I), when f is 1, g is 1, h is 1, and $R_1$ is alkyl substituted by —$NR^{A2}C(\!\!=\!\!O)R^{A2}$, provided is a compound of Formula (VI):

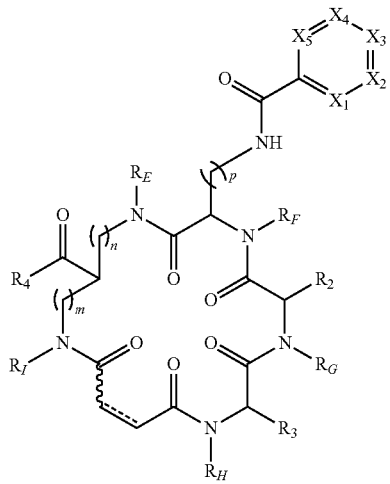

(VI)

or a pharmaceutically acceptable salt thereof, wherein ═, ⌇, $X_1$, $X_2$, $X_3$, $X_4$, $X_5$, p, $R_2$, $R_3$, $R^E$, $R^F$, $R^G$, $R^H$, $R^I$, n, and m are as defined herein. ⌇

In certain embodiments of Formula (I), when f is 1, g is 1, h is 1, $R_1$ is alkyl substituted by —$NR^{A2}C(\!\!=\!\!O)R^{A2}$, and $R_2$ is an optionally substituted arylalkyl group, provided is a compound of Formula (VII):

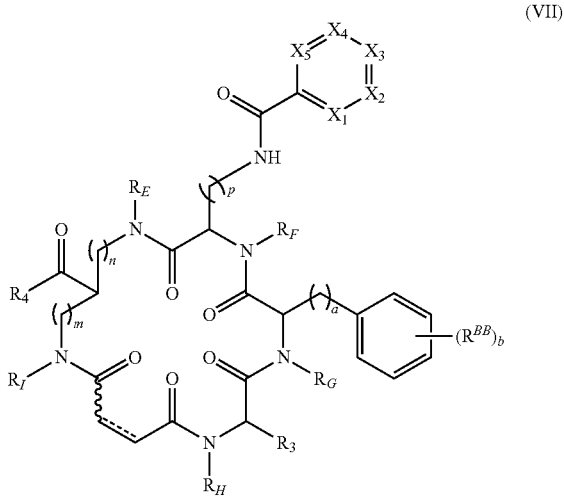

(VII)

or a pharmaceutically acceptable salt thereof, wherein ═, ⌇, $X_1$, $X_2$, $X_3$, $X_4$, $X_5$, p, $R^{BB}$, a, b, $R_3$, $R^E$, $R^F$, $R^G$, $R^H$, $R^I$, n, and m are as defined herein.

In certain embodiments of Formula (I), when f is 1, g is 1, h is 1, $R_1$ is alkyl substituted by —$NR^{A2}C(\!\!=\!\!O)R^{A2}$, and $R_3$ is an optionally substituted carbocyclyl group, provided is a compound of Formula (VIII):

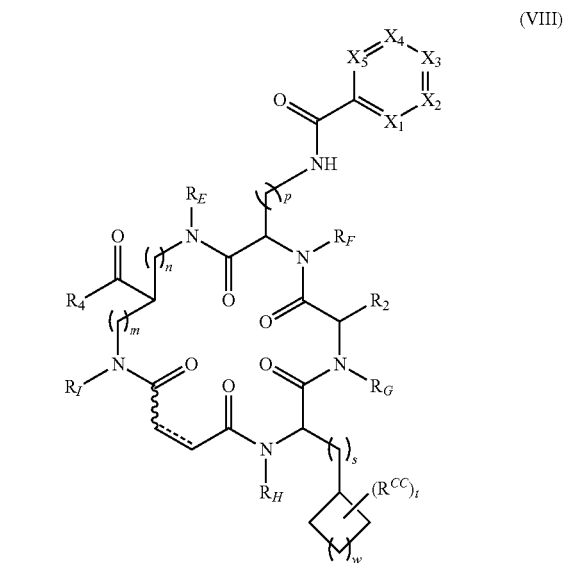

(VIII)

or a pharmaceutically acceptable salt thereof, wherein ═, ⌇, $X_1$, $X_2$, $X_3$, $X_4$, $X_5$, p, $R_2$, $R^{CC}$, s, t, w, $R^E$, $R^F$, $R^G$, $R^H$, $R^I$, n, and m are as defined herein.

In certain embodiments of Formula (I), when f is 1, g is 1, h is 1, and $R_1$ is alkyl substituted with —$SO_2R^{A1}$, provided is a compound of Formula (IX):

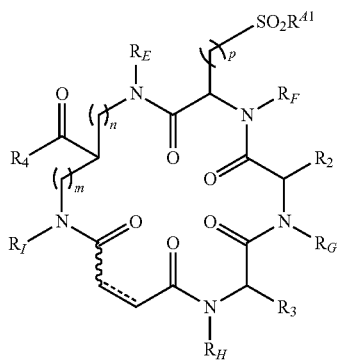

(IX)

or a pharmaceutically acceptable salt thereof, wherein ═══, ⌇⌇⌇, $R^{A1}$, p, $R_2$, $R_3$, $R^E$, $R^F$, $R^G$, $R^H$, $R^I$, n, and m are as defined herein.

In certain embodiments of Formula (I), when f is 1, g is 1, h is 1, $R_1$ is alkyl substituted with —$SO_2R^{A1}$ and $R_2$ is an optionally substituted arylalkyl group, provided is a compound of Formula (X):

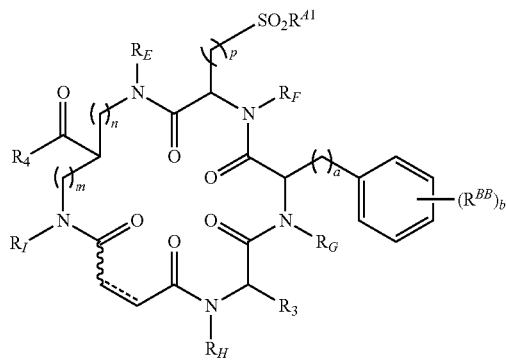

(X)

or a pharmaceutically acceptable salt thereof, wherein ═══, ⌇⌇⌇, $R^{A1}$, p, $R_2$, $R_3$, $R^E$, $R^F$, $R^G$, $R^H$, $R^I$, n, and m are as defined herein.

In certain embodiments of Formula (I), when f is 1, g is 1, h is 1, $R_1$ is alkyl substituted with —$SO_2R^{A1}$, and $R_3$ is an optionally substituted carbocyclyl group, provided is a compound of Formula (XI):

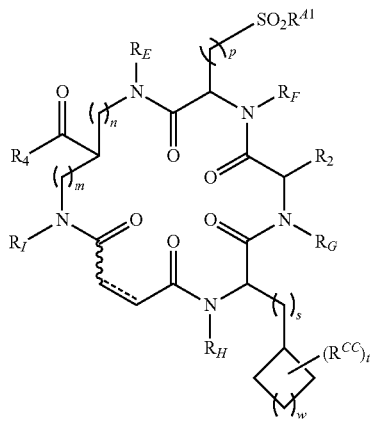

(XI)

or a pharmaceutically acceptable salt thereof, wherein ═══, ⌇⌇⌇, $R^{A1}$, p, $R_2$, $R_3$, $R^E$, $R^F$, $R^G$, $R^H$, $R^I$, n, and m are as defined herein.

In certain embodiments of Formula (I), when f is 1, g is 1, h is 1, and $R_2$ is an optionally substituted arylalkyl group, provided is a compound of Formula (XII):

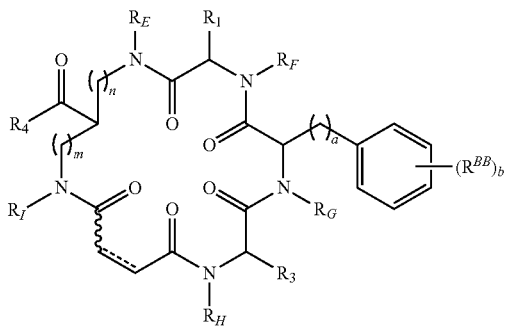

(XII)

or a pharmaceutically acceptable salt thereof, wherein ═══, ⌇⌇⌇, $R_1$, $R^{BB}$, a, b, $R_3$, $R_4$, $R^E$, $R^F$, $R^G$, $R^H$, $R^I$, n, and m are as defined herein.

In certain embodiments of Formula (I), when f is 1, g is 1, h is 1, $R_2$ is an optionally substituted arylalkyl group, and $R_3$ is an optionally substituted carbocyclyl group, provided is a compound of Formula (XIII):

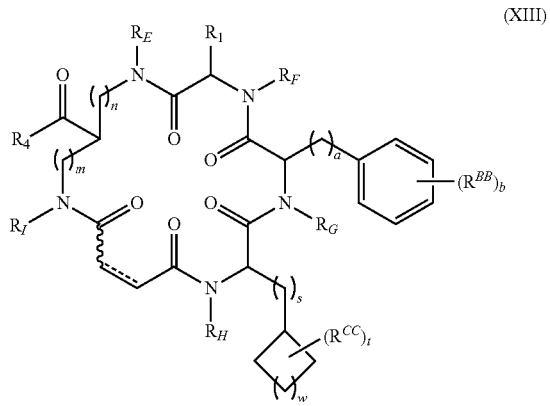

(XIII)

or a pharmaceutically acceptable salt thereof, wherein ═══, ⌇⌇⌇, $R_1$, $R^{BB}$, a, b, $R^{CC}$, s, w, $R_4$, $R^E$, $R^F$, $R^G$, $R^H$, $R^I$, n, and m are as defined herein. ⌇⌇⌇

In certain embodiments of Formula (I), when f is 1, g is 1, h is 1, and $R_3$ is an optionally substituted carbocyclyl group, provided is a compound of Formula (XIV):

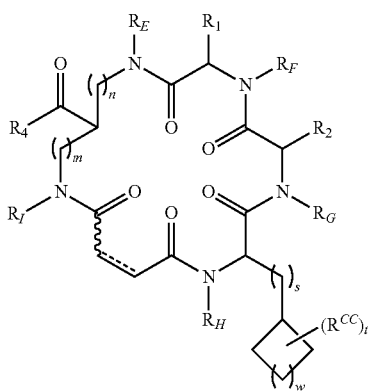

(XIV)

or a pharmaceutically acceptable salt thereof of wherein ----, ----, $R_1$, $R^{BB}$, a, b, $R^{CC}$, s, w, $R_4$, $R^E$, $R^F$, $R^G$, $R^H$, $R^I$, n, and m are as defined herein.

In certain embodiments of Formula (I), when f is 1, g is 1, h is 1, $R_1$ is an optionally substituted arylalkyl group, $R_2$ is an optionally substituted arylalkyl group, and $R_3$ is an optionally substituted carbocyclyl group, provided is a compound of Formula (XV):

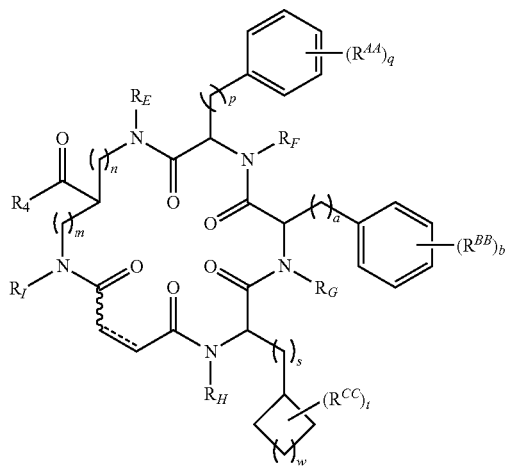

(XV)

or a pharmaceutically acceptable salt thereof, wherein ----, ----, $R^{AA}$, p, q, $R^{BB}$, a, b, $R^{CC}$, s, t, w, $R^E$, $R^F$, $R^G$, $R^H$, $R^I$, n, and m are as defined herein.

In certain embodiments of Formula (I), when f is 1, g is 1, h is 1, $R_1$ is alkyl substituted by —$NR^{A2}C(=O)R^{A2}$, $R_2$ is an optionally substituted arylalkyl group, and $R_3$ is an optionally substituted carbocyclyl group, provided is a compound of Formula (XVI):

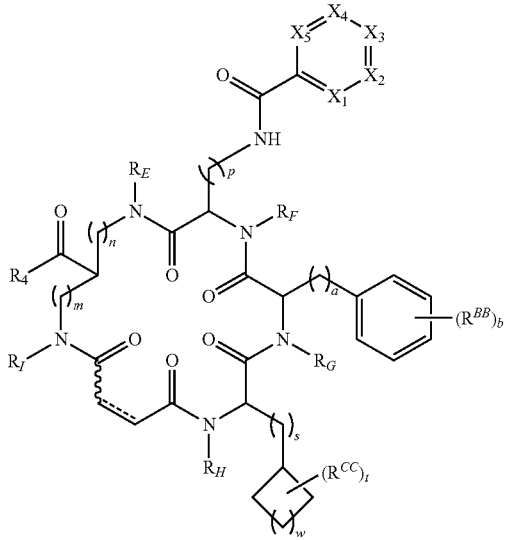

(XVI)

or a pharmaceutically acceptable salt thereof, wherein ----, ----, $X_1$, $X_2$, $X_3$, $X_4$, $X_5$, p, $R^{BB}$, a, b, $R^{CC}$, s, t, w, $R^E$, $R^F$, $R^G$, $R^H$, $R^I$, n, and m are as defined herein.

In certain embodiments of Formula (I), when f is 1, g is 1, h is 1, $R_1$ is alkyl substituted with —$SO_2R^{A1}$, $R_2$ is an optionally substituted arylalkyl group, and $R_3$ is an optionally substituted carbocyclyl group, provided is a compound of Formula (XVI):

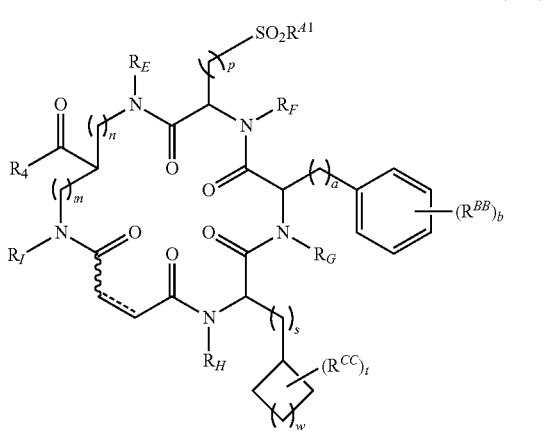

(XVI)

or a pharmaceutically acceptable salt thereof, wherein ----, ----, $R^{A1}$, p, q, $R^{BB}$, a, b, $R^{CC}$, s, t, w, $R^E$, $R^F$, $R^G$, $R^H$, $R^I$, n, and m are as defined herein.

In certain embodiments, the compound is selected from the group consisting of:

113
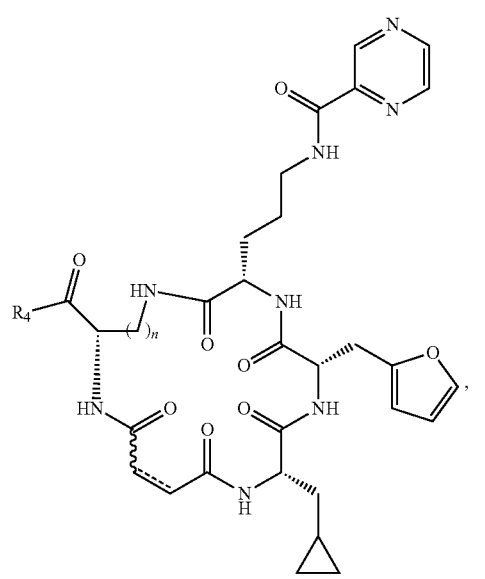
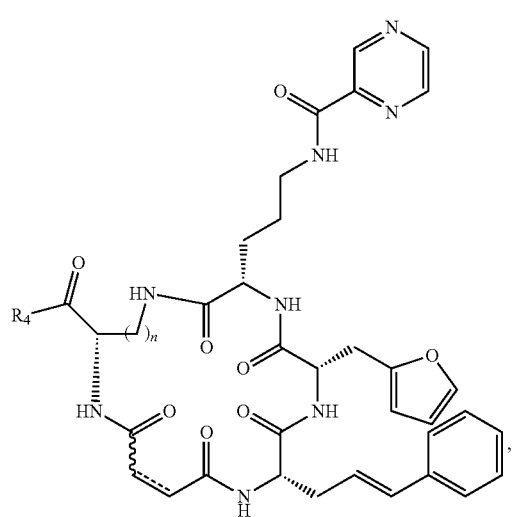
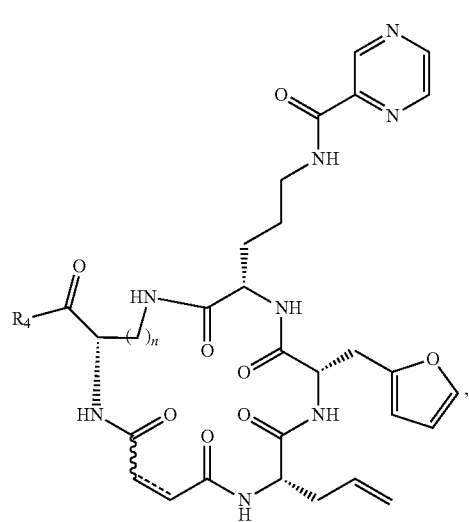
114
-continued
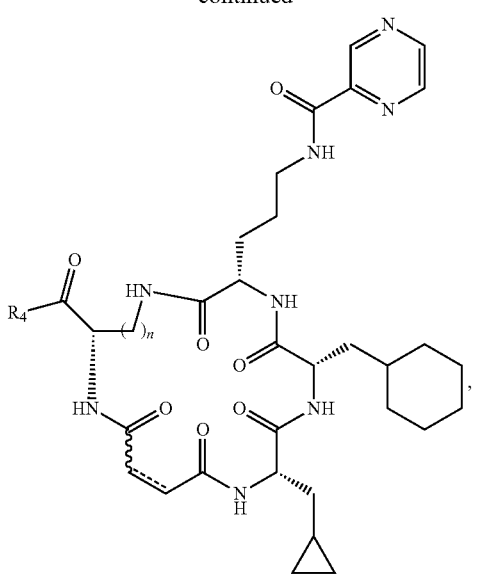
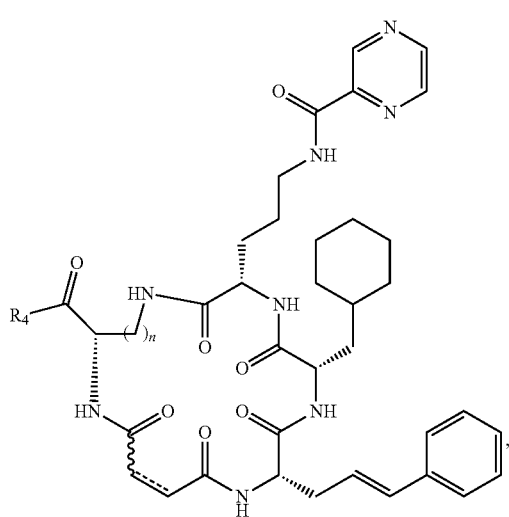
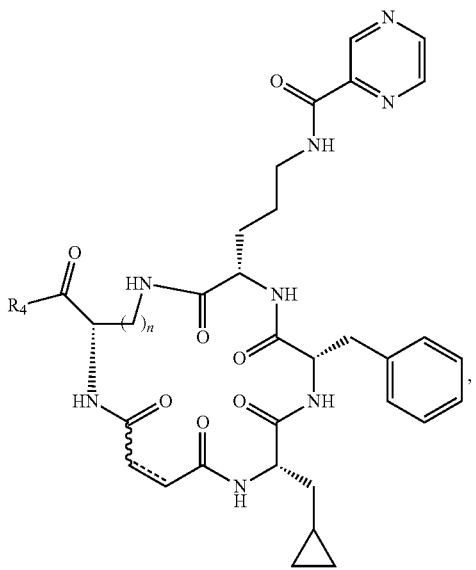

115
-continued
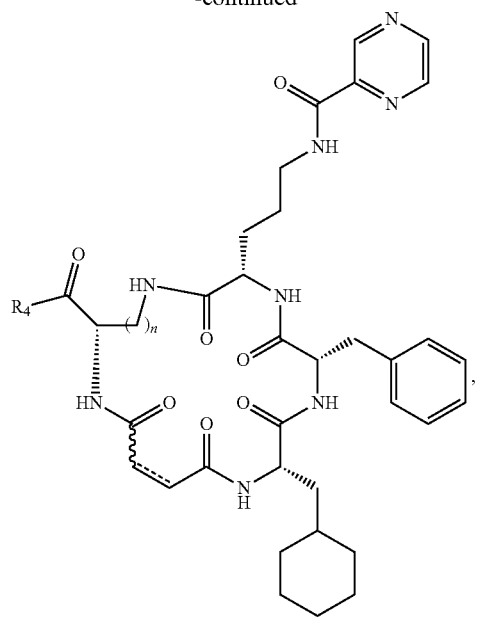
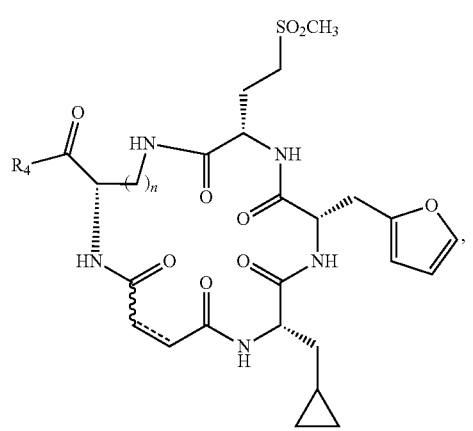
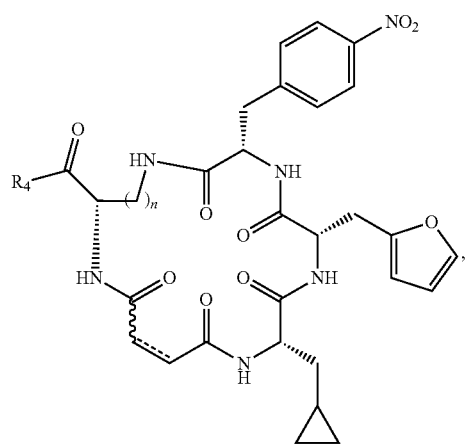
116
-continued
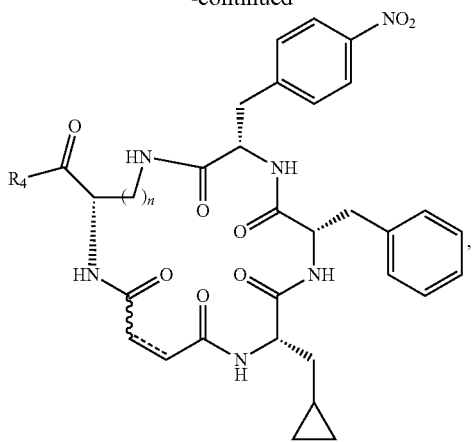
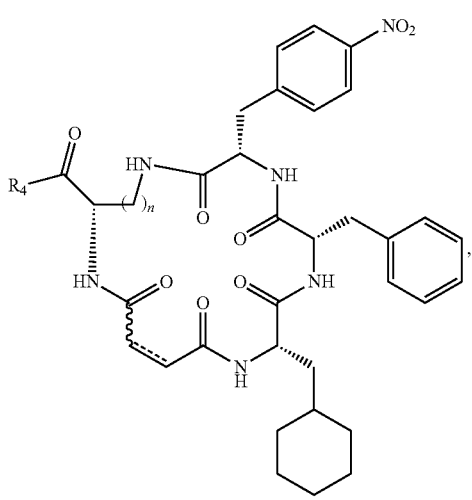
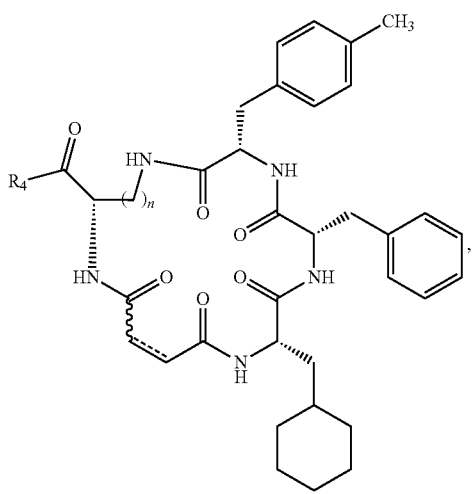

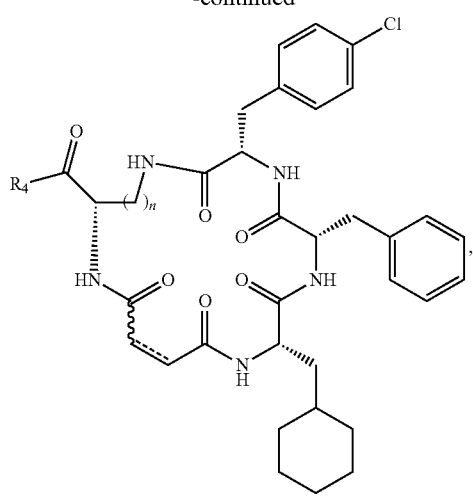
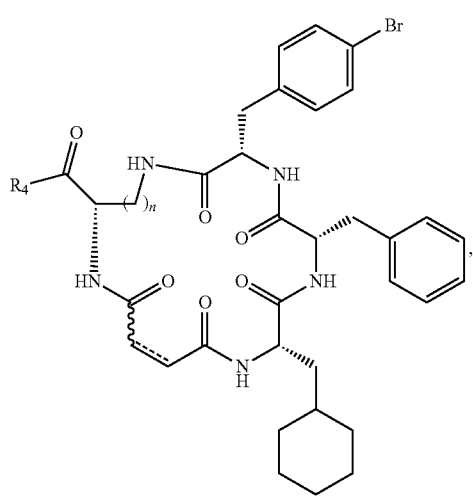
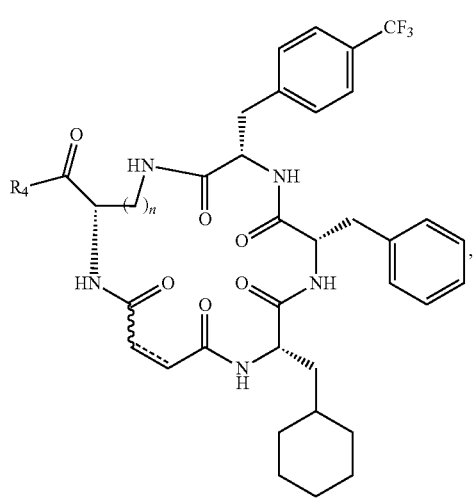
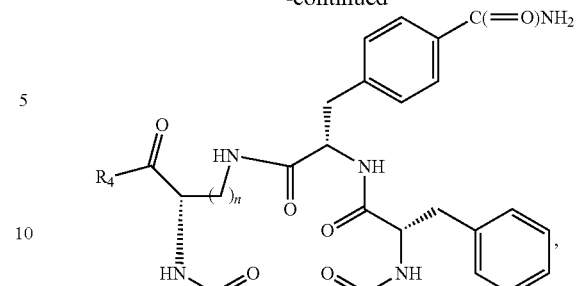
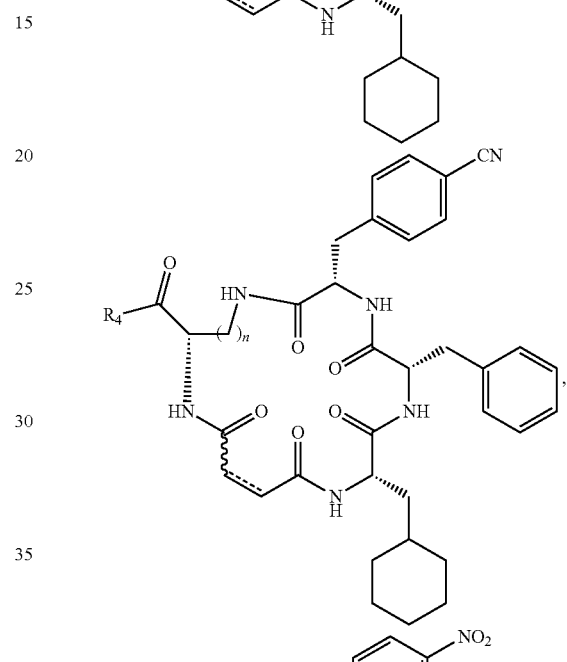
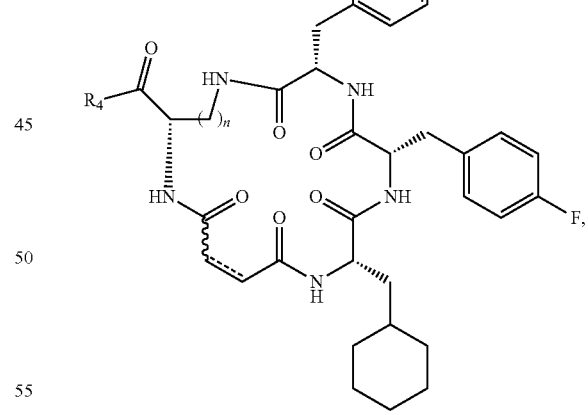

and pharmaceutically acceptable salts thereof,
wherein ═══, ⌇⌇⌇, $R^4$, and n are as defined herein. In certain embodiments, n is 2. In certain embodiments, n is 3. In certain embodiments, $R_4$ is —$NH_2$. In certain embodiments, $R_4$ is —$NHR^D$, wherein $R^D$ is a resin covalently attached thereto.

Methods of Preparation

The present invention further provides methods for preparing macrocyclic compounds of the present invention, e.g., following the syntheses depicted in below Schemes 1-6 and FIG. 7.

Scheme 1 depicts the first two steps in the synthesis of a compound of Formula (I). Step 1 (S-1) comprises providing a compound of formula (A), wherein $R^4$ is as defined herein and $R^{Y1}$ is a nitrogen protecting group, providing a compound of formula (B), wherein $R^{X1}$ is a carboxylic acid protecting group, and $R^{X2}$ and $R^{X3}$ are each independently oxygen protecting groups or are cyclized to form a 1,2-diol protecting group (e.g., a dioxolanyl group), and coupling the compound of formula (A) and the compound of formula (B) under peptide coupling conditions to provide the coupled product (C). Step 2 (S-2) comprises deprotecting the coupled product (C) to provide a compound of formula (D).

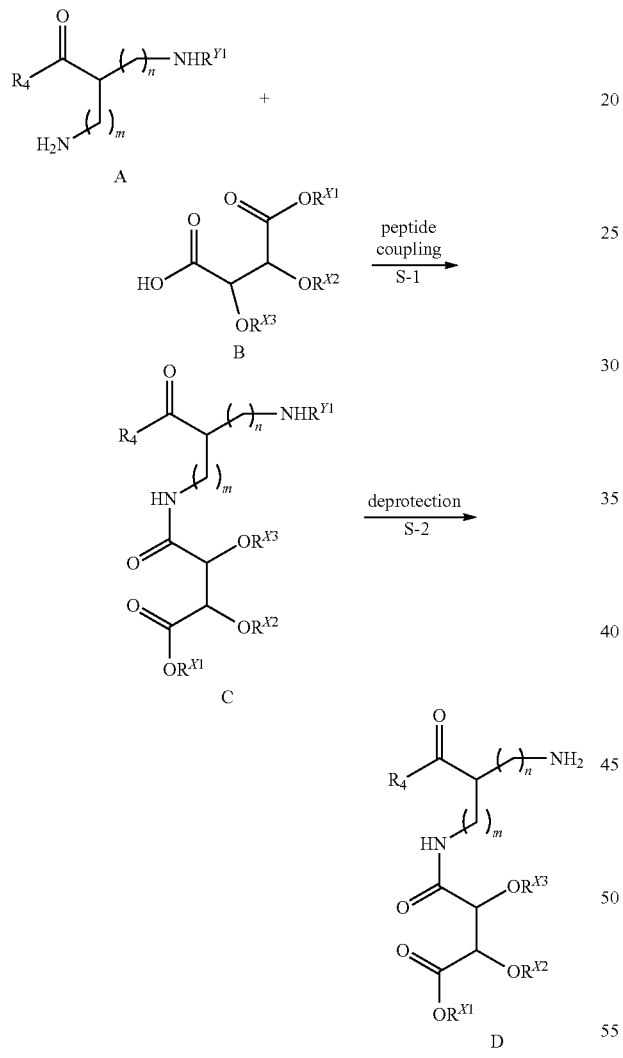

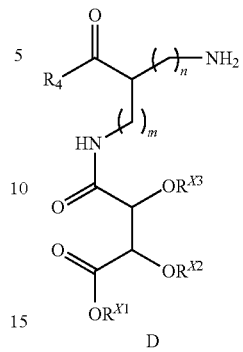

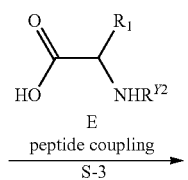

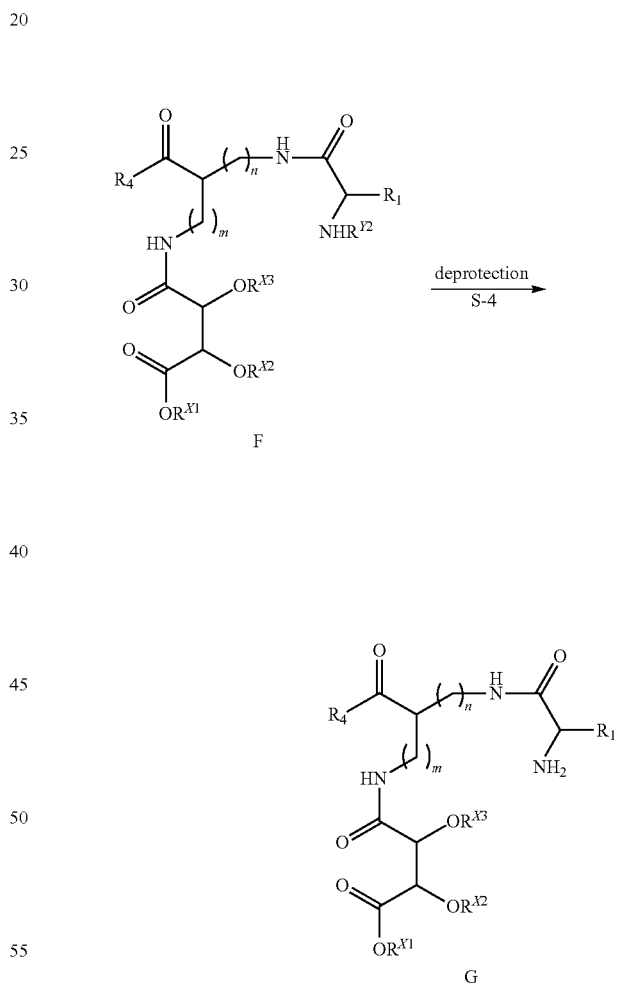

Step 3 (S-3), depicted in Scheme 2, comprises coupling the compound of fGP-98, C3 formula (D) with a compound of formula (E), wherein $R^{Y2}$ is a nitrogen protecting group, under peptide coupling conditions to provide the coupled product (F). Step 4 (S-4), also depicted in Scheme 2, comprises deprotecting the coupled product (F) to provide a compound of formula (G).

Step 5 (S-5), depicted in Scheme 3, comprises coupling the compound of formula (G) with a compound of formula (H), wherein $R^{Y3}$ is a nitrogen protecting group, under peptide coupling conditions to provide the coupled product (J). Step 6 (S-6), also depicted in Scheme 3, comprises deprotecting the coupled product (J) to provide a compound of formula (K).

Scheme 3.

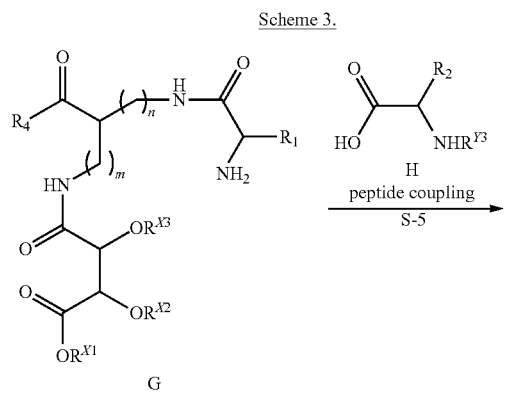

Scheme 4.

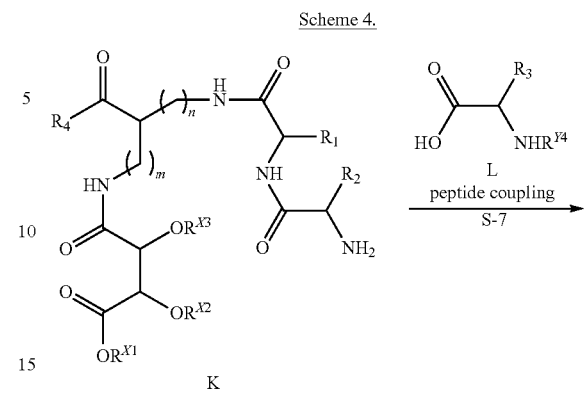

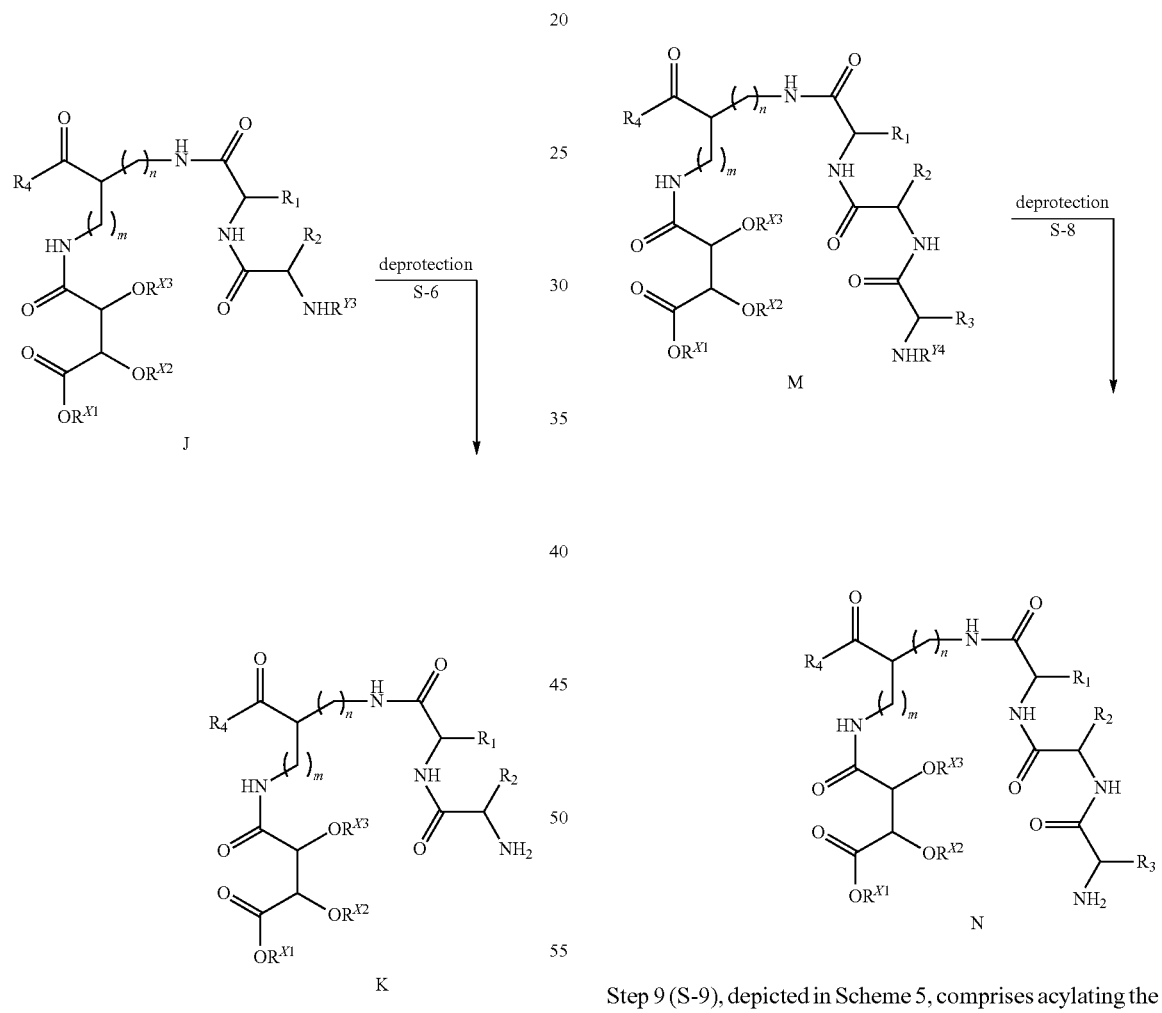

Step 7 (S-7), depicted in Scheme 4, comprises coupling the compound of formula (K) with a compound of formula (L), wherein $R^{Y4}$ is a nitrogen protecting group, under peptide coupling conditions to provide the coupled product (M). Step 8 (S-8), also depicted in Scheme 4, comprises deprotecting the coupled product (M) to provide a compound of formula (N).

Step 9 (S-9), depicted in Scheme 5, comprises acylating the compound of formula (N) to provide the acylated product (P), wherein X is —Br, —Cl, or —I. An exemplary acylating reagent is an amine reactive ester of the formula Y—C(=O)CH$_2$X, wherein Y is a N-hydroxysuccinimide (NHS) or sulfo-NHS. Step 10 (S-10) comprises contacting the acylated product (P) with a phosphine of formula $P(R^Z)_3$, wherein each $R^Z$ is independently optionally substituted aryl or optionally substituted heteroaryl, to provide a phosphonium salt of the formula (Q). Step 11 (S-11) comprises deprotecting the 1,2-diol to provide a compound of formula (R).

Scheme 5.

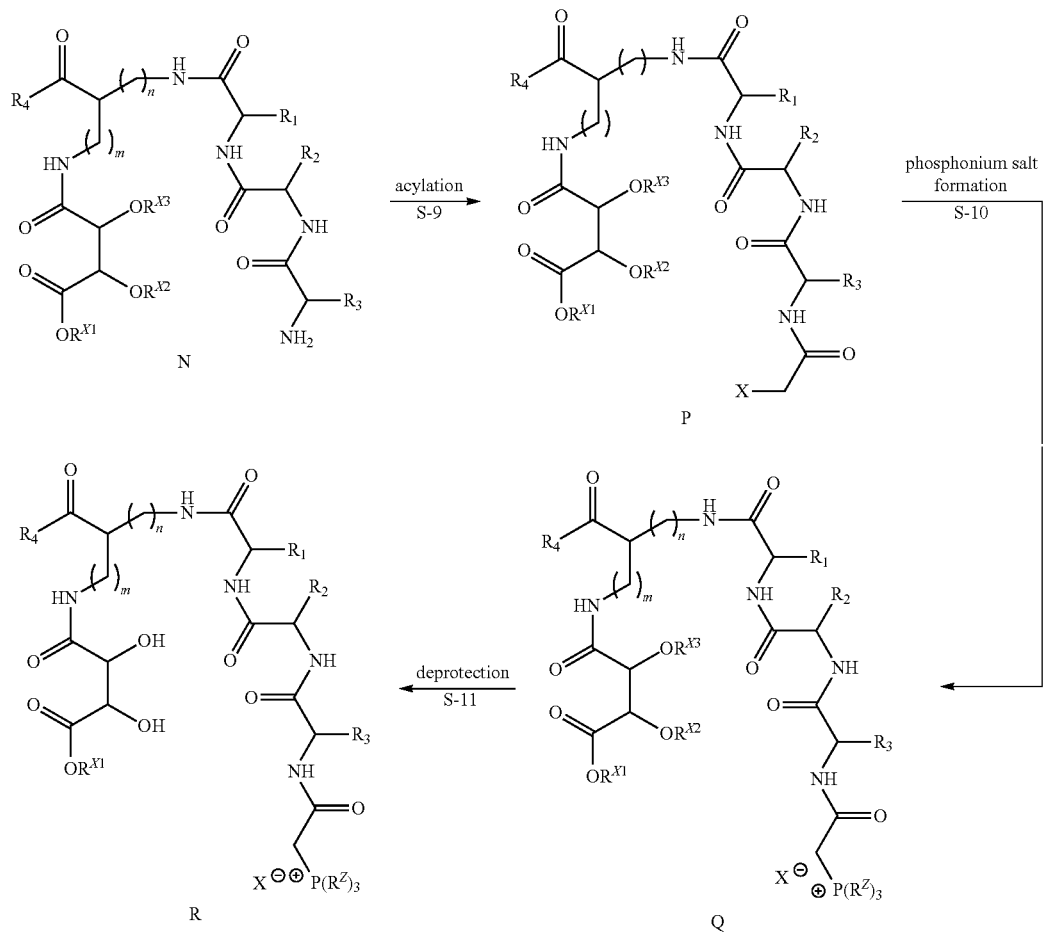

Step 12 (S-12), depicted in Scheme 6, comprises cleaving the 1,2-diol under oxidative conditions to provide the aldehyde intermediate (S) in situ. Exposure of the aldehyde intermediate (S) under basic conditions (e.g., pH>8) generates a phosphonium ylide, and the subsequent intramolecular Wittig reaction provides an exemplary macrocyclic compound of the present invention.

Scheme 6.

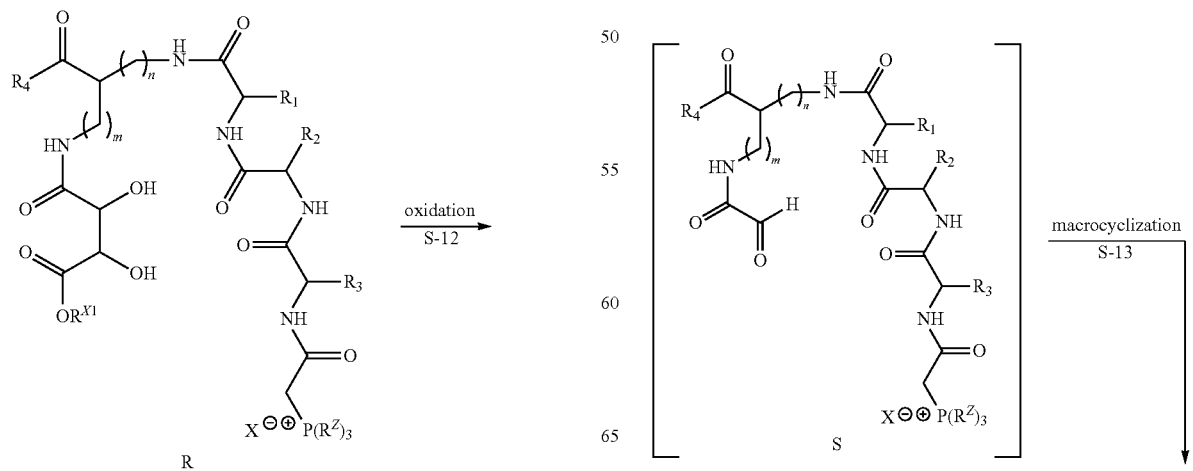

-continued

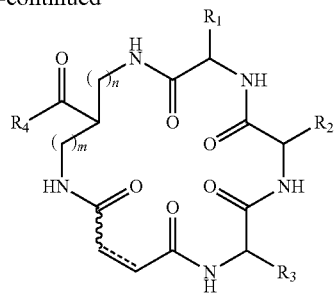

As is understood from the above, the synthesis utilizes peptide coupling methods. Such methods are known in the art, see generally, *March's Advanced Organic Chemistry: Reactions*, Mechanisms, and Structure, M. B. Smith and J. March, 5$^{th}$ Edition, John Wiley & Sons, 2001, and *Comprehensive Organic Transformations*, R. C. Larock, 2$^{nd}$ Edition, John Wiley & Sons, 1999.

The peptide coupling reaction requires a peptide coupling reagent. Exemplary peptide coupling reagents include, but are not limited to, benzotriazol-1-yloxy-tris(dimethylamino)-phosphonium hexafluorophosphate (BOP), benzotriazole-1-yl-oxy-tris-pyrrolidino-phosphonium hexafluorophosphate (PyBOP), bromo-tris-pyrrolidino phosphonium hexafluorophosphate (PyBroP), 1-ethyl-3-(3-dimethylaminopropyl) carbodiimide (EDC), N,N'-carbonyldiimidazole (CDI), 3-(diethoxyphosphoryloxy)-1,2,3-benzotriazin-4 (3H)-one (DEPBT), 1-hydroxy-7-azabenzotriazole (HOAt), 1-hydroxy-7-benzotriazole (HOBt), 2-(7-aza-1H-benzotriazole-1-yl)-1,1,3,3-tetramethyluronium hexafluorophosphate (HATU), 2-(6-chloro-1H-benzotriazole-1-yl)-1,1,3,3-tetramethylaminium hexafluorophosphate (HCTU), 2-(1H-benzotriazole-1-yl)-1,1,3,3-tetramethyluronium hexafluorophosphate (HBTU), O-(7-azabenzotriazole-1-yl)-N,N,N',N'-tetramethyluronium tetrafluoroborate (TATU), 2-(1H-benzotriazole-1-yl)-1,1,3,3-tetramethyluronium tetrafluoroborate (TBTU), N,N,N',N'-tetramethyl-O-(3,4-dihydro-4-oxo-1,2,3-benzotriazin-3-yl)uranium tetrafluoroborate (TDBTU), and O—(N-succinimidyl)-1,1,3,3-tetramethyl uranium tetrafluoroborate (TSTU)).

In certain embodiments, the peptide coupling further comprises a base, e.g., potassium carbonate, potassium hydroxide, sodium hydroxide, tetrabutylammonium hydroxide, benzyltrimethylammonium hydroxide, triethylbenzylammonium hydroxide, 1,1,3,3-tetramethylguanidine, 1,8-diazabicyclo[5.4.0]undec-7-ene (DBU), N-methylmorpholine, diisopropylethylamine (DIPEA), tetramethylethylenediamine (TMEDA), pyridine (Py), 1,4-diazabicyclo[2.2.2]octane (DABCO), N,N-dimethylamino pyridine (DMAP), or triethylamine (NEt$_3$).

In certain embodiments, the peptide coupling is solid phase peptide coupling. For example, in some embodiments, the macrocyclic compound may be synthesized using solid-phase peptide synthesis. In this particular instance, in certain embodiments, $R^4$ is —NHR$^D$, wherein R$^D$ is a resin, e.g, a Rink resin. An overview of exemplary solid phase methods can be found, for example, in Chan, W C, White, P D, *Fmoc Solid Phase Peptide Synthesis: A Practical Approach* (Practical Approach Series), Oxford University Press, USA; 1 edition (Mar. 2, 2000), ISBN-10: 0199637245; incorporated herein in its entirety for disclosure of Fmoc and solid phase Fmoc synthetic methods and related protocols). In certain embodiments, the method comprises generating the phosphonium salt (Q) on the resin, and then cleaving the compound from the resin prior to Step 12 (S-12). In certain embodiments, the phosphonium salt (Q) is cleaved from the resin by treatment with an acid (e.g., trifluoroacetic acid, TFA). In certain embodiments, the acidic conditions also cleave the 1,2-diol protecting group to provide a compound of formula (R). In certain embodiments, prior to the oxidative and cyclization steps (Steps 12 and 13), the method further comprises purifying the compound of formula (R). Methods for isolating and/or purifying synthesized peptides are well known to those of skill in the art and include, but are not limited to high performance liquid chromatography (HPLC), conventional column chromatography, or recrystallization.

However, in certain embodiments, the peptide coupling is solution phase peptide coupling, and the intermediates are not attached to a resin.

In another aspect, provided is a method of a macrocyclic compound, the method comprising:

(a) providing a differentially protected diamino acid macrocyclization precursor of the formula:

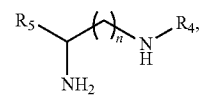

wherein:
n is 0 or is an integer between 0 and 10, inclusive;
R$_4$ is an amino protecting group;
R$_5$ is hydrogen; halogen; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; —OR$_D$; =O; —C(=O)R$_D$; —CO$_2$R$_D$; —CN; —SCN; —SR$_D$; —SOR$_D$; —SO$_2$R$_D$; —NO$_2$; —N(R$_D$)$_2$; —NHC(O)R$_D$; or —C(R$_D$)$_3$; wherein each occurrence of R$_D$ is independently hydrogen, a protecting group, aliphatic, heteroaliphatic, acyl; aryl; heteroaryl; alkoxy; aryloxy; alkylthio; arylthio; amino, alkylamino, dialkylamino, heteroaryloxy; or heteroarylthio; and optionally, wherein the macrocyclization precursor is coupled to a solid support via R$_5$;

(b) contacting the macrocyclization precursor provided under (a) with a building block of the formula:

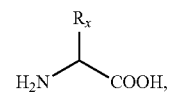

under conditions suitable for the formation of a peptide bond between the carboxyl group of the building block provided under (b) with the unprotected amino group of the macrocyclization precursor, wherein R$_x$, is hydrogen; halogen; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; —OR$_E$; =O; —C(=O)R$_E$; —CO$_2$R$_E$; —CN; —SCN; —SR$_E$; —SOR$_E$; —SO$_2$R$_E$; —NO$_2$; —N(R$_E$)$_2$; —NHC(O)R$_E$; or —C(R$_E$)$_3$; wherein each occurrence of R$_E$ is independently hydrogen, a protecting group, aliphatic, heteroaliphatic, acyl; aryl; heteroaryl; alkoxy; aryloxy; alkylthio; arylthio; amino, alkylamino, dialkylamino, heteroaryloxy; or heteroarylthio;

(c) performing 1-5 additional steps of contacting the reaction product generated under (b) with an additional building block of the formula provided in (b), wherein $R_x$ is defined for each building block separately and individually as under (b);

(d) optionally, cleaving the macrocyclization precursor from the solid support and/or purifying the macrocyclization precursor; and (e) effecting cyclization of the macrocyclization precursor.

In certain embodiments, n is an integer between 1 and 4, inclusive.

In certain embodiments, $R_4$ is an amino protecting group. In certain embodiments, $R_4$ is isopropylidene-protected tartrate monomethyl ester.

In certain embodiments, the macrocyclization precursor is coupled to an amide resin. In certain embodiments, the building blocks are added to the macrocyclization precursor by Fmoc synthesis. In certain embodiments, the method comprises generating a phosphonium salt of the macrocyclization precursor on resin.

In certain embodiments, the macrocyclization precursor is cleaved from the solid support by treatment with a strong acid. In certain embodiments, the cleavage reaction generates a carboxamide at the C-terminus and deprotects a tartrate diol group.

In certain embodiments, the macrocyclization precursor is purified before cyclization. In certain embodiments, the method further comprising a step of oxidatively cleaving the diol group, thus generating an aldehyde group. In certain embodiments, the cyclization is a Wittig cyclization. In certain embodiments, the Wittig cyclization is effected by raising the pH to generate a phosphonium ylide.

Figure 2A:
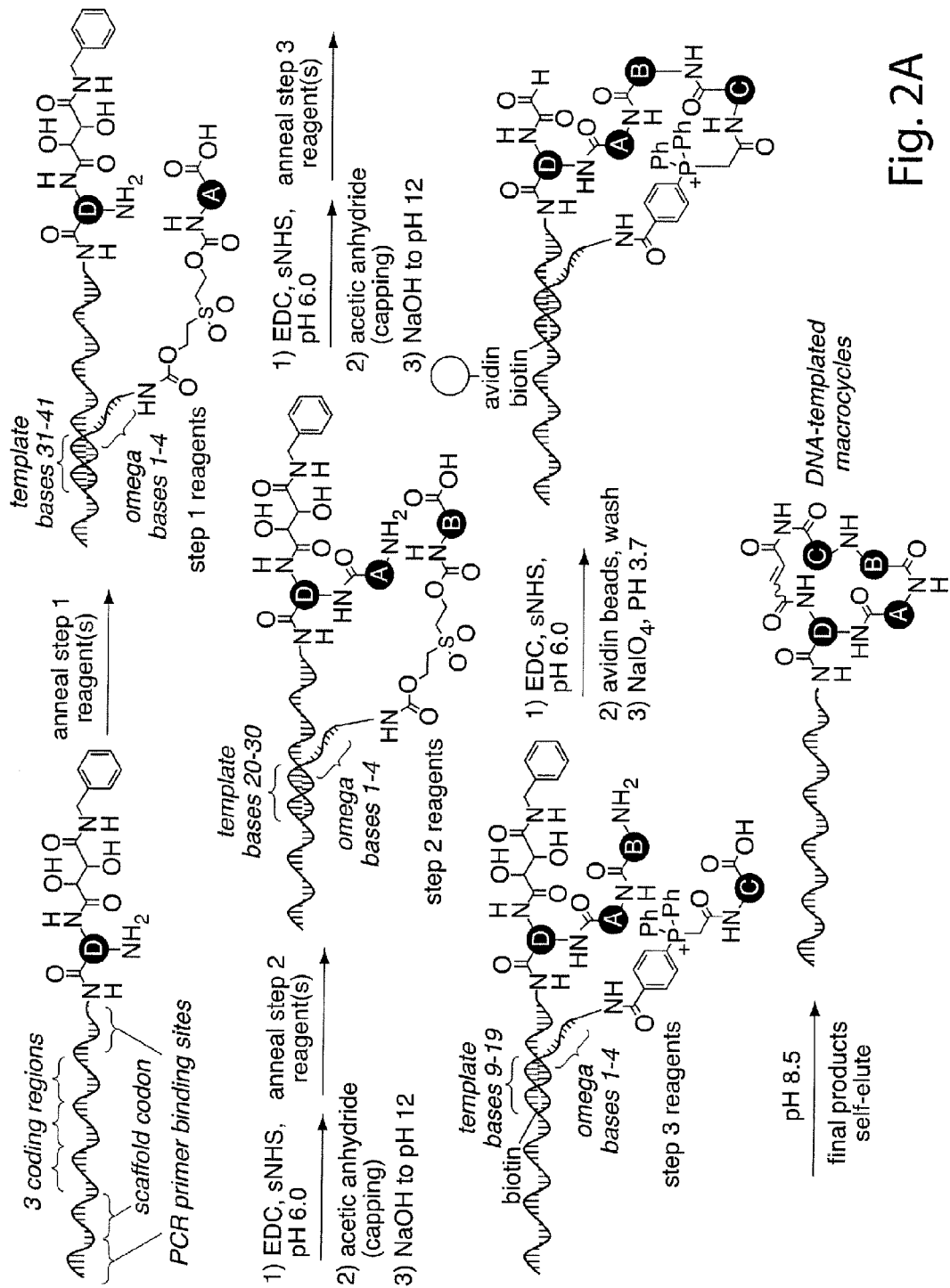
FIG. 2. 13,824-membered DNA-templated small-molecule macrocycle library. a) Scheme for the multistep DNA-templated synthesis of the macrocycle library.[24] b) Amino-acid building blocks used in the library synthesis. Step one building blocks: A1-A12 (FIG. 2B-L; step two building blocks: B1-B12 (FIG. 2B-2); step three building blocks: C1-C12 (FIG. 2B-3); and the macrocycle scaffolds: (D1-D8) (FIG. 2B-4) are shown. These 36 building blocks together with eight variable macrocycle scaffolds result in a theoretical diversity of 13,824 DNA-templated macrocycles (FIG. 2B-5). The fidelity of DNA-templated macrocycle library synthesis was extensively characterized by high-resolution LC-MS analysis (FIG. 2B-6).
Figures 1, 2B:
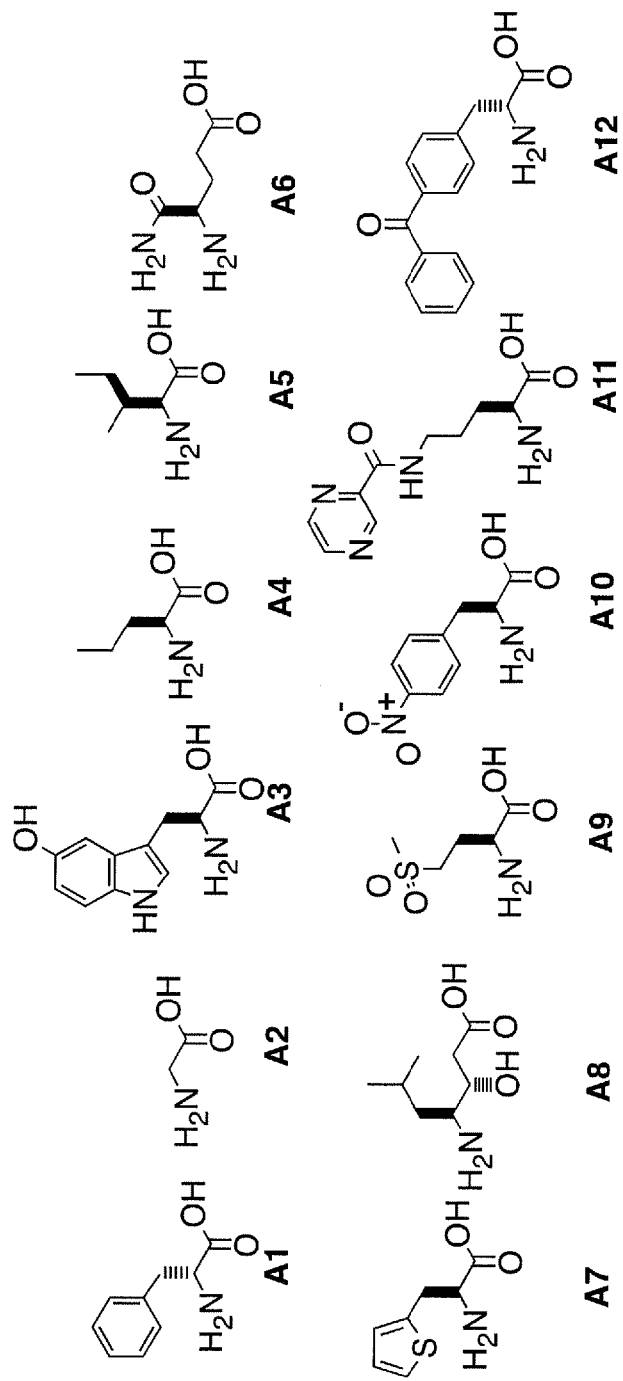
Figures 2, 2B:
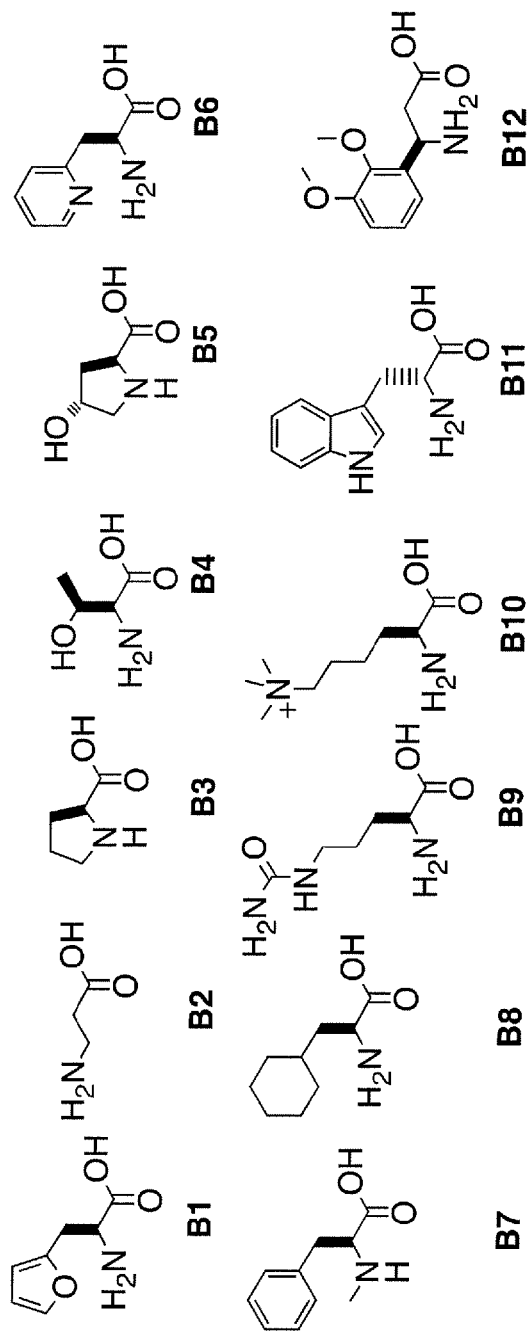
Figure 7:
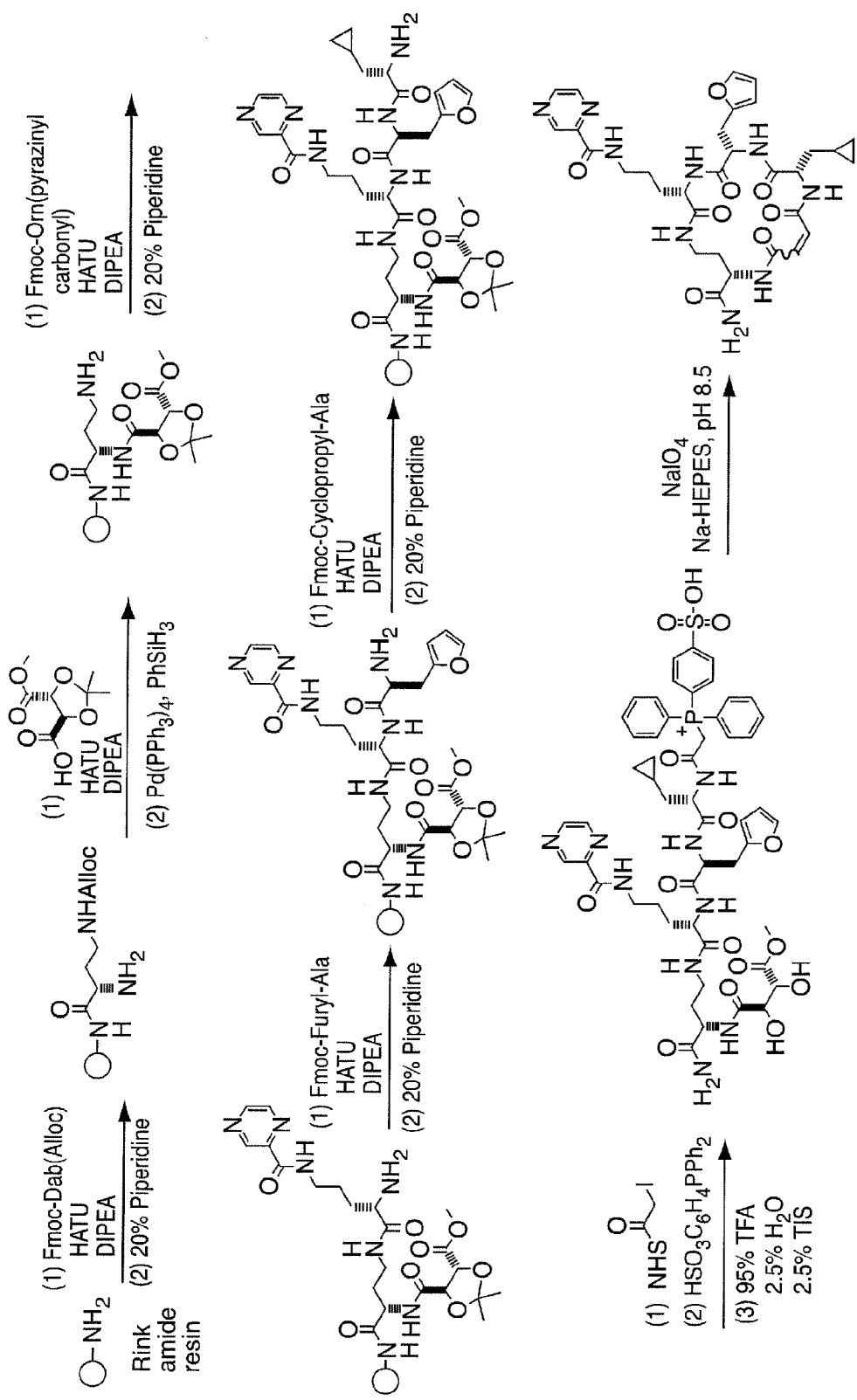
FIG. 7. Milligram-scale synthesis of macrocycle A11-B1-C5-D7. The route was adapted from Gartner et al.[20] Methyl hydrogen 2,3-O-isopropylidene-(L)-tartrate was synthesized as reported by Musich and Rapoport[69].

In some embodiments, a compound of the invention may be synthesized according to the synthetic scheme shown in FIG. 7. It will be understood by those of skill in the art that the synthesis scheme depicted is exemplary and can be used, or, where necessary, adapted with no more than routine experimentation, for the synthesis of any compound described herein by the use of the appropriate building blocks, for example, the building blocks described in FIG. 2b, reagents, protecting groups, and reaction conditions.

In some embodiments, a macrocyclic compound provided herein may be synthesized using Fmoc solid-phase peptide synthesis technology. Fmoc synthetic methods are known in the art. An overview of exemplary suitable methods can be found, for example, in Chan, W C, White, P D, *Fmoc Solid Phase Peptide Synthesis: A Practical Approach* (*Practical Approach Series*), Oxford University Press, USA; 1 edition (Mar. 2, 2000), ISBN-10: 0199637245; incorporated herein in its entirety for disclosure of Fmoc and solid phase Fmoc synthetic methods and related protocols). The synthesis of inventive macrocycles may, in some embodiments, be performed on a multi-milligram scale or a multi-gram scale. In some embodiments, a differentially protected diamino acid building block, for example, a building block described in FIG. 2b under D1-D8 may be employed as the starting material for macrocycle synthesis. In some embodiments, an isopropylidene-protected tartrate monomethyl ester may be reacted with the amine of the first building block. An additional building block may be reacted with the first building block by a round of Fmoc synthesis. In some embodiments, multiple rounds of Fmoc synthesis may be performed to synthesize multi-block peptides. For example, in some embodiments, three rounds of Fmoc synthesis are employed to generate a tripeptide. In some embodiments, a phosphonium salt of the synthesized peptide is generated for macrocyclization. In some embodiments, the synthesized peptide, or macrocyclization precursor is cleaved from a solid support, e.g. a resin, before cyclization. In some embodiments, cleavage of the macrocyclization precursor is achieved by treatment with a strong acid, e.g., TFAD. In some embodiments, a carboxamide is generated at the C-terminus of the synthesized peptide, for example, during the cleavage reaction. In some embodiments, a tartrate diol is revealed by removal of a protecting group. In some embodiments, the macrocyclization precursor is isolated and/or purified before cyclization is effected. Methods for isolating and/or purifying synthesized peptides are well known to those of skill in the art and include, but are not limited to high performance liquid chromatography (HPLC), conventional column chromatography, or recrystallization. In some embodiments, the macrocyclization precursor is characterized before cyclization, for example, by mass spectroscopy (MS) and/or NMR. In some embodiments, the deprotected diol is cleaved oxidatively to yield an aldehyde. In some embodiments, the cyclization reaction is a Wittig cyclization. In some embodiments, cyclization is effected by raising the pH of a solution comprising the macrocyclization precursor to generate a phosphonium ylide. Other cyclization reactions known in the art may also be used to yield the macrocycle.

While the compounds provided herein can be synthesized by the exemplary synthesic methods described herein, it will be understood by those of skill in the art that other synthetic methods may be used to synthesize the described compounds and the scope of the invention is not limited in this aspect.

Uses

The compounds of the invention, for example, the macrocyclic kinase inhibitors provided herein, are useful for modulating the activity of a kinase, for example, Src kinase. In some embodiments, modulating the activity of a kinase with a compound described herein involves contacting the kinase with an effective amount of the compound. In certain embodiments, the kinase is contacted in vitro. In some embodiments, an isolated or purified kinase is contacted. In some embodiments, the kinase is contacted in vivo, e.g., in a cell, tissue, or subject. In some embodiments, the cell or tissue is contacted in vitro, for example, in a cell or tissue culture environment. In some embodiments, the kinase is contacted in vivo, for example in a subject. In some embodiments, the kinase is contacted in vivo with the compound, e.g., a macrocycle described herein, or a pharmaceutically acceptable salt, solvate, or derivative thereof. In some embodiments, the subject has or is diagnosed with a disease or disorder associated with aberrant kinase activity. In some embodiments, a compound as provided herein is administered to a subject to inhibit the activity of a kinase in the subject, for example, in a cell or tissue of the subject. In some embodiments, a kinase-modulatory compound as provided herein is administered to a subject based on the subject, or a cell or tissue of the subject, exhibiting aberrant kinase activity. Methods to determine kinase activity in a subject are known to those of skill in the art. For example, such methods may, in some embodiments, include obtaining a biological sample from a subject, for example, a cell, tissue, or body fluid sample, and performing a suitable kinase assay on the sample. Suitable kinase assays are well known to those in the art. For an overview on some exemplary and non-limiting kinase assays, see Sefton and Hunter, *Protein Phosphorylation* (*Selected Methods in Enzymology*) Academic Press; 1st edition (May 1, 1998), ISBN: 0126344906; Reith, *Protein Kinase Protocols* (*Methods in Molecular Biology*), Humana Press; 1st edition (Jan. 15, 2001) ISBN: 0896037002; and Hardie, *Protein Phosphorylation: A Practical Approach* (*Practical Approach Series*), Oxford University Press, USA; 2 edition (Dec. 15, 1999), ISBN: 0199637288; all incorporated by reference in their entirety herein for disclosure of protein kinase assays). In some embodiments, the method includes determining an aberrant level of kinase activity, for example, Src kinase activity, in the subject. In some embodiments, the method includes determining an aberrant level of kinase activity in a cell or tissue of the subject. In some embodiments, the method includes obtaining a biological sample, for example, a tumor biopsy, from a subject, determining the activity level of a kinase, for example, Src kinase, in the biological sample (e.g., by performance of a suitable kinase assay (e.g. a Src kinase assay)), and comparing the kinase activity measured in the sample to a reference or control activity, wherein, if the activity level measured in the sample from the subject is higher or lower than the reference or control activity, then the biological sample is determined to exhibit an aberrant kinase activity, or if the kinase activity level in the biological sample from the subject is similar or equal to the reference or control level, then the biological sample is determined to exhibit normal kinase activity. In some embodiments, "lower" refers to a level of kinase activity that is at least 10%, at least 20%, at least 30%, at least 40%, at least 50% at least 60%, at least 70%, at least 80%, at least 90%, at least 95%, at least 98%, or at least 99% lower than a reference or control level, for example, an average level observed in healthy individuals. In some embodiments, "higher" refers to a level of kinase activity that is at least 25%, at least 50%, at least 75%, at least 100%, at least 200% at least 250%, at least 300%, at least 400%, or at least 500% higher than a reference or control level, for example, an average level observed in healthy individuals. In some embodiments, "lower" or "higher" refers to a statistically significant elevation or decrease in the level of activity. In some embodiments, the reference or control level is a level measured in a cell or tissue of the same type that is not affected by disease. For example, if the tissue from the subject is colonic tissue, then the reference or control level may, in some embodiments, be the level of activity of the respective kinase measured in healthy colonic tissue, e.g. in colonic tissue from a healthy subject or from healthy subjects or in colonic tissue that is not affected by disease from the same subject. For another example, if the tissue obtained from the subject is a tumor biopsy, the reference or control level may be the average level observed in healthy cells, or in tumors of the same tissue or organ, or in tumors of the same tissue of origin. In some embodiments, for example, where a change in kinase activity is related to a mutation in the kinase-encoding gene, the reference or control level may be a level measured in a cell, tissue, or biological sample known to have or express a non-mutated kinase gene. Accordingly, a higher level of, e.g., Src kinase activity in a colon tumor cell or tissue may, in some embodiments, be a level that is statistically significantly higher than a reference or control level of Src kinase activity, for example, an average level measured in colon tumor biopsies, or a level measured in colon tumors known to express a non-mutated Src protein.

Certain compounds of the invention are useful for modulating the activity of a mutant kinase, for example, a kinase comprising a getkeeper mutation, such as a Src kinase comprising a T338I or T341I mutation. In some embodiments, modulating the activity of a mutant kinase with a compound described herein involves contacting the kinase with an effective amount of the compound. In certain embodiments, the mutant kinase is contacted in vitro. In some embodiments, an isolated or purified mutant kinase is contacted. In some embodiments, the mutant kinase is contacted in vivo, e.g., in a cell, tissue, or subject. In some embodiments, the cell or tissue is contacted in vitro, for example, in a cell or tissue culture environment. In some embodiments, the mutant kinase is contacted in vivo, for example in a subject. In some embodiments, the subject has or is diagnosed with a disease or disorder associated with aberrant kinase activity. In some embodiments, the subject has been determined to express a mutant kinase. In some embodiments, the mutant kinase is resistant to an ATP-competitive kinase inhibitor. In some embodiments, a compound as provided herein is administered to a subject to inhibit the activity of a mutant kinase in the subject, for example, in a cell or tissue of the subject. In some embodiments, a mutant-kinase-modulatory compound as provided herein is administered to a subject based on the subject, or a cell or tissue of the subject, exhibiting aberrant kinase activity and/or being determined to express a mutant or ATP-competitive kinase inhibitor-resistant kinase. Methods to determine kinase activity and kinase mutations in a subject are known to those of skill in the art. For example, such methods may, in some embodiments, include obtaining a biological sample from a subject, for example, a cell, tissue, or body fluid sample, and performing a suitable kinase assay on the sample. Kinase mutations can be detected by sequencing the kinase-encoding genomic region or analyzing the kinase amino acid sequence, using methods well known to those of skill in the art. In some embodiments, the method includes determining an aberrant level of kinase activity, for example, Src kinase activity, in the subject, e.g., as described elsewhere herein. In some embodiments, the method includes detecting a gatekeeper mutation in a kinase in the subject, for example, in a kinase exhibting aberrant kinase activity in a cell or tissue of the subject. In some embodiments, the method includes obtaining a biological sample, for example, a tumor biopsy, from a subject, determining the activity level of a kinase, for example, Src kinase, in the biological sample (e.g., by performance of a suitable kinase assay (e.g. a Src kinase assay)), comparing the kinase activity measured in the sample to a reference or control activity, wherein, if the activity level measured in the sample from the subject is higher or lower than the reference or control activity, then the biological sample is determined to exhibit an aberrant kinase activity, or if the kinase activity level in the biological sample from the subject is similar or equal to the reference or control level, then the biological sample is determined to exhibit normal kinase activity. In some embodiments, "lower" refers to a level of kinase activity that is at least 10%, at least 20%, at least 30%, at least 40%, at least 50% at least 60%, at least 70%, at least 80%, at least 90%, at least 95%, at least 98%, or at least 99% lower than a reference or control level, for example, an average level observed in healthy individuals. In some embodiments, "higher" refers to a level of kinase activity that is at least 25%, at least 50%, at least 75%, at least 100%, at least 200% at least 250%, at least 300%, at least 400%, or at least 500% higher than a reference or control level, for example, an average level observed in healthy individuals. In some embodiments, "lower" or "higher" refers to a statistically significant elevation or decrease in the level of activity. In some embodiments, the reference or control level is a level measured in a cell or tissue of the same type that is not affected by disease. In some embodiments, for example, where a change in kinase activity is related to a mutation in the kinase-encoding gene, the reference or control level may be a level measured in a cell, tissue, or biological sample known to have or express a non-mutated kinase gene. Accordingly, a higher level of, e.g., Src kinase activity in a colon tumor cell or tissue may, in some embodiments, be a level that is statistically significantly higher than a reference or control level of Src kinase activity, for example, an average level measured in colon tumor biopsies, or a level measured in colon tumors known to express a non-mutated Src protein. In some embodiments, the method further comprises detecting a mutation, for example, a gatekeeper mutation, in a kinase expressed in the subject, e.g., a kinase determined to exhibit an aberrant activity level in the subject. In some embodiments, the method comprises administering to a cell, tissue, or subject determined to express a kinase comprising a gatekeeper mutation, for example, a src kinase with a T338I or T341I mutation, or a kinase having a homologous gatekeeper mutation, a compound provided herein that inhibits the mutated kinase. In some embodiments, a method is provided that includes administering a kinase inhibitor that inhibits the activity of a kinase comprising a gatekeeper mutation, for example, of a src kinase comprising a T338I or T341I mutation to a subject, cell, or tissue expressing such a mutated kinase. For example, in some embodiments, the cell, tissue, or subject expresses a src kinase with a T338I or T341I mutation, and the method includes administering to the cell, tissue, or subject macrocycle A10-Phe-C5-D6, [4-Me-Phe]-Phe-C5-D6, [4-Cl-Phe]-Phe-C5-D6, [4-Br-Phe]-Phe-C5-D6, [4-CF$_3$-Phe]-Phe-C5-D6, [4-CONH$_2$-Phe]-Phe-C5-D6, [4-CN-Phe]-Phe-C5-D6, A10-Phe-Cha-D6, [4-Me-Phe]-Phe-Cha-D6, [4-Cl-Phe]-Phe-Cha-D6, [4-Br-Phe]-Phe-Cha-D6, [4-CF$_3$-Phe]-Phe-Cha-D6, [4-CONH$_2$-Phe]-Phe-Cha-D6, [4-CN-Phe]-Phe-Cha-D6, A10-[4-F-Phe]-Cha-D6, [4-Me-Phe]-[4-F-Phe]-Cha-D6, [4-Cl-Phe]-[4-F-Phe]-Cha-D6, [4-Br-Phe]-[4-F-Phe]-Cha-D6, [4-CF$_3$-Phe]-[4-F-Phe]-Cha-D6, [4-CONH$_2$-Phe]-[4-F-Phe]-Cha-D6, or [4-CN-Phe]-[4-F-Phe]-Cha-D6, where Phe is phenylalanine, Cha is cyclohexylalanine, 4-Me-Phe is 4-methyl-phenylalanine, 4-F-Phe is 4-fluoro-phenylalanine, etc. (A-B-C-D nomenclature as illustrated in e.g., FIGS. 5 and 19). In some embodiments, the macrocycle is in trans-configuration.

In some embodiments, a macrocycle inhibitors provided herein is administered to a target kinase, cell, tissue, or subject in an amount effective to achieve a reduction of the activity level of the target kinase, for example, src kinase, of at least 10%, at least 20%, at least 30%, at least 40%, at least 50%, at least 60%, at least 70%, at least 80%, at least 90%, at least 95%, at least 98%, or at least 99%.

In some embodiments, methods of treating a disease using a compound described herein are provided. In some embodiments, the disease is associated with, caused by, and/or characterized by aberrant kinase activity. In some embodiments, a method provided involves the administration of a therapeutically effective amount of an inventive compound to a subject (including, but not limited to, a human or other animal) in need thereof. In some embodiments, an effective amount is an amount sufficient to decrease the level of kinase activity by at least 10%, at least 20%, at least 30%, at least 40%, at least 50%, at least 60%, at least 70%, at least 80%, at least 90%, at least 95%, at least 98%, or at least 99%, in a cell or tissue of the subject. In some embodiments, an effective amount is an amount sufficient to increase the level of kinase activity by at least 25%, at least 50%, at least 75%, at least 100%, at least 200%, at least 250%, at least 300%, at least 400%, or at least 500%.

Compounds and compositions described herein are generally useful for the modulation of kinase activity, for example, for the inhibition of the activity of a kinase, such as Src kinase or a mutant thereof, e.g., a constitutively active src mutant or a src mutant carrying a gatekeeper mutation.

The compounds and pharmaceutical compositions provided herein may be used in treating or preventing any disease or condition characterized by increased activity of a kinase, including, but not limited to, proliferative diseases (e.g., cancer, benign neoplasms, diabetic retinopathy), neurodegenerative diseases, autoimmune diseases (e.g., rheumatoid arthritis, lupus, multiple sclerosis), metabolic syndrome, diabetes mellitus, and inflammatory diseases.

The inventive compounds and pharmaceutical compositions may be administered to animals, preferably mammals (e.g., domesticated animals, cats, dogs, mice, rats), and more preferably humans. Any suitable method of administration may be used to deliver the inventive compound or pharmaceutical composition to the animal. In certain embodiments, the compound or pharmaceutical composition is administered orally. In other embodiments, the compound or pharmaceutical composition is administered parenterally.

In certain embodiments, the inventive compounds are useful in treating a proliferative disease. In some embodiments, methods for treating cancer are provided. In some embodiments, methods for treating tumorigenesis are provided. Examples of cancers that may be treated with a compound provided by some aspects of the invention include, but are not limited to, tumors of the breast; biliary tract; bladder; bone; brain, including glioblastomas and medulloblastomas; central and peripheral nervous system; cervix; colon; connective tissue; endocrine glands (e.g., thyroid and adrenal cortex); esophagus; endometrium; germ cells; gastrointestinal tract; head and neck; kidney; liver; lung; larynx and hypopharynx; mesothelioma; muscle; ovary, including those arising from epithelial cells, stromal cells, germ cells and mesenchymal cells; pancreas; prostate; rectum; renal, including adenocarcinoma and Wilm's tumor; small intestine; soft tissue; testis, including germinal tumors such as seminoma, non-seminoma (teratomas, choriocarcinomas), stromal tumors, and germ cell tumors; thyroid, including thyroid adenocarcinoma and medullar carcinoma; stomach; skin, including melanoma, Kaposi's sarcoma, basocellular cancer, and squamous cell cancer; ureter; vagina; and vulva; retinoblastoma; leukemia and lymphoma, namely non-Hodgkin's disease, lymphocytic lymphomas, chronic and acute myeloid leukemia (CML/AML), acute lymphoblastic leukemia (ALL), chronic lymphocytic leukemia (CLL), Hodgkin's disease, multiple myeloma, and T-cell lymphoma; myelodysplastic syndrome; plasma cell neoplasia; paraneoplastic syndromes; intraepithelial neoplasms including Bowen's disease and Paget's disease; neuroblastomas; oral cancer including squamous cell carcinoma; sarcomas including leiomyosarcoma, rhabdomyosarcoma, liposarcoma, fibrosarcoma, and osteosarcoma; cancers of unknown primary site; and AIDS-related malignancies. Other cancers that may be treated by administering a compound provided herein, for example, cancers that exhibit increased kinase activity (e.g., Src kinase activity) or expression, will be known to one of ordinary skill in the art or can be identified with no more than routine experimentation.

In certain embodiments, the invention provides methods for treating or lessening the severity of a proliferative disease including, but not limited to, smooth muscle cell proliferation including vascular proliferative disorders, atherosclerosis, and restenosis. In certain embodiments, the invention provides methods for treating or lessening the severity of endometriosis, uterine fibroids, endometrial hyperplasia, or benign prostate hyperplasia.

In certain embodiments, the invention provides methods for treating or lessening the severity of neurodegenerative disorders and/or tauopathies including, but not limited to, Alzheimer's disease, progressive supranuclear palsy, corticobasal degeneration, frontotemporal lobar degeneration, Pick's disease, Parkinson's disease, Lewy body disease, or amyotropic lateral sclerosis (ALS).

In some embodiments, the invention provides methods for treating or lessening the severity of autoimmune diseases including, but not limited to, inflammatory bowel disease, arthritis, systemic lupus erythematosus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

In some embodiments, the invention provides a method for treating or lessening the severity of one or more diseases and conditions, wherein the disease or condition is selected from immune-related conditions or diseases, which include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of an inflammatory disease including, but not limited to, asthma, appendicitis, Blau syndrome, blepharitis, bronchiolitis, bronchitis, bursitis, cervicitis, cholangitis, cholecystitis, chronic obstructive pulmonary disease (COPD), chronic recurrent multifocal osteomyelitis (CRMO), colitis, conjunctivitis, cryopyrin associated periodic syndrome (CAPS), cystitis, dacryoadenitis, dermatitis, dermatomyositis, dry eye syndrome, encephalitis, endocarditis, endometritis, enteritis, enterocolitis, epicondylitis, epididymitis, familial cold-induced autoinflammatory syndrome, familial Mediterranean fever (FMF), fasciitis, fibrositis, gastritis, gastroenteritis, hepatitis, hidradenitis suppurativa, laryngitis, mastitis, meningitis, mevalonate kinase deficiency (MKD), Muckle-Well syndrome, myelitis myocarditis, myositis, nephritis, oophoritis, orchitis, osteitis, inflammatory osteolysis, otitis, pancreatitis, parotitis, pericarditis, peritonitis, pharyngitis, pleuritis, phlebitis, pneumonitis, pneumonia, proctitis, prostatitis, pulmonary fibrosis, pyelonephritis, pyoderma gangrenosum and acne syndrome (PAPA), pyogenic sterile arthritis, rhinitis, salpingitis, sinusitis, stomatitis, synovitis, systemic juvenile rheumatoid arthritis, tendonitis, TNF receptor associated periodic syndrome (TRAPS), tonsillitis, undifferentiated spondyloarthropathy, undifferentiated arthropathy, uveitis, vaginitis, vasculitis, vulvitis, chronic inflammation resulting from chronic viral or bacteria infections, or psoriasis (e.g., plaque psoriasis, pustular psoriasis, erythrodermic psoriasis, guttate psoriasis or inverse psoriasis).

In some embodiments, methods are provided for treating or lessening the severity of arthropathies and osteopathological diseases including, but not limited to, rheumatoid arthritis, osteoarthrtis, gout, polyarthritis, and psoriatic arthritis.

In some embodiments, methods are provided for treating or lessening the severity of acute and chronic inflammatory diseases including, but not limited to, ulcerative colitis, inflammatory bowel disease, Crohn's disease, dry eye syndrome, allergic rhinitis, allergic dermatitis, cystic fibrosis, chronic obstructive bronchitis, and asthma.

In some embodiments, a method is provided for the treatment of mammals, including humans, which are suffering from one of the above-mentioned conditions, illnesses, disorders, or diseases. In some embodiments, the method comprises that a therapeutically effective amount of one or more of the compounds according to this invention or a composition thereof is administered to the subject in need of such treatment.

In some embodiments, a method is provided for inhibiting or activating a kinase in a cell or tissue using a compound of the invention. In some embodiments, inhibition or activation of a kinase in a cell or a tissue is achieved by contacting the cell or tissue with a compound of the invention. In some embodiments, the activity of a specific kinase, for example, Src kinase, is measured prior to contacting the cell or tissue with a compound of the invention. In some embodiments, a cell or tissue is contacted with a compound provided herein, based on the cell or tissue exhibiting abnormal kinase activity. For example, in some embodiments, a cell or tissue is contacted with a compound inhibiting Src kinase activity, as provided herein, based on the cell or tissue exhibiting increased or constitutive Src kinase activity. In some embodiments, the cell is a tumor cell. In some embodiments, the cell is a malignant cell. In some embodiments, the tissue is tumor tissue. In some embodiments, the cell or tissue are in culture. In some embodiments, the cell or the tissue are comprised within a subject. In some embodiments, the contacting is performed in vitro. In some embodiments, the contacting is performed in vivo.

In some embodiments, a method is provided comprising administering to a subject having a tumor an effective amount of a compound modulating a kinase as provided herein based on the tumor exhibiting aberrant kinase activity. In some embodiments, a method is provided comprising administering to a subject having a tumor exhibiting increased kinase activity, for example, increased Src kinase activity, a compound inhibiting a kinase as provided herein, for example, an Src-inhibitory compound, based on the tumor exhibiting aberrant kinase activity.

In some embodiments a compound modulating the activity of a kinase is a compound selectively binding the kinase. Accordingly, in some embodiments a selective kinase-inhibitory compound is provided. In some embodiments, a selective Src kinase inhibitor is provided. In some embodiments, a compound selectively binding a kinase binds the kinase with high affinity, for example, with a dissociation constant ($K_D$) of less than $10^{-7}$, less than $10^{-8}$, less than $10^{-9}$, less than $10^{-10}$, less than $10^{-11}$, less than $10^{-12}$, or less than $10^{-13}$ but does not bind with comparable affinity to other kinases. In some embodiments, a compound selectively binding a kinase binds the kinase with a dissociation constant ($K_D$) of less than $10^{-7}$, less than $10^{-8}$, less than $10^{-9}$, less than $10^{-10}$, less than $10^{-11}$, less than $10^{-12}$, or less than $10^{-13}$, but binds other proteins with a KD of more than $10^{-7}$, more than $10^{-6}$, more than $10^{-5}$, or more than $10^4$. Similarly, a compound selectively inhibiting a kinase inhibits the activity of the kinase, but does not significantly inhibit other kinases. In some embodiments, a compound provided herein that selectively inhibits a kinase, decreases the activity of the kinase by at least about 50%, at least about 60%, at least about 70%, at least about 80%, at least about 90%, at least about 95%, at least about 98%, at least about 98%, or at least about 99%, but does not decrease the activity of a different kinase by more than about 40%, more than about 30%, more than about 25%, more than about 20%, more than about 10%, or more than about 5%.

Some aspects of this invention relate to the use of the inventive compounds for the production of pharmaceutical compositions for the treatment and/or prophylaxis and/or amelioration of a disease or disorder associated with aberrant kinase activity, for example, any of the diseases, disorders, illnesses, and/or conditions as mentioned herein.

Some aspects of this invention relate to the use of the inventive compounds for the production of pharmaceutical compositions that modulate kinase activity, for example, compositions that inhibit Src kinase activity, in a subject.

Some aspects of this invention relate to the use of the inventive compounds for the production of pharmaceutical compositions which can be used for treating, preventing, or ameliorating diseases responsive to modulating kinase activity, for example, diseases responsive to the inhibition of Src kinase activity, e.g., cancers, and particularly cancers exhibiting increased or constitutive Src kinase activity.

The amount of a compound provided herein that is required for effective treatment of a disease will vary from subject to subject, depending on the species, age, and general condition of the subject, the particular compound, its mode of administration, its mode of activity, and the like. The compounds of the invention are preferably formulated in dosage unit form for ease of administration and uniformity of dosage. It will be understood, however, that the total daily usage of the compounds and compositions of the present invention will be determined by the attending physician based on sound medical judgment. The specific therapeutically effective dose level for any particular subject will depend upon a variety of factors including the disorder being treated and the severity of the disorder; the activity of the specific protein employed; the specific composition employed; the age, body weight, general health, sex, and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like. In certain embodiments, the compounds of the invention may be administered orally or parenterally at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about mg/kg, from about 0.1 mg/kg to about 10 mg/kg, and from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such polyethoxylated castor oil, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as poly(lactide-co-glycolide). Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active protein may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions such as pectin-containing formulations can be used. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

EXAMPLES

The function and advantage of these and other embodiments of the present invention will be more fully understood from the examples below. The following examples are intended to illustrate the benefits of the present invention, but do not exemplify the full scope of the invention.

Example 1

Identification of Macrocycles Having Kinase-Inhibiting Properties

DNA-linked small molecules with protein binding affinity can be enriched from complex mixtures containing predominantly non-binding DNA-linked small molecules,[20,29] and that a library of 13,824 DNA templates can be translated into a corresponding library of synthetic macrocycles through three DNA-templated synthesis reactions.[24] In this example, these capabilities are integrated into a broad effort to discover and synthetic small-molecule macrocycles that inhibit or activate protein targets of interest are characterized.

Validating the In Vitro Selection of DNA-Linked Small Molecules that Bind Proteins Fused to GST Prior to undertaking library selections, we first validated a general and efficient in vitro selection strategy that would support selections against many different protein targets. We sought to improve our earlier in vitro selection efforts that used proteins covalently bound to beads[29] by implementing a strategy that would not perturb the covalent structure of the target protein upon immobilization. Glutathione-S-transferase (GST) fusions of many biomedically relevant proteins are readily available, typically retain native function, and can be immobilized in a defined way using glutathione-linked resin. Furthermore, library members that bind targets presented in this manner can be specifically eluted under mild conditions with free glutathione. This elution strategy should minimize the enrichment of library members that bind molecules other than the target of interest, such as resins or resin-bound linkers.

We tested the ability of immobilized GST-fusion proteins to enrich known small-molecule ligands covalently linked to DNA oligonucleotides in several mock selections using GST-tagged MDM2, FKBP, Bcl-xL, cRaf-1 and HSP90 as protein targets. In brief, a known small-molecule ligand linked to DNA (the positive control) was combined with a 100- to 10,000-fold molar excess of a non-binding DNA sequence (the negative control). The negative and positive control sequences were of identical length and shared common PCR primer-binding sequences. The mixture was incubated with the corresponding protein target immobilized on glutathione-linked beads. Following several successive washes with buffer, molecules that remained bound to the resin were eluted with free glutathione and subjected to PCR amplification or carried through to another round of selection. The ratio of positive control DNA to non-binding DNA was measured using a restriction endonuclease[29] or by qPCR.[43-45] After only one round of selection, we observed substantial (~10- to 1000-fold) enrichment of the positive control-encoding DNA sequence against all five GST-linked protein targets (FIG. 1 and Table 1). These results confirmed our ability to enrich DNA-linked small-molecule protein ligands using immobilized GST-tagged proteins.

REFERENCES CITED IN TABLE 1

1. Garcia-Echeverria, C., Chene, P., Blommers, M. J. J. & Furet, P. Discovery of Potent Antagonists of the Interaction between Human Double Minute 2 and Tumor Suppressor p53. *J. Med. Chem.* 43, 3205-3208 (2000).
2. Chene, P. et al. A Small Synthetic Peptide, which Inhibits the p53-hdm2 Interaction, Stimulates the p53 Pathway in Tumour Cell Lines. *J. Mol. Biol.* 299, 245-253 (2000).
3. Bradner, J. E. et al. A Robust Small-Molecule Microarray. *Chem. Biol.* 13, 493-504 (2006).
4. Sattler, M. et al. Structure of Bcl-xL-Bak Peptide Complex: Recognition Between Regulators of Apoptosis. *Science* 275, 983-986 (1997).
5. Llauger-Bufi, L., Felts, S. J., Huezo, H., Rosen, N. & Chiosis, G. Synthesis of novel fluorescent probes for the molecular chaperone Hsp90. *Bioorg. Med. Chem. Lett.* 13, 3975-3978 (2003).
6. Barnard, D., Sun, H., Baker, L. & Marshall, M. S. In vitro inhibition of Ras-Raf association by short peptides. *Biochem. Biophys. Res. Commun.* 247, 176-180 (1998).

All references cited herein, including any references cited below, are included herein in their entirety by reference.

In Vitro Selection of 13,824 DNA-Templated Small-Molecule Macrocycles

The DNA-templated small-molecule macrocycle library used in this in vitro selection effort was generated in three DNA-templated reactions followed by a non-templated Wittig macrocyclization reaction to generate the final product (FIG. 2a).[20,24] Each DNA-templated library synthesis step relied on a set of 12 DNA-linked building blocks comprising both natural and non-natural amino acids (FIG. 2b).[24] These 36 building blocks together with eight variable diamino-acid scaffolds (FIG. 2b) result in a theoretical diversity of 13,824 DNA-templated macrocycles. The fidelity of DNA-templated macrocycle library synthesis was extensively characterized by high-resolution LC-MS analysis and by gel electrophoresis as previously described.[24]

We chose a diverse set of biomedically relevant protein targets including protein kinases, protein phosphatases, small

TABLE 1

Single round enrichment factors for positive-control DNA-small molecule conjugates after affinity selection using GST-linked MDM2, FKBP, Bcl-xL, cRaf-1, and HSP90.

| Protein | Ligand | interaction affinity (not DNA-linked) | Enrichment Factor | Analysis |
|---|---|---|---|---|
| MDM2 (1-118, N-terminal | Novartis Peptide | 5 nM[1] | 2,000 | Taqman qPCR |
| MDM2 (1-118, N-terminal | control peptide | 1.5 µM[2] | 40 | Taqman qPCR |
| FKBP (N-terminal GST-fused) | Holt ligand | 8 nM[3] | 1,100 | restriction digestion |
| BcLxL (1-209, Δ45-84, N-terminal GST-fused) | Bak peptide | 0.34 µM[4] | 200 | restriction digestion |
| Human Hsp90 (1-235, N-terminal GST-fused) | Geldanamycin | 23 nM (as FITC conjugate)[5] | 40 | Taqman qPCR |
| cRaf-1 (51-200, N-terminal | Ras peptide | ~100 µM[6] | 30 | Taqman qPCR |

GTPases, PDZ domains, SH2 domains, nuclear receptors, and anti-apoptotic proteins for in vitro selection (Table 2).

TABLE 2

Protein targets for in vitro selection. All proteins were obtained or purified as GST-tagged fusion proteins.

| Kinases | Phosphatases | PDZ domains | SH2 domains |
|---|---|---|---|
| Akt3 | DEP1 | Dvl1-3 | Abl1 |
| AMPK ERBB4 | MEG2 | Erbin G1 syntrophin Magil | Abl2 |
| MK2 | PRL2 | MUPP1 | P85αN P85αC P55γC |
| p38α | GTPases | PAR6B PSD95 | other proteins |
| MKK6 | Cdc42 | RGS3 | Bcl-xL |
| Pim1 | H-Ras-V12 | SAP97 | BIR3 (XIAP) PPARδ |
| Src | RhoA | Semcap3 | |
| VEGFR2 | | Shank3 | |

Multiple representatives were chosen from each protein class so that we could compare selection results within protein families. In total, we performed a single round of in vitro selection against 36 protein targets. Additionally, we also performed a selection for binding to GST (with no fused target protein) immobilized on glutathione-linked resin. Although successive rounds of selection (with or without DNA amplification and translation between rounds) can multiply net enrichment factors,[29] we hypothesized that recent advances in ultra high-throughput DNA sequencing would enable even modest enrichment factors to be robustly detected, and the findings in this work are the result of a single round of selection on each protein target.

Figures 2, 2B, 3:
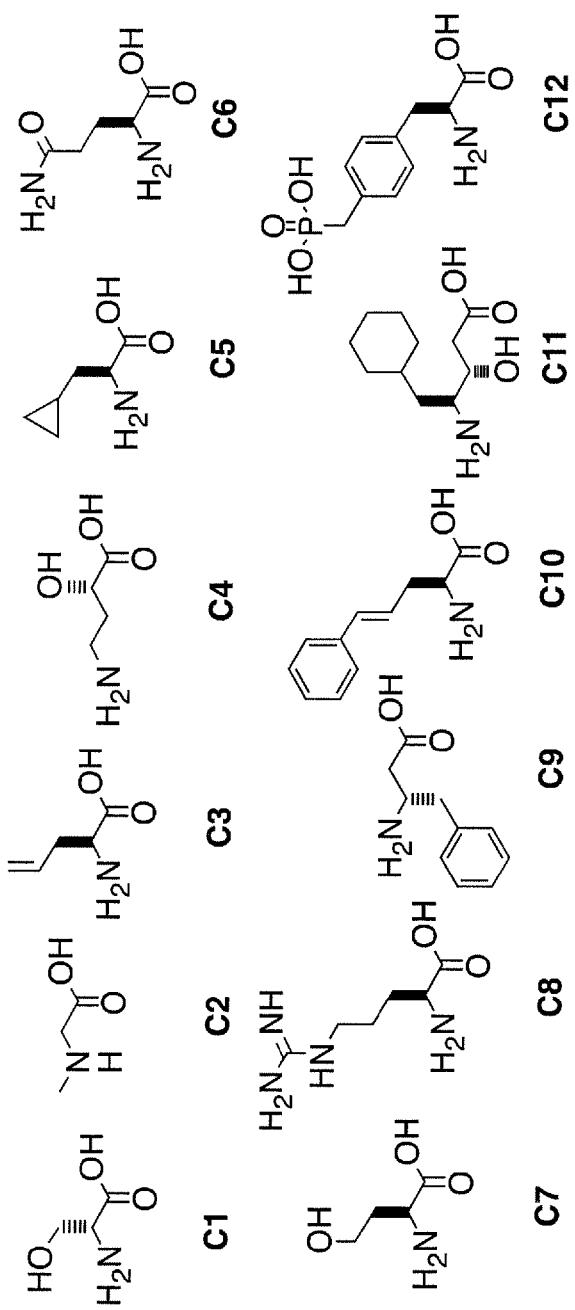
FIG. 3. In vitro selection of the DNA-templated macrocycle library against 36 protein targets. Following affinity selection of the library against an immobilized GST-fused target protein, library members possessing target affinity were eluted and their attached DNA templates were amplified by PCR using DNA primers containing a barcode sequence that uniquely identifies the protein target. Barcoded PCR amplicons from 36 target protein-binding selections, one control selection for binding immobilized GST, and eight aliquots of unselected library were pooled and submitted as one sample for ultra high-throughput DNA sequencing.
Figures 2, 2B, 3, 4:
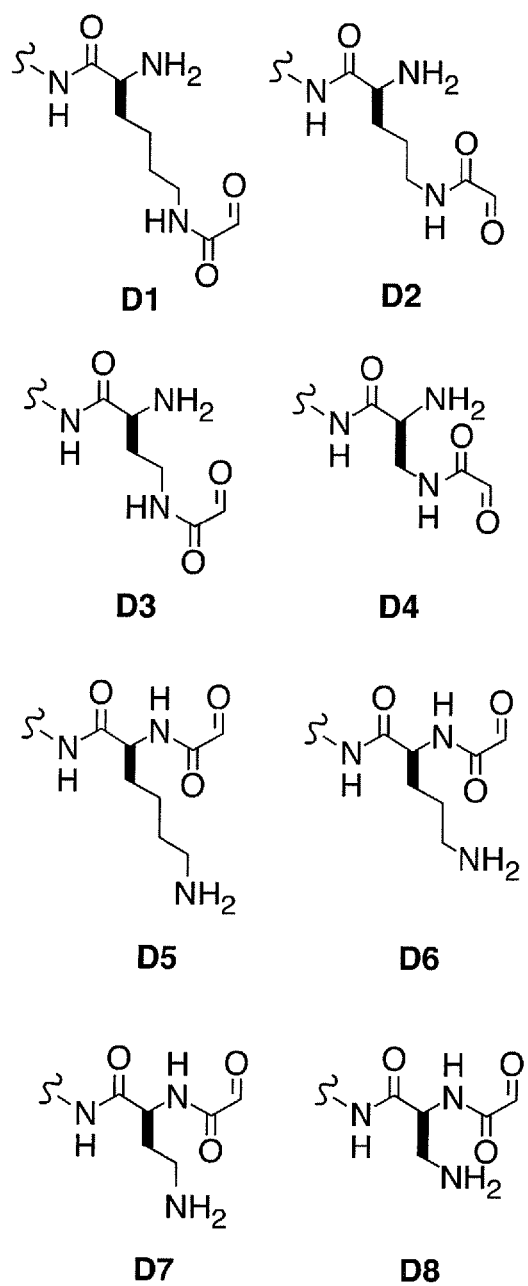
FIG. 4. Deconvolution and analysis of high-throughput sequencing results. (a) Paired-end reads were assembled and binned computationally by barcode. The enrichment factor for each library member in each selection (~497,000 total possible combinations of library member and target) were calculated as (post-selection abundance)÷(pre-selection abundance) using a PERL script (FIG. 4A). (b) Plot of enrichment factor vs. sequence abundance for library members after selection for binding to Src kinase. Each dot represents the DNA sequence corresponding to a single library member (FIG. 4B-1). The structures of macrocycles 1-9 are shown in FIG. 5. Enrichment factors for low-abundance library members vary widely due to statistical undersampling. Only enrichment factors that were substantially higher than background values were considered potential positives (FIG. 4B-1, shown as hollow dots). After one round of selection against Src kinase, macrocycle A11-B1-C5-D7 was enriched 62-fold, representing the highest degree of enrichment for any library member in any of the selections studied (See FIG. 4B-2).

Following in vitro selection, DNA templates linked to target-binding macrocycles were amplified in PCR reactions using primers containing "barcode" sequences specific to each selection (FIG. 3). We also amplified DNA templates from eight aliquots of the unselected library to determine the initial abundance of each library member. A set of 12 five-base barcodes used in pairwise combinations provided sufficient encoding complexity for one round of selection against 36 protein targets, a control selection against immobilized GST, and eight pre-selection library samples (Table 3). These barcodes were designed to differ by at least three bases from one another so that common DNA sequencing errors would not preclude barcode assignment. After affinity selection and PCR amplification, barcoded samples were combined in equimolar amounts and submitted for ultra high-throughput DNA sequencing[46,47] as a single sample.

TABLE 3

| 5'-ACTGA-3' | 5'-GTATC-3' |
|---|---|
| 5'-AGCTG-3' | 5'-GAGCT-3' |
| 5'-ATACG-3' | 5'-GTCAT-3' |
| 5'-TACGC-3' | 5'-CGTAT-3' |
| 5'-TCATG-3' | 5'-CATCG-3' |
| 5'-TCGAT-3' | 5'-CTGTA-3' |

Five-base PCR barcodes used to identify each selection during Solexa sequencing. Barcodes were appended to the 5'-terminus of the DNA-templated library-specific primers and used in pairwise combinations to provide sufficient encoding complexity.

Ultra High-Throughput DNA Sequencing and Analysis of Selection Results

Figure 4A:
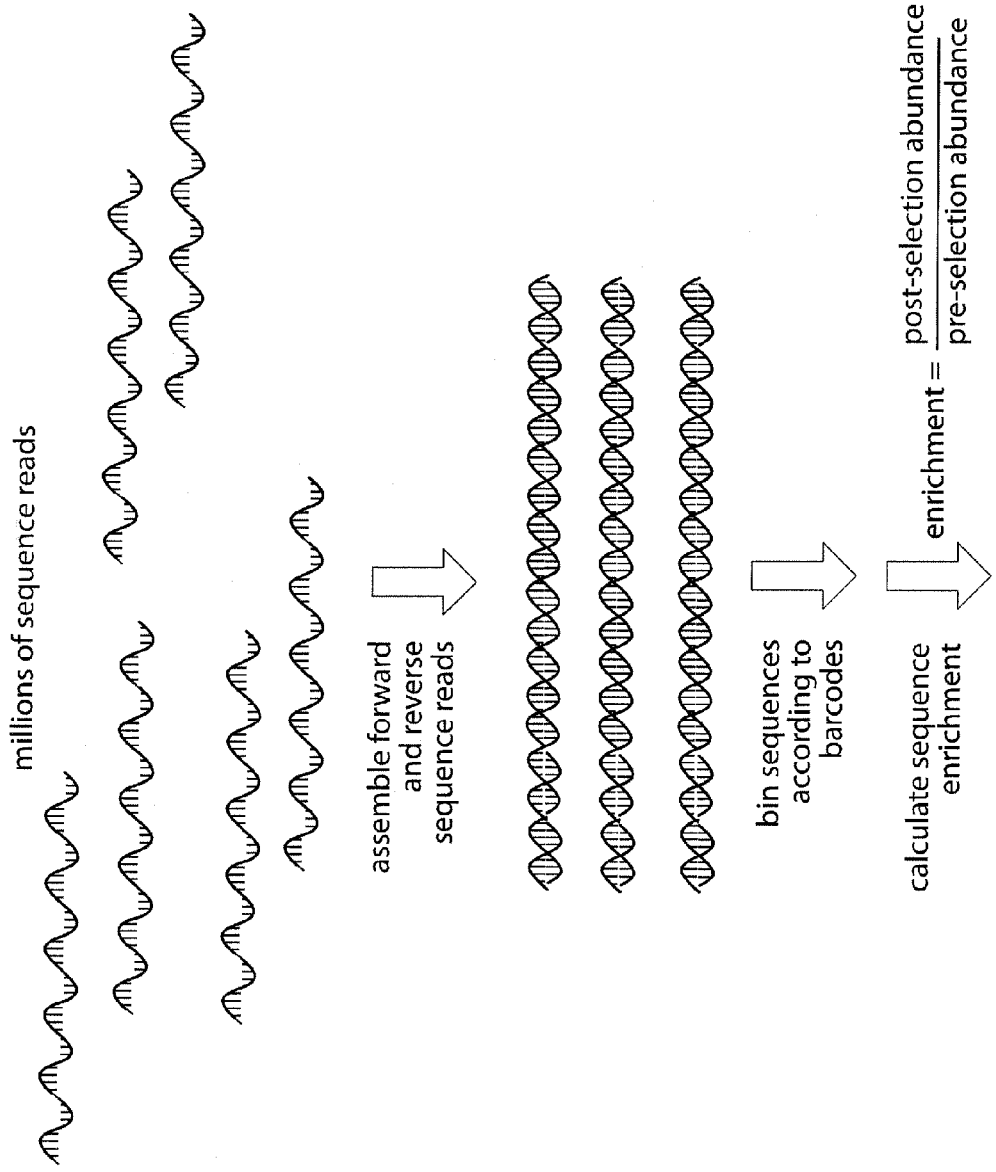

To rapidly identify the DNA-linked macrocycles that survived target affinity selection, we used Solexa (Illumina) DNA sequencing technology.[48] Because standard Solexa sequencing read lengths at the time of this experiment were shorter than the length of our barcoded library templates (84 base pairs), the paired-end sequencing method, which provides both forward and reverse sequencing reads for each template, was used. We created a PERL computer program to analyze the large amount of data emerging from high-throughput sequencing. First, forward and reverse sequence reads were merged to give complete template sequences (FIG. 4a). Each complete DNA sequence was converted into a combination of a barcode (selection identity) and three codons (building block identities). Template sequences were then binned by barcode to deconvolute the results of each selection. The abundance fraction of each library member was determined within each selection by counting the number of corresponding DNA sequence occurrences and dividing by the total number of interpretable sequence reads for that selection. Finally, enrichment factors for each library member were computed by dividing post-selection abundance fraction by pre-selection abundance fraction. In total, we received 25.6 million paired forward and reverse sequence reads from two Solexa sequencing runs. Of these, all four codons (which require five out of six correct bases per codon for the building blocks, and three out of three correct bases per codon for the scaffold[24]) and the selection barcode (which requires four out of five correct bases) could be conclusively assigned for 12.4 million sequences. As a result, we obtained ~200,000 sequence reads for each selection, and 1.7 million sequence reads of the pre-selection library.

Figures 1, 4B:
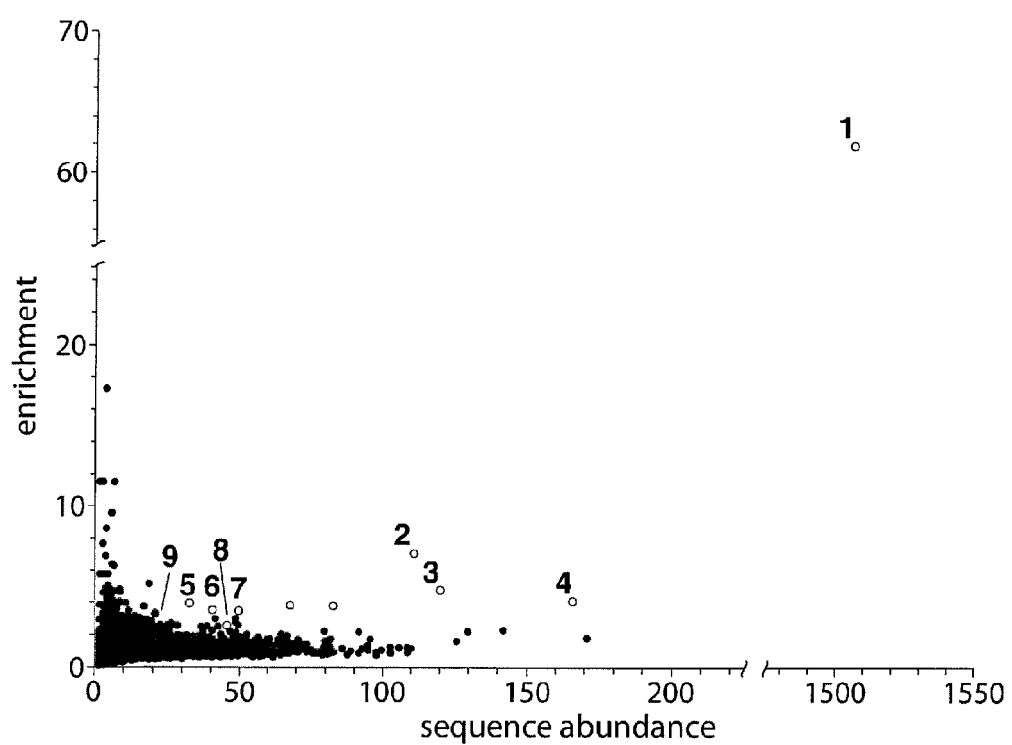
Figures 2, 4B:
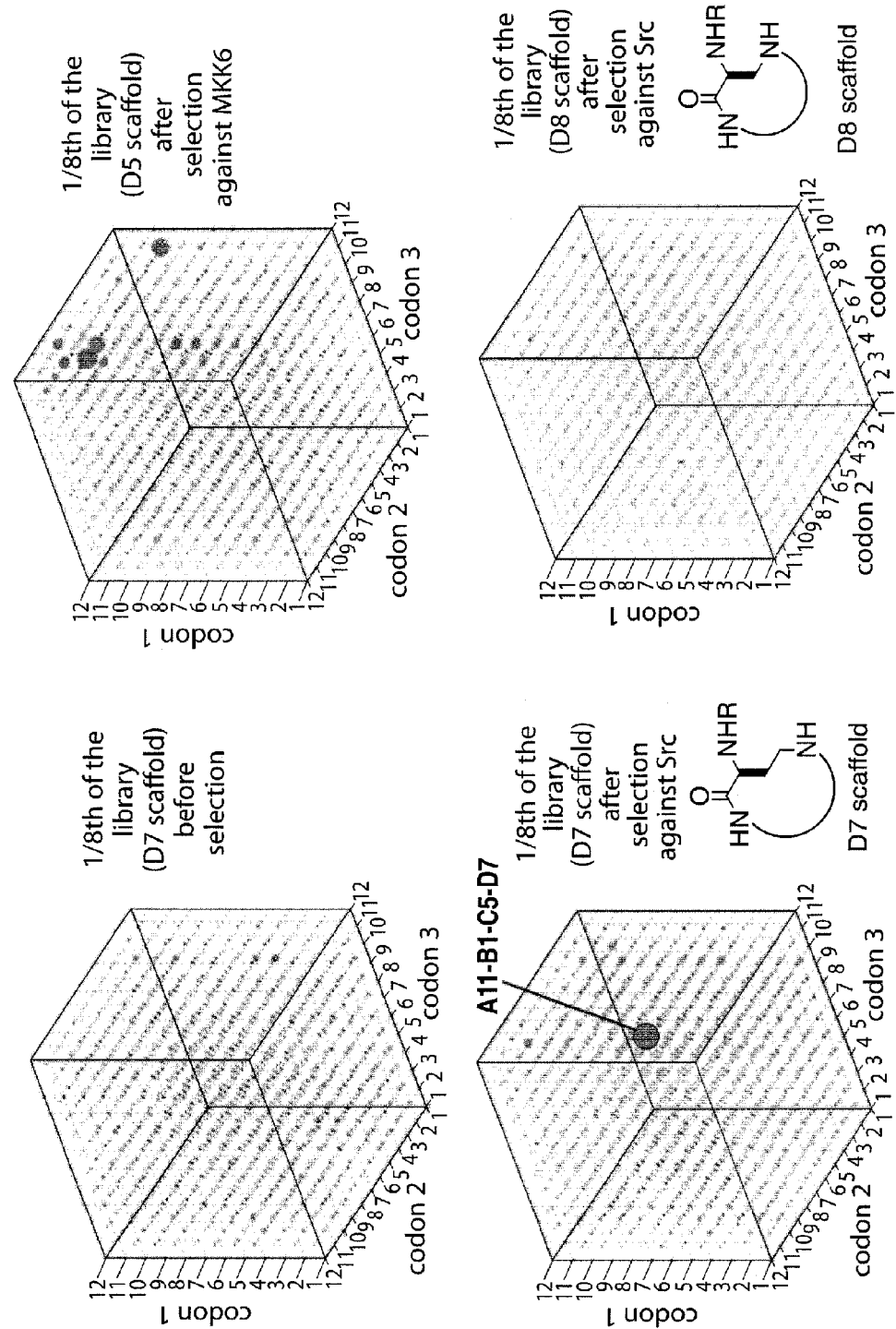
Figure 5:
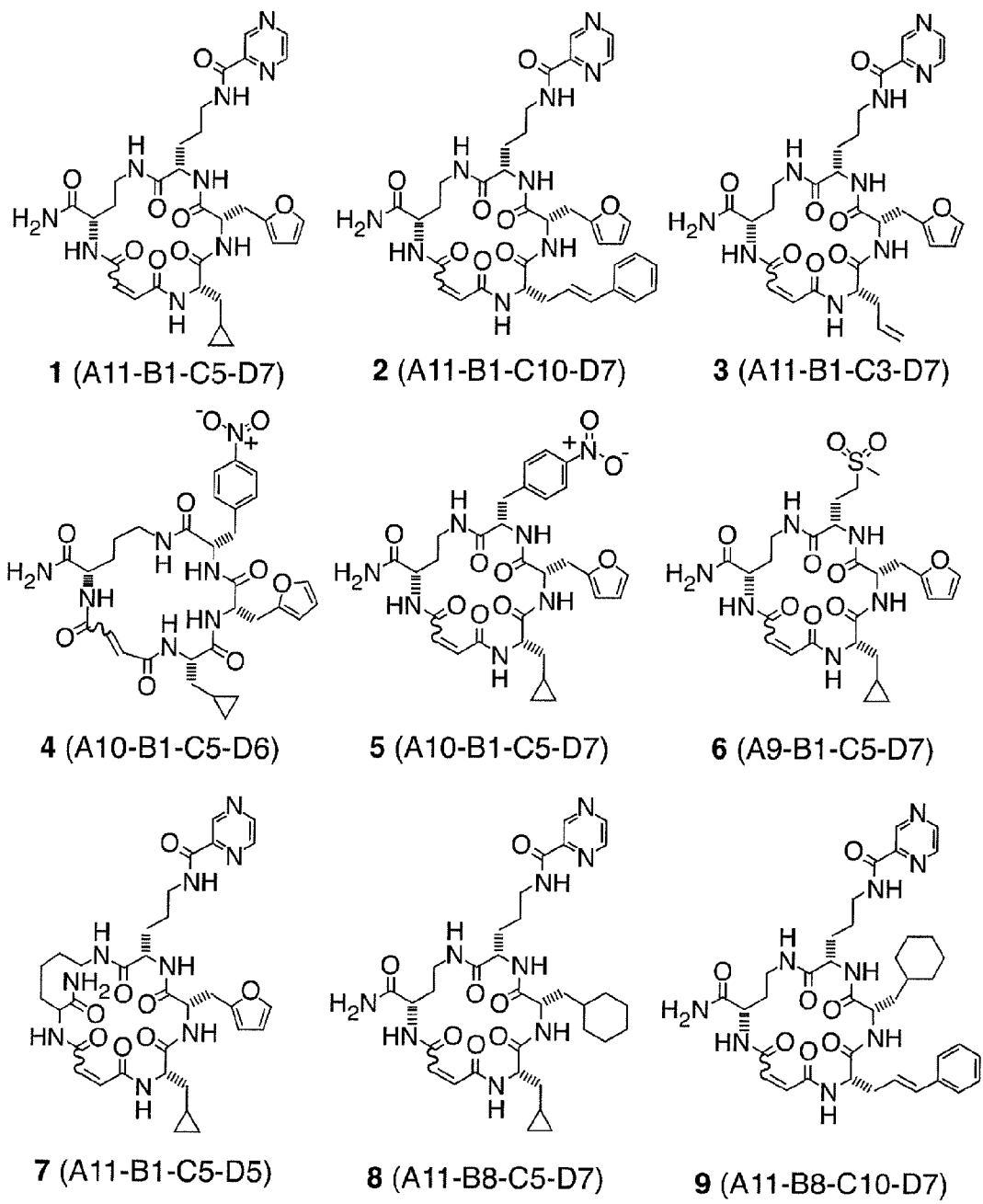
Figures 1, 6:
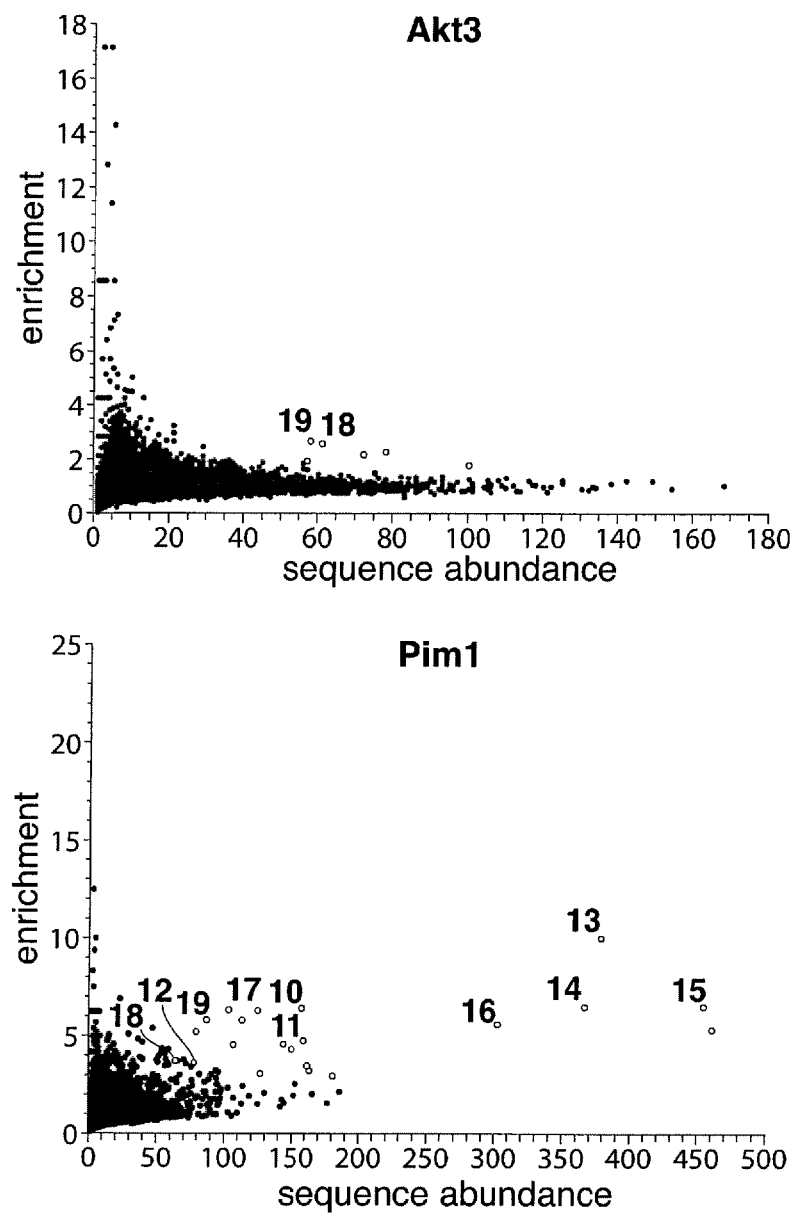
Figures 2, 6:
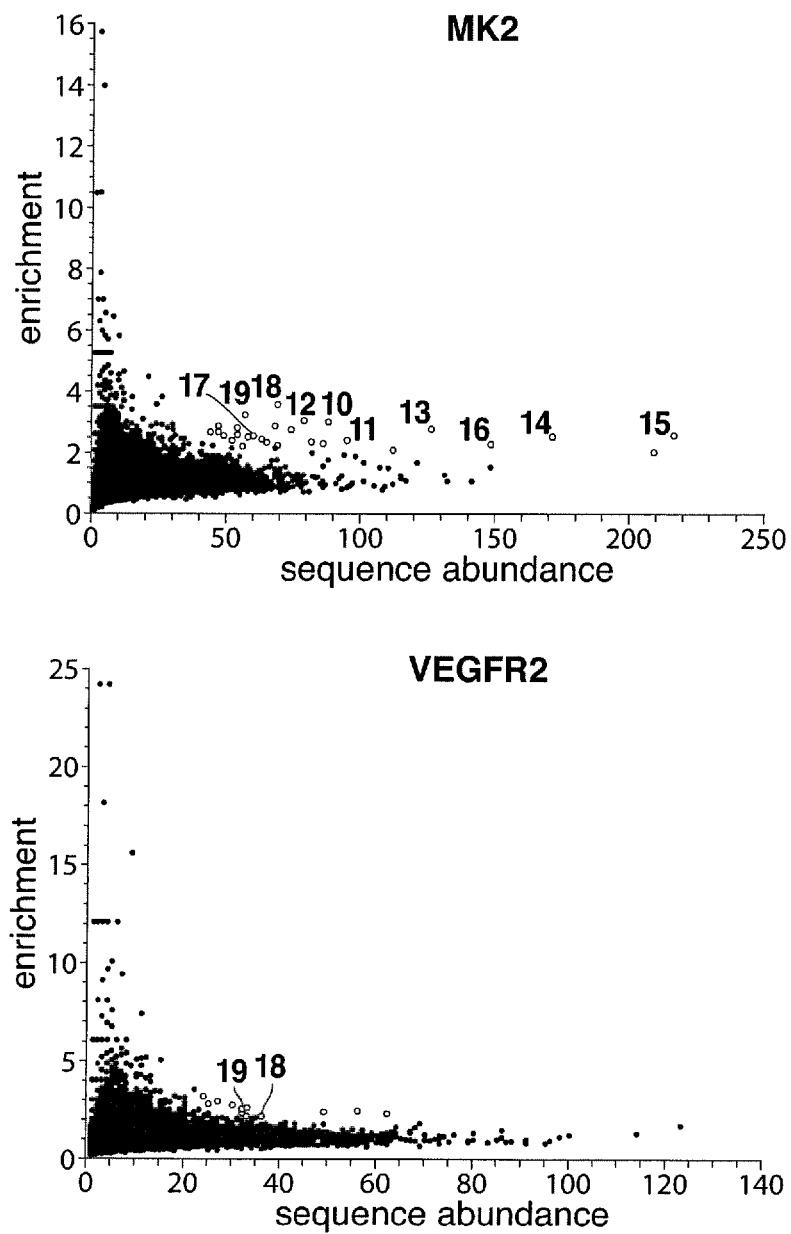

Although 100% of the 13,824 possible library DNA sequences were observed at least once, due to the varying efficiencies of library member synthesis,[24] library members in the pre-selection pool were not expected to be present in equal abundance. Since underrepresented library members are more prone to inaccurate enrichment factors arising from limited sampling, we evaluated selection results using scatter plots of enrichment factor versus sequence counts in order to better identify unusually high enrichment factors that may arise from macrocycle-target binding (FIG. 4b). Indeed, in most selections we observed that those sequences with the fewest sequence counts exhibited both the largest and the smallest enrichment factors (FIG. 4b), presumably due to statistical noise among underrepresented library members. The large number of library members enabled a general relationship between sequence abundance and typical enrichment levels to emerge for each selection. Enrichment factors were therefore deemed of interest not only on the basis of their absolute value, but also only if they fell above the typical enrichment factor range observed for sequences of that abundance.

Protein Kinase Selection Results

Because most of the significantly enriched DNA sequences arose from selections against protein kinases, we focused our characterization efforts on this class of targets. After one round of selection against Src kinase, macrocycle A11-B1-C5-D7 was enriched 62-fold, representing the highest degree of enrichment for any library member in any of the selections described above. We also identified macrocycles A11-B1-C10-D7, A11-B1-C3-D7, A10-B1-C5-D6, A10-B1-C5-D7, A11-B1-C5-D5, A9-B1-C5-D7, A11-B8-C5-D7, and A11-B8-C10-D7 (FIG. 4b and FIG. 5) as enriched between 2- to 7-fold in the Src selection. The significant enrichment factors, strong degree of structural similarity among these molecules, and lack of enrichment of these macrocycles in the other eight kinase selections performed (Table 4), collectively suggested that this class of molecules may correspond to authentic Src ligands that are selective for binding to Src over other protein kinases.

TABLE 4

Enrichment factors of positives from the Src selection in all protein kinase selections performed.

| | Src | Akt3 | AMPK | ERBB4 | MK2 | p38α | MKK6 | Pim1 | VEGFR2 |
|---|---|---|---|---|---|---|---|---|---|
| 1 | 62 | 2.2 | 0.69 | 0.63 | 2.8 | 1.1 | 2.7 | 2.4 | 2.4 |
| 2 | 7.1 | 1.2 | 0.86 | 0.82 | 1.8 | 0.84 | 1.1 | 0.91 | 0.95 |
| 3 | 4.8 | 0.97 | 0.94 | 0.91 | 1.2 | 1.0 | 0.81 | 0.93 | 1.4 |
| 4 | 4.1 | 0.81 | 0.8 | 1.1 | 0.97 | 0.91 | 1.1 | 0.89 | 0.65 |
| 5 | 4.0 | 1.5 | 1.4 | 1.7 | 2.0 | 1.7 | 2.2 | 1.3 | 1.6 |
| 6 | 3.6 | 1.3 | 1.0 | 1.0 | 0.65 | 1.1 | 1.4 | 1.1 | 0.66 |
| 7 | 3.5 | 1.5 | 1.1 | 1.2 | 1.5 | 0.99 | 1.0 | 0.39 | 1.4 |
| 8 | 2.6 | 1.5 | 1.2 | 1.2 | 2.0 | 1.6 | 1.3 | 2.2 | 1.5 |
| 9 | 2.6 | 0.98 | 0.88 | 1.3 | 2.6 | 1.4 | 2.4 | 1.9 | 1.6 |

Figures 2, 2B, 3, 4, 5:
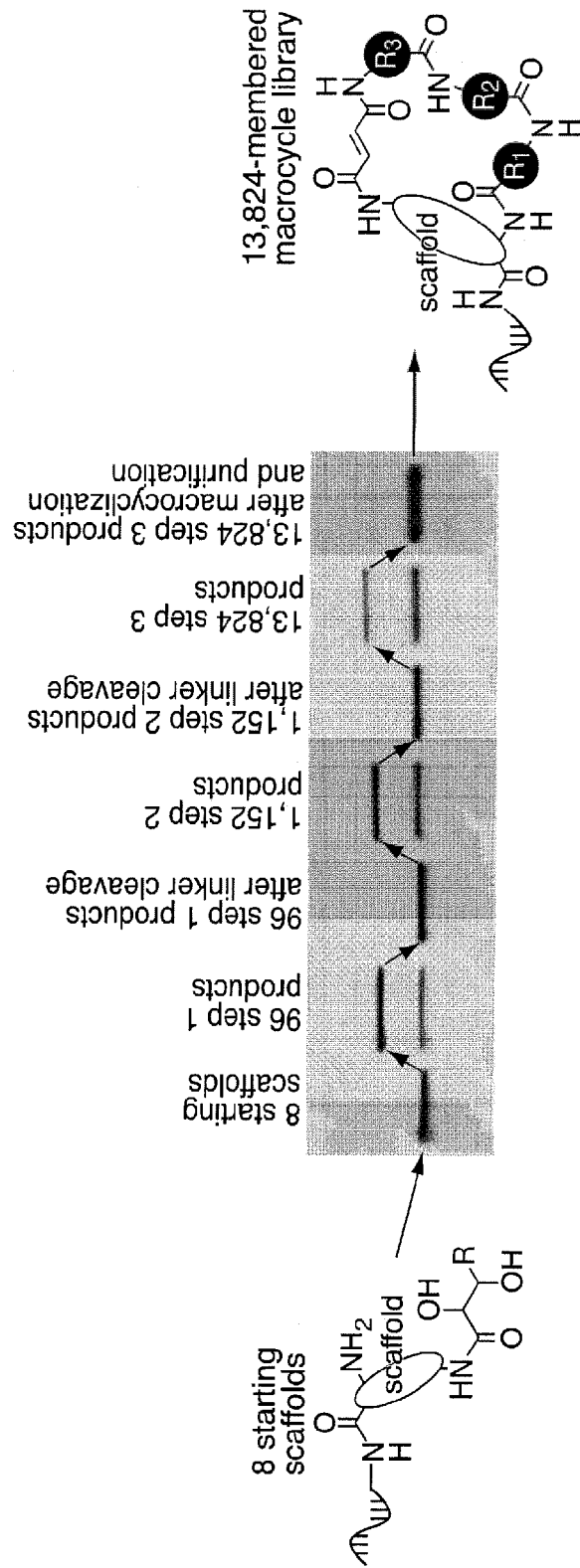
FIG. 5. Chemical structures of macrocycles exhibiting significant enrichment above background and common structural motifs after selection against Src kinase. Macrocycle numbering corresponds to that used in FIG. 4b.

Macrocycle numbering is from FIG. 5.
Enrichment factors >10 are colored red;
those >4 are colored orange;
those >2 are colored yellow.

Figures 2, 2B, 3, 4, 5, 6:
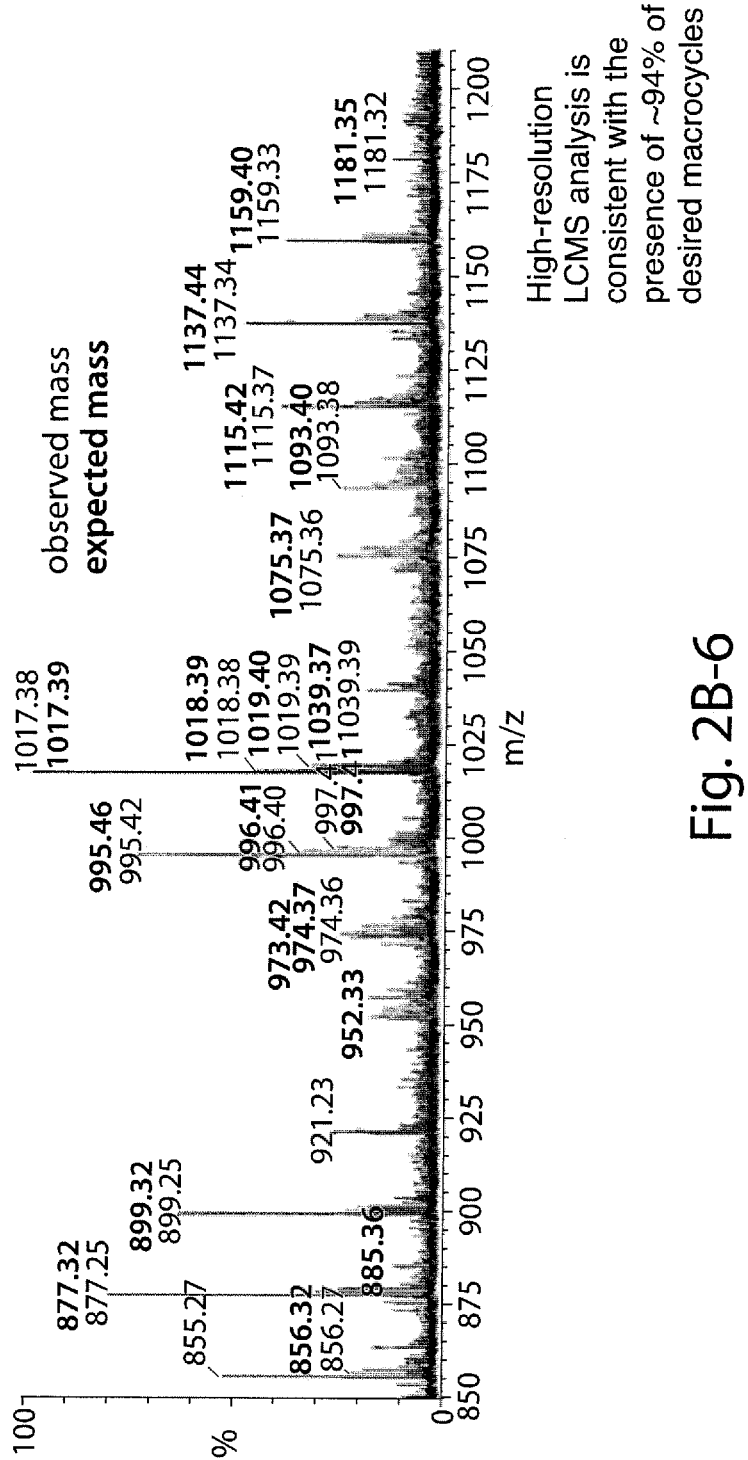
FIG. 6. Plots of enrichment factor vs. sequence abundance for macrocycles 10-19 (FIG. 6-3) after selection for binding to Akt3, MAPKAPK2, Pim1, and VEGFR2 (FIGS. 6-1 and 6-2). Macrocycles 10-19 exhibit significant enrichment above background.
Figure 3:
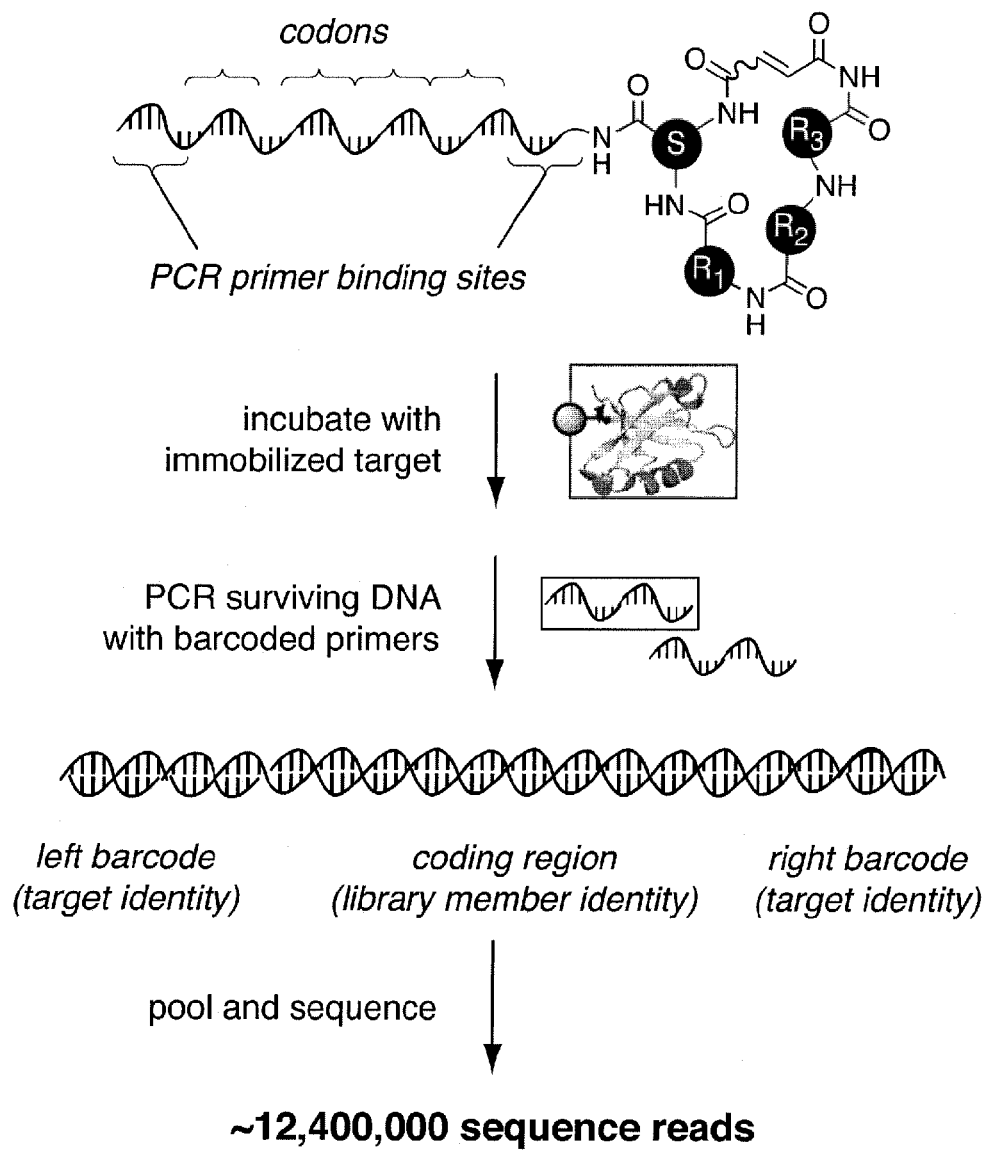

We also identified two additional families of macrocycles enriched in selections against several other kinase targets. Macrocycles A10-Y-C11-D5 (where Y=B1 or B8) were enriched against Akt3, MAPKAPK2, Pim1, and VEGFR2 (FIG. 6). Macrocycles A12-B8-C10-X (where X=D1-D8) exhibited unusually high enrichment factors in the MAPKAPK2 and Pim1 selections (FIG. 6). While we were encouraged by the ability of these molecules to bind similar targets, the high degree of hydrophobicity of the building blocks in these macrocycles raised the possibility that they may bind their targets in a non-classical mode.[49,50] Moreover, the enrichment of macrocycles of structure A12-B8-C10-X appears to be insensitive to changes in ring size (caused by substitution at the "D" scaffold position) that we anticipated would have large effects on macrocycle conformation, suggesting that these macrocycles were interacting with their targets in a non-classical binding mode.[24] The possibility that these compounds represent non-specific ligands or "promiscuous aggregators"[49,50] was examined as described below.

Solid-Phase Macrocycle Synthesis

To test if the enriched DNA sequences emerging from selection correspond to macrocycles with target-binding or target-inhibiting activities, the corresponding macrocycles were synthesized on multi-milligram scale using Fmoc solid-phase peptide synthesis (FIG. 7).[20] In brief, NovaPEG Rink amide resin (Merck) was coupled to a differentially protected diamino acid building block. An isopropylidene-protected tartrate monomethyl ester was reacted with one amine, and a tripeptide was synthesized on the other amine using three cycles of Fmoc peptide synthesis. After generating the phosphonium salt on resin, we cleaved the macrocyclization precursor from resin using strong acid. This cleavage reaction simultaneously generated a carboxamide at the C-terminus and also revealed the tartrate diol. After HPLC purification and LC/MS characterization of the linear product, we oxidatively cleaved the diol to reveal an aldehyde and effected Wittig cyclization by raising the pH of the solution to generate a phosphonium ylide. Macrocycle syntheses typically yielded two HPLC-separable isomers that were characterized as the desired cis and trans macrocycles using NMR spectroscopy and high-resolution mass spectrometry (Table 5). In total, 27 macrocycles corresponding to enriched DNA sequences were synthesized on 1-3 mg scale using this route. Overall yields for each 14-step synthesis (13 solid-phase steps and one solution-phase step) ranged from 1-12%.

TABLE 5

High-resolution ESI mass spectrometry data for macrocycles.

| Macrocycle | Expected (M + H)$^+$ | Observed (M + H)$^+$ |
|---|---|---|
| cis-A11-B1-C5-D7 | 666.2994 | 666.2995 |
| trans-A11-B1-C5-D7 | 666.2994 | 666.2986 |
| cis-A11-B1-C10-D7 | 728.3151 | 728.3120 |
| Trans-A11-B1-C10-D7 | 728.3151 | 728.3118 |
| cis-A11-B1-C3-D7 | 652.2838 | 652.2811 |
| trans-A11-B1-C3-D7 | 652.2838 | 652.2809 |
| cis-A10-B1-C5-D6 | 652.2726 | 652.2714 |
| trans-A10-B1-C5-D6 | 652.2726 | 652.2703 |
| cis-A10-B1-C5-D7 | 638.2569 | 638.2558 |
| trans-A10-B1-C5-D7 | 638.2569 | 638.2549 |
| Cis-A9-B1-C5-D7 | 609.2337 | 609.2321 |
| trans-A9-B1-C5-D7 | 609.2337 | 609.2330 |
| cis-A1 1-B1-C5-D5 | 694.3307 | 694.3289 |
| trans-A11-B1-C5-D5 | 694.3307 | 694.3298 |
| cis-A11-B8-C5-D7 | 682.3671 | 682.3647 |
| trans-A11-B8-C5-D7 | 682.3671 | 682.3654 |
| cis-A11-B8-C10-D7 | 744.3828 | 744.3802 |
| Trans-A11-B8-C10-D7 | 744.3828 | 744.3804 |
| cis-Ala-B1-C5-D7 | 517.2405 | 517.2384 |
| cis-A11-Ala-C5-D7 | 600.2889 | 600.2847 |
| cis-A11-B1-Ala-D7 | 626.2681 | 626.2674 |
| trans-Phe-B1-C5-D6 | 607.2874 | 607.2851 |
| linear-A11-B1-C5-D7 | 670.3307 | 670.3296 |
| linear-A10-B1-C5-D6 | 656.3039 | 656.3015 |
| cis-A10-B1-C11-D5 | 883.4560 | 883.4545 |
| cis-A10-B8-C11-D5 | 899.5237 | 899.5232 |
| cis-A12-B8-C10-D3 | 906.4760 | 906.4734 |
| cis-A12-B8-C10-D4 | 892.4604 | 892.4568 |
| cis-A12-B8-C10-D8 | 892.4604 | 892.4589 |

Macrocycles Selected for Binding to Src Inhibit Src Kinase Activity

Figures 2, 8:
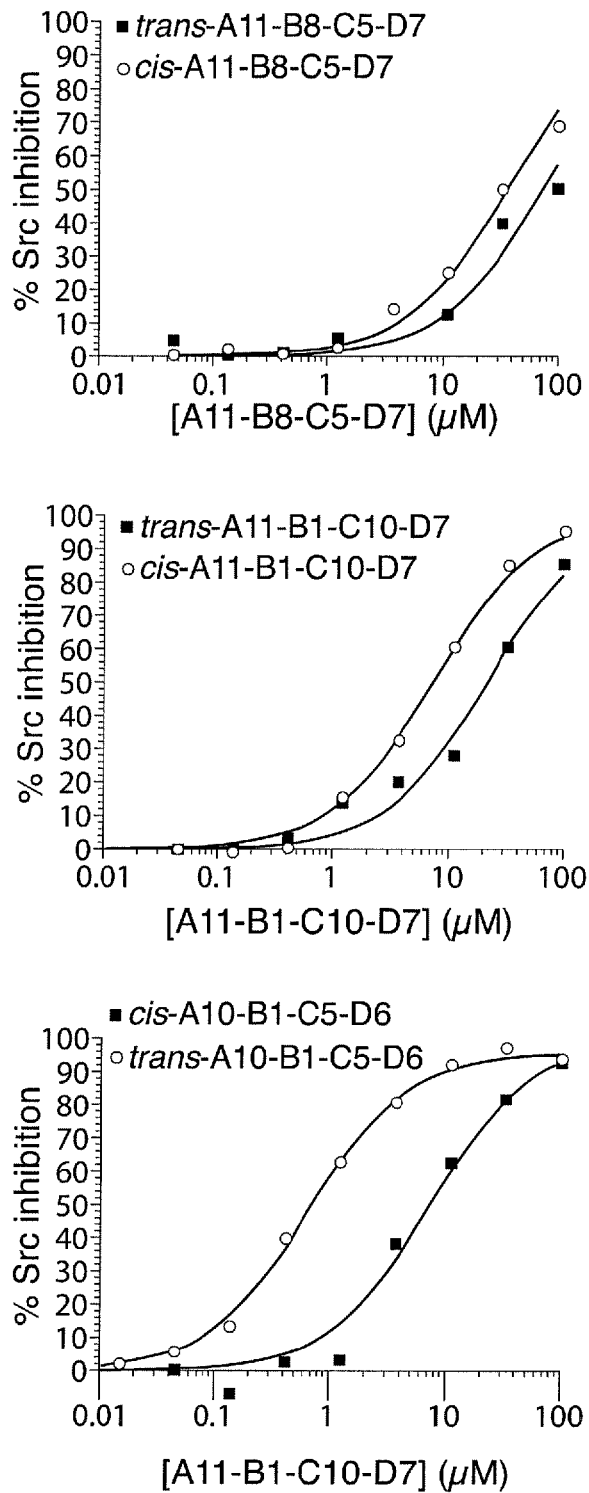
FIG. 8. A representative set of Src kinase inhibition assay data.
Figures 3, 8:
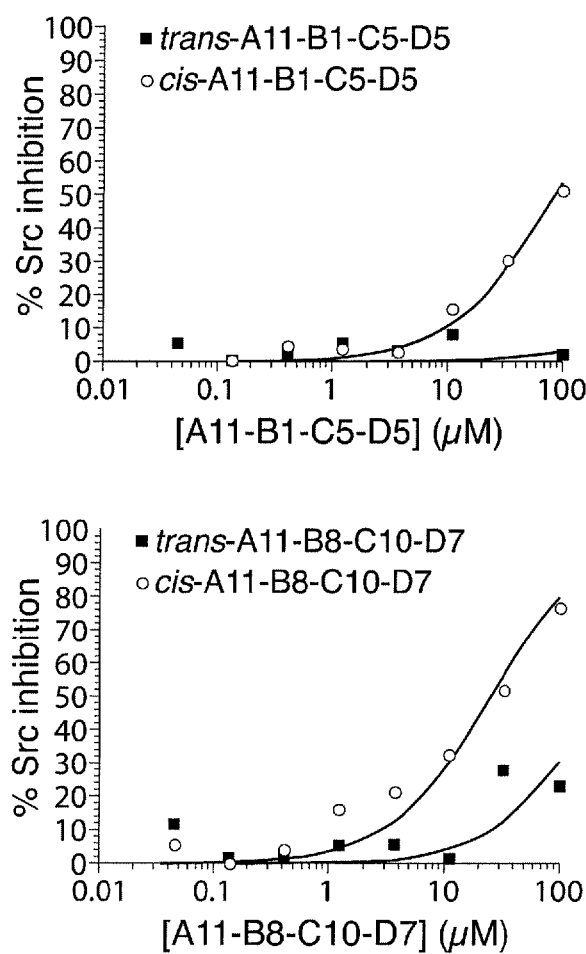

Nine macrocycles enriched in the Src selection (FIG. 5) and synthesized as described above were assayed in vitro for the ability to inhibit Src kinase activity. Kinase activity was assayed in the presence of varying concentrations of macrocycle using the FRET-based Z'-LYTE assay (Invitrogen). Although our selections did not explicitly select for target inhibition, all but one of the nine macrocycles tested inhibited Src kinase activity (Table 6 and FIG. 8). All of the assayed macrocycles with Src selection enrichment factors ≥4-fold exhibited $IC_{50}$ values in the range of ~500 nM to 10 μM. The most potent molecules, macrocycles trans-A10-B1-C5-D6 and cis-A11-B1-C5-D7, which share the furylalanine (B1) and cyclopropylalanine (C5) building blocks, but otherwise display significant structural diversity, inhibited Src with $IC_{50}$ values of 680 nM and 960 nM respectively (Table 6 and FIG. 8). We consistently observed large differences in potency between macrocycle cis and trans stereoisomers (Table 6), highlighting the importance of macrocycle stereochemistry and conformation for activity. For example, the cis and trans stereoisomers of macrocycles A11-B1-C5-D7 and A10-B1-C5-D6 exhibited a ~10-fold difference in potency (Table 6). Likewise, variants of highly-enriched macrocycles such as A11-B1-C5-D7 (62-fold enrichment) that differ by the addition or loss of a single methylene group within the macrocycle were not significantly enriched, further suggesting that even closely related library members can access significantly different three-dimensional structures.

TABLE 6

Macrocycles corresponding to Src selection survivors inhibit Src kinase. Src kinase activity was assayed in the presence of increasing concentrations of macrocycle using the Z'-LYTE assay (Invitrogen).

| Macrocycle | Src $IC_{50}$ (μM) |
| --- | --- |
| cis-A11-B1-C5-D7 | 0.96 |
| trans-A11-B1-C5-D7 | 12 |
| cis-A11-B1-C10-D7 | 7.0 |
| trans-A11-B1-C10-D7 | 21 |
| cis-A11-B1-C3-D7 | 10 |
| trans-A11-B1-C3-D7 | 48 |
| cis-A10-B1-C5-D6 | 7.4 |
| trans-A10-B1-C5-D6 | 0.68 |
| cis-A10-B1-C5-D7 | 8.9 |
| trans-A10-B1-C5-D7 | 1.5 |
| cis-A9-B1-C5-D7 | >100 |
| trans-A9-B1-C5-D7 | >100 |
| cis-A11-B1-C5-D5 | 85 |
| trans-A11-B1-C5-D5 | >100 |
| cis-A11-B8-C5-D7 | 36 |
| trans-A11-B8-C5-D7 | >100 |
| cis-A11-B8-C10-D7 | 25 |
| trans-A11-B8-C10-D7 | >100 |

Macrocycles Selected for Binding to Akt3, MAPKAPK2, Pim1, and VEGFR2 Modulate Kinase Activity Macrocycles A10-B1-C11-D5 and A10-B8-C11-D5 were enriched 2- to 6-fold upon selection for binding Akt3, MAPKAPK2, Pim1, and VEGFR2 (FIG. 6). These two macrocycles are structurally similar, sharing nitrophenylalanine (A10) and cyclohexylstatine (C11) building blocks as well as the same lysine scaffold (D5), and differ only at the B building block with either furylalanine (B1) or cyclohexylalanine (B8) (FIG. 6). For assay purposes, the macrocycles were synthesized with C-terminal PEG-diamine linkers to aid solubility, and then tested for the ability to inhibit Akt3, MAPKAPK2, Pim1 and VEGFR2. The more hydrophobic of the two compounds, macrocycle cis-A10-B8-C11-D5, inhibited Akt3, MAPKAPK2, Pim1, and p38α-MAPKAPK2 with $IC_{50}$ values of 8.7 μM, 6.8 μM, 7.5 μM, and 3.1 μM respectively (Table 7 and FIG. 9). Macrocycle cis-A10-B1-C11-D5 did not inhibit any of these kinases when assayed with isolated kinase enzymes; however we observed inhibition of the p38α-MAPKAPK2 kinase cascade with an $IC_{50}$ value of 6.4 μM (Table 7 and FIG. 9), suggesting that the molecule may interact with either or both kinases but only in a conformation that is adopted upon formation of the p38α-MAPKAPK2 complex. Interestingly, we observed strong, dose-dependent activation of VEGFR2 in the presence of cis-A10-B1-C11-D5 (FIG. 10) with enzyme activity increasing 70% upon treatment with 10 μM of this macrocycle and 300% upon treatment with 100 μM compound, suggesting that this macrocycle may bind to VEGFR2 in a manner that enhances kinase activity.

TABLE 7

Enriched macrocycles inhibit Pim1, MK2, Akt3, and p38a-MK2. Kinase activity was assayed in the presence of increasing concentrations of macrocycles using Invitrogen's Z-LYTE assay.

| Macrocycle | Kinase | $IC_{50}$ (μM) |
| --- | --- | --- |
| cis-A10-B1-C11-D5 | P38α-MK2 | 6.5 |
| cis-A10-B1-C11-D5 | Pim1 | 21 |
| cis-A10-B8-C11-D5 | Akt3 | 8.4 |
| cis-A10-B8-C11-D5 | MK2 | 6.1 |
| cis-A10-B8-C11-D5 | P38α-MK2 | 3.4 |
| cis-A10-B8-C11-D5 | Pim1 | 7.3 |
| cis-A12-B8-C10-D3 | P38α-MK2 | 12 |
| cis-A12-B8-C10-D3 | Pim1 | 25 |
| cis-A12-B8-C10-D4 | P38α-MK2 | 20 |
| cis-A12-B8-C10-D4 | Pim1 | 100 |
| cis-A12-B8-C10-D8 | MK2 | 47 |
| cis-A12-B8-C10-D8 | P38α-MK2 | 14 |
| cis-A12-B8-C10-D8 | Pim1 | 17 |

Figure 11:
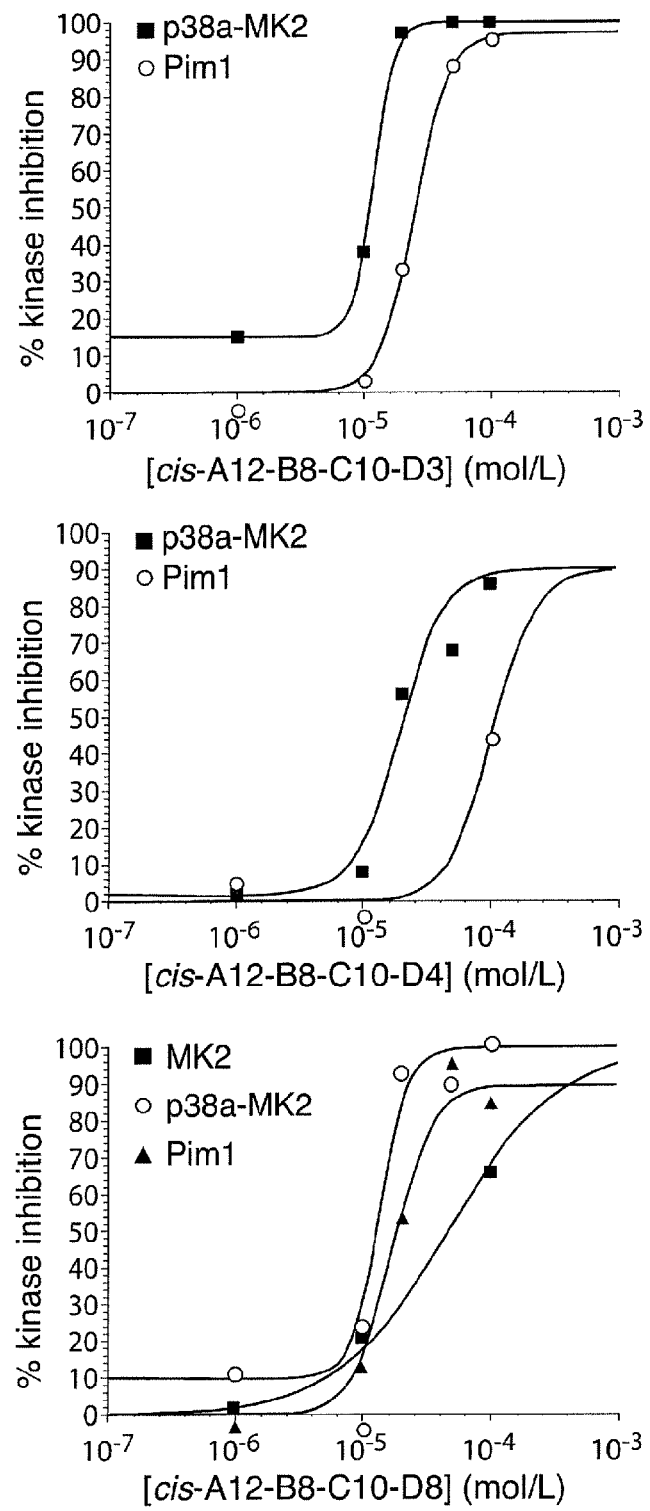
FIG. 11. Kinase inhibition activities of macrocycles of the cis-A12-B8-C10-DX family.
Figure 12A:
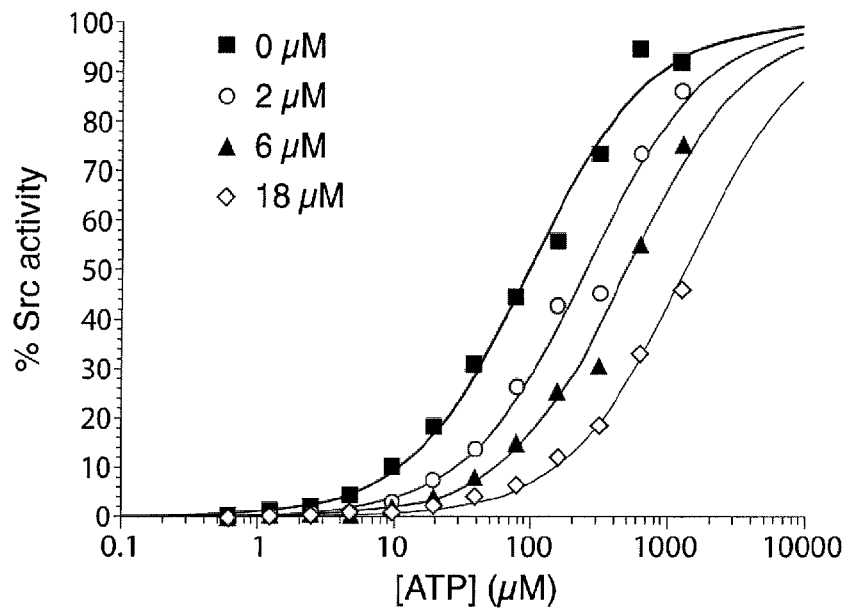
FIG. 12. Macrocycle cis-A11-B1-C5-D7 is an ATP-competitive inhibitor of Src kinase. a) The apparent $K_M$ of Src for ATP was measured in the presence of increasing concentrations of macrocycle cis-A11-B1-C5-D7. Kinase activity was measured as in Table 6. b) The resulting relationship is linear in accord with the following equation for a classical competitive inhibitor: apparent $K_M=K_M*(1+[\text{inhibitor}]/K_i)$.
Figure 12B:
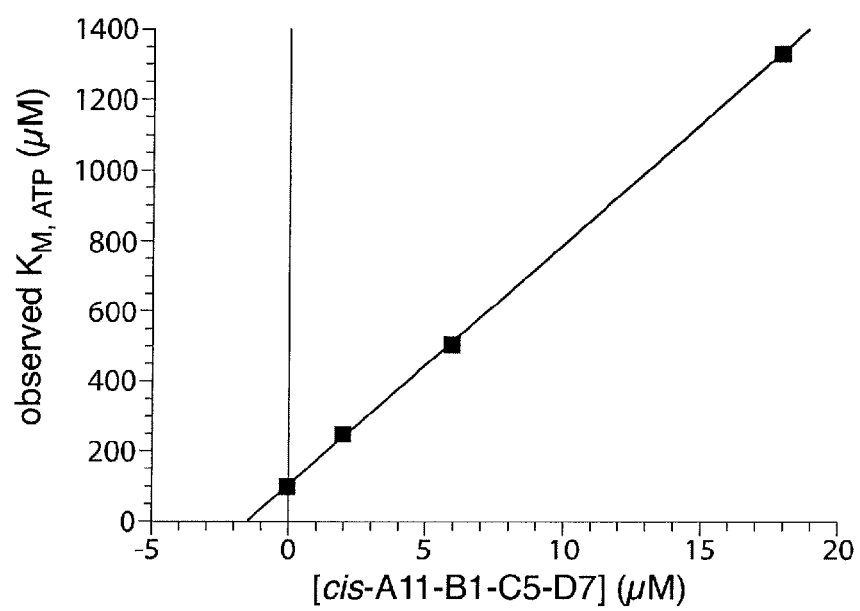

We also synthesized and assayed three macrocycles from the A12-B8-C10-X series that were enriched 2- to 10-fold after in vitro selection against MAPKAPK2 and Pim1 (FIG. 6). These macrocycles possess three hydrophobic building blocks, benzoyl-D-phenylalanine (A12), cyclohexylalanine (B8), and styrylalanine (C10), with variable scaffold diamino acid building blocks. Macrocycles A12-B8-C10-D3, enriched 3-fold against MAPKAPK2 and 3.5-fold against Pim1; A12-B8-C10-D4, enriched 3-fold against MAPKAPK2 and 10-fold against Pim1; and A12-B8-C10-D8, enriched 2.5-fold against MAPKAPK2 and 6-fold against Pim1 (FIG. 6), were synthesized and assayed for inhibition of MAPKAPK2, Pim1, and the p38α-MAPKAPK2 cascade. We observed modest inhibition of these kinase targets, with the most potent molecules being cis-A12-B8-C10-D3 against the p38α-MAPKAPK2 cascade ($IC_{50}$=11 μM) and cis-A12-B8-C10-D8 against Pim1 ($IC_{50}$=19 μM) (FIG. 11 and Table 7).

Taken together, these results indicate that DNA-templated macrocycles that are enriched from in vitro selections for kinase affinity frequently possess the ability to inhibit protein kinases with reasonable potency (low- to mid-micromolar $IC_{50}$ values) when synthesized and assayed in a non-DNA-linked form. Among the nine macrocycles chosen based on the magnitude of their enrichment during Src selection, or based on their structurally similarity to the highly enriched A11-B1-C5-D7, we characterized only one enriched macrocycle (A9-B1-C5-D7) that did not inhibit Src, representing a false positive rate of 11%. While we characterized only five molecules from selections against Akt3, MAPKAPK2, Pim1, and VEGFR2, due to enrichment of the same molecule against multiple targets, we validated 12 distinct protein-macrocycle interactions. One molecule, macrocycle A10-B9-C11-D5 (B9=citrulline), similar to the validated A10-Y-C11-D5 family of hits, was observed enriched above background in the Pim1 (3.5-fold enrichment) and VEGFR2 (2.4-fold enrichment) selections, but did not inhibit either kinase when assayed in its non-DNA-linked form. In total, we observed a similarly low false positive rate of 14% (2/14) from the Akt3, MAPKAPK2, Pim1, and VEGFR2 selections.

Kinase Inhibition Selectivity of Enriched Src-Inhibiting Macrocycles

Figure 13:
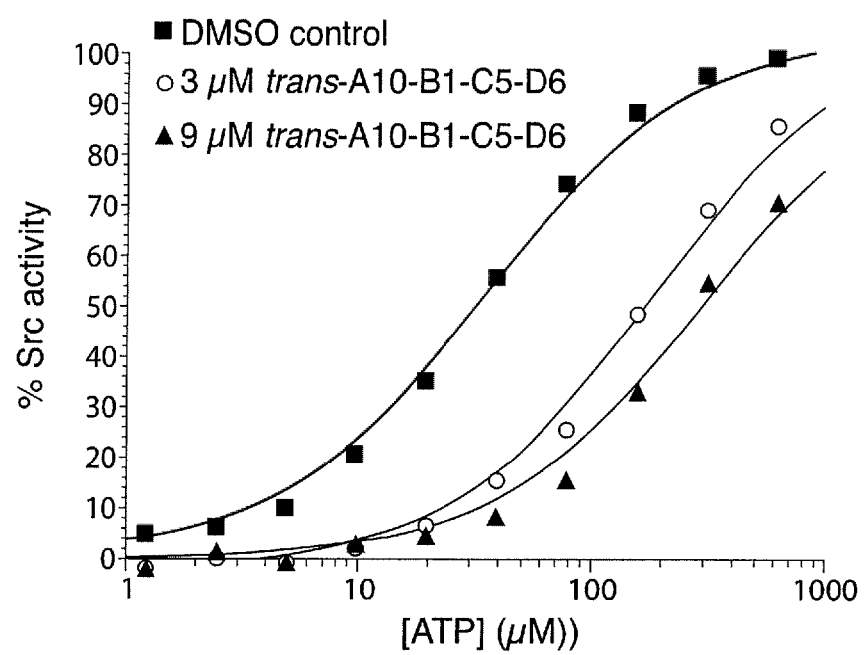
FIG. 13. Macrocycle trans-A10-B1-C5-D6 is an ATP-competitive Src inhibitor. Src kinase activity was measured as a function of ATP concentration at 3 µM and 9 µM concentrations of macrocycle trans-A10-B1-C5-D6 and compared against Src activity in the presence of DMSO control. Macrocycle trans-A10-B1-C5-D6 induces a shift in the observed $K_{M, ATP}$ indicating ATP-competitive inhibition. Kinase activity was measured as described in Table 6.
Figures 1, 18:
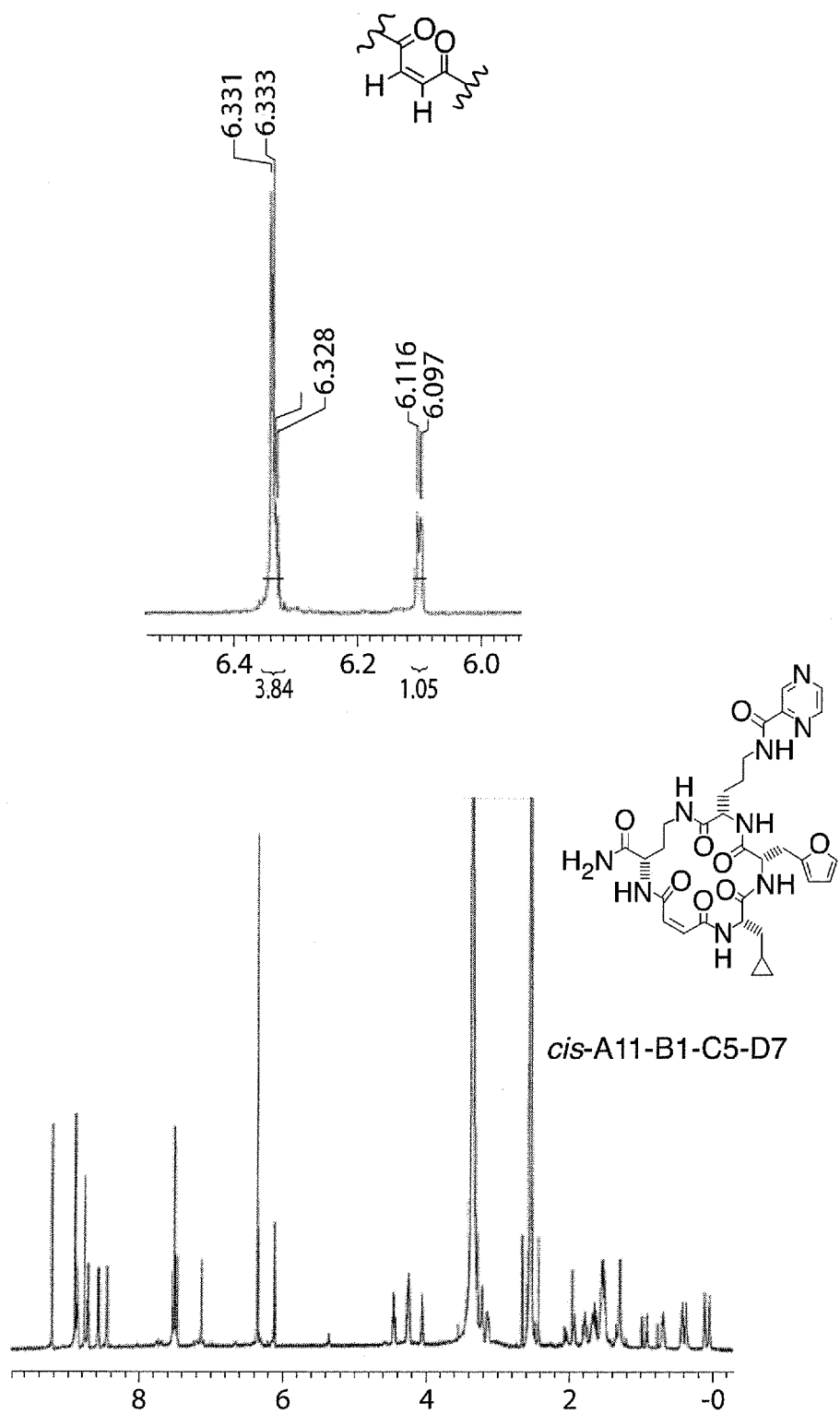
FIG. 18. NMR spectra and LC/MS data for certain macrocycles.
Figures 2, 18:
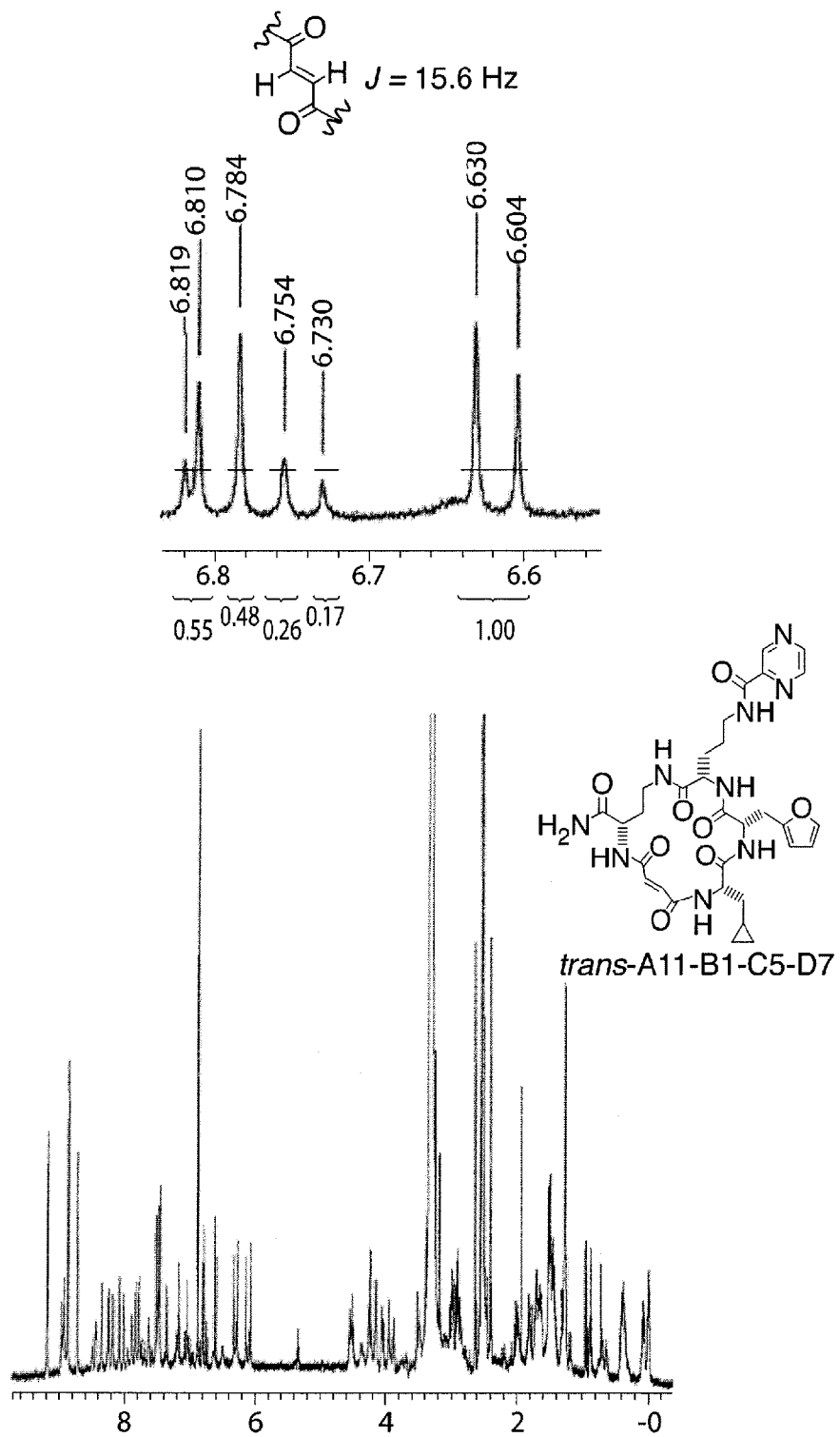
Figures 3, 18:
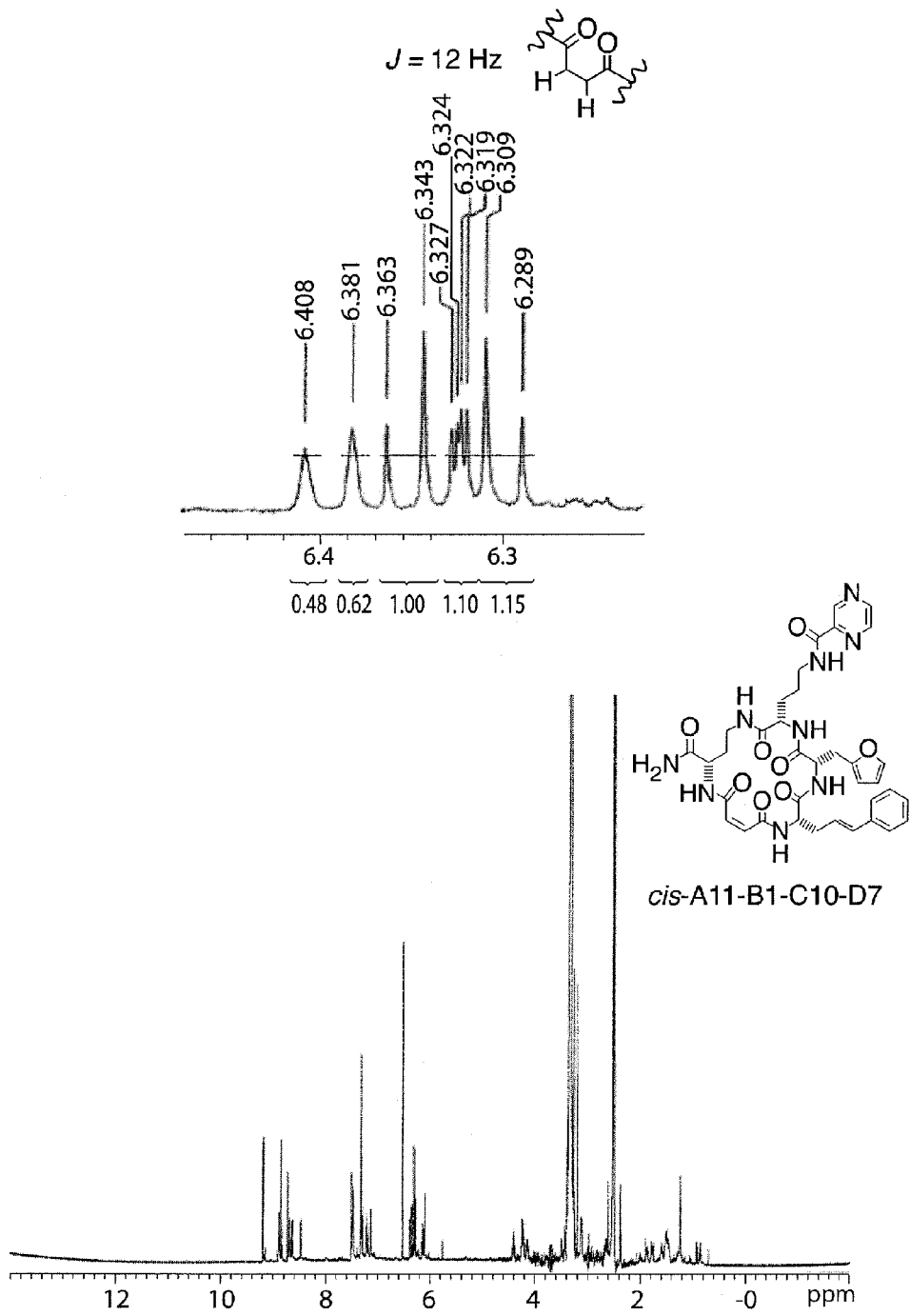
Figures 4, 18:
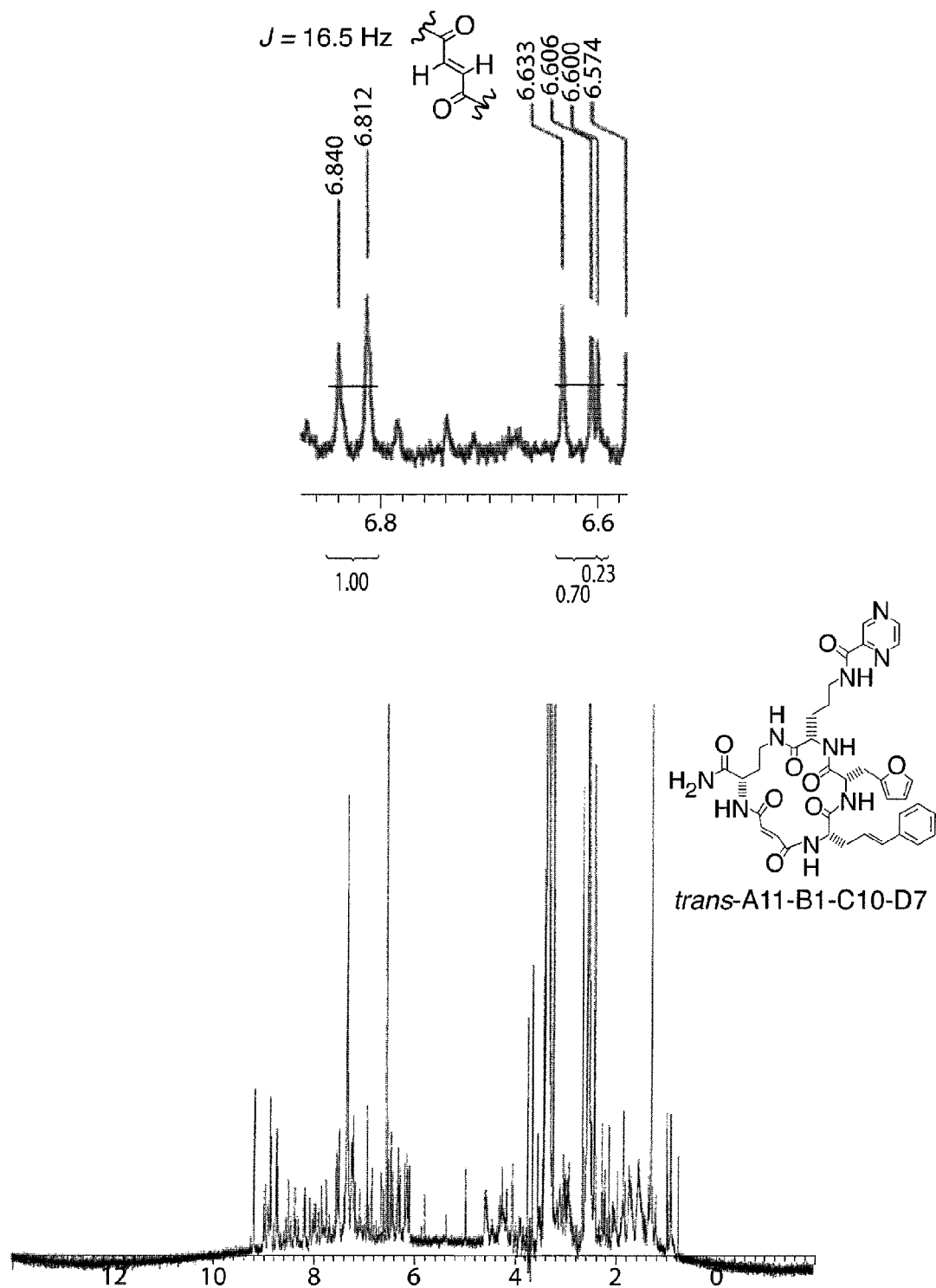
Figures 5, 18:
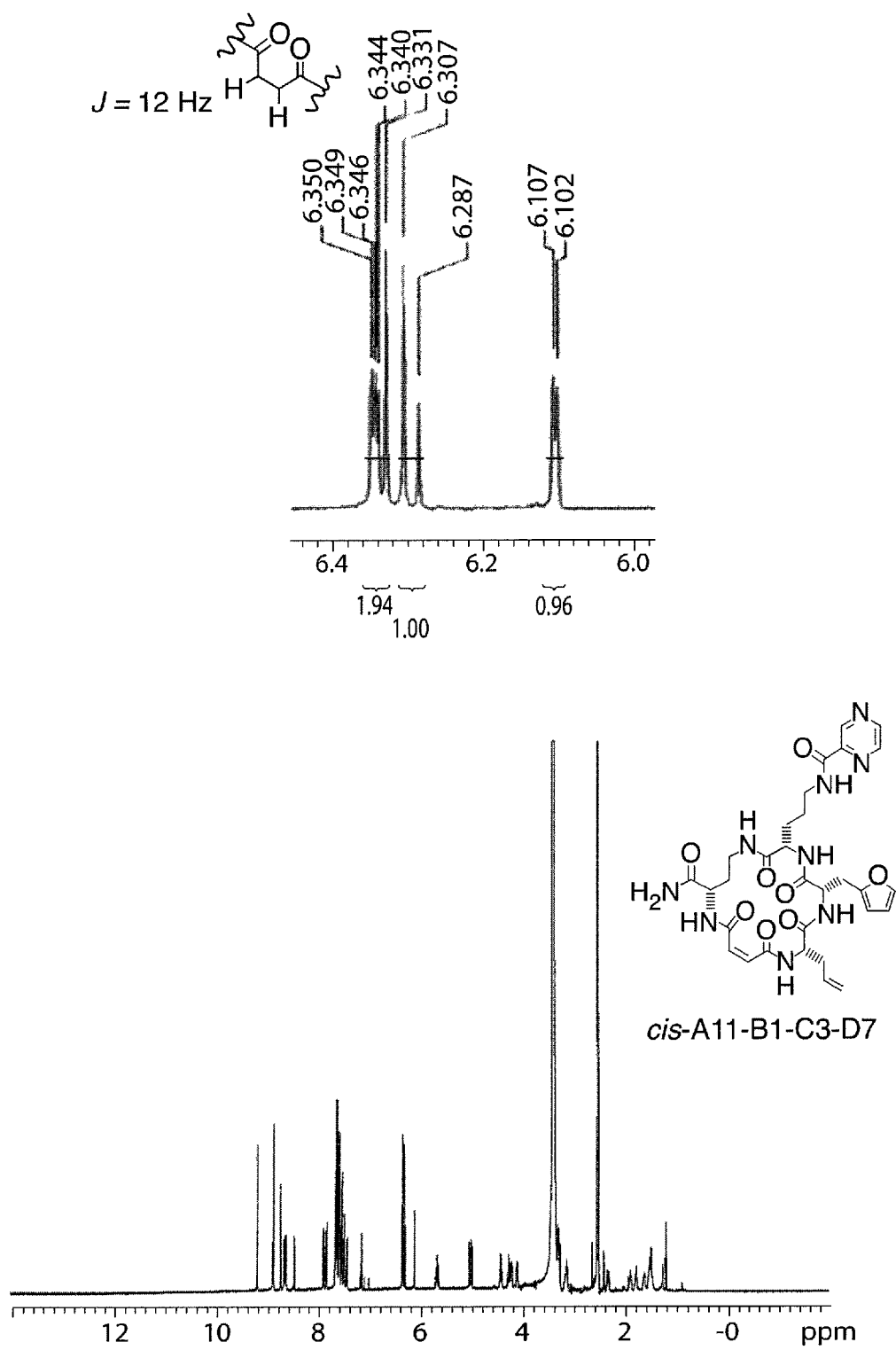
Figures 6, 18:
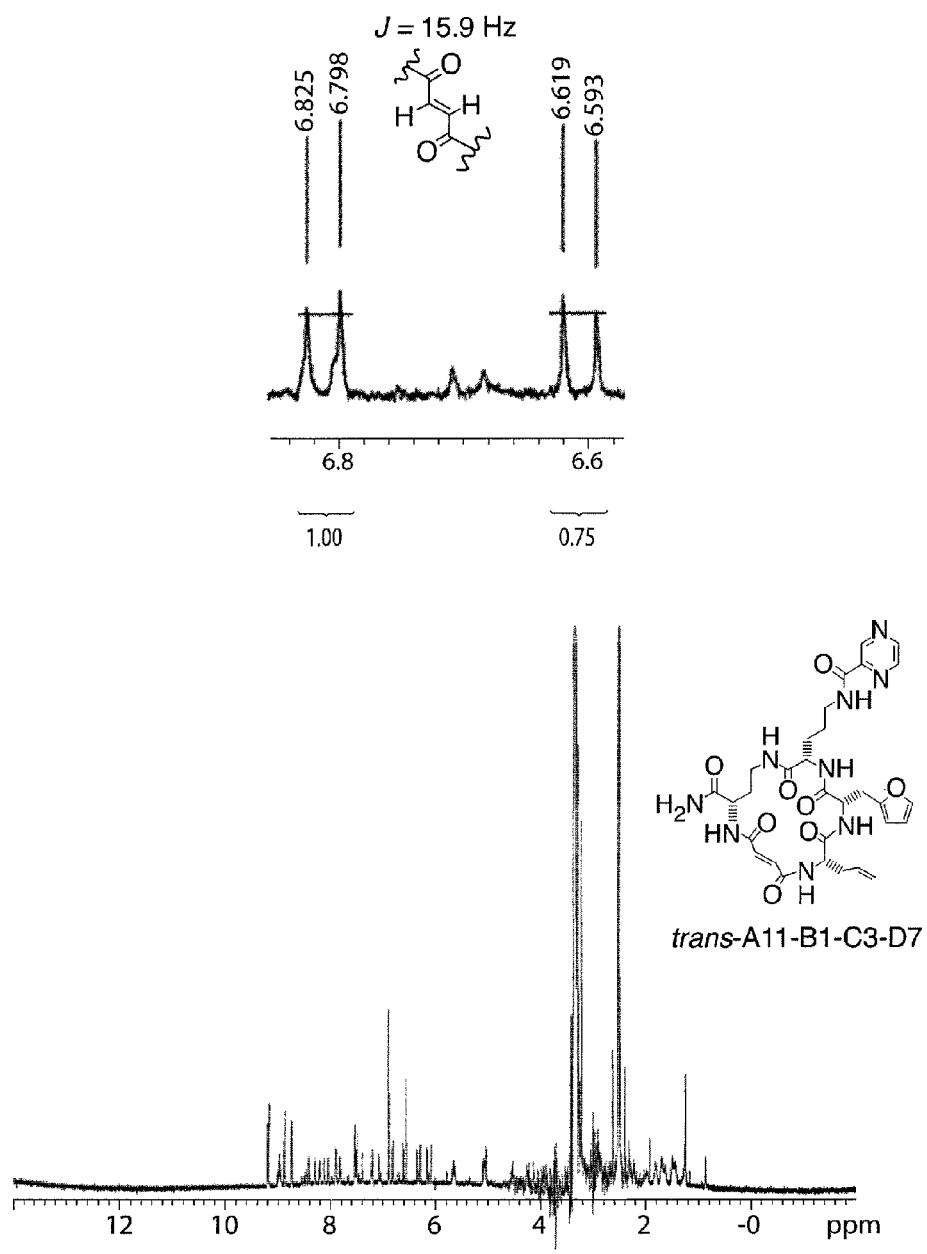
Figures 7, 18:
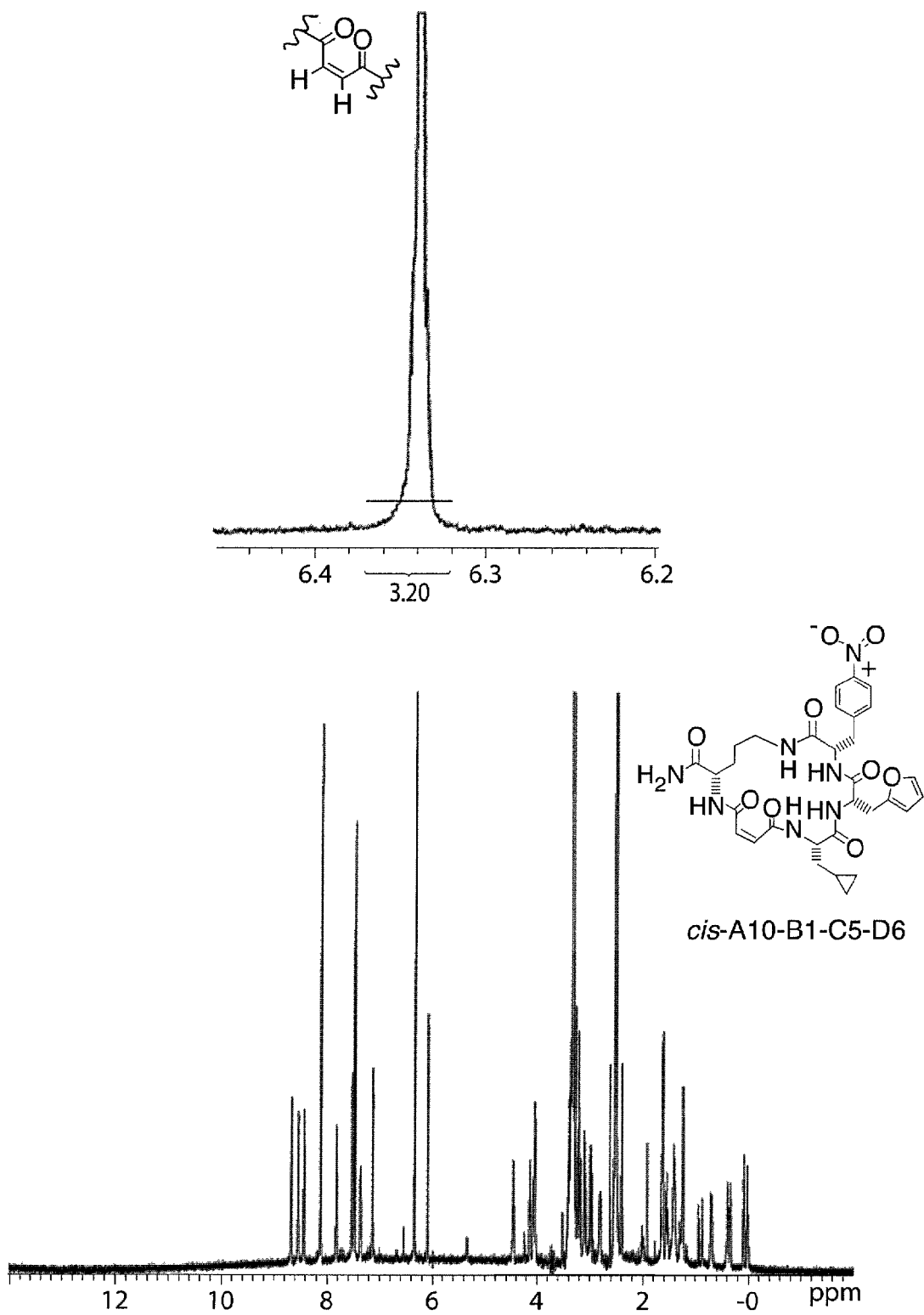
Figures 8, 18:
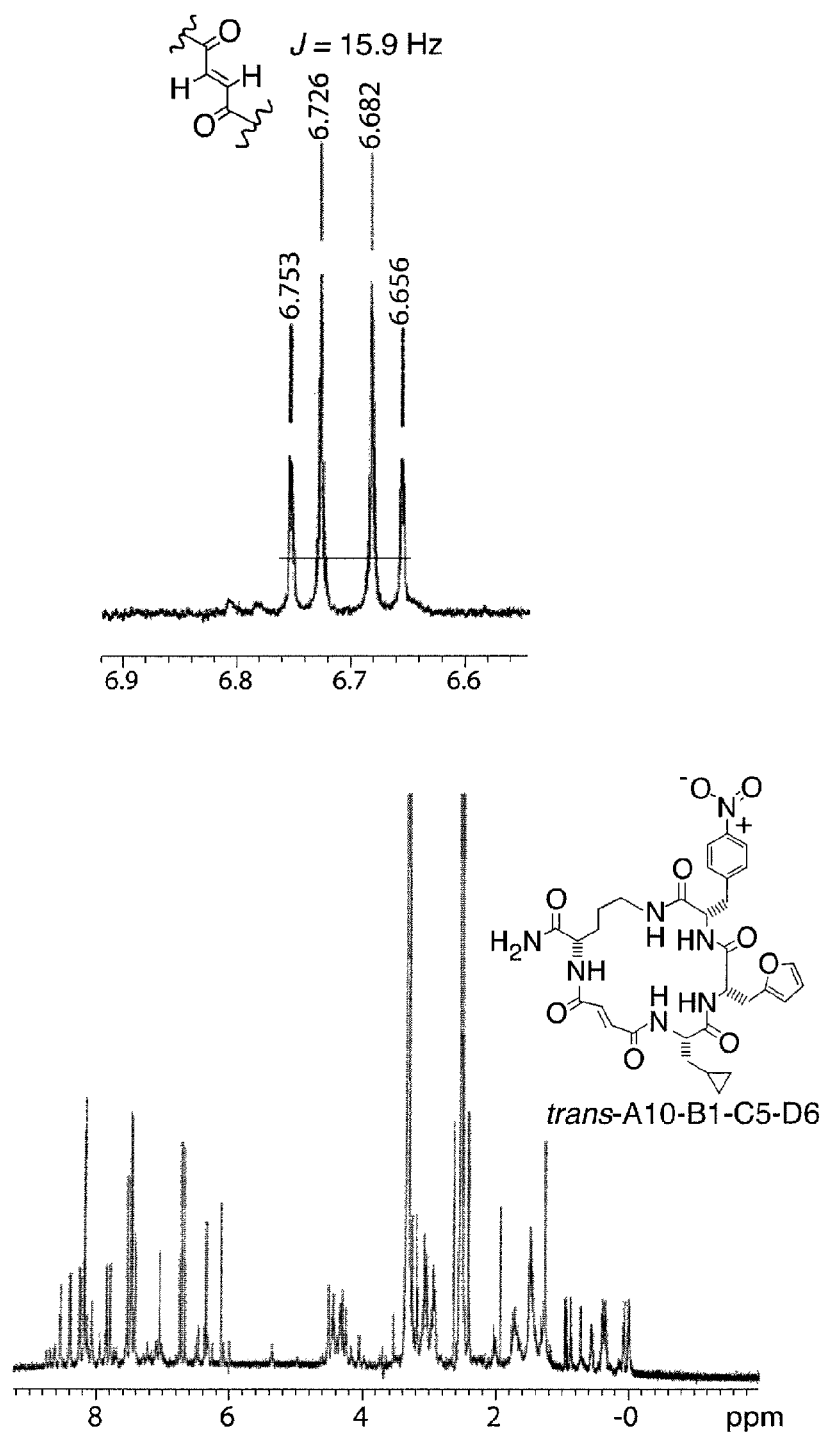
Figures 9, 18:
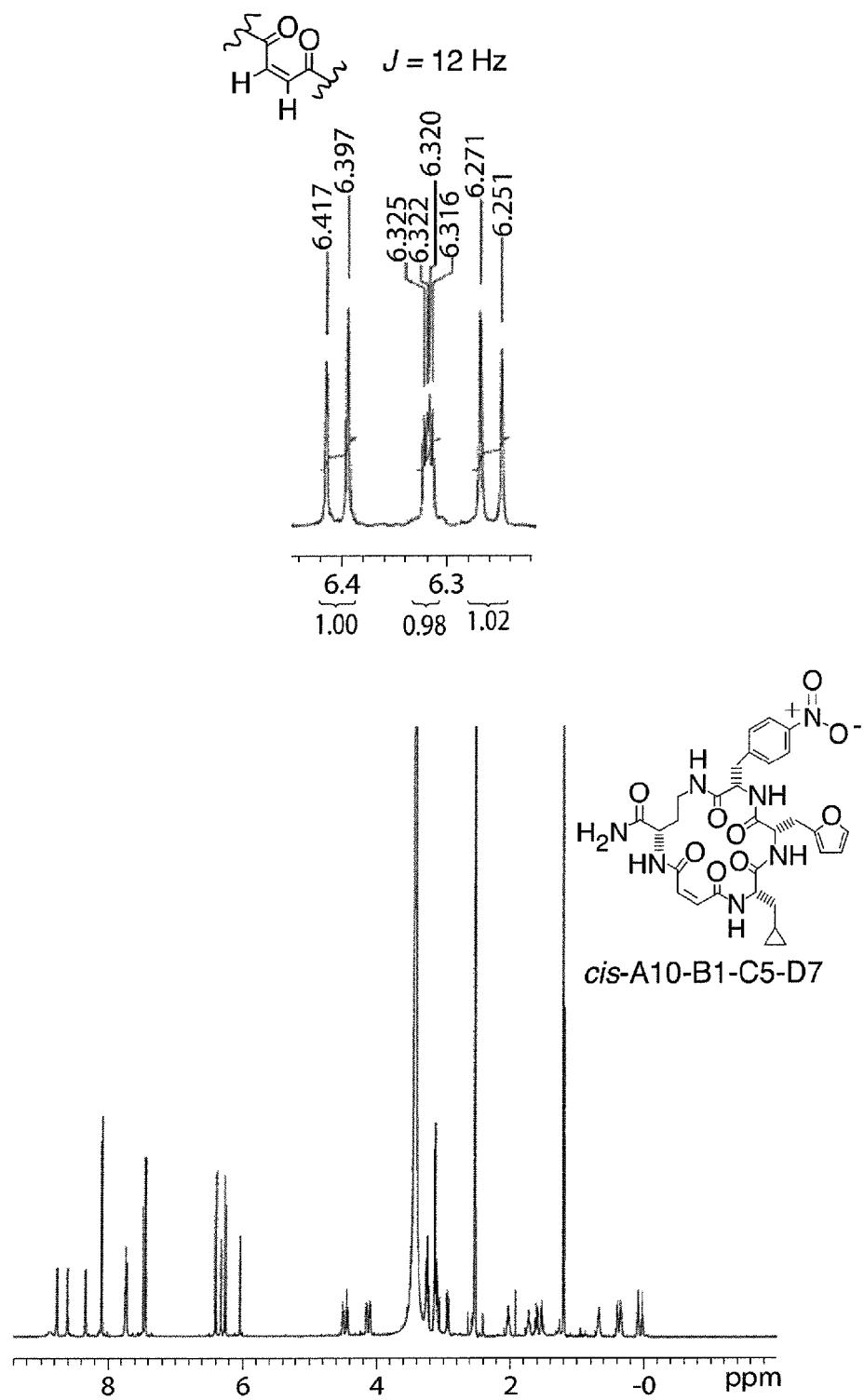
Figures 10, 18:
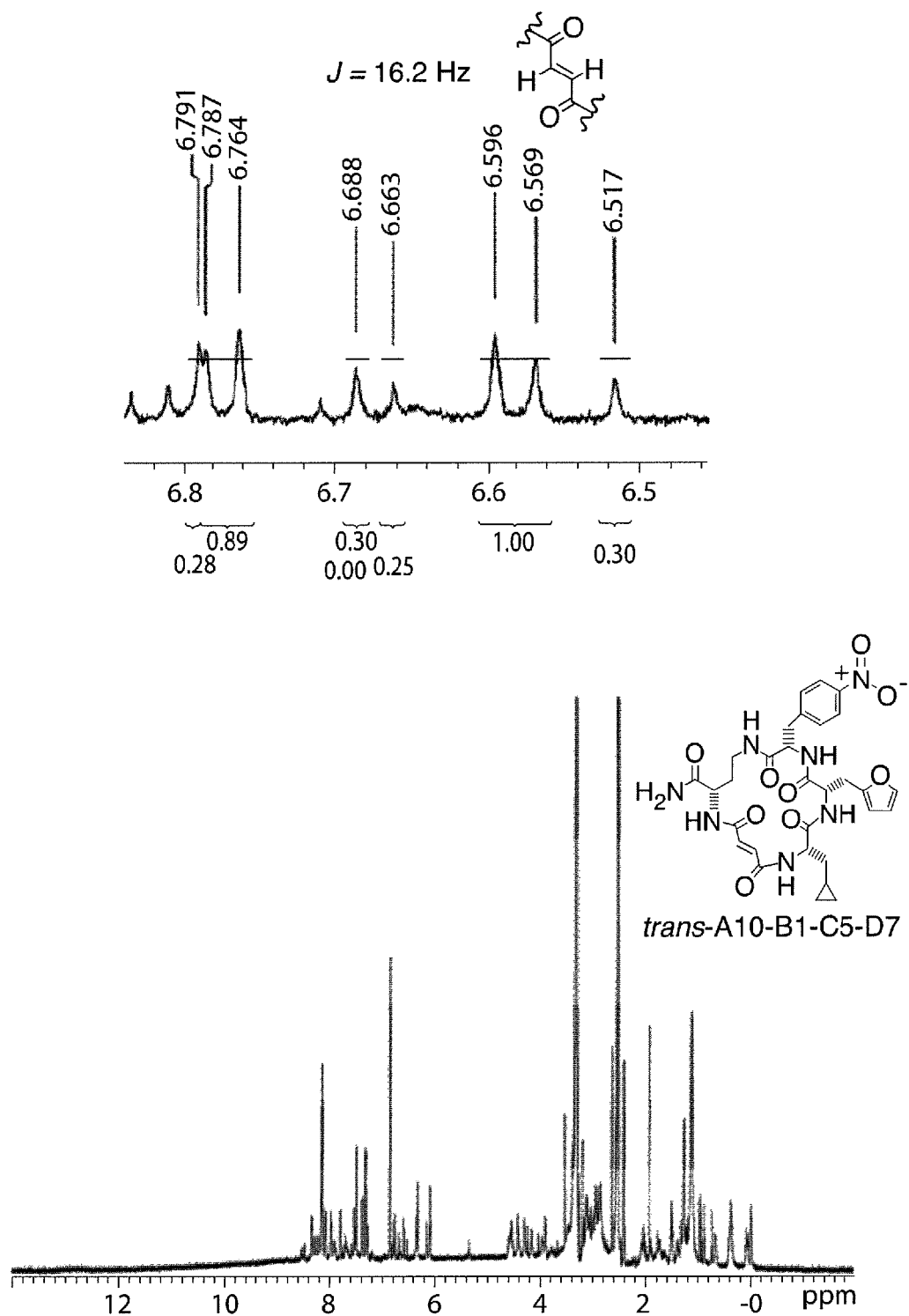
Figures 11, 18:
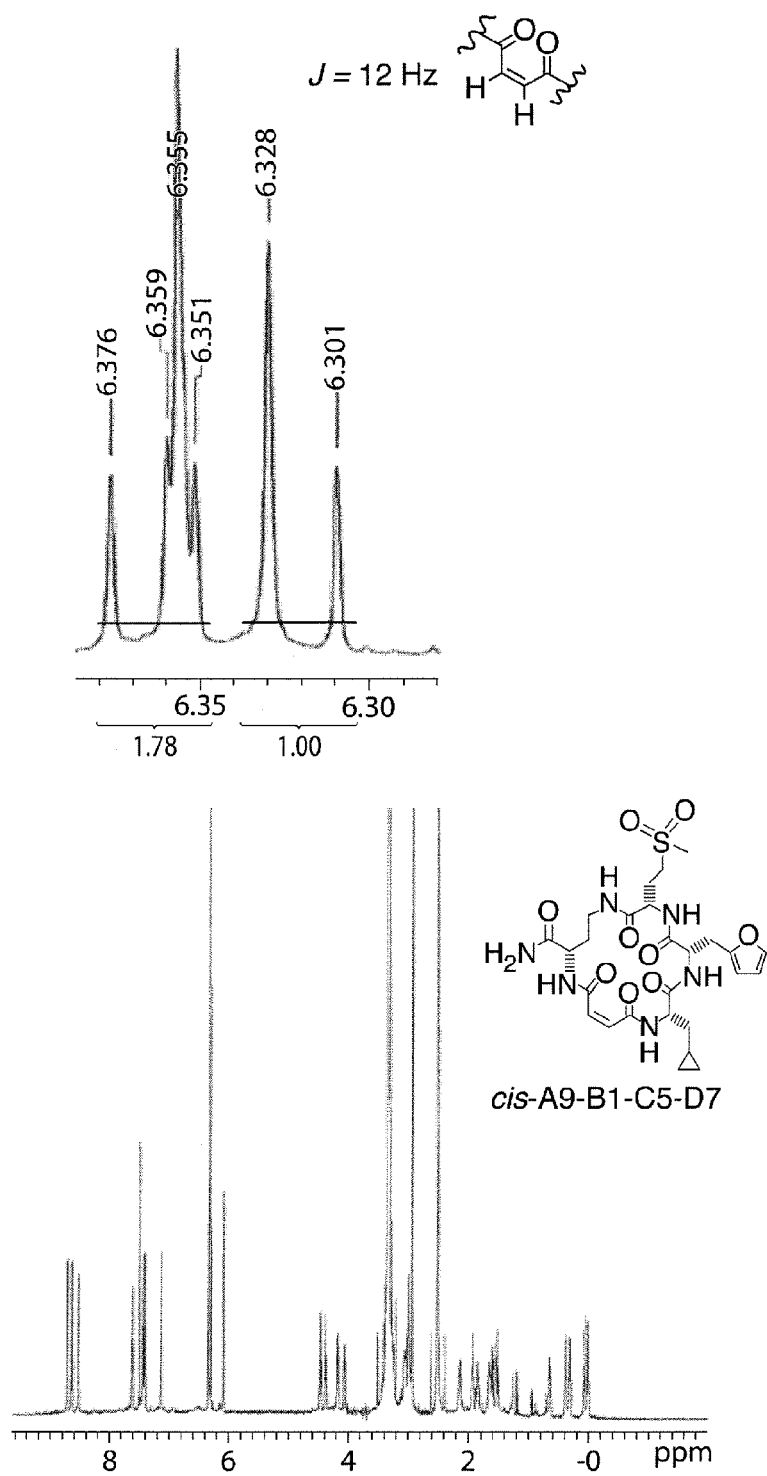
Figures 12, 18:
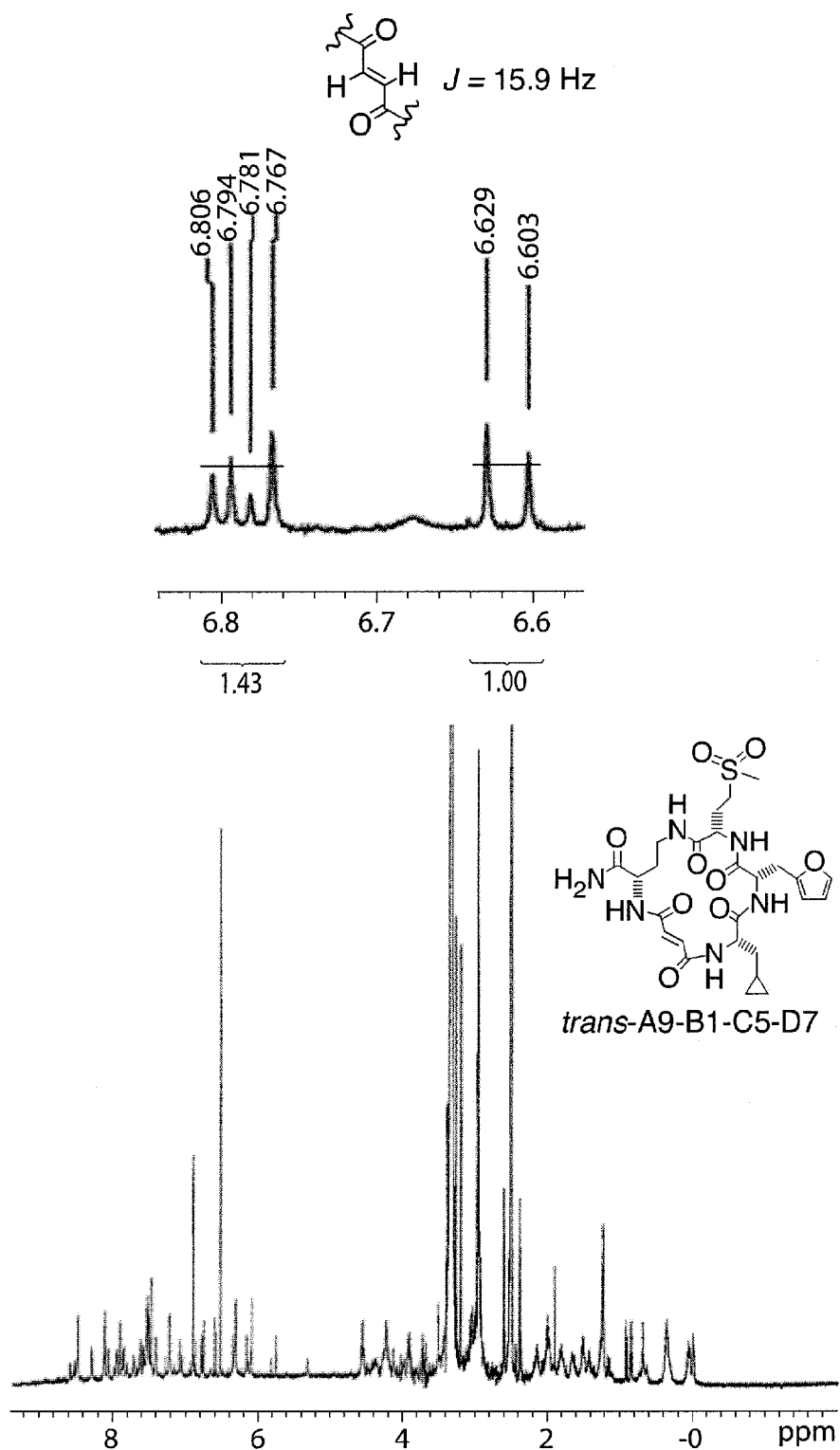
Figures 13, 18:
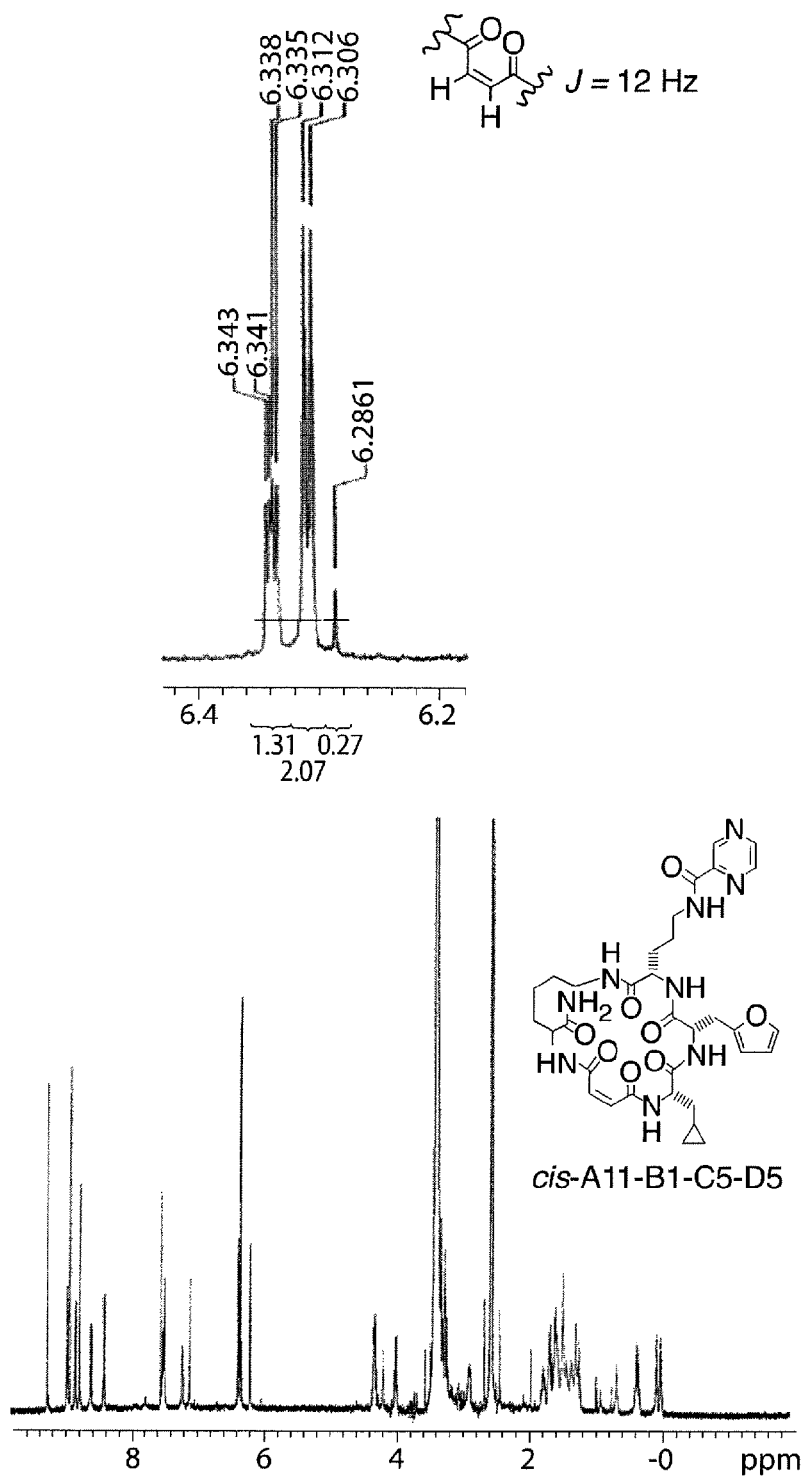
Figures 14, 18:
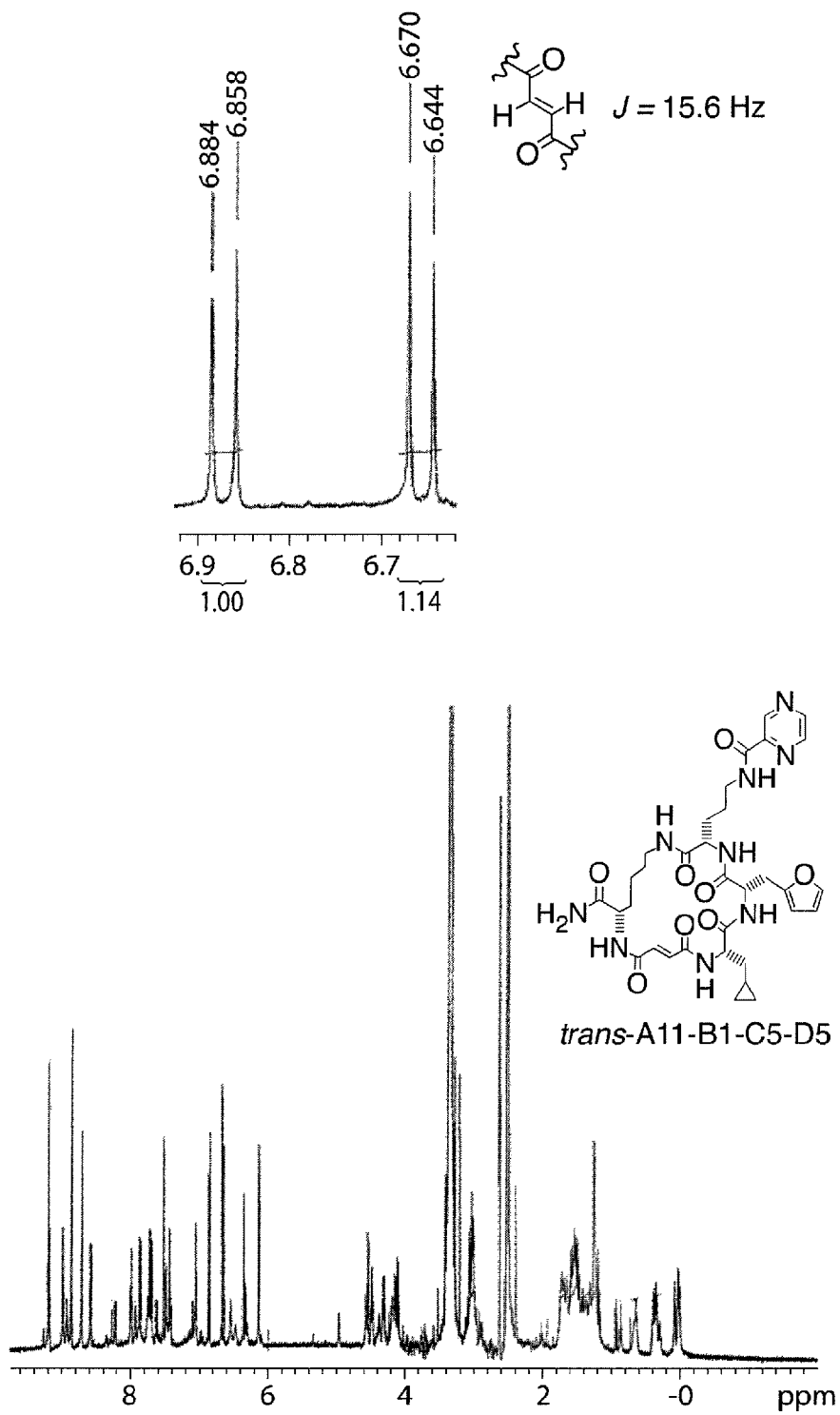
Figures 15, 18:
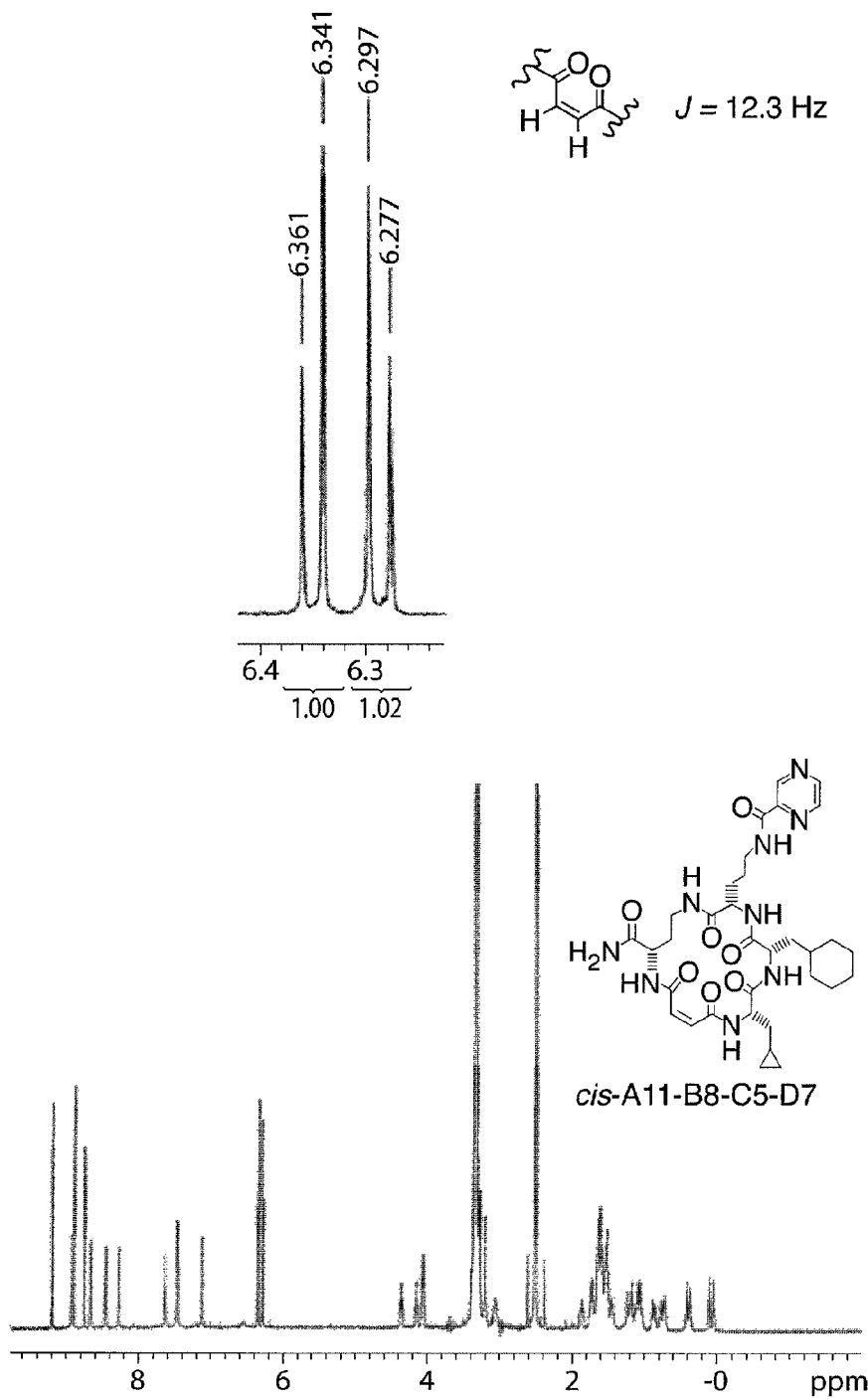
Figures 16, 18:
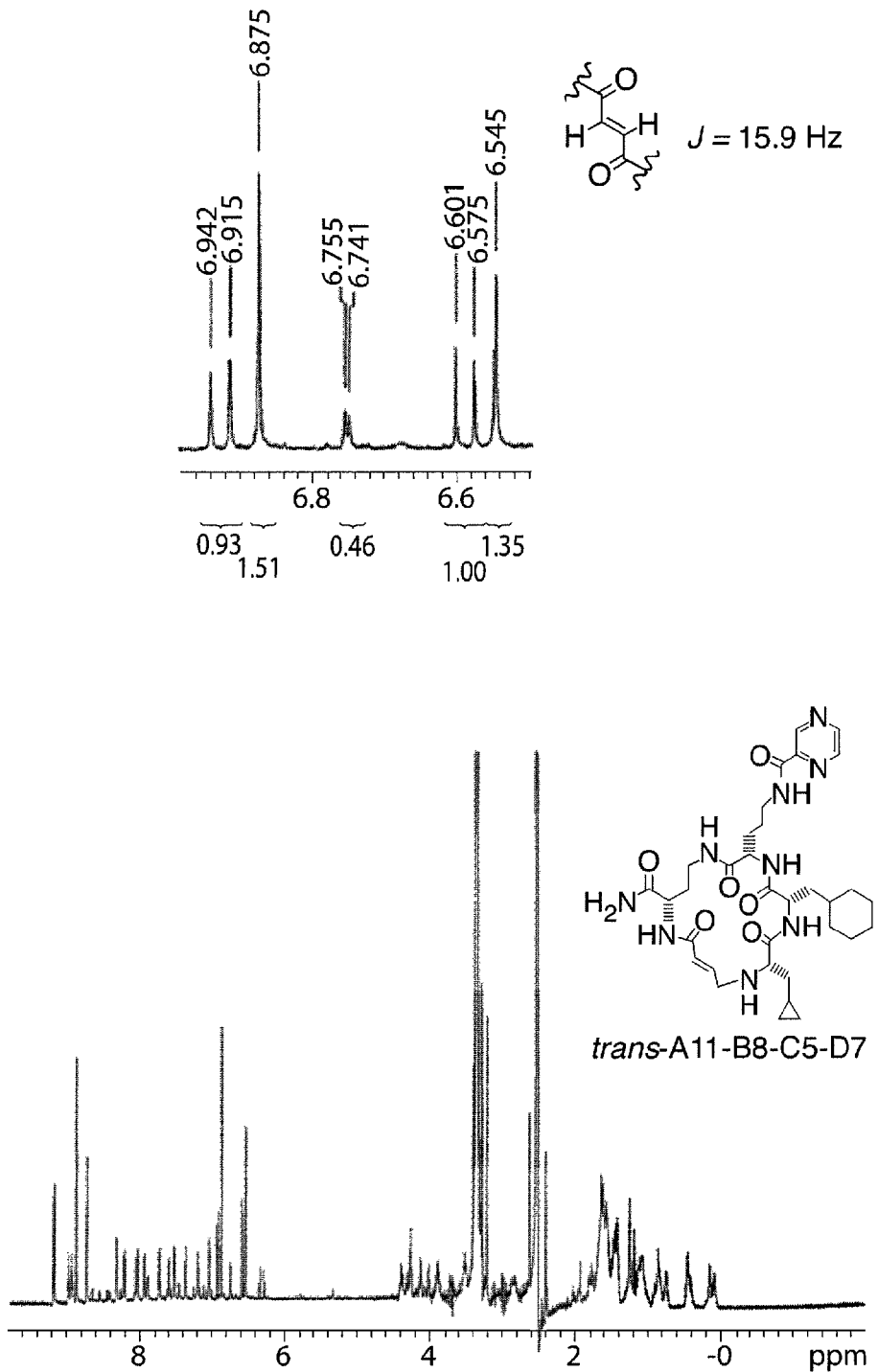

We chose to characterize in greater depth macrocycles cis-A11-B1-C5-D7 and trans-A10-B1-C5-D6 (FIG. 5 and Table 6) since they represent potent and structurally diverse inhibitors that are both predicted based on in vitro selection results (Table 4) to be selective for Src kinase. We first characterized their mode of inhibition. Although the selection used to identify the inhibitors is agnostic with respect to target binding site, we determined that cis-A11-B1-C5-D7 and trans-A10-B1-C5-D6 are ATP-competitive inhibitors (FIG. 12 and FIG. 13). We next determined the selectivity of these molecules against a representative set of human kinases. Although kinase selectivity can be modest for ATP-competitive inhibitors since the ATP-binding site is highly conserved among protein kinases,[51-54] our selection data (Table 4) suggested that the Src-inhibiting macrocycles may exhibit unusual selectivity.

Macrocycle cis-A11-B1-C5-D7 was assayed at 50 μM against a representative panel of 58 commercially available human protein kinases including all nine mammalian Src family kinases (Table 8). For those kinases that displayed significant inhibition (>40%) at 50 μM cis-A11-B1-C5-D7, we re-assayed at 5 μM compound concentration to estimate rough $IC_{50}$ values and performed 10-point $IC_{50}$ titrations for the most potently inhibited kinases (Table 8). Using this data, we calculated a selectivity score[55] for the macrocycle based on the number of non-target proteins exhibiting $IC_{50}$ values within 10-fold of the 960 nM $IC_{50}$ of cis-A11-B1-C5-D7 for Src. Macrocycle cis-A11-B1-C5-D7 displayed a selectivity score of 0.05, indicating that only 5% of the kinases assayed were inhibited with $IC_{50}$ values within 10-fold of the $IC_{50}$ for Src. When judged by similar criteria, cis-A11-B1-C5-D7 is significantly more selective than the promiscuous ATP-competitive inhibitor staurosporine (selectivity score=0.50), and slightly more selective than two kinase inhibitor drugs: sorafenib (selectivity score=0.10) and dasatanib (selectivity score=0.10).[55] The most potently inhibited proteins other than Src were closely related kinases such as Fgr (a Src family kinase, $IC_{50}$=4.0 μM) and RET (a tyrosine kinase, $IC_{50}$=5.7 μM), as well as Aurora A, a serine/threonine kinase which shares close structural homology to Src-family kinases ($IC_{50}$=1.7 μM)[56].

TABLE 8

Inhibition activity of cis-A11-B1-C5-D7 against a panel of human kinase enzymes.

| kinase | % inhibition (50 μM) | % inhibition (5 μM) | $IC_{50}$ |
|---|---|---|---|
| ABL1 | 7 | | >50 μM |
| ACVR1B (ALK4) | 5 | | >50 μM |
| AKT1 (PKB alpha) | 83 | | 19.4 μM |
| AMPK A1/B1/G1 | 57 | 7 | 40 μM |
| AURKA | 105 | | 1.7 μM |
| BLK | 42 | 13 | >50 μM |
| BTK | 59 | 20 | 31 μM |
| CDK1/cyclin B | 6 | | >50 μM |
| CHEK1 (CHK1) | 18 | | >50 μM |
| CSNK1G2 (CK1 gamma 2) | 2 | | >50 μM |
| CSNK2A1 (CK2 alpha 1) | 4 | | >50 μM |
| DYRK3 | 44 | 8 | >50 μM |
| EGFR (ErbB1) | -1 | | >50 μM |
| EPHA2 | 6 | | >50 μM |
| ERBB2 (HER2) | -1 | | >50 μM |
| FGFR1 | 2 | | >50 μM |
| FGR | 96 | | 4.0 μM |
| FLT3 | 53 | 16 | 41 μM |
| FRAP1 (mTOR) | 0 | | >50 μM |
| FRK (PTK5) | 71 | 23 | 19 μM |
| FYN | 39 | 8 | >50 μM |
| GSK3B (GSK3 beta) | 85 | | 26.8 μM |
| HCK | 18 | | >50 μM |
| IGF1R | 11 | | >50 μM |
| IKBKB (IKK beta) | 78 | | 43.9 μM |
| INSR | 4 | | >50 μM |
| IRAK4 | -5 | | >50 μM |
| JAK3 | 58 | 11 | 37 μM |
| KDR (VEGFR2) | 80 | | 15.9 μM |
| KIT | -6 | | >50 μM |
| LCK | 70 | 25 | 18 μM |
| LYN A | 67 | 21 | 23 μM |
| LYN B | 75 | 14 | 21 μM |
| MAP2K1 (MEK1) | 14 | | >50 μM |
| MAP4K4 (HGK) | 40 | -19 | >50 μM |
| MAPK1 (ERK2) | 18 | | >50 μM |
| MAPK14 (p38 alpha) | 102 | | 10.0 μM |
| MAPK8 (JNK1) | 1 | | >50 μM |
| MAPKAPK2 | 63 | 14 | 30 μM |
| MARK2 | 15 | | >50 μM |
| MET (cMet) | 35 | 11 | >50 μM |
| NEK1 | -17 | | >50 μM |
| NTRK1 (TRKA) | 4 | | >50 μM |
| PAK4 | 26 | | >50 μM |
| PDGFRB (PDGFR beta) | 6 | | >50 μM |
| PHKG2 | 4 | | >50 μM |
| PIM1 | 3 | | >50 μM |
| PLK1 | 2 | | >50 μM |
| PRKACA (PKA) | 27 | | >50 μM |
| PAKCB1 (PKC beta 1) | 4 | | >50 μM |
| RET | 82 | | 5.7 μM |
| ROCK1 | 11 | | >50 μM |
| RPS6KA3 (RSK2) | 87 | | 10.6 μM |
| RPS6KB1 (p70S6K) | 4 | | >50 μM |
| SRC | 100 | 82 | 960 nM |
| SYK | 18 | | >50 μM |
| TEK (Tie2) | 6 | | >50 μM |
| YES1 | 56 | 36 | 23 μM |

>80% inhibition is highlighted in red,
<40% inhibition is highlighted in blue.
$IC_{50}$ values falling within 10-fold of the Src $IC_{50}$ (960 nM) are highlighted in orange.
Assay data for Src kinase is from FIG. 8 and Table 6.
All non-Src assay points were measured by the Invitrogen Select Screen Profiling Service.
$IC_{50}$ values <18 μM were calculated from 10-point titrations.
All other $IC_{50}$ values were estimated from % inhibition at 5 and 50 μM.

Figure 14:
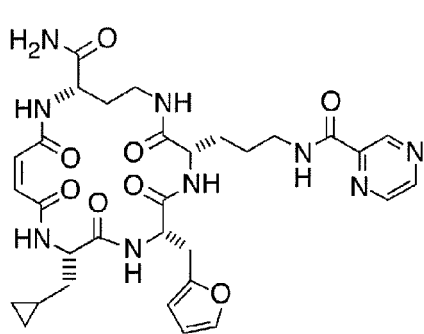
FIG. 14. Selectivity of macrocycles cis-A11-B1-C5-D7 and trans-A10-B1-C5-D6 among Src-related kinases, including all nine Src-family kinases. Both macrocycles were assayed at 5 µM concentration against the indicated kinases. Assays of cis-A11-B1-C5-D7 against Abl and Hck were performed at 50 µM macrocycle concentration instead of 5 µM. Assay data for Src kinase is from FIG. 8 and Table 6. All non-Src assay points were measured by the Invitrogen Select Screen Profiling Service FIG. 15. Structure-activity relationship (SAR) analysis of Src-inhibiting macrocycles. a) Single-alanine mutants of cis-A11-B1-C5-D7 were assayed against Src-family kinases Src and Fgr at 5 µM concentration as described previously. b) Linear diacetylated peptides corresponding to macrocycles A11-B1-C5-D7 and A10-B1-C5-D6 were synthesized by Fmoc solid-phase peptide synthesis and assayed against Src kinase. c) Macrocycle trans-Phe-B1-C5-D6 (replacing nitrophenylalanine with phenylalanine) was assayed against Src as described previously.
Figure 14:
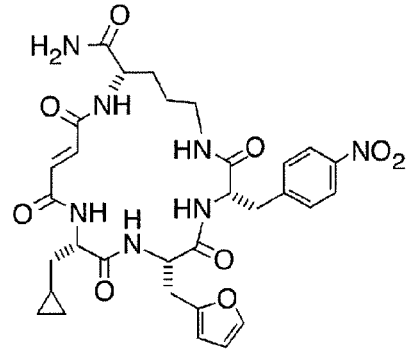
Figure 14:
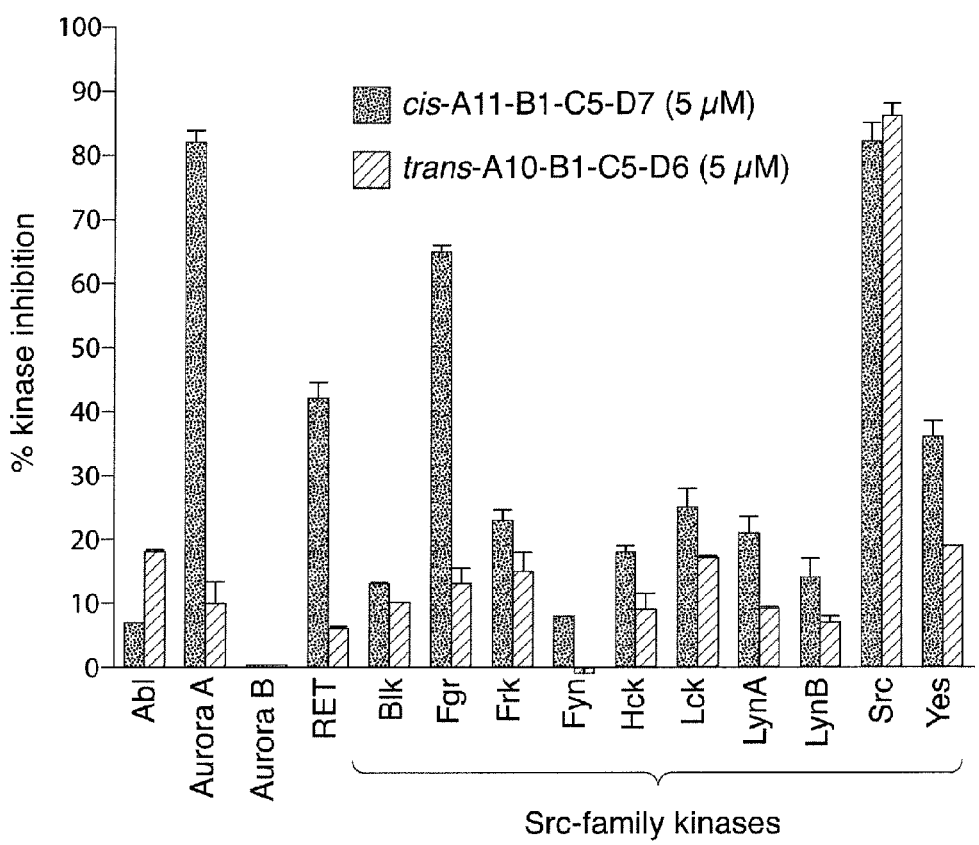

In addition to good overall selectivity, cis-A11-B1-C5-D7 exhibited exceptional selectivity among Src-like protein kinases that have traditionally been difficult to distinguish by small-molecule inhibition (FIG. 14). For example, this macrocycle exhibits >50-fold selectivity for Src over Abl kinase, >50-fold selectivity for Src over the Src-family kinases Hck and Fyn, and >10-fold selectivity for Src over all remaining Src-family kinases with the exception of Fgr (FIG. 14 and Table 8). Similarly, among the closely related Aurora kinases we observed >50-fold selectivity for Aurora A over Aurora B (Table 9 and Table 8).

We also investigated the selectivity of the nitrophenylalanine (A10)-containing macrocycle trans-A10-B1-C5-D6. While it shares two out of four building blocks in common with cis-A11-B1-C5-D7 and also inhibits Src in an ATP-competitive manner, building block composition in this macrocycle is strikingly different at the A position and the trans stereochemistry of the olefin contrasts with the olefin geometry of the active isomer of A11-B1-C5-D7. The differences between these two molecules were further revealed upon assays against a kinase panel, in which trans-A10-B1-C5-D6 exhibited even greater selectivity for Src than macrocycle cis-A11-B1-C5-D7 (FIG. 14). Macrocycle trans-A10-B1-C5-D6 did not significantly inhibit Aurora A, RET, or any of the other Src-family kinases (the primary kinases beyond Src that are inhibited by cis-A11-B1-C5-D7) at the concentration tested (5 µM) (FIG. 14). Indeed, of all 44 human kinases against which this macrocycle was assayed, Src was the only kinase observed to be significantly inhibited by this macrocycle (FIG. 14 and Table 10). This level of Src selectivity is unprecedented among currently available Src-selective kinase inhibitors such as PP1 and PP2,[57] which are significantly more potent against Src-family members Fyn, Hck and Lyn than against Src itself. Taken together, these results establish that macrocycles emerging from the in vitro selection of a DNA-templated small-molecule library include kinase inhibitors that exhibit unusual selectivity.

TABLE 10

Inhibition activity of trans-A10-B1-C5-D6 at 5 µM against a set of human kinase enzymes. Assay data for Src kinase is from FIG. 8 and Table 6. All non-Src assay points were measured by the Invitrogen Select Screen Profiling Service.

| KINASE | % inhibition |
| --- | --- |
| ABL1 | 18 |
| AKT1 (PKB alpha) | −7 |
| AKT3 (PKB gamma) | 11 |
| AMPK A1/B1/G1 | −1 |
| AURKA (Aurora A) | 10 |
| AURKB (Aurora B) | 0 |
| AURKC (Aurora C) | 2 |
| BLK | 10 |
| BTK | 4 |
| CHEK1 (CHK1) | −15 |
| DYRK3 | 4 |
| ERBB4 (HER4) | 4 |
| FGR | 13 |
| FLT3 | 7 |
| FRK (PTK5) | 15 |
| FYN | −1 |
| GSK3B (GSK3 beta) | −6 |
| HCK | 9 |
| IGF1R | 9 |
| IKBKB (IKK beta) | −1 |
| JAK3 | −7 |
| KDR (VEGFR2) | 7 |
| LCK | 17 |
| LYN A | 9 |
| LYN B | 7 |
| MAP2K1 (MEK1) | −6 |
| MAP2K6 (MKK6) | −1 |
| MAP4K4 (HGK) | −1 |
| MAPK1 (ERK2) | −3 |
| MAPK14 (p38 alpha) | 32 |
| MAPK14 (p38 alpha) Direct | −9 |
| MAPKAPK2 | −3 |
| MARK2 | 1 |
| MET (cMet) | −8 |
| PAK4 | −2 |
| PIM1 | −3 |
| PRKACA (PKA) | −1 |
| RET | 6 |
| ROCK1 | 12 |
| RPS6KA3 (RSK2) | −4 |
| SRC | 86 |
| SYK | −1 |
| YES1 | 19 |

SAR Analysis of Src-Inhibiting Macrocycles

Figure 15A:
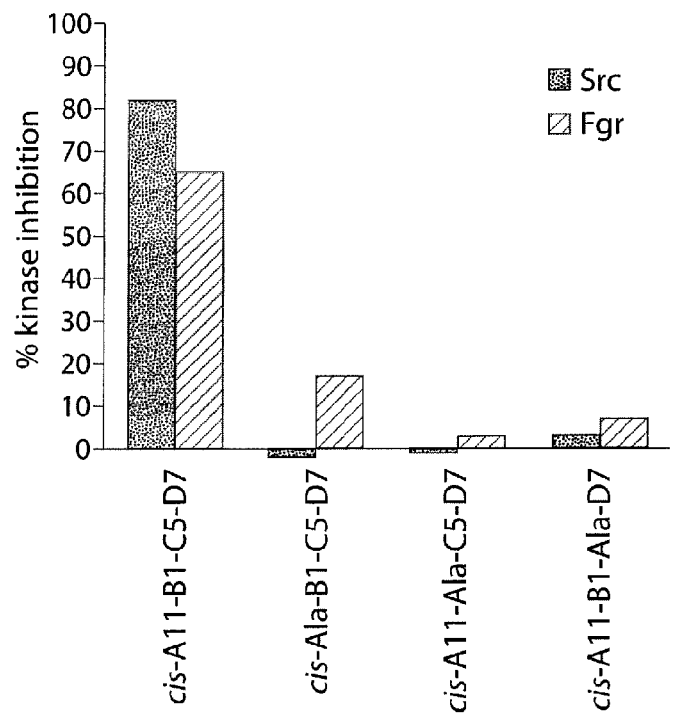

We analyzed the set of macrocycles enriched in the Src selection to develop basic structure-activity relationships for Src inhibition. Our selection data shows a strong preference for a small set of building blocks at each non-scaffold position (FIG. 5), suggesting that all three macrocyclic building blocks are important for binding. To test this hypothesis, we synthesized three derivatives of macrocycle cis-A11-B1-C5-D7 by systematically replacing each of the non-scaffold building blocks (positions A, B, and C) with alanine, in analogy to alanine-scanning mutagenesis of proteins. We assayed the resulting three single-alanine mutants for Src inhibition and observed that none of the three mutant macrocycles at 5 µM significantly inhibit Src or the Src-family kinase Fgr (FIG. 15a), indicating that all three building blocks contribute to the kinase inhibition activity of cis-A11-B1-C5-D7.

Figure 15B:
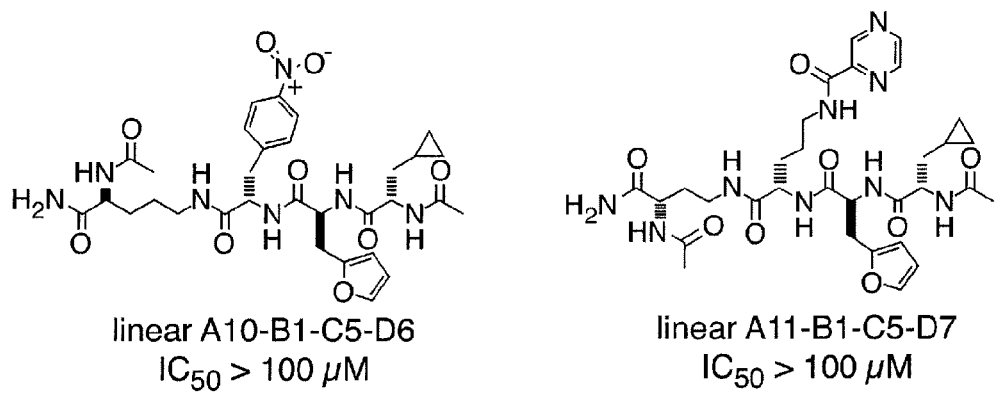

To evaluate the importance of the macrocyclic nature of these molecules for kinase inhibition, we synthesized two diacetylated linear peptides as linear versions of macrocycles A11-B1-C5-D7 and A10-B1-C5-D6 (FIG. 15b) and assayed their abilities to inhibit Src. These two compounds are identical to their corresponding macrocycles with the exception that the olefin group resulting from Wittig macrocyclization is replaced by two methyl groups in the linear peptides. Both linear peptides were virtually inactive against Src kinase, confirming the necessity of a cyclic scaffold to pre-organize these sets of building blocks into a three-dimensional conformation capable of binding to and inhibiting the kinase.

Olefin stereochemistry plays a role in the ability of these compounds to inhibit Src kinase activity. Macrocycles possessing the ornithine(pyrazinylcarbonyl) building block (A11) and diaminobutyric acid scaffold (D7) are more potent Src inhibitors in their cis-isomeric form (Table 6). These macrocycles favor furylalanine (B1) over cyclohexylalanine (B8) at the B position, as evidenced by the weakened potency of macrocycles cis-A11-B8-C5-D7 and cis-A11-B8-C10-D7 compared to cis-A11-B1-C5-D7 and cis-A11-B1-C10-D7 (Table 6), respectively. All of these compounds exhibit hydrophobic building blocks at the C position, especially cyclopropylalanine (C5) (FIG. 5 and Table 6).

Figure 15C:
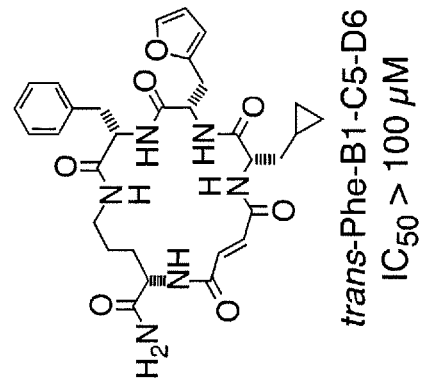
Figure 15C:
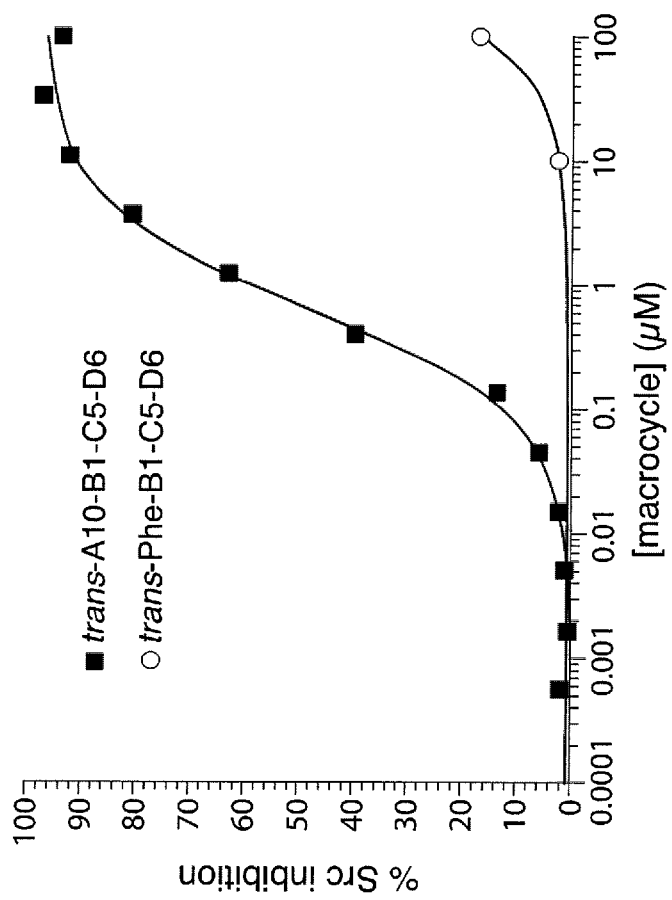
Figure 16:
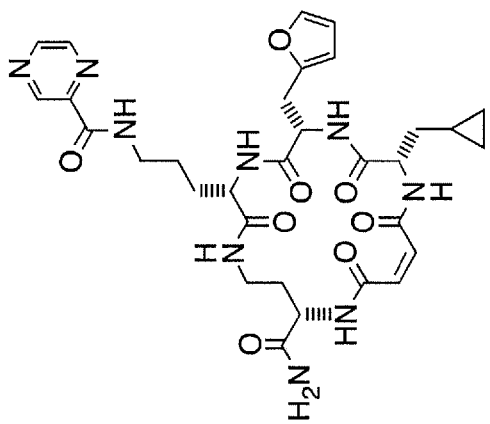
FIG. 16. MM2 energy-minimized (Chem3D, CambridgeSoft) models of macrocycles cis-A11-B1-C5-D7 and trans-A10-B1-C5-D6. The models are oriented such that the a carbon of each scaffold amino acid is in the same spatial orientation.
Figure 16:
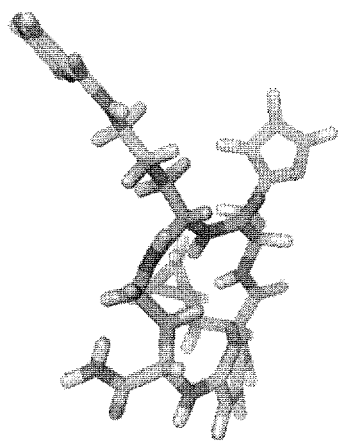
Figure 16:
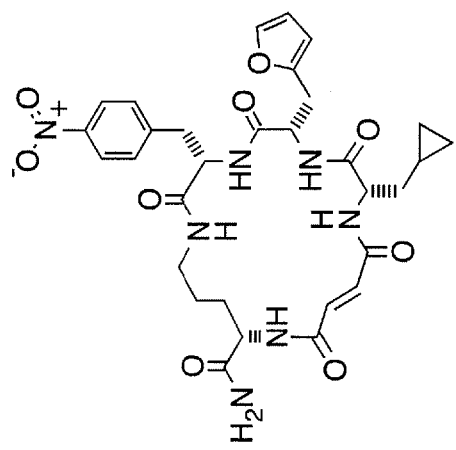
Figure 16:
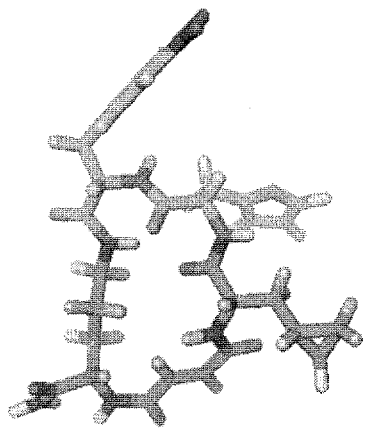

In contrast, macrocycles with nitrophenylalanine (A10) at the A position are more active Src inhibitors in their trans-isomeric form (Table 6). The ornithine (D6) scaffold also supports more potent Src inhibition than the diaminobutyric acid (D7) scaffold that differs by the loss of a single methylene group (Table 6). We assayed the importance of the nitrophenylalanine (A10) building block for Src inhibition by replacing it with phenylalanine in macrocycle trans-A10-B1-C5-D6 to create macrocycle trans-Phe-B1-C5-D6. This substitution abolished Src inhibition (FIG. 15c), indicating the importance of the nitro group among A10 macrocycle subfamily kinase inhibitors. Due to the altered olefin stereochemistry of the nitrophenylalanine (A10)-containing macrocycles, the difference in macrocycle ring size, and the structural differences between the nitrophenylalanine (A10) and ornithine(pyrazinylcarbonyl) (A11) building blocks, we believe that these two classes of macrocycles interact in distinct ways with the Src active site. Indeed, modeling the three-dimensional conformations adopted by cis-A11-B1-C5-D7 and trans-A10-B1-C5-D6 using an MM2 energy-minimization algorithm (Chem3D, CambridgeSoft) predicts large differences in both preferred backbone conformation and preferred side-chain orientation for these two macrocycles (FIG. 16). This hypothesis is further supported by the substantial differences in kinase selectivity (FIG. 14) exhibited by cis-A11-B1-C5-D7 and trans-A10-B1-C5-D6.

Src-Inhibiting Macrocycles do not Resemble Promiscuous Aggregators

Figure 9:
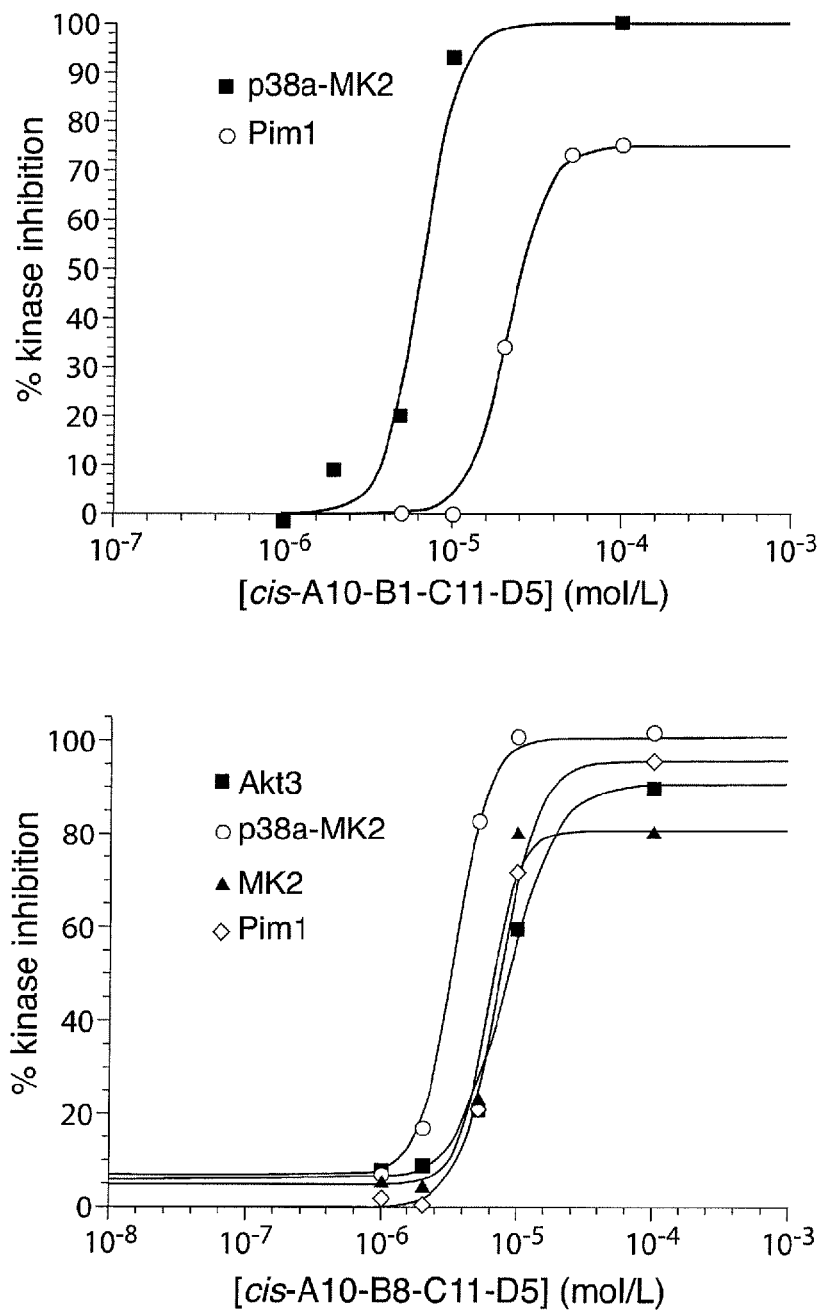
FIG. 9. Inhibition of kinase activity using macrocycles cis-A10-B1-C11-D5 and cis-A10-B8-C11-D5.
Figure 10:
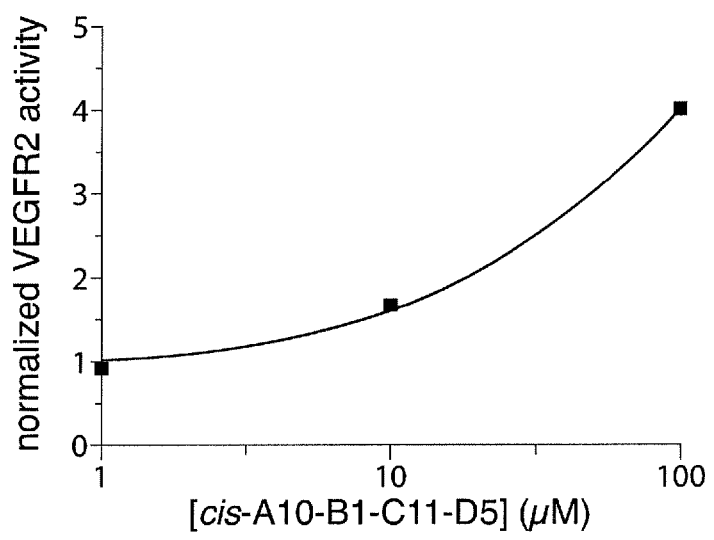
FIG. 10. VEGFR2 activity increases upon treatment with macrocycle cis-A10-B1-C11-D5. Kinase activity was measured as in Table 6. Activation was calculated by dividing the amount of substrate phosphorylation observed in the presence of the macrocycle by the amount of substrate phosphorylation observed in the absence of the macrocycle.

High-throughput screening can result in the discovery of non-canonical ligands known as promiscuous aggregators that form colloidal aggregates in aqueous solution and inhibit enzymes by a non-specific sequestration mechanism rather than through a classical one-to-one binding mode.[49] A common property of promiscuous aggregators is a steep dose-response curve that can result from the enzyme concentration in the kinase assay exceeding the $K_i$ of the aggregated species, which is typically present at significantly lower concentrations than that of the small molecule itself.[49] We suspected that A10-Y-C11-D5 and A12-B8-C10-X macrocycles (FIG. 6 and Table 7) might be promiscuous aggregators due to their high hydrophobicity, broad specificity, and steep dose-response curves (FIGS. 9 and 11).

To test this hypothesis, we assayed macrocycle cis-A10-B8-C11-D5 against Akt3, MAPKAPK2, and Pim1 and assayed macrocycle cis-A12-B8-C100-D3 against Pim1 while varying the concentration of kinase in the reactions. If aggregate formation results in stoichiometric titration of the kinase, the observed $IC_{50}$ value should vary linearly with enzyme concentration.[49]

Despite their steep dose-response curves, inhibition of MAPKAPK2 and Pim1 did not vary with kinase concentration (FIG. 17), suggesting a different mechanism of inhibition. For example, steep dose-response curves can also be caused by multi-site binding or by a phase transition in the inhibitor that is coupled with inhibition.[49] In contrast, we observed that inhibition of Akt3 by cis-A10-B8-C11-D5 varied linearly with the kinase concentration used in the assay (FIG. 17), indicating that this macrocycle may be inhibiting Akt3 through a promiscuous aggregator mechanism.

Figures 17, 18:
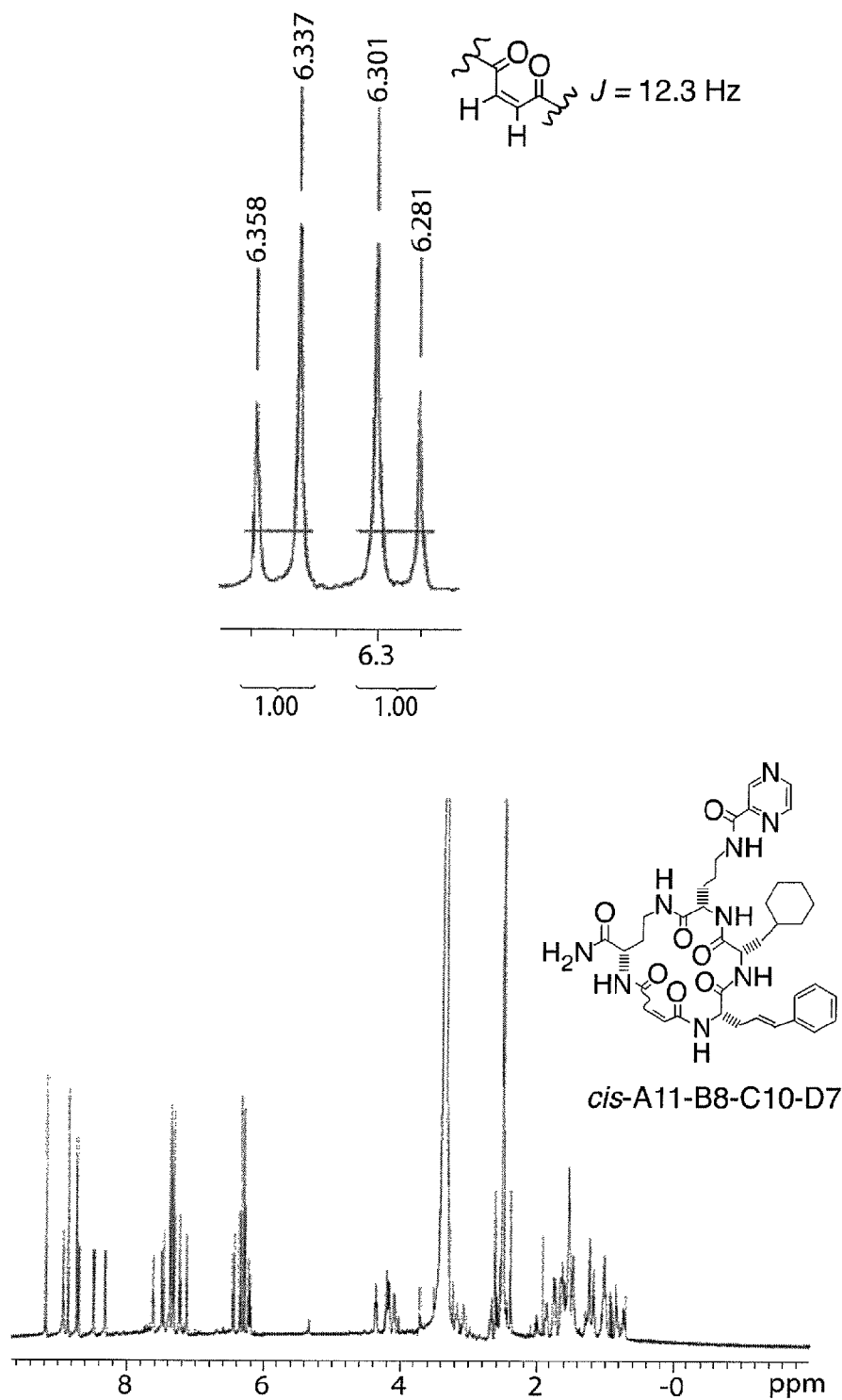
FIG. 17. Enzyme titration test for promiscuous aggregator behavior. The specified macrocycles were assayed in the presence of varying concentrations of enzyme (shown in the legend). Significant dependence of apparent $IC_{50}$ on enzyme concentration was observed for macrocycle cis-A11-B8-C10-D5 when assayed against Akt3, consistent with the behavior of a promiscuous aggregator, but not for the other macrocycles assayed.
Figure 18:
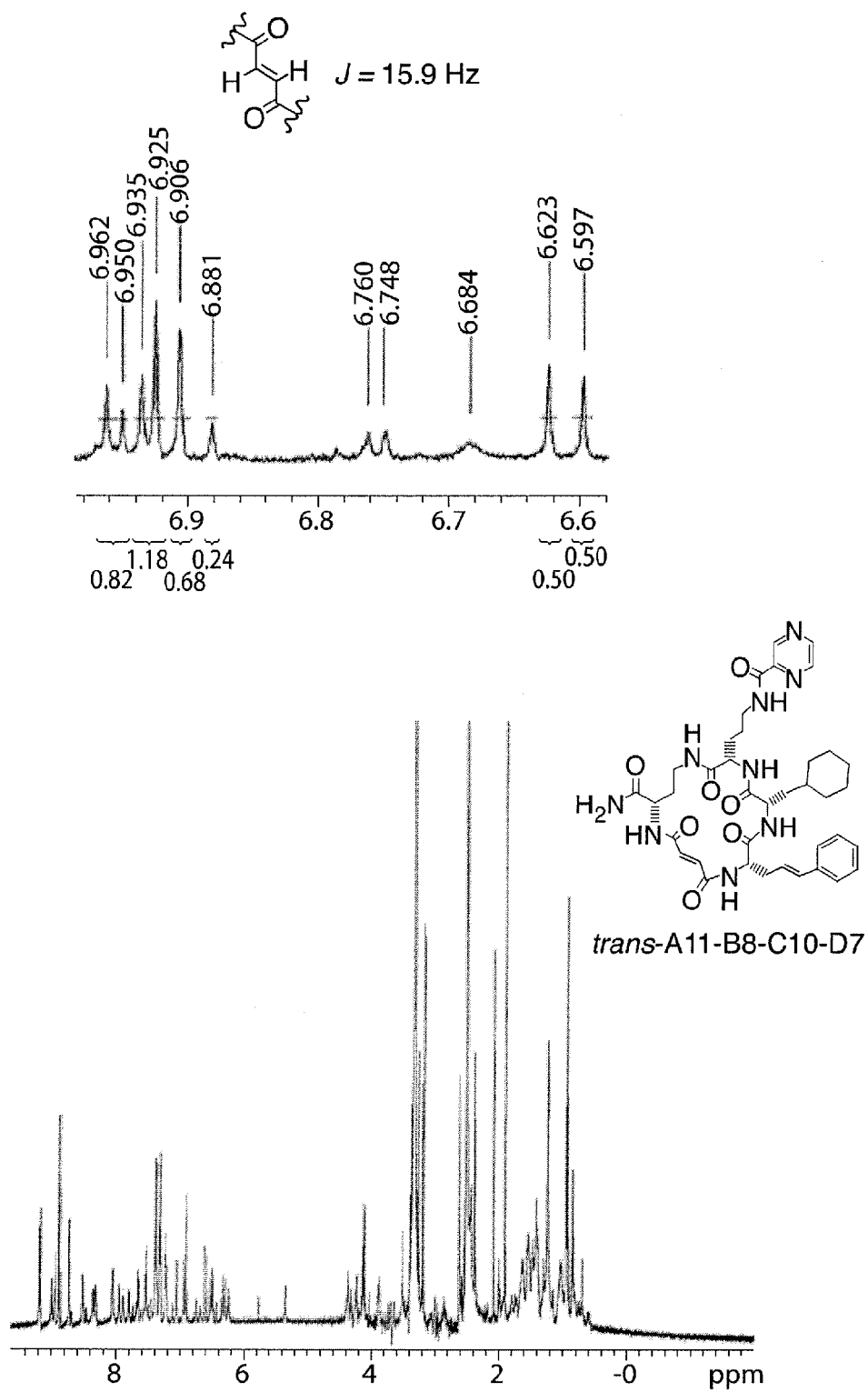

In contrast, the family of Src-inhibiting macrocycles discovered in this work do not exhibit steep dose-response curves (FIG. 8), bind in an ATP-competitive manner (FIG. 12 and FIG. 13), and do not vary significantly in observed inhibitory potency as a function of enzyme concentration (FIG. 17). These results collectively indicate that the Src-inhibiting macrocycles described above are not promiscuous aggregators.

Discussion

A 13,824-membered DNA-templated macrocycle library was subjected to 36 protein affinity-based selections in a parallel manner. PCR-installed DNA barcodes enabled all of the selections to be sequenced as one sample and deconvoluted for analysis by binning sequence data by barcode. The ability of current DNA sequencing technology to detect even modestly enriched library members is demonstrated here, obviating the need to perform multiple rounds of selection for the library members characterized in this work. The low false positive rate among the macrocycles enriched during selections studied here suggests that the evaluation of small molecule-protein interactions based on in vitro selection and modern DNA sequencing methods is robust.

After one round of in vitro binding selection, high-throughput sequencing enabled the identification of three families of enriched macrocycles in the protein kinase selections, despite enrichment factors that were as low as ~2- to 3-fold. All three families of macrocycles enriched after selection were shown to possess the ability to inhibit their target kinase Macrocycles enriched in the Src selection possessed classical single-site dose response curves with $IC_{50}$ values as low as 680 nM. The potency of these compounds is promising given that they emerged from the broad selection of an untargeted 13,824-membered library.

Consistent with the highly target-specific in vitro selection results, assays of Src-enriched macrocycles against a broad set of human kinases revealed that these molecules indeed possess very good overall selectivity among a panel of human kinases. The specificity of these macrocycles is especially intriguing since these macrocycles are ATP-competitive inhibitors and the ATP-binding site is highly conserved among protein kinases.[51-53] Furthermore, in addition to possessing good overall selectivity, the molecules were exceptionally selective among kinases that have been traditionally very difficult to distinguish by small-molecule inhibitors. For example, Src and Abl are two closely related non-receptor tyrosine kinases that have exhibited very similar small-molecule binding specificities.[58-61]

Towards the goal of distinguishing Src and Abl using a small molecule, Maly and co-workers[62] recently generated bivalent kinase inhibitors that rely on peptidic recognition outside of the ATP-binding cleft to generate binding selectivity. Macrocycle A1-B1-C5-D7 displays >50-fold selectivity for Src over Abl kinase while binding in an ATP-competitive manner. We also observed >100-fold selectivity for Aurora A among the closely-related Aurora family of serine/threonine protein kinases.[63] Most reported small molecule Aurora A inhibitors also inhibit Aurora B and/or Aurora C with comparable affinity[64-67] although examples of Aurora A selective inhibitors have begun to emerge.[68]

Macrocycle trans-A10-B1-C5-D6 exhibited even better selectivity for Src, with no significant off-target inhibition in the panel of 44 human kinases against which this compound was assayed. This panel included all nine highly-related Src-family kinases. The generation of small molecules that are selective among the Src-family kinases has posed a significant challenge to academic and pharmaceutical drug-discovery efforts, and the new class of macrocyclic kinase inhibitors described here represent promising starting points for future probe or therapeutic development efforts.

The observed selectivity may arise at least in part from the design of the library to contain rigid macrocyclic structures with a high ratio of atoms derived from varying building blocks to atoms shared in common by all library members. Kinase selectivity may also result from the larger size of these molecules compared with traditional ATP-competitive kinase inhibitors; the presence of additional groups may support interactions both inside and outside of the ATP-binding site. The macrocyclic kinase inhibitors discovered in this work share very few chemical features with classical ATP-competitive kinase inhibitors, which are typically planar heterocycles based on adenine. In contrast, our peptidic macrocycles contain several stereocenters and can adopt distinct three-dimensional conformations required for selective target binding. These findings also demonstrate that changes in building block composition that do not abrogate Src inhibition can modulate the selectivity of these macrocycles among human kinases.

Materials and Methods

General Methods

Macrocycles were purified by reverse-phase HPLC using a C18 stationary phase and an acetonitrile/0.1% trifluoroacetic acid gradient. All $^1$H NMR spectra were recorded on a Varian INOVA 600 (600 MHz) instrument (FIG. 18).

In Vitro Selections with Known Protein-Binding Ligands

A stock solution of GST-labeled protein target was diluted in protein-binding buffer (50 mM Tris-HCl, pH 7.5, 50 mM NaCl, 10 mM β-mercaptoethanol) to a final concentration of 1 µM. The protein target (200 µmol) was incubated with 2 µL MagneGST (Promega) glutathione-linked magnetic particles for one hour at 4° C. with gentle shaking. The beads were washed three times with 100 µL TBST buffer supplemented with 1 M NaCl, followed by two washes with 300 µL protein-binding buffer. The beads were then diluted in 20 µL selection buffer (TBST, 3 mg/mL yeast tRNA, 1 mM DTT) and 10 µL of resulting protein bead solution was combined with 1 pmol of a non-binding DNA sequence and 1/10, 1/100, 1/1000, or 1/10,000 pmol of the known protein-binding ligand conjugated to DNA. After removing unbound molecules, the beads were washed three times with 200 µL selection buffer, and bound molecules were eluted in 20 µL of 0.1 mM glutathione in 50 mM Tris pH 8.0 buffer for 15 minutes. Of this eluant, 5 µL was subjected to PCR amplification.

Positive Control Selection Analysis

Positive-control selections were analyzed using either a Taqman qPCR assay or restriction-endonuclease digestion. Taqman qPCR was performed according to the manufacturer's protocols. For restriction-endonuclease analysis, 20 µL of PCR reaction were combined with 5 units of Earl restriction endonuclease (NEB), and incubated for two hours at 37° C. Digested PCR amplicons were separated by agarose gel electrophoresis and stained with EtBr. The ratio of digested to undigested DNA was determined by ethidium bromide staining and densitometry using UV light.

In Vitro Selections with the DNA-Templated Macrocycle Library

In vitro selections of the 13,824-membered library were conducted exactly as described above for the positive control selections. For each selection, 5 pmol of library were used. PCR amplification of selection survivors was performed with 5'-barcoded forward and reverse primers. Barcoded PCR amplicons were quantitated using Picogreen dsDNA quantitation reagent (Invitrogen), mixed in equimolar amounts, and submitted for high-throughput DNA sequencing.

Kinase Assays

Src IC$_{50}$ determinations and single-point inhibition measurements were performed using Invitrogen's Z'-LYTE Tyr 02 assay kit according to the manufacturer's protocols. All kinase assays were performed at ATP concentrations near K$_{M,ATP}$ values, except where noted otherwise. Active human Src kinase was obtained from Millipore. For kinome profiling and IC$_{50}$ determinations against non-Src kinases, compounds were submitted to Invitrogen's SelectScreen Kinase Profiling Service.

REFERENCES (1) Lam, K. S.; Lebl, M.; Krchnak, V. *Chem. Rev.* 1997, 97, 411-448.
(2) Pirrung, M. C. *Chem. Rev.* 1997, 97, 473-488.
(3) Tan, D. S, *Nat. Chem. Biol.* 2005, 1, 74-84.
(4) Walters, W. P.; Namchuk, M. *Nat. Rev. Drug Discov.* 2003, 2, 259-266.
(5) Joyce, G. F. *Annu. Rev. Biochem.* 2004, 73, 791-836.
(6) Lin, H.; Comish, V. W. *Angew. Chem. Int. Ed. Egl.* 2002, 41, 4402-4425.
(7) Taylor, S. V.; Kast, P.; Hilvert, D. *Angew. Chem. Int. Ed. Engl.* 2001, 40, 3310-3335.
(8) Wilson, D. S.; Szostak, J. W. *Annu. Rev. Biochem.* 1999, 68, 611-648.
(9) Dewey, T. M.; Mundt, A. A.; Crouch, G. J.; Zyzniewski, M. C.; Eaton, B. E. *J. Am. Chem. Soc.* 1995, 117, 8474-8475.
(10) Forster, A. C.; Tan, Z.; Tan, M. N.; Nalam, H.; Lin, H.; Qu, H.; Cornish, V. W.; Blacklow, S. C. *Proc. Natl. Acad. Sci. USA* 2003, 100, 6353-6357.
(11) Horhota, A.; Zou, K.; Ichida, J. K.; Yu, B.; McLaughlin, L. W.; Szostak, J. W.; Chaput, J. C. *J. Am. Chem. Soc.* 2005, 127, 7427-7434.
(12) Josephson, K.; Hartman, M. C. T.; Szostak, J. W. *J. Am. Chem. Soc.* 2005, 127, 11727-11735.
(13) Latham, J. A.; Johnson, R.; Toole, J. J. *Nucleic Acids Res.* 1994, 22, 2817-2822.
(14) Lee, S. E.; Sidorov, A.; Gourlain, T.; Thorpe, S. J.; Brazier, J. A.; Dickman, M. J.; Hornby, D. P.; Grasby, J. A.; Williams, D. M. *Nucleic Acids Res.* 2001, 29, 1565-1573.
(15) Matulic-Adamic, J.; Daniher, A. T.; Karpeisky, A.; Haeberli, P.; Sweedler, D.; Beigelman, L. *Bioorg. Med. Chem. Lett.* 2000, 10, 1299-1302.
(16) Perrin, D. M.; Garestier, T.; Helène, C. *J. Am. Chem. Soc.* 2001, 123, 1556-1663.
(17) Gartner, Z. J.; Liu, D. R. *J. Am. Chem. Soc.* 2001, 123, 6961-6963.
(18) Gartner, Z. J.; Kanan, M. W.; Liu, D. R. *Angew. Chem. Int. Ed.* 2002, 41, 1796-1800.
(19) Gartner, Z. J.; Kanan, M. W.; Liu, D. R. *J. Am. Chem. Soc.* 2002, 124, 10304-10306.
(20) Gartner, Z. J.; Tse, B. N.; Grubina, R.; Doyon, J. B.; Snyder, T. M.; Liu, D. R. *Science* 2004, 305, 1601-1605.
(21) Calderone, C. T.; Liu, D. R. *Angew. Chem. Int. Ed.* 2005, 44, 7383-7386.
(22) Snyder, T. M.; Liu, D. R. *Angew. Chem. Int. Ed.* 2005, 44, 7379-7382.
(23) Kanan, M. W.; Rozenman, M. M.; Sakurai, K.; Snyder, T. M.; Liu, D. R. *Nature* 2004, 431, 545-549.
(24) Tse, B. N.; Snyder, T. M.; Shen, Y. S.; Liu, D. R. *J. Am. Chem. Soc.* 2008, 130, 15611-15626.
(25) Li, X.; Liu, D. R. *Angew. Chem. Int. Ed.* 2004, 43, 4848-4870.
(26) Kleiner, R. E.; Brudno, Y.; Birnbau, M. E.; Liu, D. R. *J. Am. Chem. Soc.* 2008, 130, 4646-4659.
(27) Rosenbaum, D. M.; Liu, D. R. *J. Am. Chem. Soc.* 2003, 125, 13924-13925.
(28) Brudno, Y.; Birnbaum, M. E.; Kleiner, R. E.; Liu, D. R. *Nat. Chem. Bio.* 2010, 6, 148-155.
(29) Doyon, J. B.; Snyder, T. M.; Liu, D. R. *J. Am. Chem. Soc.* 2003, 125, 12372-12373.
(30) Dumelin, C. E.; Scheuermann, J.; Melkko, S.; Neri, D. *Bioconjug. Chem.* 2006, 17, 366-370.
(31) Halpin, D. R.; Harbury, P. B. *PLOS Biol.* 2004, 2, 1015-1021.
(32) Halpin, D. R.; Harbury, P. B. *PLOS Biol.* 2004, 2, 1022-1030.
(33) Halpin, D. R.; Lee, J. A.; Wrenn, S. J.; Harbury, P. B. *PLOS Biol.* 2004, 2, 1031-1038.

(34) Melkko, S.; Scheuermann, J.; Dumelin, C. E.; Neri, D. *Nat. Biotechnol.* 2004, 22, 568-574.
(35) Melkko, S.; Zhang, Y.; Dumelin, C. E.; Scheuermann, J.; Neri, D. *Angew. Chem. Int. Ed.* 2007, 46, 4671-4674.
(36) Scheuermann, J.; Dumelin, C. E.; Melkko, S.; Zhang, Y.; Mannocci, L.; Jaggi, M.; Sobek, J.; Neri, D. *Bioconjug. Chem.* 2008, 19, 778-785.
(37) Wrenn, S. J.; Weisinger, R. M.; Halpin, D. R.; Harbury, P. B. *J. Am. Chem. Soc.* 2007, 129, 13137-13143.
(38) Clark, M. A.; Acharya, R. A.; Arico-Muendel, C. C.; Belyanskaya, S. L.; Benjamin, D. R.; Carlson, N. R.; Centrella, P. A.; Chiu, C. H.; Creaser, S. P.; Cuozzo, J. W.; Davie, C. P.; Ding, Y.; Franklin, G. J.; Franzen, K. D.; Gefter, M. L.; Hale, S. P.; Hansen, N. J. V.; Israel, D. I.; Jiang, J.; Kavarana, M. J.; Kelley, M. S.; Kollmann, C. S.; Li, F.; Lind, K.; Mataruse, S.; Medeiros, P. F.; Messer, J. A.; Myers, P.; O'Keefe, H.; Oliff, M. C.; Rise, C. E.; Satz, A. L.; Skinner, S. R.; Svendsen, J. L.; Tang, L.; Vloten, K. v.; Wagner, R. W.; Yao, G.; Zhao, B.; Morgan, B. A. *Nat. Chem. Biol.* 2009, 5, 647-654.
(39) Hansen, M. H.; Blakskjaer, P.; Petersen, L. K.; Hansen, T. H.; Hojfeldt, J. W.; Gothelf, K. V.; Hansen, N. J. V. *J. Am. Chem. Soc.* 2009, 131, 1322-1327.
(40) Driggers, E. M.; Hale, S. P.; Lee, J.; Terrett, N. K. *Nat. Rev. Drug Discovery* 2008, 7, 608-624.
(41) Hruby, V.; Ahn, J. M.; Liao, S. *Curr. Opin. Chem. Biol.* 1997, 1, 114-119.
(42) Spatola, A. F.; Romanovskis, P. In *Combinatorial Peptide and Nonpeptide Libraries: A Handbook*; Jung, G., Ed.; VCH Publishers: New York, 1996, p 327-347.
(43) Heid, C. A.; Stevens, J.; Livak, K. J.; Williams, P. M. *Genome Res.* 1996, 6, 986-994.
(44) Higuchi, R.; Dollinger, G.; Walsh, P. S.; Griffith, P. R. *Biotechnology* 1992, 10, 413-417.
(45) Livak, K. J.; Flood, S. J. A.; Marmaro, J.; Giusti, W.; Deetz, K. *PCR Methods Appl.* 1995, 4, 357-362.
(46) Church, G. M. *Sci. Am.* 2006, 294, 46-54.
(47) Hall, N. *J. Exp. Biol.* 2007, 210, 1518-1525.
(48) Bentley, D. R.; Balasubramanian, S.; Swerdlow, H. P.; Smith, G. P.; Milton, J.; Brown, C. G.; Hall, K. P.; Evers, D. J.; Barnes, C. L.; Bignell, H. R. *Nature* 2008, 456, 53-59.
(49) Shoichet, B. K. *J. Med. Chem.* 2006, 49, 7274-7277.
(50) Coan, K. E.; Shoichet, B. K. *J. Am. Chem. Soc.* 2008, 130, 9606-9612.
(51) Hanks, S. K.; Hunter, T. *FASEB J.* 1995, 9, 576-596.
(52) Hanks, S. K.; Quinn, A. M. *Meth. Enzymol.* 1991, 200, 38-62.
(53) Hanks, S. K.; Quinn, A. M.; Hunter, T. *Science* 1988, 241, 42-52.
(54) Stout, T. J.; Foster, P. G.; Mathews, D. J. *Curr. Pharm. Des.* 2004, 10, 1069-1082.
(55) Karaman, M. W.; Herrgard, S.; Treiber, D. K.; Gallant, P.; Atteridge, C. E.; Campbell, B. T.; Chan, K. W.; Ciceri, P.; Davis, M. I.; Edeen, P.; Faraoni, R.; etc. *Nat. Biotech.* 2008, 26, 127-132.
(56) Cheetham, G. M. T.; Knegtel, R. M. A.; Coll, J. T.; Renwick, S. B.; Swenson, L.; Weber, P.; Lippke, J. A.; Austen, D. A. *J. Biol. Chem.* 2002, 277, 42419-42422.
(57) Hanke, J. H.; Gardner, J. P.; Dow, R. L.; Changelian, P. S.; Brissette, W. H.; Weringer, E. J.; Pollok, B. A.; Connelly, P. A. *J. Biol. Chem.* 1996, 271, 695-701.
(58) Azam, M.; Nardi, V.; Shakespeare, W. C.; III, C. A. M.; Bohacek, R. S.; Wang, Y.; Sundaramoorthi, R.; Sliz, P.; Veach, D. R.; Bornmann, W. G.; Clarkson, B.; Dalgarno, D. C.; Sawyer, T. K.; Daley, G. Q. *Proc. Natl. Acad. Sci. USA* 2006, 103, 9244-9249.
(59) Das, J.; Chen, P.; Norris, D.; Padmanabha, R.; Lin, J.; Moquin, R. V.; Shen, Z.; Cook, L. S.; Doweyko, A. M.; Pitt, S.; Pang, S.; Shen, D. R.; Fang, Q.; Fex, H. F. d.; McIntyre, K. W.; Shuster, D. J.; Gillooly, K. M.; Behnia, K.; Schieven, G. L.; Wityak, J.; Barrish, J. C. *J. Med. Chem.* 2006, 49, 6819-6832.
(60) Golas, J. M.; Lucas, J.; Etienne, C.; Golas, J.; Discafani, C.; Sridharan, L.; Boghaert, E.; Arndt, K.; Ye, F.; Boschelli, D. H.; Li, F.; Titsch, C.; Huselton, C.; Chaudary, I.; Boschelli, F. *Cancer Res.* 2005, 65, 5358-5364.
(61) Tatton, L.; Morley, G. M.; Chopra, R.; Khwaja, A. *J. Biol. Chem.* 2003, 278, 4847-4853.
(62) Hill, Z. B.; Gayani, B.; Perara, K.; Maly, D. J. *J. Am. Chem. Soc.* 2009, 131, 6686-6688.
(63) Fu, J.; Bian, M.; Jian, Q.; Zhang, C. Mol. *Cancer. Res.* 2007, 5, 1-10.
(64) Andersen, C. B.; Wan, Y.; Chang, J. W.; Riggs, B.; Lee, C.; Liu, Y.; Sessa, F.; Villa, F.; Kwiatkowski, N.; Suzuki, M.; Nallan, L.; Heald, R.; Musacchio, A.; Gray, N. S. *ACS Chem. Biol.* 2008, 3, 180-192.
(65) Ditchfield, C.; Johnson, V. L.; Tighe, A.; Ellston, R.; Haworth, C.; Johnson, T.; Mortlock, A.; Keen, N.; Taylor, S. S. *J. Cell. Biol.* 2003, 161, 267-280.
(66) Fancelli, D.; Berta, D.; Bindi, S.; Cameron, A.; Cappella, P.; Carpinelli, P.; Catana, C.; Forte, B.; Giordano, P.; Giorgini, M. L.; Mategani, S.; Marsiglio, A.; Meroni, M.; Moll, J.; Pittala, V.; Roletto, F.; Severino, D.; Soncini, C.; Storici, P.; Tonani, R.; Varasi, M.; Vulpetti, A.; Vianello, P. *J. Med. Chem.* 2005, 48, 3080-3084.
(67) Harrington, E. A.; Bebbington, D.; Moore, J.; Rasmussen, R. K.; Ajose-Adeogun, A. O.; Nakayama, T.; Graham, J. A.; Demur, C.; Hercend, T.; Diu-Hercend, A.; Su, M.; Golec, J. M. C.; Miller, K. M. *Nat. Med.* 2004, 10, 262-267.
(68) Manfredi, M. G.; Ecsedy, J. A.; Meetze, K. A.; Balani, S. K.; Burenkova, O.; Chen, W.; Galvin, K. M.; Hoar, K. M.; Huck, J. J.; LeRoy, P. J.; Ray, E. T.; Sells, T. B.; Stringer, B.; Stroud, S. G.; Vos, T. J.; Weatherhead, G. S.; Wysong, D. R.; Zhang, M.; Bolen, J. B.; Claiborne, C. F. *Proc. Natl. Acad. Sci. USA* 2007, 104, 4106-4111.
(69) Musich, J. A.; Rapoport, H. *J. Am. Chem. Soc.* 1978, 100, 4865-4872.

All publications, patents and sequence database entries mentioned herein, including those items listed below, are hereby incorporated by reference in their entirety for disclosure of the teachings relevant to this invention, as if each individual publication or patent was specifically and individually indicated to be incorporated by reference. In case of the present specification and a document incorporated by reference including conflicting disclosure, the present specification shall control.

Example 2

Development of Macrocyclic Src Inhibitors

Since protein kinases play a central role in cell signaling, the discovery and development of protein kinase inhibitors have become the focus of intensive chemical and biological research over the past two decades (Cohen 2002). Currently, all FDA-approved small-molecule inhibitors of protein kinases target the binding site for ATP, the common substrate in the enzymatic reaction of all 518 kinases in the human kinome (Manning, Whyte et al. 2002). The high sequence conservation within the kinase domain and in particular around the ATP binding pocket makes it challenging to develop specific inhibitors of protein kinases. However, when such specificity can be achieved, kinase inhibitors can become effective drugs. The small-molecule inhibitor IMATINIB™ (GLEEVEC™, Novartis) is selective for c-Abl, PDFGR and c-Kit kinases, which makes imatinib a powerful therapeutic for the treatment of chronic myelogenic leukemia (CML), hypereosinophile syndrome (HES) and gastrointestinal stromal tumors (GIST), respectively (Capdeville, Buchdunger et al. 2002; Cools, Stover et al. 2003; Bikker, Brooijmans et al. 2009). The importance of high specificity is further illustrated by the second-generation drugs approved for the treatment of CML. Dasatinib (Sprycel, Bristol-Meyers Squibb) inhibits a broader spectrum of protein kinases than imatinib, including the Src-family tyrosine kinases (SFKs), and consequently dasatinib has more side effects and increased toxicity (Lombardo, Lee et al. 2004; Bikker, Brooijmans et al. 2009). Since the introduction of imatinib, another ten small-molecule kinase inhibitors have been approved for clinic use and 80 are in clinical trials (Bikker, Brooijmans et al. 2009; Zhang, Yang et al. 2009; Krishnamurty and Maly 2010). The application of these inhibitors ranges from the treatment of chronic myeloid leukemia and renal cell carcinoma to non-small-cell lung cancers (Bikker, Brooijmans et al. 2009; Zhang, Yang et al. 2009).

The catalytic domains of protein kinases can adopt multiple conformations as illustrated by the model tyrosine kinases Src and Abl. The active conformation of the Src and Abl kinase domains is characterized by two hallmarks: (i) a salt bridge between a glutamate in helix αC (Glu310, chicken c-Src numbering) and the catalytic lysine in the amino terminal N-lobe of the kinase (Lys295) and (ii) an aspartate side chain (Asp404) facing into the active site of the kinase where it coordinates $Mg^{2+}$/ATP during the catalytic cycle (Azam, Seeliger et al. 2008). Disruption of either structural hallmark of the active conformation renders the kinases inactive. The outward rotation of helix αC disrupts this first hallmark by breaking the Lys295-Glu310 salt bridge. This conformation was first observed in the structures of Src and Cdk2 and is referred to as the "Src/Cdk-like" or the "helix αC-out" inactive conformation. The second hallmark of the active conformation can be disrupted by a crankshaft-like 180° rotation of the Asp-Phe-Gly (DFG) motif at the beginning of the activation loop. This rotation forces Asp404 out of the active side and Phe405 into the active site, thereby preventing the coordination of $Mg^{2+}$/ATP for catalysis. The movement of Phe405 opens up the specificity pocket—a hydrophobic pocket with low sequence homology among kinases. This conformation is termed the "c-Kit/Abl-like" or the "DFG-Asp-out" inactive conformation as it was described first in the complex of c-Abl and c-Kit with imatinib (Schindler, Bornmann et al. 2000; Mol, Dougan et al. 2004; Levinson, Kuchment et al. 2006). While it is not clear whether all kinases can access these three distinct conformations, Src and Abl kinase (Sicheri, Moarefi et al. 1997; Xu, Harrison et al. 1997; Azam, Seeliger et al. 2008) have been observed in all three conformations indicating that these conformations are relevant for the function of these kinases.

ATP competitive kinase inhibitors can be classified into two groups: (i) type I inhibitors (such as PP1) that bind deeply into the binding pocket of adenine and mimic the hydrogen bonding pattern of the base (Zhang, Yang et al. 2009) and (ii) type II inhibitors such as imatinib, nilotinib and the DSA series of compounds (Seeliger, Ranjitkar et al. 2009) that bind to the specificity pocket of Src and Abl kinase that only opens upon rotation of the Asp-Phe-Gly motif.

Non-ATP competitive inhibitors have the potential for excellent specificity. Type III kinase inhibitors bind to allosteric sites, which exist in a number of kinases. The small-molecule inhibitors GNF-2 (targeting Abl kinase) and CI-1040 (targeting MEK kinases) have been shown to be potent and highly specific (Ohren, Chen et al. 2004; Adrian, Ding et al. 2006; Zhang, Yang et al. 2009). One of the main challenges in finding type III inhibitors is the identification of allosteric sites. Recently we used unusually long computer simulations that may help to predict such allosteric binding sites for Src kinase (Shan, Kim et al. 2011).

Finally, substrate-peptide-competitive inhibitors can potentially be highly specific because of the sequence variation in the substrate-peptide binding sites of protein kinases. For example, tyrphostins potently and specifically inhibit EGFR activity by targeting the substrate binding site (Gazit, Yaish et al. 1989; Levitzki 1999).

The identification of macrocyclic kinase inhibitors that bind to Src kinase and potently inhibit the enzyme activity from a library of macrocyclic compounds is described elsewhere herein. Interestingly, two of these macrocyclic compounds, cis-A11-B1-C5-D7 and trans-A10-B1-C5-D6 (referred to also herein as MC1 and MC4, respectively) displayed a remarkable level of specificity, inhibiting Src kinase but not Abl kinase or the highly-related Src-family kinases Hck (68% identical to Src kinase domain in sequence), Blk, Frk, Fyn, and Lyn (see FIG. 14).

Macrocycle derivatives of MC1 and MC4 with potencies as high as Kd=4 nM were developed by systematic modulation of individual macrocycle building blocks. Some of the most potent of these macrocycle derivatives inhibit Src kinase activity in mammalian cells. The mechanism of inhibition of the macrocycle kinase inhibitors was investigated, and it was determined that the src kinase inhibiting macrocycles compete with both ATP and substrate peptide for binding to and inhibition of Src kinase domain.

Further, two amino acid substitutions between Src and Hck were identified that explain the specificity of the macrocycles described herein for Src over Hck. Finally, the ability of macrocycles to inhibit the Thr338Ile Src gatekeeper mutation was characterized, and it was discovered that MC4-based but not MC1-based macrocycles are insensitive to this mutation and inhibit Thr338Ile Src kinase with similar potency as wild type Src kinase. Taken together, these findings establish that macrocycles can serve as potent Src kinase inhibitors that demonstrate uncommon kinase selectivity, insensitivity to common drug-resistant forms of tyrosine kinases, and src kinase inhibitory activity when administered to human cells.

Materials and Methods

Macrocycle Synthesis:

Carboxamide-containing macrocycles were synthesized on multi-milligram scale using Fmoc solid-phase peptide synthesis as described in Kleiner et al.(Kleiner, Dumelin et al. 2010) Carboxylate-containing macrocycles were synthesized using standard macrocycle synthesis protocols substituting 2-chlorotrityl resin (EMD Biosciences) in place of Rink amide resin. Fluorescein-macrocycle conjugates were synthesized using standard macrocycle synthesis protocols substituting 1,6-diaminohexane trityl resin (EMD Biosciences) in place of Rink amide resin. After HPLC purification, the 6-aminohexane-conjugate was reacted with 5 equivalents of 5-carboxyfluorescein N-succinimidyl ester (Sigma-Aldrich) and 10 equivalents of DIPEA in DMF. The fluorescein-macrocycle was then purified by reverse-phase HPLC using a C18 stationary phase and eluting with a gradient of water/acetonitrile.

Protein Purification:

Kinase domain constructs of human c-Abl (residues 229-512), chicken c-Src (residues 251-533 and residues 83-533), murine Lck (residues 227-509), and human Hck (residues 166-445) were expressed as previously described (Seeliger, Young et al. 2005; Seeliger, Nagar et al. 2007; the entire contents of each of which are incorporated by reference herein). Mutations were introduced into chicken c-Src (residues 251-533) (T338I, C277Q, L297M) by site-directed mutagenesis and verified by DNA sequencing.

Kinase Activity Assays:

In vitro kinase inhibition assays were performed using either a continuous spectrophotometric assay or a FRET-based endpoint assay. For the continuous assay (Barker, Kassel et al. 1995), 100 µM of a Src optimal substrate peptide (AEEEIYGEFAKKK, SEQ ID NO: 16) or 200 µM of an Abl optimal substrate peptide (EAIYAAPFAKKK, SEQ ID NO: 17) (Songyang and Cantley 1995; Songyang, Carraway et al. 1995) were combined with 50 µM ATP, unless stated otherwise. Titrations of MC1, MC1.2, MC4, MC4.1, and MC9 (ranging from 0 µM to 83.3 µM) were performed at 30° C. as described before for imatinib (Seeliger, Nagar et al. 2007) to determine the concentration at which 50% of the initial kinase activity is inhibited (IC50).

For the FRET-based endpoint assay, kinase assays were performed using Invitrogen's Z'-LYTE kinase assay using the Tyr 02 substrate peptide (based upon the optimal Abl substrate peptide EAIYAAPF) according to the manufacturer's instructions. Assays were performed at near KM ATP concentrations for full-length c-Src and full-length c-Src T338I-50 µM and 7 µM, respectively.

KM Assays:

The Michaelis constant (KM) of the kinases for ATP, Src optimal peptide and Abl optimal peptide were determined for each of the kinases through use of the continuous spectrophotometric assay (Barker, Kassel et al. 1995). Concentrations of ATP ranged from 0 to 250 µM and ranged from 0 to 1.2 mM for Src optimal peptide and 0 to 2.4 mM for Abl optimal peptide. All experiments were performed in triplicate.

Anisotropy Binding Assay:

The change in fluorescence anisotropy of fluorescein-labeled MC1, MC4 and MC9 at 518 nm upon excitation at 492 nm was monitored with a HORIBA JobinYvon FluoroMax-4 (Edison, N.J.) spectrofluorimeter. Kinase was titrated to 0.5 µM of the fluorescently labeled macrocycle in 100 mM Tris pH 8.0, 10 mM MgCl2 at 25° C. After equilibration, the increase in the fluorescence anisotropy of the fluorescently labeled ligand was recorded and fitted against a quadratic binding equation in Kaleidagraph (Synergy Software, Reading Pa.) to yield the dissociation constant KD.

Cell Culture Assays and Western Blots:

Cells were cultured in 48-well tissue culture plates in DMEM+10% FBS until they reached confluence. After removing serum-containing medium, cells were washed with serum-free DMEM, and small molecule inhibitor in serum-free DMEM with 2% DMSO was added to each well and incubated overnight. After incubation with compound, cells were washed once with PBS and lysed in Cell Extraction Buffer (Invitrogen), a modified RIPA buffer, supplemented with PMSF and protease inhibitors according to the manufacturer's instruction. Cell lysates were quantified by BCA assay (Pierce Biotechnology) and an equivalent amount of lysate was loaded into each lane of a 4-12% polyacrylamide gel, and separated by SDS-PAGE. Separated proteins were transferred onto a PVDF membrane, and blocked for one hour with 5% BSA in TBST buffer. The membrane was then incubated overnight at 4° C. with 4G10 anti-phosphotyrosine antibody (Millipore) and a β-tubulin antibody (Sigma) as a loading control. Fluorescent anti-mouse and anti-rabbit secondary antibodies (LI-COR) were added prior to imaging the membrane.

Results and Discussion

Figures 18, 19:
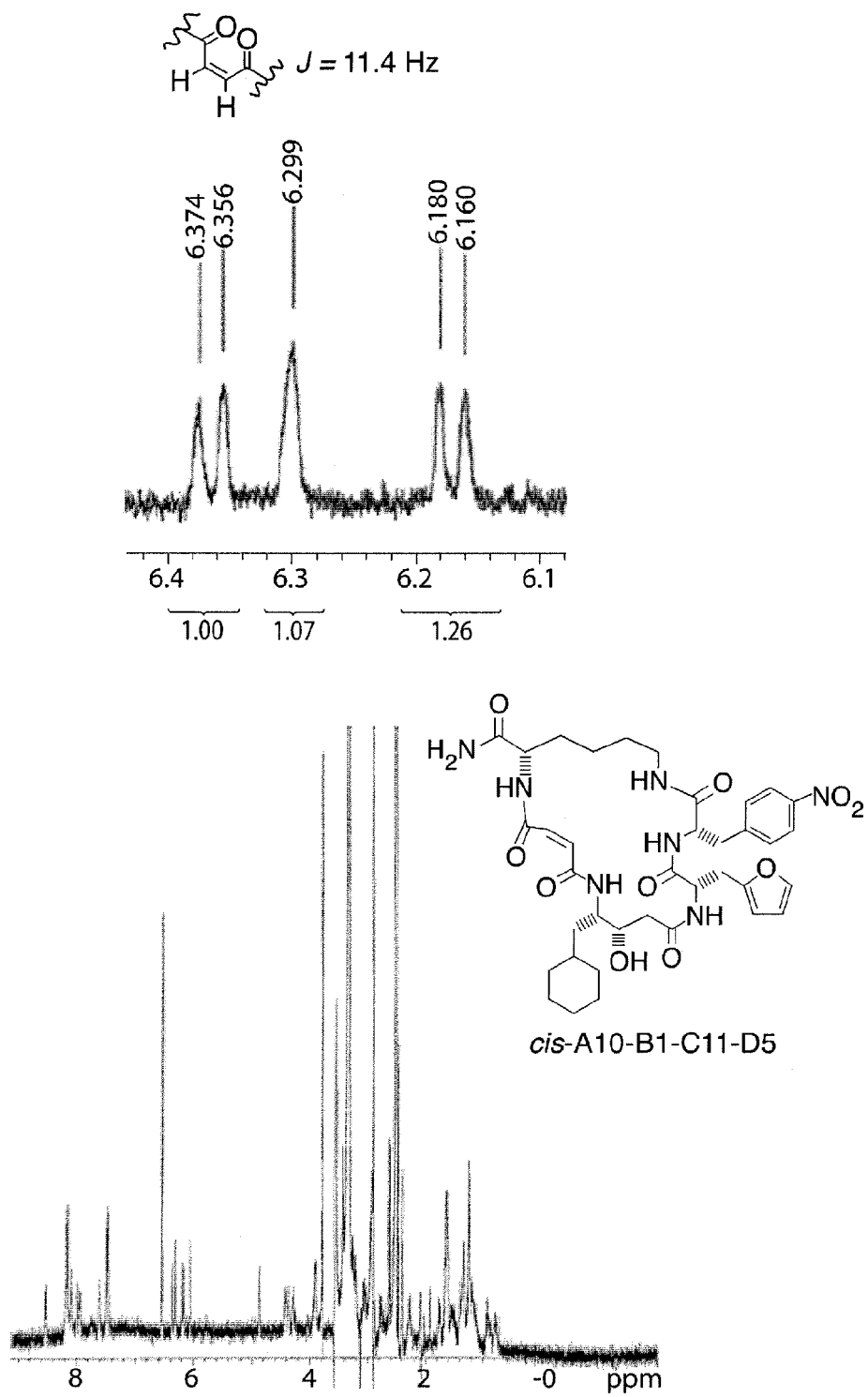
FIG. 19. Macrocycle kinase inhibitors with improved inhibition potency. Macrocycle compounds MC1 (trans A11-B1-C5-D7), MC1.2 (trans A11-Phe-Cha-D7), MC4 (cis A10-B1-C5-D6), MC4.1 (trans A10-Phe-Cha-D6), MC4.3 (trans A10-[4-F-Phe]-Cha-D6),—and MC9 (trans A11-B8-C10-D7). Macrocycles MC1, MC1.2, and MC9 are based off a diaminobutyric acid scaffold, and contain a pyrazine group in the A position (shown in red). Macrocycles MC4, MC4.1, MC4.2, and MC4.3 are based off an ornithine scaffold, and contains a nitrophenylalanine in position A. Positions B and C varied for each compound, resulting in different affinities for Src kinase. Adapted from Kleiner, et al. JACS (2010).

Development of Src-Inhibiting Macrocycles with Improved Potency:

Since ATP-competitive kinase inhibitors must compete with millimolar ATP concentrations in the cell, high in vitro potency, e.g., an $IC_{50}$ in the low nM range, is often required for a kinase inhibitor to demonstrate cellular efficacy at micromolar concentrations (Knight and Shokat 2005). It was therefore sought to improve the potency of the inhibitors identified herein, for example, of the pyrazine-containing MC1 (MC stands for "macrocycle," sometimes also referred to as "macro" herein; MC1 is also referred to as cis-A11-B1-C5-D7 herein) and p-nitrophenylalanine-containing MC4 (also referred to as trans-A10-B1-C5-D6 herein) by the systematic replacement of macrocycle amino acids with modified building blocks. FIG. 19, upper panel displays the structures of some exemplary macrocycles mentioned herein.

Derivatives of MC4 were synthesized by Fmoc solid-phase peptide synthesis and assayed against full-length chicken c-Src using Invitrogen's Z'-LYTE kinase assay. Improvement of building blocks at the B and C positions were investigated first (FIG. 19, middle panel). Holding the amino acids at the A and C positions constant, variants of MC4 containing phenylalanine, cyclohexylalanine, pentafluorophenylalanine, and N-methyl-phenylalanine at the B position in place of furylalanine were synthesized and assayed. Substituting pentafluorophenylalanine and N-methylphenylalanine at this position abolished activity ($IC_{50}$>10 µM), and cyclohexylalanine resulted in a ~10-fold decrease in potency. The phenylalanine derivative MC4.1, also referred to herein as trans-A10-Phe-C5-D6, wherein Phe is phenylalanine, in contrast, resulted in a 3-fold increase in Src inhibition potency to $IC_{50}$=80 nM.

With this improved macrocycle in hand, building blocks at the C position were varied next. Holding the A and B positions constant as p-nitrophenylalanine and phenylalanine, respectively, phenylalanine, diphenylalanine, 1-naphthylalanine, and cyclohexylalanine were substituted at the C position in place of cyclopropylalanine (FIG. 19, middle panel). Of these derivatives, phenylalanine and naphthylalanine decreased Src inhibition potency by ~3-5-fold, and diphenylalanine decreased inhibition potency by ~16-fold. The cyclohexylalanine derivative, MC4.2, also referred to herein as trans-A10-Phe-Cha-D6, wherein Cha refers to cyclohexylalanine, as illustrated in FIG. 19, middle panel, on the right, however, exhibited an inhibition potency that was improved by >10-fold, with Src $IC_{50}$=6 nM. These results collectively establish that modest modifications in the size and shape of the macrocycle side chains can result in significant gains in potency. Changes to the peptide backbone, such as N-methylation, however, did not appear to be tolerated, as substitution of N-methyl amino acids at some positions resulted in a decrease in inhibition potency. Notably, none of the amino acids that increased potency of Src inhibition were present at the appropriate position in the DNA-templated macrocycle library from which the initial macrocyclic Src inhibitors were discovered, consistent with the quality of the structure-activity relationships resulting from the in vitro selection for Src binding. (Tse, Snyder et al. 2008)

Next, more subtly altered building blocks were installed into the partially optimized macrocycle structures. The importance of p-nitrophenylalanine at the A position of MC4.2 was probed by replacing the nitro group at the para position with a methyl, chloro, bromo, trifluoromethyl, cyano, carbamoyl, or tert-butyl substituent (FIG. 19, middle panel). Remarkably, all but the electronically similar p-cyanophenylalanine exhibited substantial reductions in potency (see Table in FIG. 19, middle panel).

A similar series of subtle changes was introduced to the optimized B position building block, phenylalanine, of MC4.2 by replacing it with tyrosine, p-fluorophenylalanine or p-methylphenylalanine. Introduction of a methyl or hydroxyl group onto the phenyl ring resulted in a substantial decreases in Src inhibition. In contrast, the p-fluorophenylalanine derivative, also referred to herin as MC4.3, or trans-A10-[4-F-Phe]-Cha-D6, wherein 4-F-Phe is p-fluorophenylalanine, a very conservative change, retained all of the parent compound activity.

Surprisingly, the analogous building block substitutions in the pyrazine-containing macrocycle structure MC1, changing furylalanine to phenylalanine (MC1.1) and cyclopropylalanine to cyclohexylalanine, resulted in a macrocycle, MC1.2 (cis-A11-Phe-Cha-D7), with >150-fold greater potency against Src kinase than the parent compound (FIG. 19, lower panel). The potency of MC1.2 could not accurately be measured since its $IC_{50}$ of ≤4 nM was lower than the enzyme concentration required by our in vitro kinase assay. These findings support a similar mode of binding for the B and C building blocks in MC1 and MC4 derivatives.

Exceptionally Specific Inhibitors of Src Kinase with an ATP and Substrate Peptide Competitive Mode of Inhibition.

The exceptional specificity with which some of the macrocycles described herein inhibited Src kinase activity without inhibiting the activity of the closely related Src family kinase Hck or the activity of human c-Abl kinase, as described in Kleiner, Dumelin et al. 2010, is intriguing. To understand the origin of this unusual specificity, the activity and specificity of the following compounds was characterized: MC1, MC4 and MC9 (MC9 is also referred to herein as cis-A11-B8-C10-D7, see, e.g., FIG. 5) as well as three second-generation compounds with greatly improved potency—MC1.2, MC4.1 and MC4.3. MC1, MC1.2 and MC9 share a diaminobutyric acid scaffold, cis-olefin stereochemistry, and a pyrazine group in position A, whereas MC4, MC4.1, and MC4.3 contain an ornithine scaffold and nitrophenylalanine in position A.

The original characterization of kinase inhibition was performed with a commercial kinase assay that relies on a fluorescently labeled peptide kinase substrate (Z-LYTE, Invitrogen). For further characterization, a continuous spectrophotometric kinase activity assay was employed that is easily adapted to different substrate peptides as well as a wider range of peptide and ATP concentrations. Using this assay, we found that the original compounds MC1, MC4 and MC9 inhibited 50% of Src kinase domain activity ($IC_{50}$) at 16 μM, 11 μM and 69 μM respectively (FIG. 20A). The $IC_{50}$ values of these compounds for Hck, Lck and Abl kinase were over 100 μM and could not be determined accurately. Consistent with their improved potency in the Z'-LYTE assay, the second generation compounds MC1.2, MC4.1, and MC4.3 exhibited more than 200-fold higher potency than the first generation compounds. MC1.2 and MC4.2 inhibited Src kinase domain with $IC_{50}$-values of 0.07 μM and 0.6 μM, respectively (FIG. 20B). This overall increase in potency resulted in micromolar potency of MC1.2 and MC4.1 against Hck ($IC_{50}$ of 0.36 μM and 0.87 μM, respectively) and Lck ($IC_{50}$ of 4 μM and 5.2 μM, respectively).

While these results are in qualitative agreement with the Z'-LYTE assays (Kleiner, Dumelin et al. 2010), the absolute $IC_{50}$ values observed in the spectrophotometric assay are approximately 10-fold higher. To address this discrepancy, the two major differences between the fluorescent peptide-based Z'-LYTE assay and the continuous spectrophotometric assay employed here were investigated: the kinase construct used (full-length kinase in the Z-LYTE assay vs. kinase domain in the current study) and the peptide identity and concentration (5 μM fluorescent Abl-optimal substrate peptide in the previous study vs. 100 μM Src-optimal substrate peptide in the current study). Surprisingly, it was discovered that the macrocycle compounds inhibited longer Src kinase constructs including the regulatory SH3 and SH2 domains (chicken c-Src 83-533) approximately 10-fold more potently than isolated kinase domains (chicken c-Src 248-533) (FIG. 20B). The $IC_{50}$ values determined for MC1.2 and MC4.1 were close to the concentration of the kinase used in the assay and therefore these values only represent an upper estimate of the real potency of these compounds.

The effect of substrate peptide on inhibitory potency of the macrocycle compounds was investigated next. An Src optimal substrate peptide (AEEEIYGEFAKKK, SEQ ID NO: 16 (Songyang and Cantley 1995; Songyang, Carraway et al. 1995)) was employed in the assays at 100 μM concentration (FIG. 20C). Upon increasing the substrate peptide concentration 3-fold to 300 μM a 50% increase in IC50 was measured for MC1 and MC1.2, indicating that the macrocycle compounds could be substrate peptide competitive. For comparison, when the ATP concentration was raised 50-fold, for all macrocycles a 2-fold to 5-fold increase in $IC_{50}$ was measured consistent with the ATP competitive behavior of the compounds (FIG. 20C).

The $IC_{50}$ values of macrocycles MC1, MC1.2, MC44, and MC4.1 for Src, Hck, Lck, and Abl kinases in response to a 3-fold increase in Src optimal substrate, and a 50-fold

TABLE 11

$IC_{50}$ values of Macrocycles 1, 1.2, 4, and 4.1 for Src, Hck, Lck, and Abl kinases in response to a 3-fold increase in Src optimal substrate, and a 50-fold increase in ATP.

|  | 5 μM ATP<br>100 μM Src optimal peptide | 5 μM ATP<br>300 μM Src optimal peptide | 250 μM ATP<br>300 μM Src optimal peptide |
|---|---|---|---|
| Macrocycle 1 | | | |
| Src | 16 μM | 26 μM | 89 μM |
| Hck | >100 μM | >100 μM | >100 μM |
| Lck | >100 μM | >100 μM | >100 μM |
| Abl | >100 μM | >100 μM | >100 μM |
| Macrocycle 1.2 | | | |
| Src | 0.07 μM* | 0.12 μM | 0.14 μM |
| Hck | 0.36 μM* | 0.46 μM | 1.0 μM |
| Lck | 0.87 μM* | 1.9 μM | 2.4 μM |
| Abl | >100 μM | >100 μM | >100 μM |

TABLE 11-continued

IC$_{50}$ values of Macrocycles 1, 1.2, 4, and 4.1 for Src, Hck, Lck, and Abl kinases
in response to a 3-fold increase in Src optimal substrate, and a 50-fold increase in ATP.

| | 5 µM ATP<br>100 µM Src optimal peptide | 5 µM ATP<br>300 µM Src optimal peptide | 250 µM ATP<br>300 µM Src optimal peptide |
|---|---|---|---|
| | Macrocycle 4 | | |
| Src | 11 µM | 11 µM | 21 µM |
| Hck | >100 µM | >100 µM | >100 µM |
| Lck | >100 µM | >100 µM | >100 µM |
| Abl | >100 µM | >100 µM | >100 µM |
| | Macromple 4.1 | | |
| Src | 0.6 µM | 0.8 µM | 1.8 µM |
| Hck | 4.6 µM | 6.3 µM | 11 µM |
| Lck | 5.2 µM | 5.5 µM | 10 µM |
| Abl | >100 µM | >100 µM | >100 µM |

*values are an upper estimate of the IC$^{50}$ because it is 2-fold less than the concentration of kinase used.

Figures 18, 19, 20, 21:
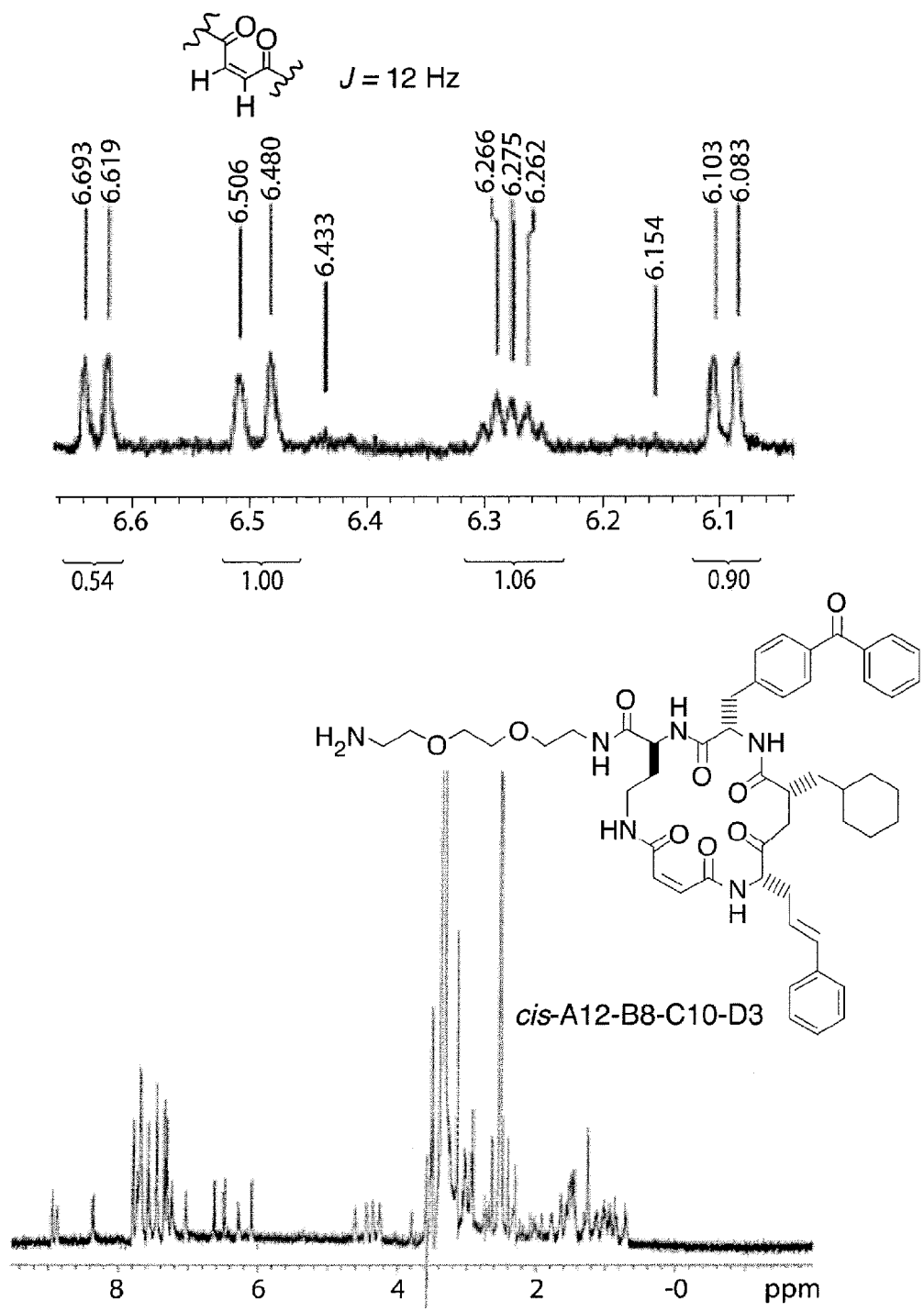
FIG. 20. The macrocycle compounds specificity for Src kinase over Hck, Lck, and Abl kinases. (A) $IC_{50}$ values of macrocycles MC1, MC1.2, MC4, MC4.1, and MC9. $IC_{50}$ values of the macrocycle compounds were determined in the presence of 5 µM ATP and 100 µM Src optimal substrate peptide. Concentrations of kinase used were 0.25 µM for Src, 0.042 µM for Hck, 0.5 µM for Lck, and 0.5 µM for Abl. (B) Src83-533 is more potently inhibited by the Macrocycle compounds than the kinase domain of Src. $IC_{50}$ values of the macrocycle compounds were determined in the presence of 5 µM ATP and 100 µM Src optimal substrate peptide and 0.66 µM of Src83-533. *value is an upper estimate of the $IC_{50}$ because it is 2-fold less than the concentration of kinase used. (C) Macrocycle compounds are mixed inhibitors. $IC_{50}$ values of the Macrocycle compounds for Src kinase domain in response to a 50-fold decrease in ATP (5 µM to 250 µM), and a 3-fold change in Src optimal peptide (100 µM to 300 µM). $IC_{50}$ values decrease as ATP and substrate peptide decrease, showing that the macrocycle compounds compete with both ATP and substrate peptide. *values are an upper estimate of the $IC_{50}$ because it is 2-fold less than the concentration of kinase used.
FIG. 21. (A) Macrocylces A11-B1-C5-D7 and A10-B1-C5-D6 are ATP- and substrate-competitive Src kinase inhibitors. Inhibition of Src decreases for both compounds with increasing ATP concentration. $K_D$ of fluorescein-tagged macrocycles increases with increasing concentrations of src substrate peptide. (B) $K_D$ of the fluorescein labeled Macrocycles MC1, MC4, and MC9 for Src kinase domain in the presence of 250 µM AMP-PNP and 300 µM Src optimal peptide. In the presence of AMP-PNP, or Src optimal peptide, the KD increases, showing that the macrocycles compete with both ATP and peptide for binding.
Figure 21A:
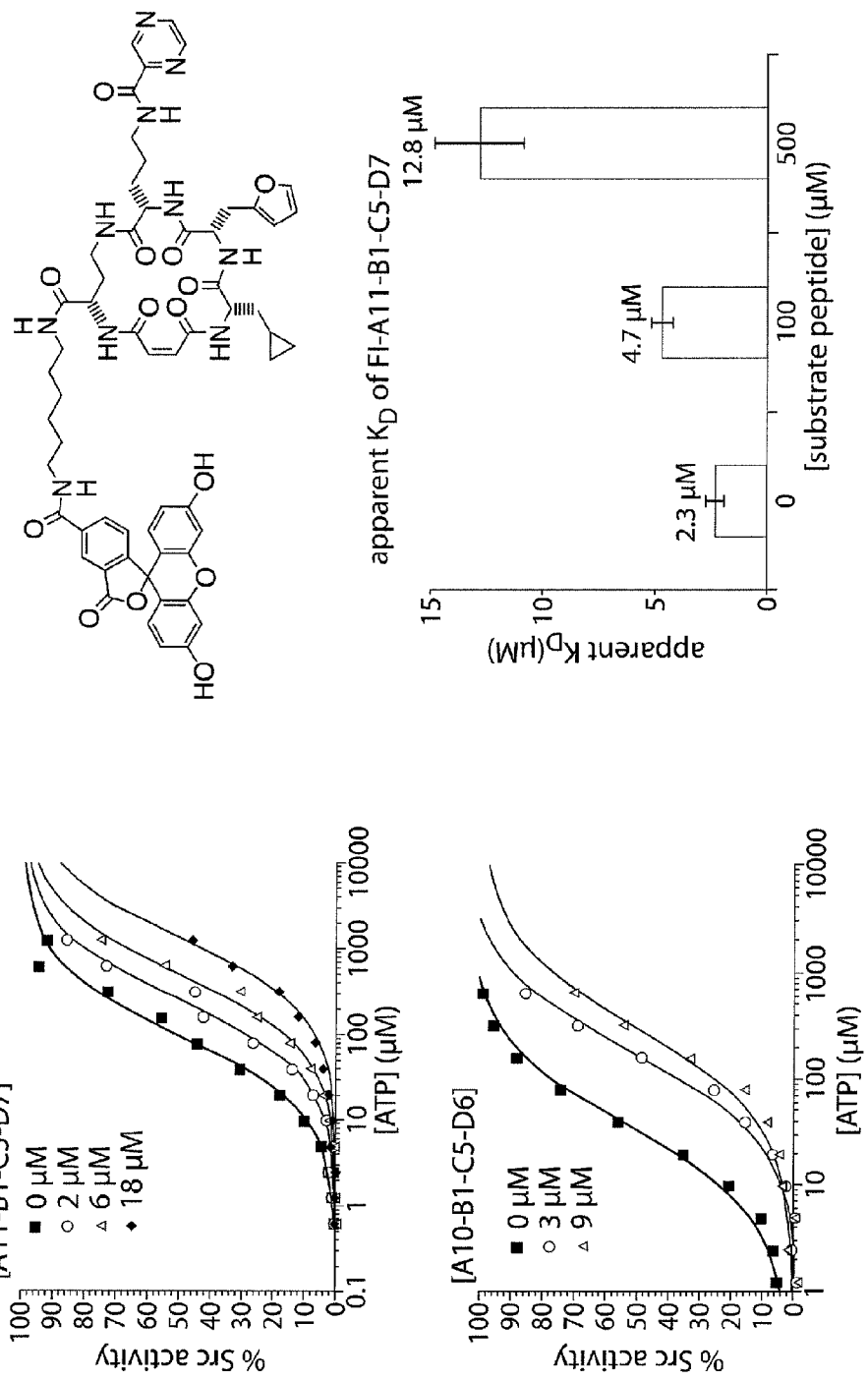
Figure 21B:
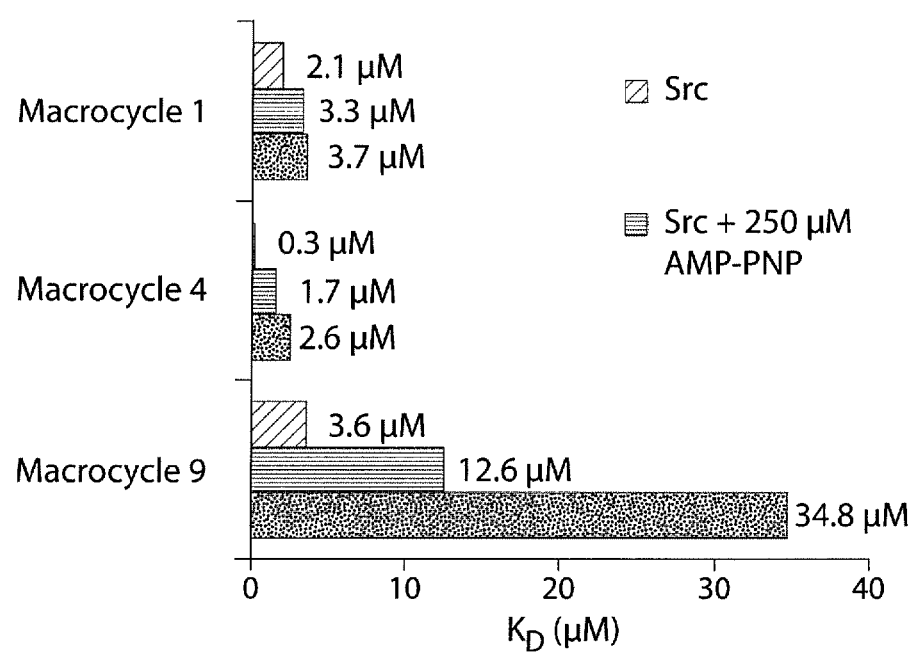
Figure 22:
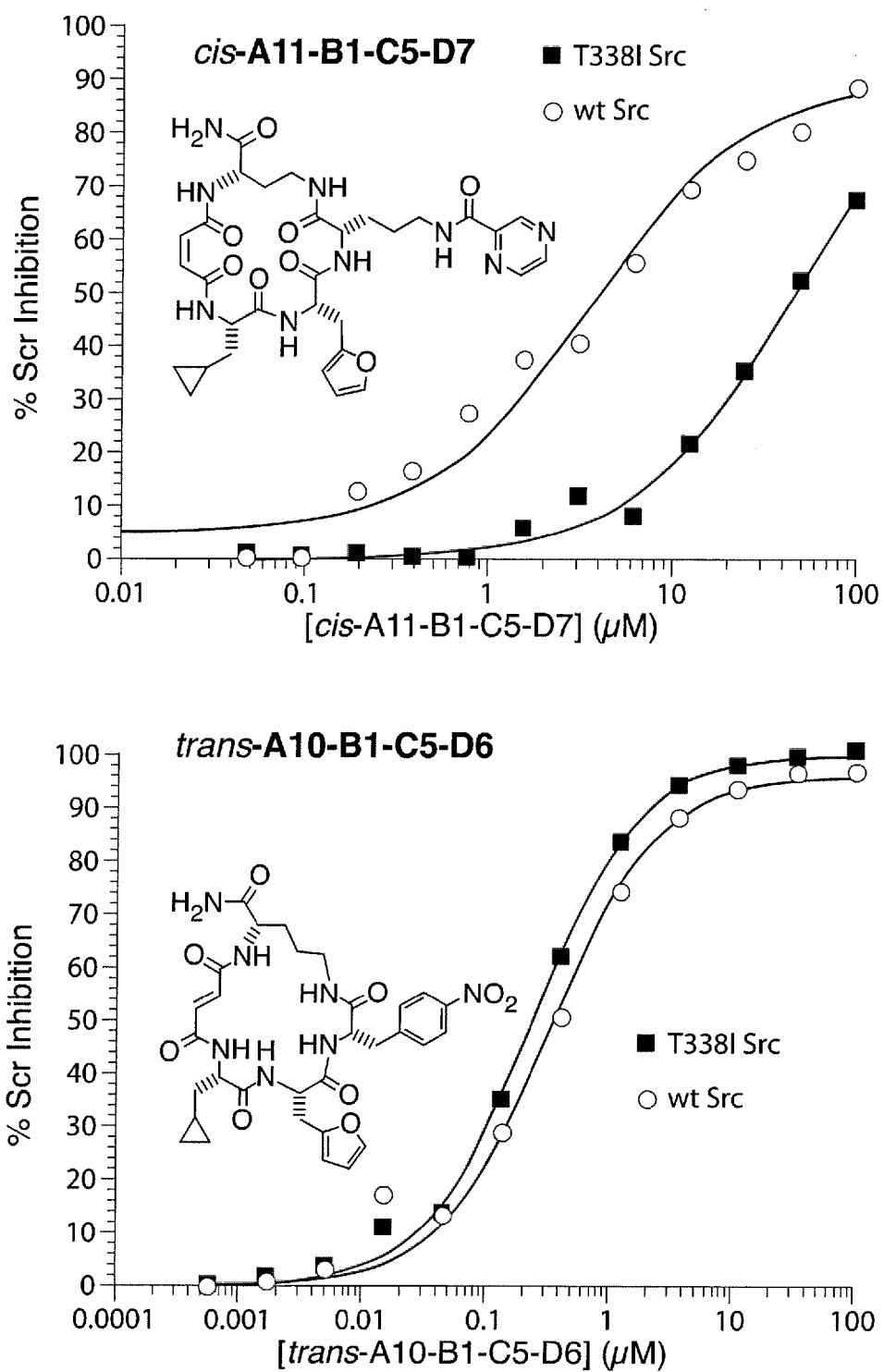
Figure 23:
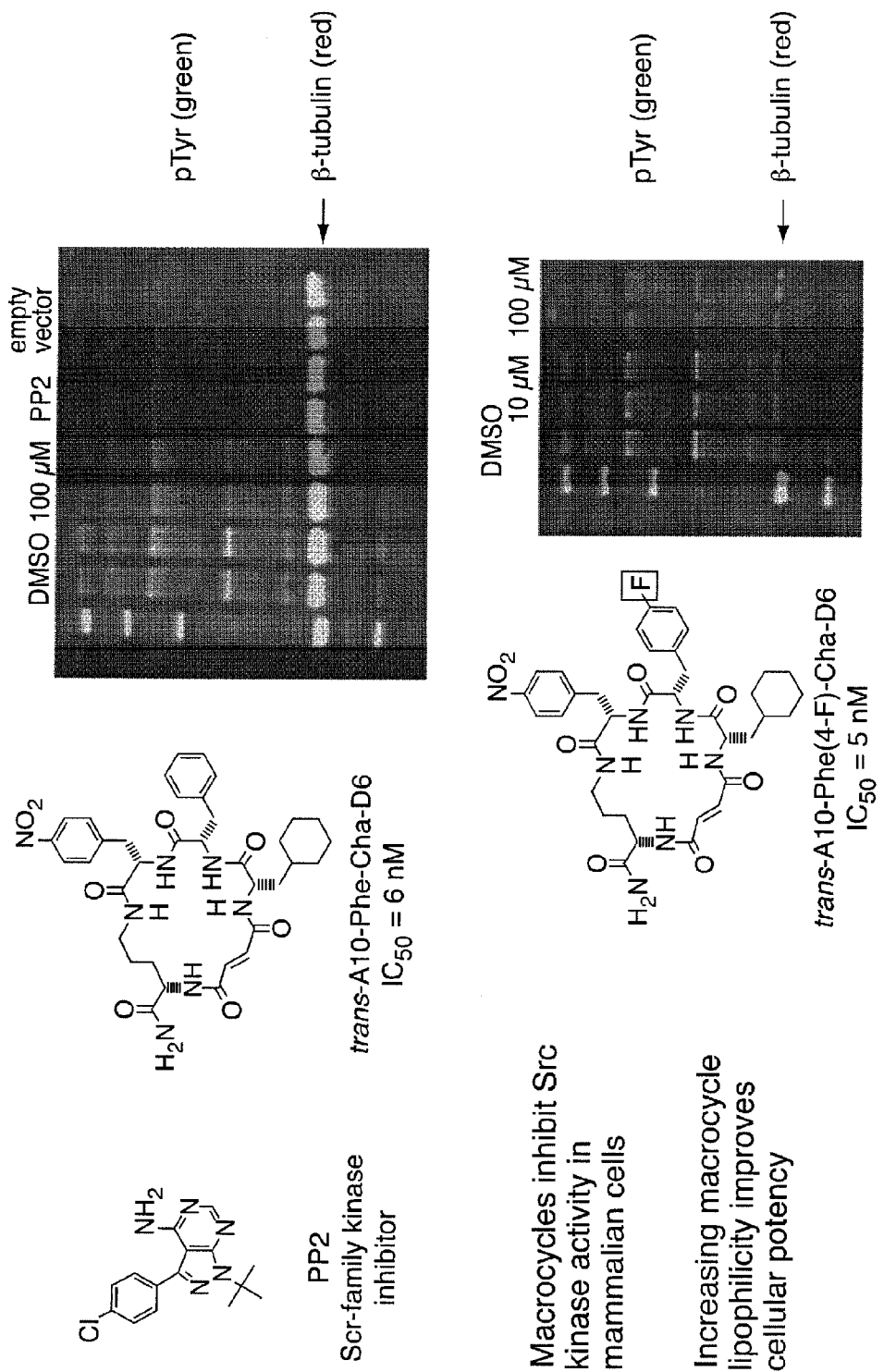

To clarify the inhibitory mechanism of the compounds further, the binding affinity of fluorescently labeled MC1, MC4, and MC9 to Src kinase domain was determined in a fluorescence anisotropy assay (FIG. 21). An exemplary structure of a fluorescently labeled macrocycle is provided in FIG. 21A. It was found that both MC1 and MC4 inhibition potency decreased with increased ATP concentrations (FIG. 21A). It was further observed that Src kinase domain binds MC1, MC4 and MC9 with a dissociation constant (KD) of 2.1 µM, 0.3 µM and 3.6 µM, respectively (FIG. 21B). Binding affinity of the compounds decreased in the presence of 250 µM of the non-hydrolyzable ATP analog AMP-PNP to 3.3 µM, 1.7 µM and 12.6 µM consistent with ATP competitive inhibitor characteristics (FIG. 21B). Consistent with the decrease in IC$_{50}$ observed in the kinase assay, the presence of 300 µM Src optimal substrate peptide decreased the apparent affinities of the fluorescent-macrocycle conjugates up to 10-fold (FIG. 21B, lowest column in each group). From these results, it was concluded that the macrocycle compounds are both ATP-competitive and substrate peptide-competitive kinase inhibitors.

Macrocycles are Active Against the Src Gatekeeper Mutation Thr338Ile.

The emergence of resistance of an aberrant kinase to a therapeutic kinase inhibitor after therapy has commenced is a common problem in kinase inhibition therapy. For example ~30% of all CML patients undergoing imatinib treatment develop resistance mutations in the kinase domain of the BCR-Abl fusion protein. Some mutated kinases that are resistant to inhibition by imatinib, can be inhibited with certain second generation kinase inhibitors such as nilotinib or dasatinib. However, some of the most common mutations conferring resistance against kinase inhibition, so-called gatekeeper residue mutations, e.g., Thr315Ile (human Abl1a numbering), Thr338Ile in chicken c-Src, or Thr34Ile, cannot be overcome with currently available kinase inhibitor therapeutics. The gatekeeper residue in Src kinase regulates access to a hydrophobic binding pocket adjacent to the ATP binding pocket. This particular residue is of great interest because it is mutated to a threonine residue in almost all isoforms of viral Src, because it renders the mutated Src resistant to most ATP-competitive inhibitors (including GLEEVEC™, IRESSA™, and TARCEVA™), and because the corresponding mutation in Abl kinase (Thr315Ile, human Abl 1a numbering) is a common basis for IMATINIB™ resistance among CML patients. Currently, no small-molecule kinase inhibitor is available in the clinic to treat patients with this particular resistance mutation.

Figures 18, 19, 20, 21, 22:
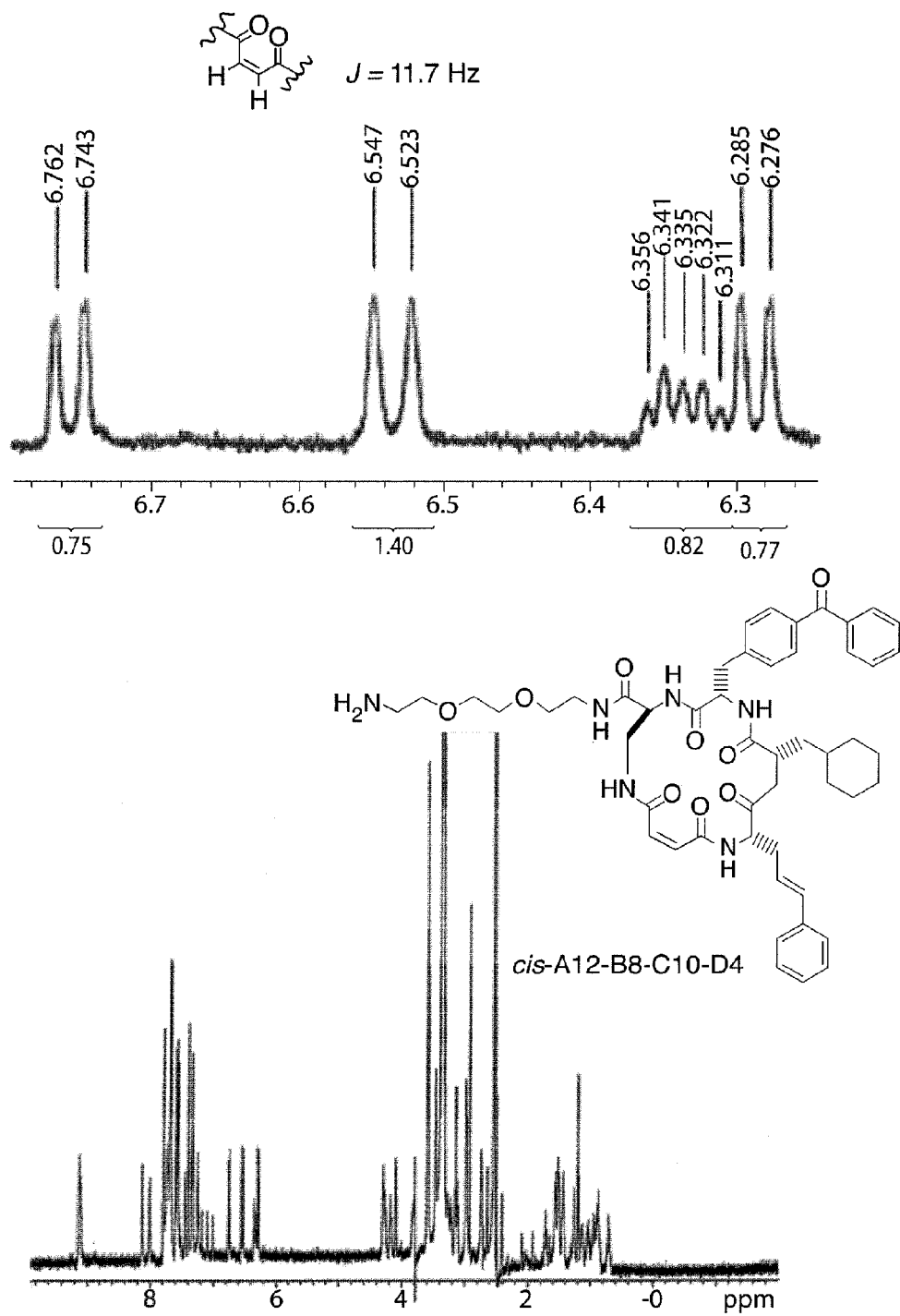
FIG. 22. Inhibition of the Src gatekeeper mutant T338I by cis-A11-B1-C5-D7 and trans-A10-B1-C5-D6. The T338I mutation ("gatekeeper" residue) confers resistance to most ATP-competitive inhibitors and promotes oncogenic activation of Src.

It was observed that that the gatekeeper mutation had a stronger impact on the potency of macrocycles based on the diaminobutyric acid scaffold, e.g., compounds MC1 and MC1.2, which were at least 100-fold less potent against the gatekeeper mutant than against Src wild-type (FIG. 22, left panel, showing data for MC1). In contrast, MC9 inhibited Src Thr338Ile containing SH3 and SH2 domains with high potency (IC50 1.0 µM), which was only about 3-fold lower than the inhibition potency of MC9 against the corresponding Src wild-type construct (IC50 0.39 µM) (FIG. 22, right panel). Similarly, MC4 and its derivatives, e.g., MC4.2 and MC4.3 retained their inhibition potency against the Src Thr338Ile gatekeeper mutation.

Src Kinase Inhibition in Cell Culture.

Figures 18, 19, 20, 21, 22, 23:
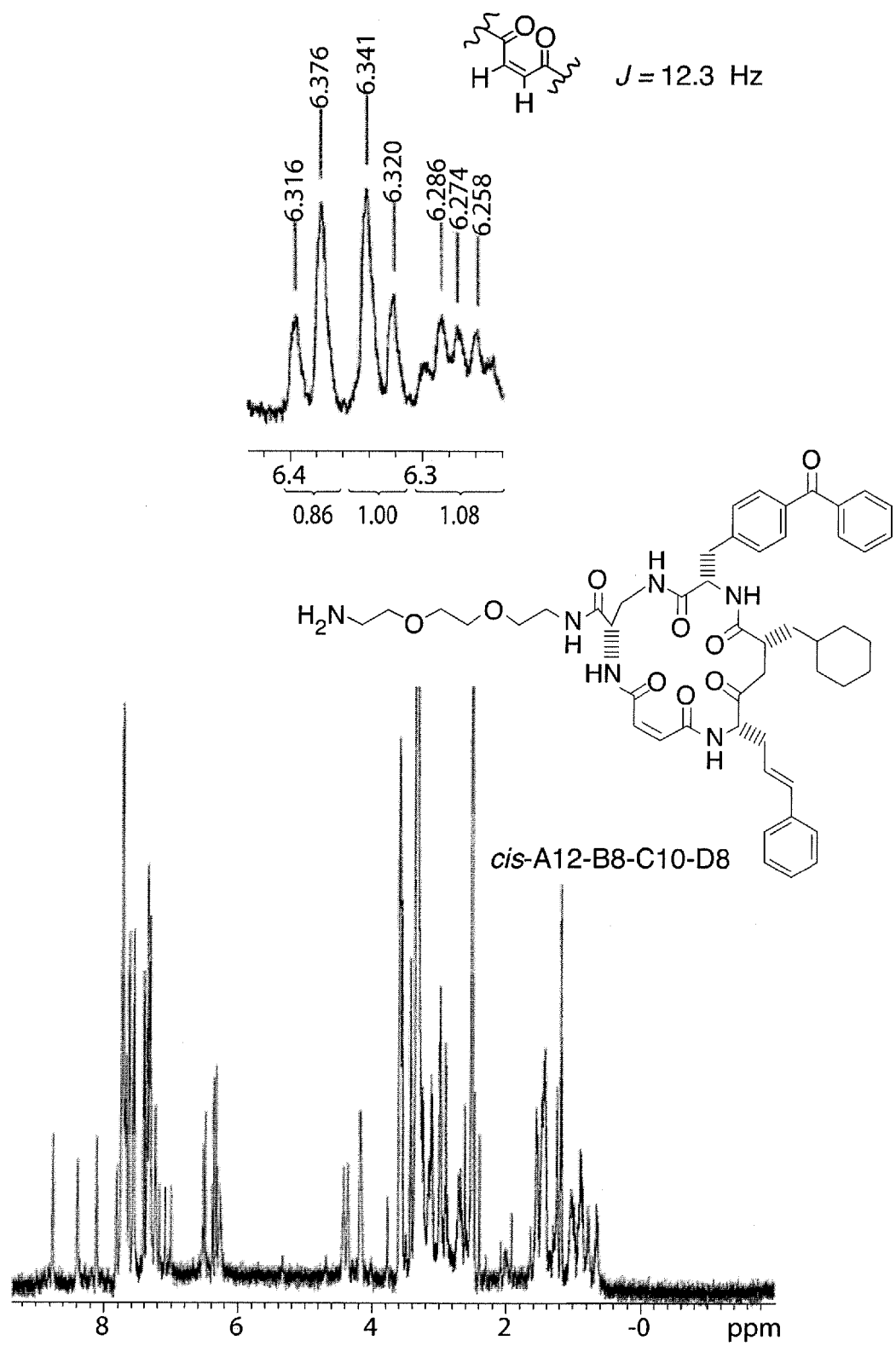
FIG. 23. Src kinase inhibition in mammalian cells.
Figures 18, 19, 20, 21, 22, 23, 24:
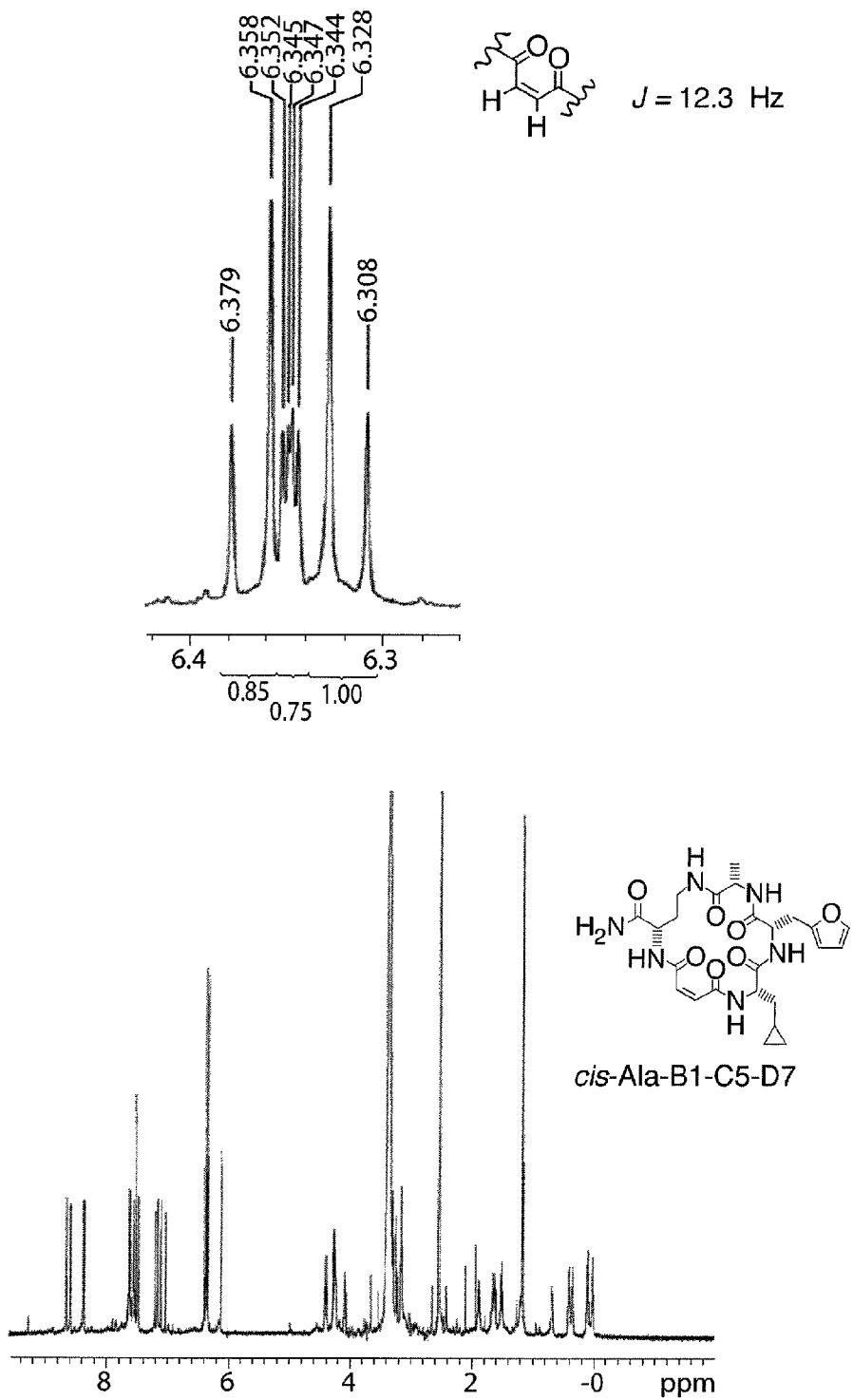
Figures 18, 19, 20, 21, 22, 23, 24, 25:
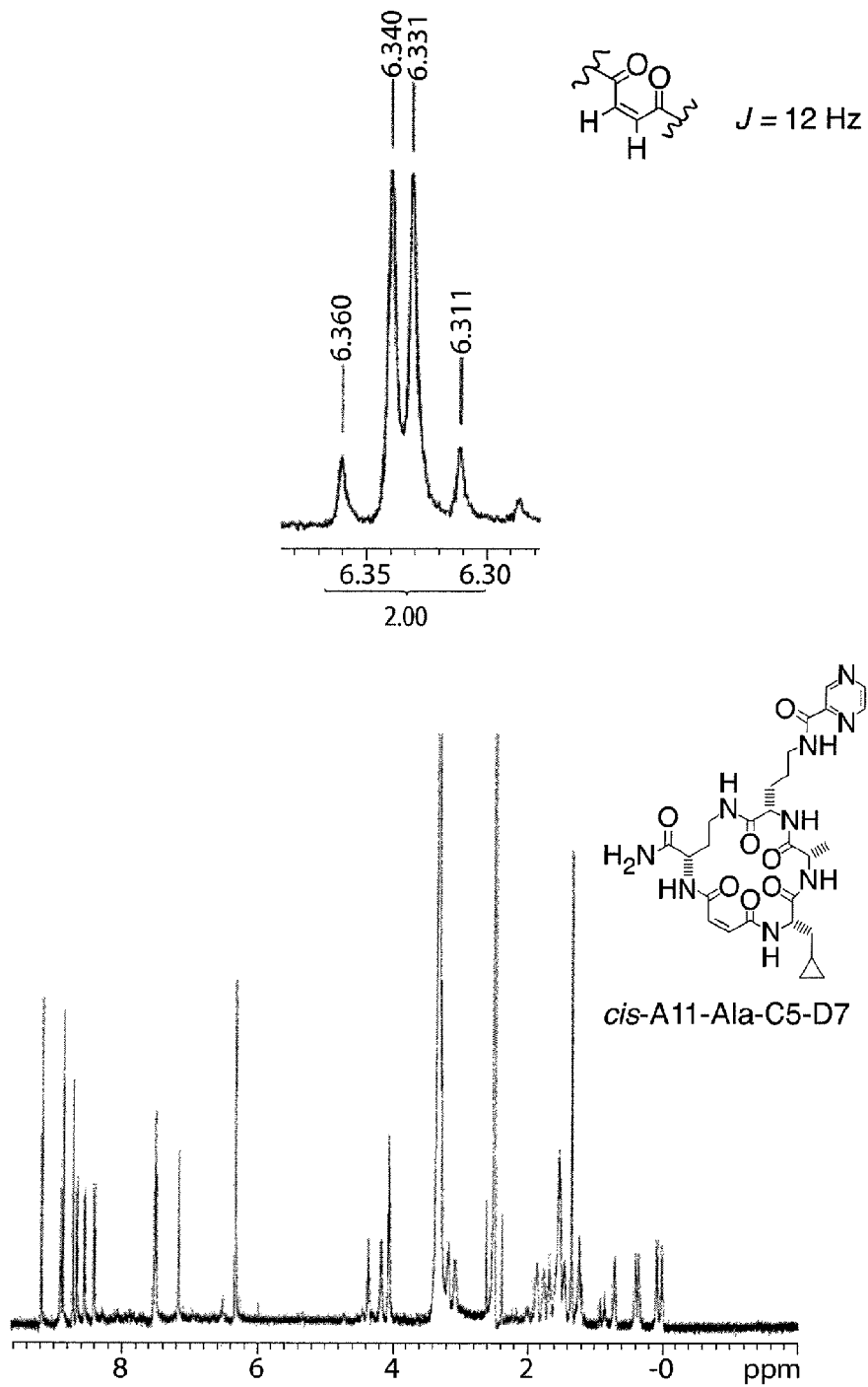
Figures 18, 19, 20, 21, 22, 23, 24, 25, 26:
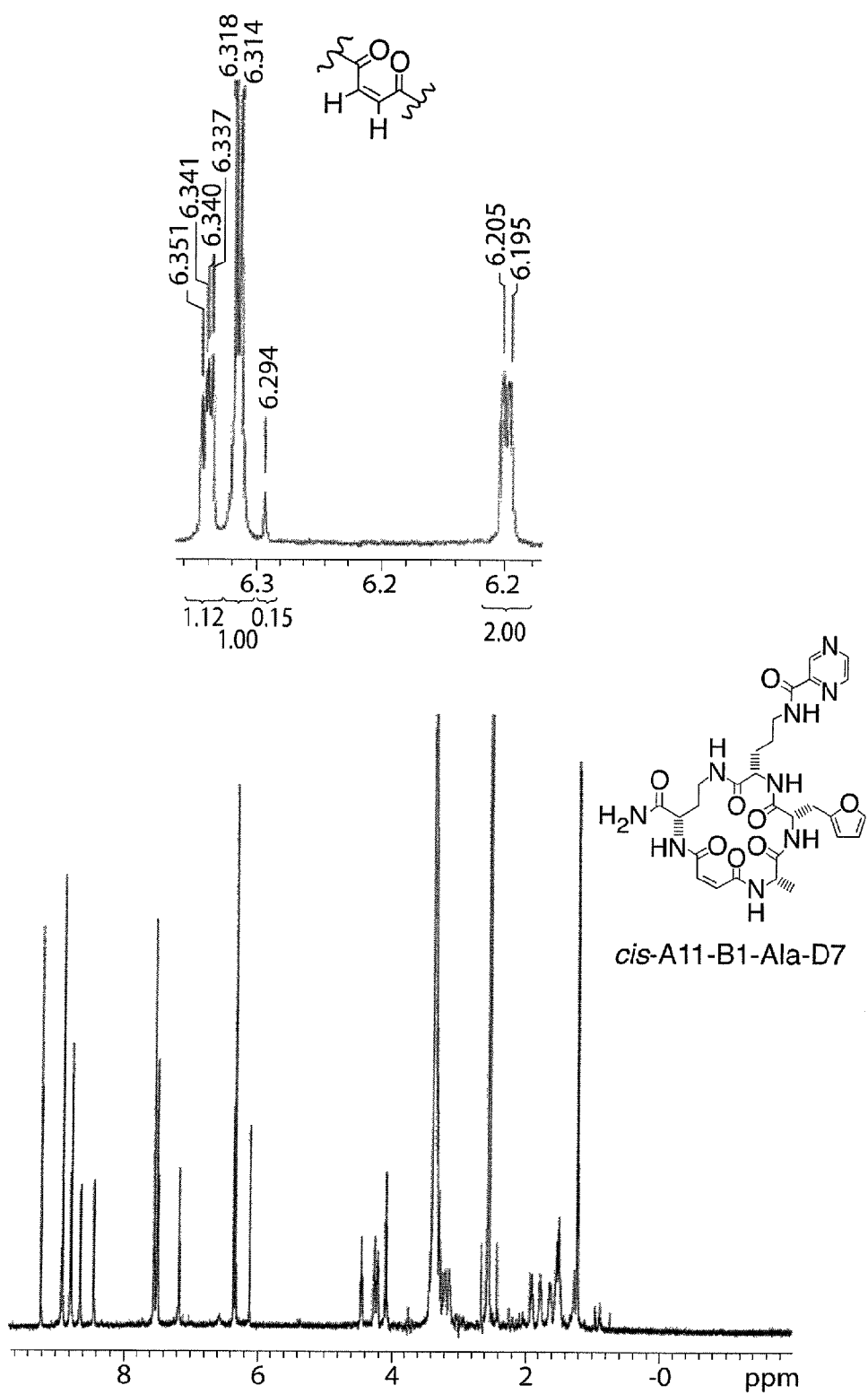
Figures 18, 19, 20, 21, 22, 23, 24, 25, 26, 27:
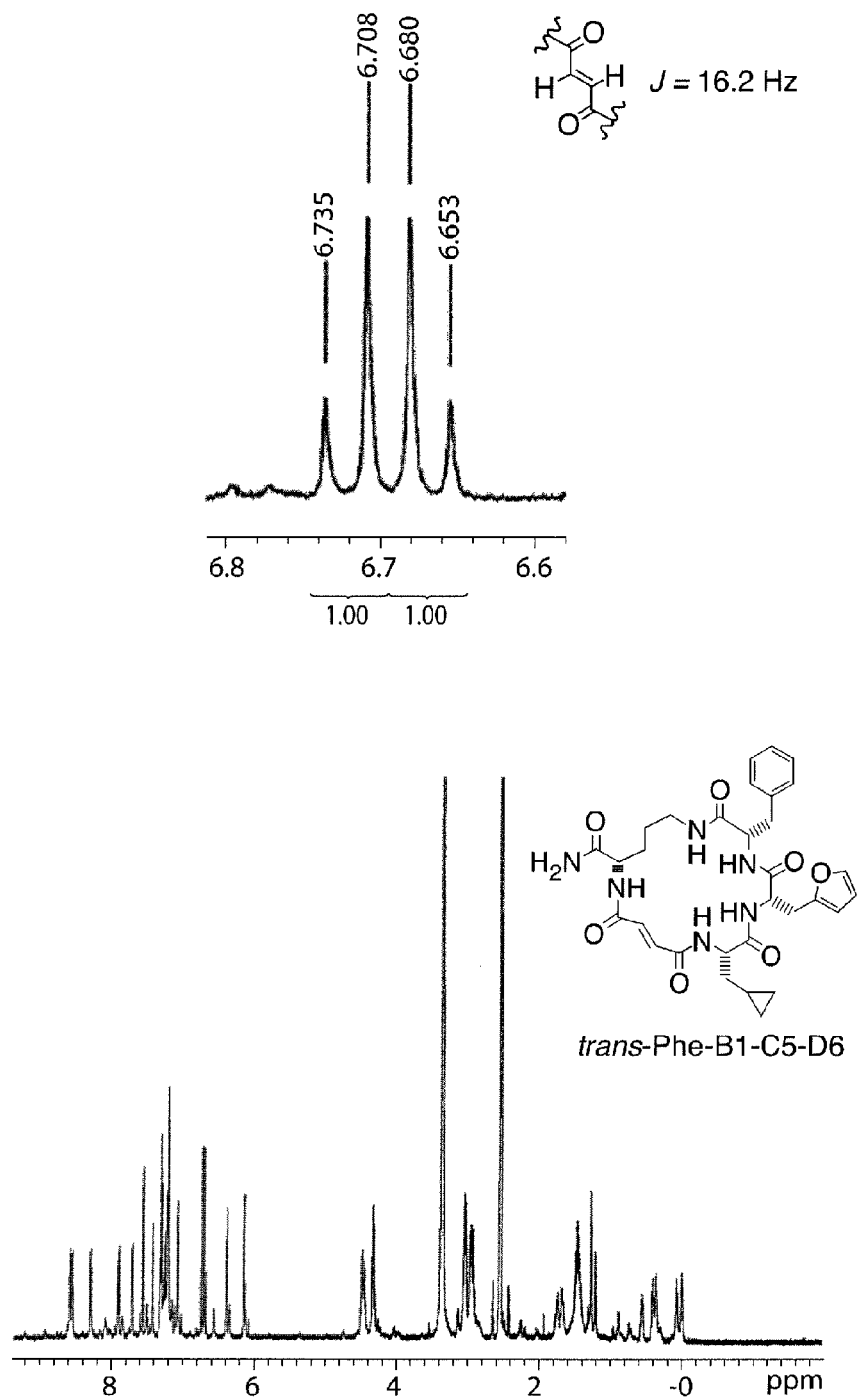
Figures 18, 19, 20, 21, 22, 23, 24, 25, 26, 27, 28:
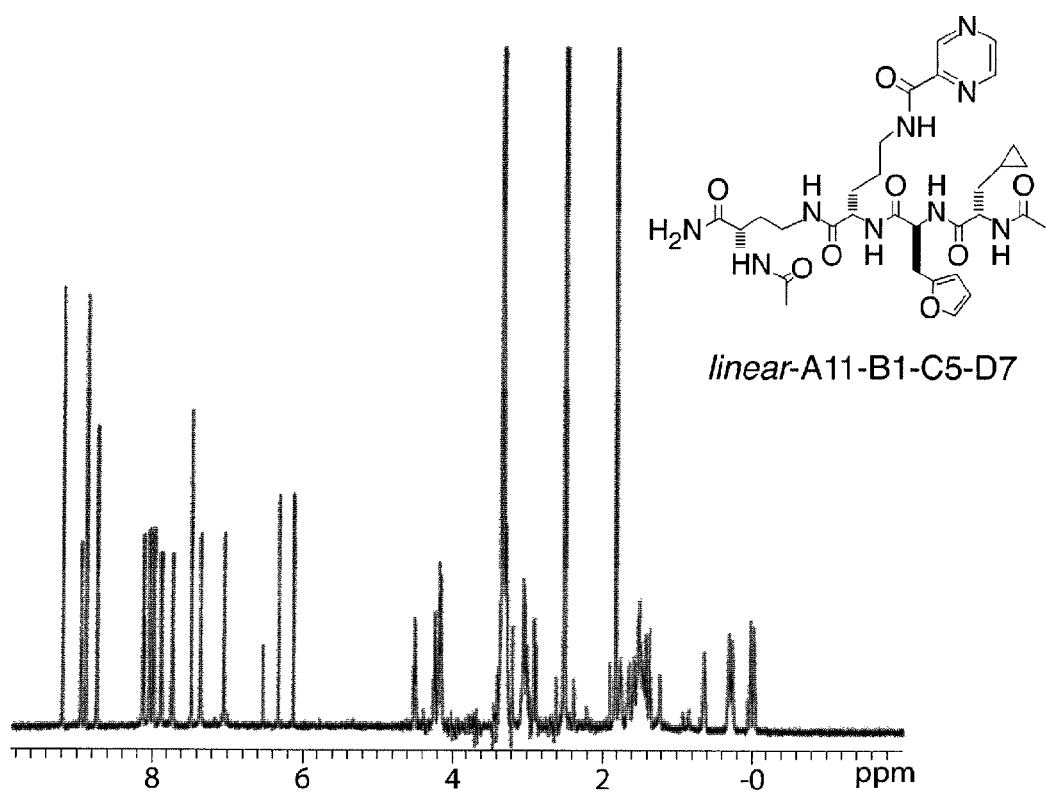
Figures 18, 19, 20, 21, 22, 23, 24, 25, 26, 27, 28, 29:
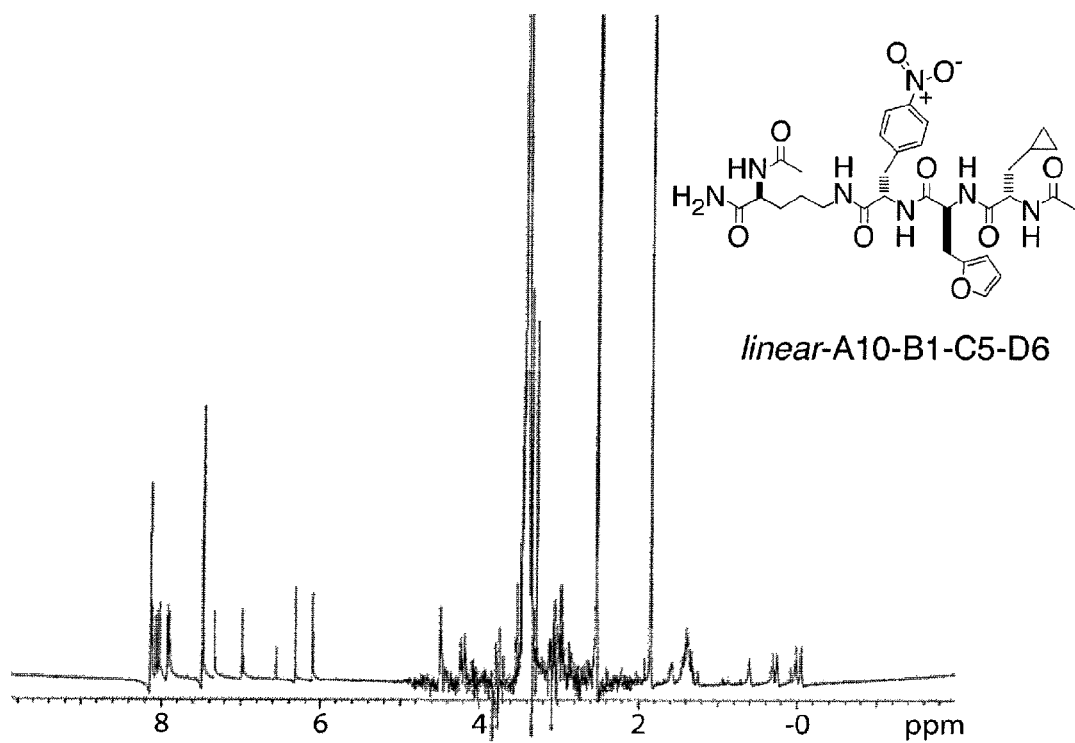
Figures 1, 19:
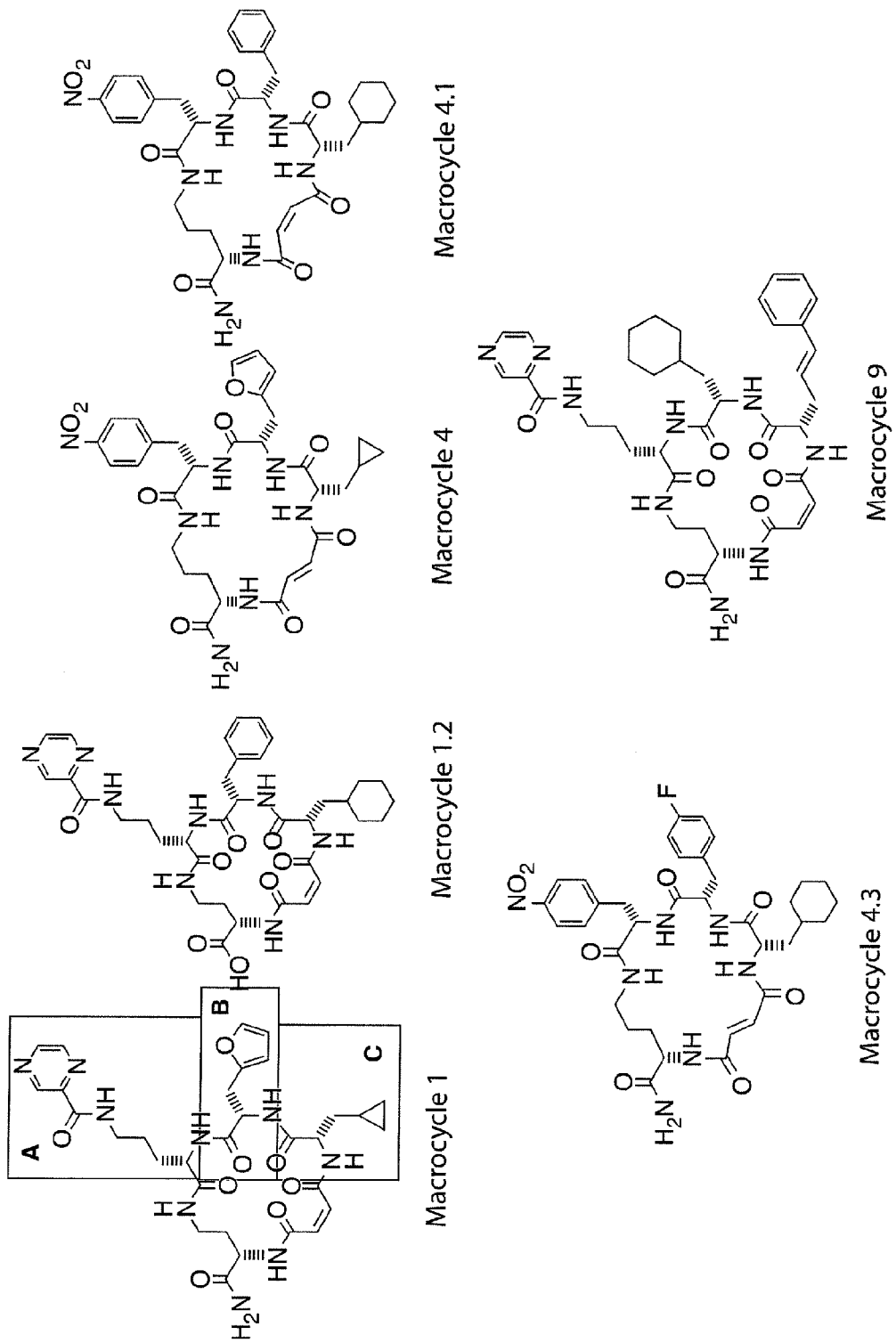
Figures 2, 19:
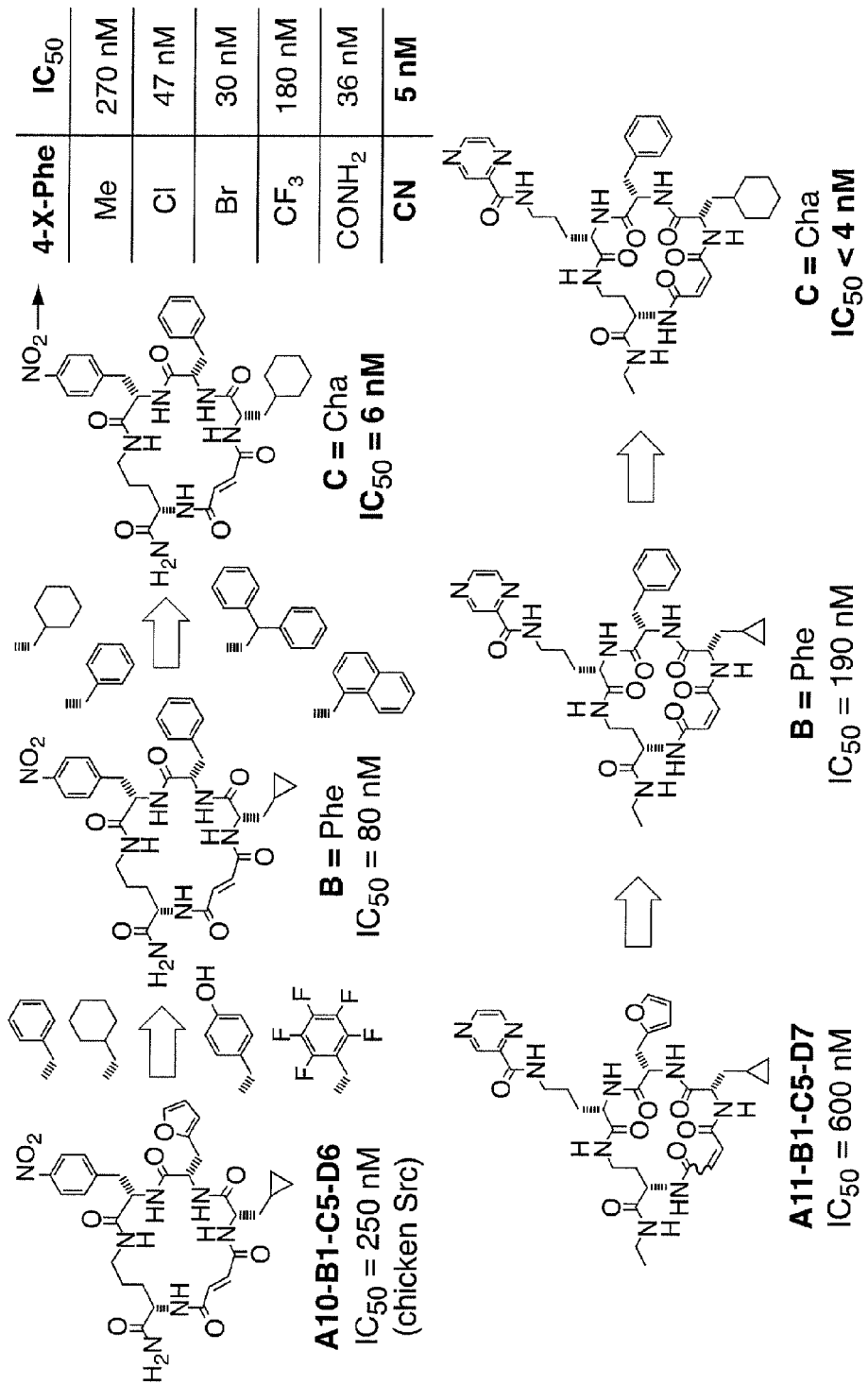

Having obtained macrocycle Src kinase inhibitors with nanomolar in vitro potency, the potency for inhibition of Src kinase activity in living cells was assessed. Since intracellular Src kinase signaling is complex and tightly regulated, a cell culture line transfected with a constitutively active form of murine c-Src was chosen. 3T3 cells (src–/–) stably transfected with c-Src Y529F were compared to 3T3 cells (src–/–) transfected with empty vector. Anti-phosphotryosine Western blotting with the 4G10 antibody (Millipore) indicated a marked difference between global phosphotyrosine levels in the c-Src Y529F transfected cells compared to those transfected with empty vector; in fact, almost all detectable intracellular phosphotyrosine in the Src-transfected cell line was a result of c-Src Y529F and downstream signaling (FIG. 23, upper panel, compare lanes 2 and 3, transfected and trated with DMSO, against lanes 8 and 9, transfected with empty vector). In addition, treatment of the c-Src Y529F expressing cells with 10 µM PP2 (Hanke, Gardner et al. 1996) a known Src-family kinase inhibitor, prior to Western blotting resulted in reduction of global phosphotyrosine to levels comparable with those observed in the cells transfected with empty vector (FIG. 23, compare lanes 6 and 7, treated with PP2, with lanes 8 and 9). These results implied that depletion of global tyrosine phosphorylation in the cells transfected with c-Src Y529F was indicative of specific inhibition of Src kinase activity in this cell line.

The effect of the most potent macrocycles, MC1.2, MC4.2, and MC4.3 were assayed in the c-Src Y529F-transfected cells. Briefly, cells were seeded in a 48-well plate and grown to confluence in Dulbecco's Modified Eagle Medium (DMEM) supplemented with 10% fetal bovine serum (FBS).

Individual wells were then treated with 10 or 100 μM concentration of macrocycle in serum-free DMEM overnight. After removing the small molecule and washing with phosphate-buffered saline, cells were lysed in radioimmunoprecipitation assay (RIPA) buffer, and global phosphotyrosine levels were quantified by Western blot. After overnight treatment with the p-nitrophenylalanine-containing MC4.2 global phosphotyrosine levels showed a modest reduction, with an $EC_{50}$ of >100 μM (FIG. 23, upper panel, lanes 4 and 5). Surprisingly, treating cells with MC4.3 (FIG. 23, lower panel), which differs in structure from MC4.2 by a single fluorine atom (boxed in the figure), resulted in higher levels of tyrosine phosphorylation inhibition at comparable small molecule concentrations. The pyrazine-containing MC1.2 did not reduce global tyrosine phosphorylation at 100 μM concentration, possibly because of low membrane permeability.

REFERENCES

Adams, P. D., R. W. Grosse-Kunstleve, et al. (2002). "PHENIX: building new software for automated crystallographic structure determination." Acta Crystallogr D Biol Crystallogr 58(Pt 11): 1948-1954.

Adrian, F. J., Q. Ding, et al. (2006). "Allosteric inhibitors of Bcr-abl-dependent cell proliferation." Nat Chem Biol 2(2): 95-102.

Azam, M., M. A. Seeliger, et al. (2008). "Activation of tyrosine kinases by mutation of the gatekeeper threonine." Nat Struct Mol Biol 15(10): 1109-1118.

Barker, S. C., D. B. Kassel, et al. (1995). "Characterization of pp 60c-src tyrosine kinase activities using a continuous assay: autoactivation of the enzyme is an intermolecular autophosphorylation process." Biochemistry 34(45): 14843-14851.

Barouch-Bentov, R., J. Che, et al. (2009). "A Conserved Salt Bridge in the G Loop of Multiple Protein Kinases Is Important for Catalysis and for In Vivo Lyn Function." Molecular Cell 33(1): 43-52.

Bikker, J. A., N. Brooijmans, et al. (2009). "Kinase domain mutations in cancer: implications for small molecule drug design strategies." J Med Chem 52(6): 1493-1509.

Capdeville, R., E. Buchdunger, et al. (2002). "Glivec (STI571, imatinib), a rationally developed, targeted anticancer drug." Nat. Rev. Drug Disc. 1(7): 493-502.

Cohen, P. (2002). "Protein kinases—the major drug targets of the twenty-first century?" Nat Rev Drug Discov 1(4): 309-315.

Cools, J., E. H. Stover, et al. (2003). "PKC412 overcomes resistance to imatinib in a murine model of FIP1L1-PDGFR[alpha]-induced myeloproliferative disease." Cancer Cell 3(5): 459-469.

Cowan-Jacob, S. W., G. Fendrich, et al. (2005). "The crystal structure of a c-Src complex in an active conformation suggests possible steps in c-Src activation." Structure 13(6): 861-871. Emsley, P. and K. Cowtan (2004). "Coot: model-building tools for molecular graphics." Acta Crystallogr D Biol Crystallogr 60(Pt 12 Pt 1): 2126-2132.

Gartner, Z. J. and D. R. Liu (2001). "The Generality of DNA-Templated Synthesis as a Basis for Evolving Non-Natural Small Molecules." J Am Chem Soc 123: 6961-6963.

Gartner, Z. J., B. N. Tse, et al. (2004). "DNA-Templated Organic Synthesis and Selection of a Library of Macrocycles." Science 305: 1601-1605.

Gazit, A., P. Yaish, et al. (1989). "Tyrphostins I: synthesis and biological activity of protein tyrosine kinase inhibitors." J Med Chem 32(10): 2344-2352.

Hanke, J. H., J. P. Gardner, et al. (1996). "Discovery of a novel, potent, and Src family-selective tyrosine kinase Inhibitor. Study of Lck- and FynT-dependent T cell activation." J. Biol. Chem. 271(2): 695-701.

Hubbard, S. R. (1997). "Crystal structure of the activated insulin receptor tyrosine kinase in complex with peptide substrate and ATP analog." EMBO J. 16(18): 5572-5581.

Kansy, M., F. Sunner, et al. (1998). "Physicochemical High Throughput Screening: Parallel Artificial Membrane Permeation Assay in the Description of Passive Absorption Processes." J. Med. Chem. 41: 1007-1010.

Kleiner, R. E., C. E. Dumelin, et al. (2011). "Small-molecule discovery from DNA-encoded chemical libraries" Chem Soc Rev.

Kleiner, R. E., C. E. Dumelin, et al. (2010). "In Vitro Selection of a DNA-Templated Macrocycle Library Reveals a Class of Macrocyclic Kinase Inhibitors." J. Am. Chem. Soc. 132: 11779-11791.

Kleiner, R. E., C. E. Dumelin, et al. (2010). "In vitro selection of a DNA-templated small-molecule library reveals a class of macrocyclic kinase inhibitors." J Am Chem Soc 132 (33): 11779-11791.

Knight, Z. A. and K. M. Shokat (2005). "Features of selective kinase inhibitors." Chem. Biol. 12: 621-637.

Krishnamurty, R. and D. J. Maly (2010). "Biochemical Mechanisms of Resistance to Small-Molecule Protein Kinase Inhibitors." ACS Chemical Biology 5(1): 121-138.

Leslie, A. G. W. (1992). "Recent changes to the MOSFLM package for processing film and image plate data" Joint CCP4+ESF-EAMCB Newsletter on Protein Crystallography(26).

Levinson, N. M., O. Kuchment, et al. (2006). "A Src-like inactive conformation in the abl tyrosine kinase domain." PLoS Biol 4(5): e144.

Levitzki, A. (1999). "Protein tyrosine kinase inhibitors as novel therapeutic agents." Pharmacol Ther 82(2-3): 231-239.

Lombardo, L. J., F. Y. Lee, et al. (2004). "Discovery of N-(2-Chloro-6-methyl-phenyl)-2-(6-(4-(2-hydroxyethyl)-piperazin-1-yl)-2-methylpyrimidin-4-ylamino)thiazole-5-carboxamide (BMS-354825), a Dual Src/Abl Kinase Inhibitor with Potent Antitumor Activity in Preclinical Assays." Journal of Medicinal Chemistry 47(27): 6658-6661.

Manning, G., D. B. Whyte, et al. (2002). "The protein kinase complement of the human genome." Science 298(5600): 1912-1934.

McCoy, A. J., R. W. Grosse-Kunstleve, et al. (2005). "Likelihood-enhanced fast translation functions." Acta Crystallogr D Biol Crystallogr 61(Pt 4): 458-464.

Mol, C. D., D. R. Dougan, et al. (2004). "Structural basis for the autoinhibition and STI-571 inhibition of c-Kit tyrosine kinase." J Biol Chem 279(30): 31655-31663.

Ohren, J. F., H. Chen, et al. (2004). "Structures of human MAP kinase kinase 1 (MEK1) and MEK2 describe novel noncompetitive kinase inhibition." Nat Struct Mol Biol 11(12): 1192-1197.

Otwinowski, Z. and W. Minor (1997). "Processing of X-ray Diffraction Data Collected in Oscillation Mode." Methods in Enzymology 276 (Macromolecular Crystallography, Part A): 307-326.

Schindler, T., W. Bornmann, et al. (2000). "Structural mechanism for STI-571 inhibition of abelson tyrosine kinase." Science 289(5486): 1938-1942.

Seeliger, M. A., B. Nagar, et al. (2007). "c-Src binds to the cancer drug imatinib with an inactive Abl/c-Kit conformation and a distributed thermodynamic penalty." Structure 15(3): 299-311.

Seeliger, M. A., P. Ranjitkar, et al. (2009). "Equally potent inhibition of c-Src and Abl by compounds that recognize inactive kinase conformations." Cancer Res 69(6): 2384-2392.

Seeliger, M. A., M. Young, et al. (2005). "High yield bacterial expression of active c-Abl and c-Src tyrosine kinases." Protein Sci 14(12): 3135-3139.

Shan, Y., E. T. Kim, et al. (2011). "How Does a Drug Molecule Find Its Target Binding Site?" J Am Chem. Soc.

Sicheri, F., I. Moarefi, et al. (1997). "Crystal structure of the Src family tyrosine kinase Hck." Nature 385(6617): 602-609.

Songyang, Z. and L. C. Cantley (1995). "Recognition and specificity in protein tyrosine kinase-mediated signalling." Trends Biochem Sci 20(11): 470-475.

Songyang, Z., K. L. Carraway, et al. (1995). "Catalytic specificity of protein-tyrosine kinases is critical for selective signalling." Nature 373(6514): 536-539.

Tse, B. N., T. M. Snyder, et al. (2008). "Translation of DNA into a Library of 13,000 Synthetic Small-Molecule Macrocycles Suitable for in Vitro Selection." J. Am. Chem. Soc. 130: 15611-15626.

Xu, W., A. Doshi, et al. (1999). "Crystal structures of c-Src reveal features of its autoinhibitory mechanism." Mol Cell 3(5): 629-638.

Xu, W., S. C. Harrison, et al. (1997). "Three-dimensional structure of the tyrosine kinase c-Src." Nature 385(6617): 595-602.

Zhang, J., P. L. Yang, et al. (2009). "Targeting cancer with small molecule kinase inhibitors." Nat Rev Cancer 9(1): 28-39.

Other Embodiments

All publications, patents and sequence database entries mentioned herein, including those items listed below, are hereby incorporated by reference in their entirety for disclosure of the teachings relevant to this invention, as if each individual publication or patent was specifically and individually indicated to be incorporated by reference. In case of the present specification and a document incorporated by reference including conflicting disclosure, the present specification shall control.

While several embodiments of the present invention have been described and illustrated herein, those of ordinary skill in the art will readily envision a variety of other methods and/or structures for performing the functions and/or obtaining the results and/or one or more of the advantages described herein, and each of such variations and/or modifications is deemed to be within the scope of the present invention. More generally, those skilled in the art will readily appreciate that all structures, reagents, methods, features, parameters, materials, and configurations described herein are meant to be exemplary and that the actual structures, reagents, methods, features, parameters, materials, and configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual structure, reagent, method, feature, parameter, material, and configuration described herein. In addition, any combination of two or more such structures, reagents, methods, features, parameters, materials, and configurations, if such are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an", as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:
1. A compound of Formula (XV):

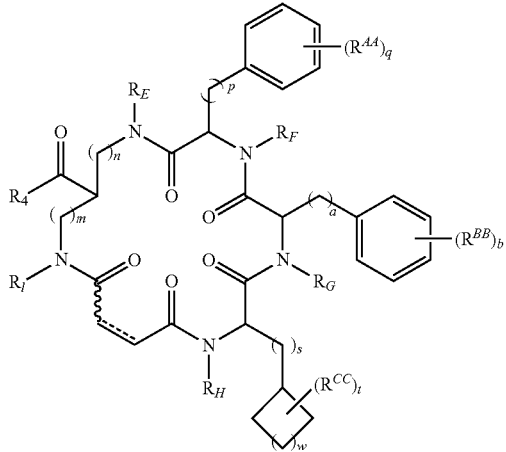

(XV)

or a pharmaceutically acceptable salt thereof;
wherein:
n is 2 or 3;
m is 0;
╌╌ represents a double bond in the cis or trans configuration;
p is an integer between 1 and 6, inclusive;
q is an integer between 1 and 5, inclusive;
each instance of $R^{AA}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A3}$, —$N(R^{A4})_2$, —$SR^{A3}$, —$C(=O)R^{A3}$, —$C(=O)OR^{A3}$, —$C(=O)SR^{A3}$, —$C(=O)N(R^{A4})_2$, —$OC(=O)R^{A3}$, —$OC(=O)OR^{A3}$, —$OC(=O)SR^{A3}$, —$OC(=O)N(R^{A4})_2$, —$NR^{A4}C(=O)R^{A4}$, —$NR^{A4}C(=O)OR^{A3}$, —$NR^{A4}C(=O)SR^{A3}$, —$NR^{A4}C(=O)N(R^{A4})_2$, —$SC(=O)R^{A3}$, —$SC(=O)OR^{A3}$, —$SC(=O)SR^{A3}$, —$SC(=O)N(R^{A4})_2$, —$C(=NR^{A4})R^{A3}$, —$C(=NR^{A4})OR^{A3}$, —$C(=NR^{A4})SR^{A3}$, —$C(=NR^{A4})N(R^{A4})_2$, —$OC(=NR^{A4})R^{A3}$, —$OC(=NR^{A4})OR^{A3}$, —$OC(=NR^{A4})SR^{A3}$, —$OC(=NR^{A4})N(R^{A4})_2$, —$NR^{A4}C(=NR^{A4})R^{A2}$, —$NR^{A4}C(=NR^{A4})OR^{A3}$, —$NR^{A4}C(=NR^{A4})SR^{A3}$, —$NR^{A4}C(=NR^{A4})N(R^{A4})_2$, —$SC(=NR^{A4})R^{A3}$, —$SC(=NR^{A4})OR^{A3}$, —$SC(=NR^{A4})SR^{A3}$, —$SC(=NR^{A4})N(R^{A4})_2$, —$C(=S)R^{A3}$, —$C(=S)OR^{A3}$, —$C(=S)SR^{A3}$, —$C(=S)N(R^{A4})_2$, —$OC(=S)R^{A3}$, —$OC(=S)OR^{A3}$, —$OC(=S)SR^{A3}$, —$OC(=S)N(R^{A4})_2$, —$NR^{A4}C(=S)R^{A4}$, —$NR^{A4}C(=S)OR^{A3}$, —$NR^{A4}C(=S)SR^{A3}$, —$NR^{A4}C(=S)N(R^{A4})_2$, —$SC(=S)R^{A3}$, —$SC(=S)OR^{A3}$, —$SC(=S)SR^{A3}$, —$SC(=S)N(R^{A4})_2$, —$S(=O)R^{A3}$, —$SO_2R^{A3}$, —$NR^{A4}SO_2R^{A3}$, —$SO_2N(R^{A4})_2$, —$N_3$, —CN, —SCN, and —$NO_2$, wherein each occurrence of $R^{A3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{A4}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{A4}$ groups are joined to form an substituted or unsubstituted heterocyclic ring,
provided at least one $R^{AA}$ is selected from the group consisting of halogen, perhaloalkyl, —$C(=O)N(R^{A2})_2$, —CN, —SCN, and —$NO_2$;
a is an integer between 1 and 6, inclusive;
b is 0 or an integer between 1 and 5, inclusive;
each instance of $R^{BB}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B3}$, —$N(R^{B4})_2$, —$SR^{B3}$, —$C(=O)R^{B3}$, —$C(=O)OR^{B3}$, —$C(=O)SR^{B3}$, —$C(=O)N(R^{B4})_2$, —$OC(=O)R^{B3}$, —$OC(=O)OR^{B3}$, —$OC(=O)SR^{B3}$, —$OC(=O)N(R^{B4})_2$, —$NR^{B4}C(=O)R^{B4}$, —$NR^{B4}C(=O)OR^{B3}$, —$NR^{B4}C(=O)SR^{B3}$, —$NR^{B4}C(=O)N(R^{B4})_2$, —$SC(=O)R^{B3}$, —$SC(=O)OR^{B3}$, —$SC(=O)SR^{B3}$, —$SC(=O)N(R^{B4})_2$, —$C(=NR^{B4})R^{B3}$, —$C(=NR^{B4})OR^{B3}$, —$C(=NR^{B4})SR^{B3}$, —$C(=NR^{B4})N(R^{B4})_2$, —$OC(=NR^{B4})R^{B3}$, —$OC(=NR^{B4})OR^{B3}$, —$OC(=NR^{B4})SR^{B3}$, —$OC(=NR^{B4})N(R^{B4})_2$, —$NR^{B4}C(=NR^{B4})R^{B2}$, —$NR^{B4}C(=NR^{B4})OR^{B3}$, —$NR^{B4}C(=NR^{B4})SR^{B3}$, —$NR^{B4}C(=NR^{B4})N(R^{B4})_2$, —$SC(=NR^{B4})R^{B3}$, —$SC(=NR^{B4})OR^{B3}$, —$SC(=NR^{B4})SR^{B3}$, —$SC(=NR^{B4})N(R^{B4})_2$, —$C(=S)R^{B3}$, —$C(=S)OR^{B3}$, —$C(=S)SR^{B3}$, —$C(=S)N(R^{B4})_2$, —$OC(=S)R^{B3}$, —$OC(=S)OR^{B3}$, —$OC(=S)SR^{B3}$, —$OC(=S)N(R^{B4})_2$, —$NR^{B4}C(=S)R^{B4}$, —$NR^{B4}C(=S)OR^{B3}$, —$NR^{B4}C(=S)SR^{B3}$, —$NR^{B4}C(=S)N(R^{B4})_2$, —$SC(=S)R^{B3}$, —$SC(=S)OR^{B3}$, —$SC(=S)SR^{B3}$, —$SC(=S)N(R^{B4})_2$, —$S(=O)R^{B3}$, —$SO_2R^{B3}$, —$NR^{B4}SO_2R^{B3}$, —$SO_2N(R^{B4})_2$, —$N_3$, —CN, —SCN, and —$NO_2$, wherein each occurrence of $R^{B3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{B4}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{B4}$ groups are joined to form an substituted or unsubstituted heterocyclic ring;

s is an integer between 1 and 10, inclusive;

w is 3;

t is 0, 1, or 2;

each instance of $R^{CC}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{C3}$, —$N(R^{C4})_2$, —$SR^{C3}$, —$C(=O)R^{C3}$, —$C(=O)OR^{C3}$, —$C(=O)SR^{C3}$, —$C(=O)N(R^{C4})_2$, —$OC(=O)R^{C3}$, —$OC(=O)OR^{C3}$, —$OC(=O)SR^{C3}$, —$OC(=O)N(R^{C4})_2$, —$NR^{C4}C(=O)R^{C4}$, —$NR^{C4}C(=O)OR^{C3}$, —$NR^{C4}C(=O)SR^{C3}$, —$NR^{C4}C(=O)N(R^{C4})_2$, —$SC(=O)R^{C3}$, —$SC(=O)OR^{C3}$, —$SC(=O)SR^{C3}$, —$SC(=O)N(R^{C4})_2$, —$C(=NR^{C4})R^{C3}$, —$C(=NR^{C4})OR^{C3}$, —$C(=NR^{C4})SR^{C3}$, —$C(=NR^{C4})N(R^{C4})_2$, —$OC(=NR^{C4})R^{C3}$, —$OC(=NR^{C4})OR^{C3}$, —$OC(=NR^{C4})SR^{C3}$, —$OC(=NR^{C4})N(R^{C4})_2$, $NR^{C4}C(=NR^{C4})R^{C2}$, —$NR^{C4}C(=NR^{C4})OR^{C3}$, —$NR^{C4}C(=NR^{C4})SR^{C3}$, —$NR^{C4}C(=NR^{C4})N(R^{C4})_2$, —$SC(=NR^{C4})R^{C3}$, —$SC(=NR^{C4})OR^{C3}$, —$SC(=NR^{C4})SR^{C3}$, —$SC(=NR^{C4})N(R^{C4})_2$, —$C(=S)R^{C3}$, —$C(=S)OR^{C3}$, —$C(=S)SR^{C3}$, —$C(=S)N(R^{C4})_2$, —$OC(=S)R^{C3}$, —$OC(=S)OR^{C3}$, —$OC(=S)SR^{C3}$, —$OC(=S)N(R^{C4})_2$, —$NR^{C4}C(=S)R^{C4}$, —$NR^{C4}C(=S)OR^{C3}$, —$NR^{C4}C(=S)SR^{C3}$, —$NR^{C4}C(=S)N(R^{C4})_2$, —$SC(=S)R^{C3}$, —$SC(=S)OR^{C3}$, —$SC(=S)SR^{C3}$, —$SC(=S)N(R^{C4})_2$, —$S(=O)R^{C3}$, —$SO_2R^{C3}$, —$NR^{C4}SO_2R^{C3}$, —$SO_2N(R^{C4})_2$, —$N_3$, —$CN$, —$SCN$, or —$NO_2$, wherein each occurrence of $R^{C3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{C4}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{C4}$ groups are joined to form an substituted or unsubstituted heterocyclic ring;

$R_4$ is —$N(R_D)_2$; —$OR_D$; or —$SR_D$; wherein each occurrence of $R_D$ is independently independently hydrogen; a protecting group; substituted or unsubstituted aliphatic; substituted or unsubstituted heteroaliphatic; acyl; substituted or unsubstituted aryl; or substituted or unsubstituted heteroaryl; or two $R_D$ groups are joined to form a substituted or unsubstituted heterocyclic group; optionally wherein at least one $R_D$ is a label, a resin, or a therapeutic agent, or at least one $R^D$ is substituted aliphatic, substituted heteroaliphatic, substituted aryl, or substituted heteroaryl, wherein the substituent covalently or non-covalently attached thereto is a resin, a label, or therapeutic agent; and each instance of $R_E$, $R_F$, $R_G$, $R_H$, and $R_I$ is independently hydrogen; acyl; a nitrogen protecting group; or substituted or unsubstituted aliphatic.

2. The compound of claim 1, wherein $R_4$ is —$N(R_D)_2$.

3. The compound of claim 1, wherein each occurrence of $R_E$, $R_F$, $R_G$, $R_H$, and $R_I$ is hydrogen.

4. The compound of claim 1, wherein n is 3.

5. The compound of claim 1, wherein the compound is selected from the group consisting of:

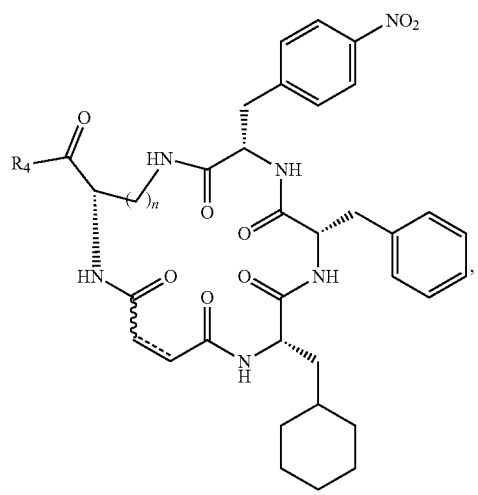

,

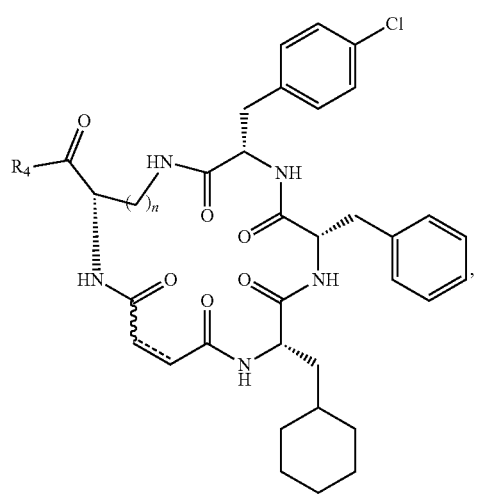

,

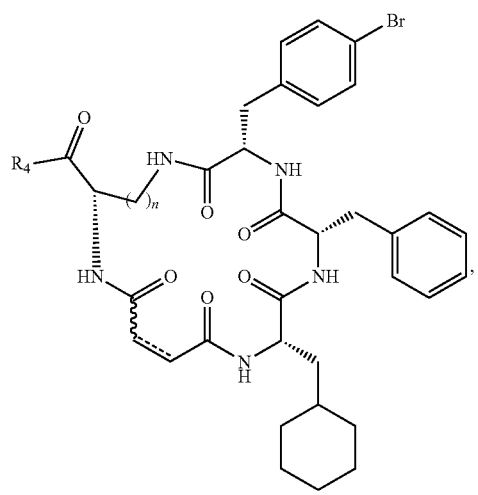

,

221
-continued

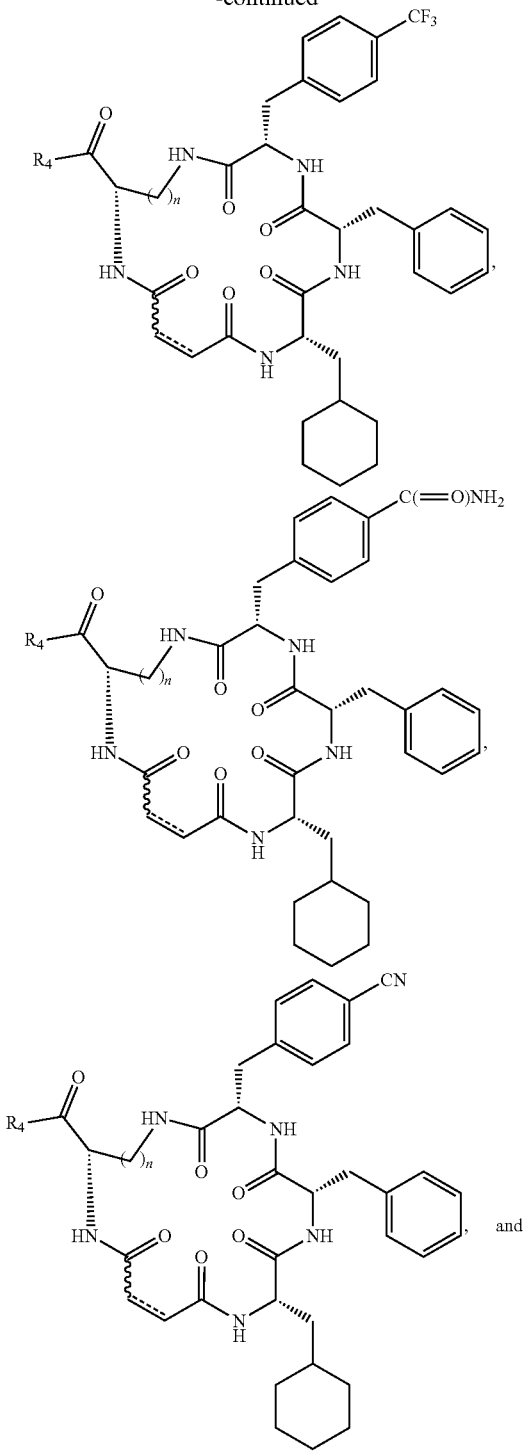

222
-continued

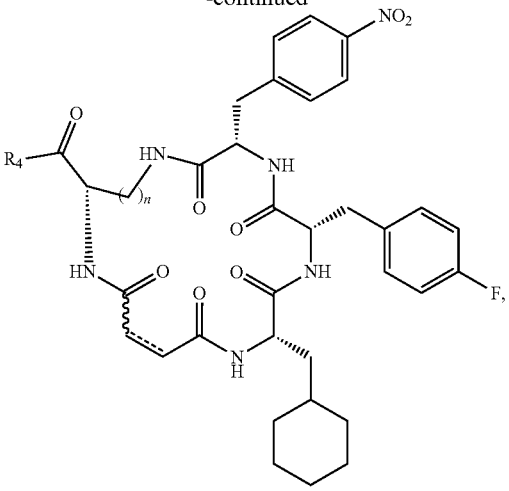

and pharmaceutically acceptable salts thereof.

6. A pharmaceutical composition comprising a therapeutically effective amount of a compound of claim 1 and a pharmaceutically acceptable carrier.

7. The compound of claim 1, wherein n is 2.

8. The compound of claim 1, wherein q is 1; and $R^{AA}$ is halogen, perhaloalkyl, —C(=O)N($R^{A2}$)$_2$, —CN, —SCN, or —NO$_2$ located at the para position relative to the point of attachment.

9. The compound of claim 8, wherein $R^{AA}$ is —NO$_2$.

10. The compound of claim 1, wherein b is 1; and $R^{BB}$ is halogen located in the para position relative to the point of attachment.

11. The compound of claim 10, wherein $R^{BB}$ is —F.

12. The compound of claim 1, wherein t is 0.

13. The compound of claim 5, wherein $R_4$ is —NH$_2$, n is 3, and ⋍ represents a double bond in the trans configuration.

14. The compound of claim 5, wherein $R_4$ is —NH$_2$, n is 3, and ⋍ represents a double bond in the cis configuration.

15. The compound of claim 5, wherein $R_4$ is —NH$_2$, n is 2, and ⋍ represents a double bond in the trans configuration.

16. The compound of claim 5, wherein $R_4$ is —NH$_2$, n is 2, and ⋍ represents a double bond in the cis configuration.

* * * * *

SEQUENCE LISTING

<160> NUMBER OF SEQ ID NOS: 18

<210> SEQ ID NO 1
<211> LENGTH: 4145
<212> TYPE: DNA
<213> ORGANISM: Homo sapiens

<400> SEQUENCE: 1

```
caaacaagtg cggccatttc accagcccag gctggcttct gctgttgact ggctgtggca      60
cctcaagcag ccccttttccc ctctagcctc agtttatcac cgcaagagct accattcatc    120
tagcacaacc tgaccatcct cacactggtc agttccaacc ttcccaggaa tcttctgtgg    180
ccatgttcac tccggtttta cagaacagag aacagaagct cagagaagtg aagcaacttg    240
cccagctatg agagacagag ccaggatttg aaaccagatg aggacgctga ggcccagaga    300
gggaaagcca cttgcctagg gacacacagc ggggagaggt ggagcagggc ctctatttcg    360 agaccctga ctccacacct ggtgtttgtg ccaagacccc aggctgcctc ccaggtcctc      420
tgggacagcc cctgccttct accaggacca tgggtagcaa caagagcaag cccaaggatg    480
ccagccagcg gcgccgcagc ctggagcccg ccgagaacgt gcacggcgct ggcggggggcg    540 cttcccccgc ctcgcagacc cccagcaagc cagcctcggc cgacgccac cgcggcccca    600 gcgcggcctt cgcccccgcg gccgccgagc ccaagctgtt cggaggcttc aactcctcgg    660
acaccgtcac ctccccgcag agggcgggcc cgctggccgg tggagtgacc acctttgtgg    720
ccctctatga ctatgagtct aggacggaga cagacctgtc cttcaagaaa ggcgagcggc    780
tccagattgt caacaacaca gagggagact ggtggctggc ccactcgctc agcacaggac    840
agacaggcta catccccagc aactacgtgg cgccctccga ctccatccag gctgaggagt    900
ggtattttgg caagatcacc agacgggagt cagagcggtt actgctcaat gcagagaacc    960
cgagagggac cttcctcgtg cgagaaagtg agaccacgaa aggtgcctac tgcctctcag   1020
tgtctgactt cgacaacgcc aagggcctca acgtgaagca ctacaagatc cgcaagctgg   1080
acagcggcgg cttctacatc acctcccgca cccagttcaa cagcctgcag cagctggtgg   1140
cctactactc caaacacgcc gatggcctgt gccaccgcct caccaccgtg tgccccacgt   1200
ccaagccgca gactcagggc ctggccaagg atgcctggga gatccctcgg gagtcgctgc   1260
ggctggaggt caagctgggc cagggctgct ttggcgaggt gtggatgggg acctggaacg   1320
gtaccaccag ggtggccatc aaaaccctga gcctggcac gatgtctcca gaggccttcc   1380
tgcaggaggc ccaggtcatg aagaagctga ggcatgagaa gctggtgcag ttgtatgctg   1440
tggtttcaga ggagcccatt tacatcgtca cggagtacat gagcaagggg agtttgctgg   1500
actttctcaa gggggagaca ggcaagtacc tgcggctgcc tcagctggtg gacatggctg   1560
ctcagatcgc ctcaggcatg gcgtacgtgg agcggatgaa ctacgtccac cgggaccttc   1620
gtgcagccaa catcctggtg ggagagaacc tggtgtgcaa agtggccgac tttgggctgg   1680
ctcggctcat tgaagacaat gagtacacgg cgcggcaagg tgccaaattc cccatcaagt   1740
ggacggctcc agaagctgcc ctctatggcc gcttcaccat caagtcggac gtgtggtcct   1800
```

```
tcgggatcct gctgactgag ctcaccacaa agggacgggt gccctaccct gggatggtga    1860
accgcgaggt gctggaccag gtggagcggg gctaccggat gccctgcccg ccggagtgtc    1920
ccgagtccct gcacgacctc atgtgccagt gctggcggaa ggagcctgag gagcggccca    1980
ccttcgagta cctgcaggcc ttcctggagg actacttcac gtccaccgag ccccagtacc    2040
agcccgggga gaacctctag gcacaggcgg gcccagaccg gcttctcggc ttggatcctg    2100
ggctgggtgg ccctgtctc ggggcttgcc ccactctgcc tgcctgctgt tggtcctctc    2160 tctgtgggc tgaattgcca ggggcgaggc ccttcctctt tggtggcatg gaagggctt    2220 ctggacctag ggtggcctga gagggcggtg ggtatgcgag accagcacgg tgactctgtc    2280
cagctcccgc tgtggccgca cgcctctccc tgcactccct cctggagctc tgtgggtctc    2340
tggaagagga accaggagaa gggctggggc cggggctgag ggtgcccttt ccagcctca    2400 gcctactccg ctcactgaac tccttcccca cttctgtgcc accccggtc tatgtcgaga    2460 gctggccaaa gagcctttcc aaagaggagc gatgggcccc tggccccgcc tgcctgccac    2520
cctgcccctt gccatccatt ctggaaacac ctgtaggcag aggctgccga acagaccct    2580 ctgccgctgc ttccaggctg ggcagcacaa ggccttgcct ggcctgatga tggtgggtgg    2640
gtgggatgag taccccctca aaccctgccc tccttagacc tgaggaccc ttcgagatca    2700 tcacttcctt gcccccattt cacccatggg gagacagttg agagcgggga tgtgacatgc    2760
ccaaggccac ggagcagttc agagtggagg cgggcttgga acccggtgct ccctctgtca    2820
tcctcaggaa ccaacaattc gtcggaggca tcatggaaag actgggacag cccaggaaac    2880 aagggggtctg aggatgcatt cgagatggca gattcccact gccgctgccc gctcagccca    2940
gctgttggga acagcatgga ggcagatgtg ggctgagct ggggaatcag ggtaaaaggt    3000
gcaggtgtgg agagagaggc ttcaatcggc ttgtgggtga tgtttgacct tcagagccag    3060
ccggctatga aagggagcga gccctcggc tctggaggca atcaagcaga catagaagag    3120
ccaagagtcc aggaggccct ggtcctgcc tccttcccg tactttgtcc cgtggcattt    3180
caattcctgg ccctgttctc ctccccaagt cggcacccct taactcatga ggagggaaaa    3240
gagtgcctaa gcggggggtga aagaggacgt gttacccact gccatgcacc aggactggct    3300
gtgtaacctt gggtggcccc tgctgtctct ctgggctgca gagtctgccc cacatgtggc    3360 catgcctct gcaactgctc agctctggtc caggccctgt ggcaggacac acatggtgag    3420
cctagccctg ggacatcagg agactgggct ctggctctgt tcggccttg ggtgtgtggt    3480 ggattctccc tgggcctcag tgtgcccatc tgtaaagggg cagctgacag tttgtggcat    3540
cttgccaagg gtccctgtgt gtgtgtatgt gtgtgcatgt gtgcgtgtct ccatgtgcgt    3600
ccatatttaa catgtaaaaa tgtccccccc gctccgtccc ccaaacatgt tgtacatttc    3660
accatggccc cctcatcata gcaataacat tcccactgcc aggggttctt gagccagcca    3720
ggccctgcca gtggggaagg aggccaagca gtgcctgcct atgaaatttc aacttttcct    3780
ttcatacgtc tttattaccc aagtcttctc ccgtccattc cagtcaaatc tgggctcact    3840
caccccagcg agctctcaaa tccctctcca actgcctaag gcccttttgtg taaggtgtct    3900 taatactgtc ctttttttt ttttaacagt gttttgtaga tttcagatga ctatgcagag    3960
gcctggggga cccctggctc tgggccgggc ctggggctcc gaaattccaa ggcccagact    4020 tgcgggggt gggggggtat ccagaattgg ttgtaaatac tttgcatatt gtctgattaa    4080
acacaaacag acctcagaaa aaaaaaaaa aaaaaaaaa aaaaaaaaa aaaaaaaaa    4140 aaaaa                                                              4145
```

-continued

<210> SEQ ID NO 2
<211> LENGTH: 4044
<212> TYPE: DNA
<213> ORGANISM: Homo sapiens

<400> SEQUENCE: 2

| | | | | | |
|---|---|---|---|---|---|
| gccggagcgg | ccaggccgcc | gtctgcccgt | cccgctggac | gtcccgcggt | ccgccctccc | 60 |
| gtgcgtccgt | ctgccggtga | gcccgcccgc | ccgccggccc | agaacagaga | acagaagctc | 120 |
| agagaagtga | agcaacttgc | ccagctatga | gagacagagc | caggatttga | aaccagatga | 180 |
| ggacgctgag | gcccagagag | ggaaagccac | ttgcctaggg | acacacagcg | gggagaggtg | 240 |
| gagcagggcc | tctatttcga | gacccctgac | tccacacctg | gtgtttgtgc | caagacccca | 300 |
| ggctgcctcc | caggtcctct | gggacagccc | ctgccttcta | ccaggaccat | gggtagcaac | 360 |
| aagagcaagc | ccaaggatgc | cagccagcgg | cgccgcagcc | tggagcccgc | cgagaacgtg | 420 |
| cacgcgctg | gcggggcgc | tttcccgcc | tcgcagaccc | ccagcaagcc | agcctcggcc | 480 |
| gacggccacc | gcggccccag | cgcggccttc | gccccgcgg | ccgccgagcc | caagctgttc | 540 |
| ggaggcttca | actcctcgga | caccgtcacc | tccccgcaga | gggcgggccc | gctggccggt | 600 |
| ggagtgacca | cctttgtggc | cctctatgac | tatgagtcta | ggacggagac | agacctgtcc | 660 |
| ttcaagaaag | gcgagcggct | ccagattgtc | aacaacacag | agggagactg | gtggctggcc | 720 |
| cactcgctca | gcacaggaca | gacaggctac | atccccagca | actacgtggc | gccctccgac | 780 |
| tccatccagg | ctgaggagtg | gtattttggc | aagatcacca | gacgggagtc | agagcggtta | 840 |
| ctgctcaatg | cagagaaccc | gagagggacc | ttcctcgtgc | gagaaagtga | gaccacgaaa | 900 |
| ggtgcctact | gcctctcagt | gtctgacttc | gacaacgcca | agggcctcaa | cgtgaagcac | 960 |
| tacaagatcc | gcaagctgga | cagcggcggc | ttctacatca | cctcccgcac | ccagttcaac | 1020 |
| agcctgcagc | agctggtggc | ctactactcc | aaacacgccg | atggcctgtg | ccaccgcctc | 1080 |
| accaccgtgt | gccccacgtc | caagccgcag | actcagggcc | tggccaagga | tgcctgggag | 1140 |
| atccctcggg | agtcgctgcg | gctggaggtc | aagctgggcc | agggctgctt | tggcgaggtg | 1200 |
| tggatgggga | cctggaacgg | taccaccagg | gtggccatca | aaaccctgaa | gcctggcacg | 1260 |
| atgtctccag | aggccttcct | gcaggaggcc | caggtcatga | agaagctgag | gcatgagaag | 1320 |
| ctggtgcagt | tgtatgctgt | ggtttcagag | gagcccattt | acatcgtcac | ggagtacatg | 1380 |
| agcaagggga | gtttgctgga | ctttctcaag | ggggagacag | gcaagtacct | gcggctgcct | 1440 |
| cagctggtgg | acatggctgc | tcagatcgcc | tcaggcatgg | cgtacgtgga | gcggatgaac | 1500 |
| tacgtccacc | gggaccttcg | tgcagccaac | atcctggtgg | agagaacct | ggtgtgcaaa | 1560 |
| gtggccgact | ttgggctggc | tcggctcatt | gaagacaatg | agtacacggc | gcggcaaggt | 1620 |
| gccaaattcc | ccatcaagtg | gacggctcca | gaagctgccc | tctatggccg | cttcaccatc | 1680 |
| aagtcggacg | tgtggtcctt | cgggatcctg | ctgactgagc | tcaccacaaa | gggacgggtg | 1740 |
| ccctacccctg | ggatggtgaa | ccgcgaggtg | ctggaccagg | tggagcgggg | ctaccggatg | 1800 |
| ccctgccgc | cggagtgtcc | cgagtccctg | cacgacctca | tgtgccagtg | ctggcggaag | 1860 |
| gagcctgagg | agcggcccac | cttcgagtac | ctgcaggcct | tcctggagga | ctacttcacg | 1920 |
| tccaccgagc | cccagtacca | gcccgggag | aacctctagg | cacaggcggg | cccagaccgg | 1980 |
| cttctcggct | tggatcctgg | gctggtggc | cctgtctcg | gggcttgccc | cactctgcct | 2040 |
| gcctgctgtt | ggtcctctct | ctgtggggct | gaattgccag | gggcgaggcc | cttcctcttt | 2100 |

-continued

```
ggtggcatgg aagggcttc tggacctagg gtggcctgag agggcggtgg gtatgcgaga    2160
ccagcacggt gactctgtcc agctcccgct gtggccgcac gcctctccct gcactccctc    2220
ctggagctct gtgggtctct ggaagaggaa ccaggagaag ggctggggcc ggggctgagg    2280
gtgccctttt ccagcctcag cctactccgc tcactgaact ccttccccac ttctgtgcca    2340
ccccggtct atgtcgagag ctggccaaag agcctttcca agaggagcg atgggcccct     2400
ggccccgcct gcctgccacc ctgccccttg ccatccattc tggaaacacc tgtaggcaga    2460
ggctgccgag acagaccctc tgccgctgct tccaggctgg gcagcacaag gccttgcctg    2520
gcctgatgat ggtgggtggg tgggatgagt accccctcaa accctgccct ccttagacct    2580
gagggaccct tcgagatcat cacttccttg cccccatttc acccatgggg agacagttga    2640
gagcggggat gtgacatgcc caaggccacg gagcagttca gagtggaggc gggcttggaa    2700
cccggtgctc cctctgtcat cctcaggaac caacaattcg tcggaggcat catggaaaga    2760
ctggacagc ccaggaaaca aggggtctga ggatgcattc gagatggcag attcccactg      2820
ccgctgcccg ctcagcccag ctgttgggaa cagcatggag gcagatgtgg ggctgagctg    2880
gggaatcagg gtaaaaggtg caggtgtgga gagagaggct tcaatcggct tgtgggtgat    2940
gtttgaccctt cagagccagc cggctatgaa agggagcgag cccctcggct ctggaggcaa   3000
tcaagcagac atagaagagc caagagtcca ggaggccctg gtcctggcct ccttccccgt    3060
actttgtccc gtggcatttc aattcctggc cctgttctcc tccccaagtc ggcacccttt    3120
aactcatgag gagggaaaag agtgcctaag cggggggtgaa agaggacgtg ttacccactg    3180
ccatgcacca ggactggctg tgtaaccttg ggtggcccct gctgtctctc tgggctgcag    3240
agtctgcccc acatgtggcc atggcctctg caactgctca gctctggtcc aggccctgtg    3300
gcaggacaca catggtgagc ctagccctgg gacatcagga gactgggctc tggctctgtt    3360
cggcctttgg gtgtgtggtg gattctccct gggcctcagt gtgcccatct gtaaaggggc    3420
agctgacagt ttgtggcatc ttgccaaggg tccctgtgtg tgtgtatgtg tgtgcatgtg    3480
tgcgtgtctc catgtgcgtc catatttaac atgtaaaaat gtcccccccg ctccgtcccc    3540
caaacatgtt gtacatttca ccatggcccc ctcatcatag caataacatt cccactgcca    3600
ggggttcttg agccagccag gccctgccag tggggaagga ggccaagcag tgcctgccta    3660
tgaaatttca acttttcctt tcatacgtct ttattaccca agtcttctcc cgtccattcc    3720
agtcaaatct gggctcactc accccagcga gctctcaaat ccctctccaa ctgcctaagg    3780
ccctttgtgt aaggtgtctt aatactgtcc tttttttttt tttaacagtg ttttgtagat    3840
ttcagatgac tatgcagagg cctgggggac ccctggctct gggccgggcc tggggctccg    3900
aaattccaag gcccagactt gcgggggtg ggggggtatc cagaattggt tgtaaatact     3960
ttgcatattg tctgattaaa cacaaacaga cctcagaaaa aaaaaaaaa aaaaaaaaa      4020
aaaaaaaaa aaaaaaaaa aaaa                                             4044
```

<210> SEQ ID NO 3
<211> LENGTH: 536
<212> TYPE: PRT
<213> ORGANISM: Homo sapiens

<400> SEQUENCE: 3

```
Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
            20                  25                  30
```

```
Pro Ala Ser Gln Thr Pro Ser Lys Pro Ala Ser Ala Asp Gly His Arg
            35                  40                  45

Gly Pro Ser Ala Ala Phe Ala Pro Ala Ala Glu Pro Lys Leu Phe
 50                  55                  60

Gly Gly Phe Asn Ser Ser Asp Thr Val Thr Ser Pro Gln Arg Ala Gly
 65                  70                  75                  80

Pro Leu Ala Gly Gly Val Thr Thr Phe Val Ala Leu Tyr Asp Tyr Glu
                 85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
            115                 120                 125

Thr Gly Gln Thr Gly Tyr Ile Pro Ser Asn Tyr Val Ala Pro Ser Asp
130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
            195                 200                 205

Lys Leu Asp Ser Gly Gly Phe Tyr Ile Thr Ser Arg Thr Gln Phe Asn
            210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
            275                 280                 285

Trp Asn Gly Thr Thr Arg Val Ala Ile Lys Thr Leu Lys Pro Gly Thr
290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
            355                 360                 365

Met Ala Ala Gln Ile Ala Ser Gly Met Ala Tyr Val Glu Arg Met Asn
            370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
            435                 440                 445
```

```
Trp Ser Phe Gly Ile Leu Leu Thr Glu Leu Thr Thr Lys Gly Arg Val
    450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
            500                 505                 510

Glu Tyr Leu Gln Ala Phe Leu Glu Asp Tyr Phe Thr Ser Thr Glu Pro
        515                 520                 525

Gln Tyr Gln Pro Gly Glu Asn Leu
    530                 535

<210> SEQ ID NO 4
<211> LENGTH: 3588
<212> TYPE: DNA
<213> ORGANISM: Homo sapiens

<400> SEQUENCE: 4
```

| | | | | | |
|---|---|---|---|---|---|
| gcagcagcag | agaatccaaa | ccctaaagct | gatatcacaa | agtaccattt | ctccaagttg   60 |
| ggggctcaga | ggggagtcat | catgagcgat | gttaccattg | tgaaagaagg | ttgggttcag  120 |
| aagaggggag | aatatataaa | aaactggagg | ccaagatact | tccttttgaa | gacagatggc  180 |
| tcattcatag | gatataaaga | gaaacctcaa | gatgtggatt | taccttatcc | cctcaacaac  240 |
| ttttcagtgg | caaaatgcca | gttaatgaaa | acagaacgac | caaagccaaa | cacatttata  300 |
| atcagatgtc | tccagtggac | tactgttata | gagagaacat | tcatgtaga  | tactccagag  360 |
| gaaagggaag | aatggacaga | agctatccag | gctgtagcag | acagactgca | gaggcaagaa  420 |
| gaggagagaa | tgaattgtag | tccaacttca | caaattgata | atataggaga | ggaagagatg  480 |
| gatgcctcta | caacccatca | taaaagaaag | acaatgaatg | attttgacta | tttgaaacta  540 |
| ctaggtaaag | gcacttttgg | gaaagttatt | ttggttcgag | agaaggcaag | tggaaaatac  600 |
| tatgctatga | agattctgaa | gaaagaagtc | attattgcaa | aggatgaagt | ggcacacact  660 |
| ctaactgaaa | gcagagtatt | aaagaacact | agacatccct | ttttaacatc | cttgaaatat  720 |
| tccttccaga | caaaagaccg | tttgtgtttt | gtgatggaat | atgttaatgg | gggcgagctg  780 |
| ttttccatt  | tgtcgagaga | gcgggtgttc | tctgaggacc | gcacacgttt | ctatggtgca  840 |
| gaaattgtct | ctgccttgga | ctatctacat | tccggaaaga | ttgtgtaccg | tgatctcaag  900 |
| ttggagaatc | taatgctgga | caaagatggc | cacataaaaa | ttacagattt | tggactttgc  960 |
| aaagaaggga | tcacagatgc | agccaccatg | aagacattct | gtggcactcc | agaatatctg 1020 |
| gcaccagagg | tgttagaaga | taatgactat | ggccgagcag | tagactggtg | gggcctaggg 1080 |
| gttgtcatgt | atgaaatgat | gtgtgggagg | ttaccttct  | acaaccagga | ccatgagaaa 1140 |
| cttttttgaat | taatattaat | ggaagacatt | aaatttcctc | gaacactctc | ttcagatgca 1200 |
| aaatcattgc | tttcagggct | cttgataaag | gatccaaata | aacgccttgg | tggaggacca 1260 |
| gatgatgcaa | agaaattat  | gagacacagt | ttcttctctg | gagtaaactg | gcaagatgta 1320 |
| tatgataaaa | agcttgtacc | tccttttaaa | cctcaagtaa | catctgagac | agatactaga 1380 |
| tattttgatg | aagaatttac | agctcagact | attacaataa | caccacctga | aaaatatgat 1440 |
| gaggatggta | tggactgcat | ggacaatgag | aggcggccgc | atttccctca | atttttcctac 1500 |
| tctgcaagtg | gacgagaata | agtctctttc | attctgctac | ttcactgtca | tcttcaattt 1560 |
| attactgaaa | atgattcctg | gacatcacca | gtcctagctc | ttacacatag | cagggggcacc 1620 |

```
ttccgacatc ccagaccagc caagggtcct caccccctcgc cacctttcac cctcatgaaa     1680
acacacatac acgcaaatac actccagttt ttgttttttgc atgaaattgt atctcagtct     1740
aaggtctcat gctgttgctg ctactgtctt actattatag caactttaag aagtaatttt     1800 ccaaccttg gaagtcatga gcccaccatt gttcatttgt gcaccaatta tcatcttttg     1860
atcttttagt ttttccctca gtgaaggcta aatgagatac actgattcta ggtacatttt     1920
ttaactttct agaagagaaa aactaactag actaagaaga tttagtttat aaattcagaa     1980
caagcaattg tggaagggtg gtggcgtgca tatgtaaagc acatcagatc cgtgcgtgaa     2040
gtaggcatat atcactaagc tgtggctgga attgattagg aagcatttgg tagaaggact     2100
gaacaactgt tgggatatat atatatatat ataattttt ttttttaaat tcctggtgga     2160
tactgtagaa gaagcccata tcacatgtgg atgtcgagac ttcacgggca atcatgagca     2220
agtgaacact gttctaccaa gaactgaagg catatgcaca gtcaaggtca cttaaagggt     2280
cttatgaaac aatttgagcc agagagcatc tttccctgt gcttggaaac ctttttccct     2340
tcttgacatt tatcacctct gatggctgaa gaatgtagac aggtataatg atactgcttt     2400
tcaccaaaat ttctacacca aggtaaacag gtgtttgcct tatttaattt tttactttca     2460
gttctacgtg aattagcttt ttctcagatg ttgaaacttt gaatgtcctt ttatgattt     2520 gtttatattg cagtagtatt tattttttag tgatgagaat tgtatgtcat gttagcaaac     2580
gcagctccaa cttatataaa atagacttac tgcagttact tttgacccat gtgcaaggat     2640
tgtacacgct gatgagaatc atgcactttt tctcctctgt taaaaaaaat gataaggctc     2700
tgaaatggaa tatattggtt agaatttggc tttgggagaa gagatgctgc catttaaccc     2760
cttggtactg aaaatgagaa aatccccaac tatgcatgcc aagggggttaa tgaaacaaat     2820 agctgttgac gtttgctcat ttaagaattt gaaacgttat gatgacctgg caacaaaaag     2880
taatgaagaa aattgagacc tgagtgaaga taagaaatga tctttacgtg gcaaaatgaa     2940
cacatcttga gtatttagga aatgggcagt gaaggctaag aacctggtgt gtttcttggg     3000
atcatggtac atttatcact gaattaagcc atcagggaaa aaacaacaaa aaaagagaac     3060
acctccagct tttcttttc tgtatatact catgtccccc agattccaac atttctcact     3120 gaaaggggc atgtatgcaa acctcatctt tctccttcat taatgatgat cttcagatta     3180 aacccttgg tgctaggagc tgacaatttc caaagcagcc tgtgaagtcc tagggctgg     3240 gggccactct tgcggcaagc agaaggccat cctactccgc ggagtgatca tggaaatgta     3300
ttttagttaa actctgacag ctcccaaacg gaagactaca gcatgacgta gtattatgat     3360
tgcattgtat gaaagagcaa gtgactttct aagtaggatg aatcatattc atatgcagat     3420
gtcttagcct cttgacgctg gaagtgtgga tttatagcta tgaaaccact gctggcagtg     3480
ggtgggccac tgggactgac gggggttaaa gggcatttta ctaaggcagc taagacatat     3540
tcagacatca acgttatcct tctttttcat atttctacct gagtgaag                  3588
```

<210> SEQ ID NO 5
<211> LENGTH: 1703
<212> TYPE: DNA
<213> ORGANISM: Homo sapiens

<400> SEQUENCE: 5

```
gcagcagcag agaatccaaa ccctaaagct gatatcacaa agtaccattt ctccaagttg       60
ggggctcaga ggggagtcat catgagcgat gttaccattg tgaaagaagg ttgggttcag      120
```

```
aagaggggag aatatataaa aaactggagg ccaagatact tccttttgaa gacagatggc    180
tcattcatag gatataaaga gaaacctcaa gatgtggatt taccttatcc cctcaacaac    240
ttttcagtgg caaaatgcca gttaatgaaa acagaacgac caaagccaaa cacatttata    300
atcagatgtc tccagtggac tactgttata gagagaacat tcatgtaga tactccagag     360 gaaagggaag aatggacaga agctatccag gctgtagcag acagactgca gaggcaagaa    420
gaggagagaa tgaattgtag tccaacttca caaattgata atataggaga ggaagagatg    480
gatgcctcta caacccatca taaaagaaag acaatgaatg attttgacta tttgaaacta    540
ctaggtaaag gcacttttgg gaaagttatt ttggttcgag agaaggcaag tggaaaatac    600
tatgctatga agattctgaa gaaagaagtc attattgcaa aggatgaagt ggcacacact    660
ctaactgaaa gcagagtatt aaagaacact agacatccct ttttaacatc cttgaaatat    720
tccttccaga caaaagaccg tttgtgtttt gtgatggaat atgttaatgg gggcgagctg    780
tttttccatt tgtcgagaga gcgggtgttc tctgaggacc gcacacgttt ctatggtgca    840
gaaattgtct ctgccttgga ctatctacat tccggaaaga ttgtgtaccg tgatctcaag    900
ttggagaatc taatgctgga caaagatggc cacataaaaa ttacagattt tggactttgc    960
aaagaaggga tcacagatgc agccaccatg aagacattct gtggcactcc agaatatctg   1020
gcaccagagg tgttagaaga taatgactat ggccgagcag tagactggtg gggcctaggg   1080
gttgtcatgt atgaaatgat gtgtgggagg ttacctttct acaaccagga ccatgagaaa   1140 cttttgaat taatattaat ggaagacatt aaatttcctc gaacactctc ttcagatgca   1200
aaatcattgc tttcagggct cttgataaag gatccaaata aacgccttgg tggaggacca   1260
gatgatgcaa agaaattat gagacacagt ttcttctctg gagtaaactg gcaagatgta   1320
tatgataaaa agcttgtacc tccttttaaa cctcaagtaa catctgagac agatactaga   1380
tattttgatg aagaatttac agctcagact attacaataa caccacctga aaaatgtcag   1440
caatcagatt gtggcatgct gggtaactgg aaaaaataat aaaaatcggc ttcctacagc   1500
cagcagcaca gtcacccatg gaactgttgg ctttggatta aatgtggaat tgaacgacta   1560
cccagaagtg ttctggaaag aagcgagatg tgtggcctgc ctcaccgtcc tcacccatca   1620
aaagcaccag caggcacgtt aactcgaatt ctcacaagga aaaggccatt aaagctcaag   1680
gtgcatttca aactccaggc tac                                           1703
```

<210> SEQ ID NO 6
<211> LENGTH: 479
<212> TYPE: PRT
<213> ORGANISM: Homo sapiens

<400> SEQUENCE: 6

```
Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95
```

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Glu Met Asp Ala Ser Thr Thr His His Lys Arg Lys Thr
130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
        435                 440                 445

Pro Glu Lys Tyr Asp Glu Asp Gly Met Asp Cys Met Asp Asn Glu Arg
450                 455                 460

Arg Pro His Phe Pro Gln Phe Ser Tyr Ser Ala Ser Gly Arg Glu
465                 470                 475

<210> SEQ ID NO 7
<211> LENGTH: 465
<212> TYPE: PRT
<213> ORGANISM: Homo sapiens

<400> SEQUENCE: 7

```
Met Ser Asp Val Thr Ile Val Lys Glu Gly Trp Val Gln Lys Arg Gly
1               5                  10                 15
Glu Tyr Ile Lys Asn Trp Arg Pro Arg Tyr Phe Leu Leu Lys Thr Asp
                20                 25                  30
Gly Ser Phe Ile Gly Tyr Lys Glu Lys Pro Gln Asp Val Asp Leu Pro
            35                  40                  45
Tyr Pro Leu Asn Asn Phe Ser Val Ala Lys Cys Gln Leu Met Lys Thr
        50                  55                  60
Glu Arg Pro Lys Pro Asn Thr Phe Ile Ile Arg Cys Leu Gln Trp Thr
65                  70                  75                  80
Thr Val Ile Glu Arg Thr Phe His Val Asp Thr Pro Glu Glu Arg Glu
                85                  90                  95
Glu Trp Thr Glu Ala Ile Gln Ala Val Ala Asp Arg Leu Gln Arg Gln
            100                 105                 110
Glu Glu Glu Arg Met Asn Cys Ser Pro Thr Ser Gln Ile Asp Asn Ile
        115                 120                 125
Gly Glu Glu Glu Met Asp Ala Ser Thr Thr His His Lys Arg Lys Thr
130                 135                 140
Met Asn Asp Phe Asp Tyr Leu Lys Leu Leu Gly Lys Gly Thr Phe Gly
145                 150                 155                 160
Lys Val Ile Leu Val Arg Glu Lys Ala Ser Gly Lys Tyr Tyr Ala Met
                165                 170                 175
Lys Ile Leu Lys Lys Glu Val Ile Ile Ala Lys Asp Glu Val Ala His
            180                 185                 190
Thr Leu Thr Glu Ser Arg Val Leu Lys Asn Thr Arg His Pro Phe Leu
        195                 200                 205
Thr Ser Leu Lys Tyr Ser Phe Gln Thr Lys Asp Arg Leu Cys Phe Val
210                 215                 220
Met Glu Tyr Val Asn Gly Gly Glu Leu Phe Phe His Leu Ser Arg Glu
225                 230                 235                 240
Arg Val Phe Ser Glu Asp Arg Thr Arg Phe Tyr Gly Ala Glu Ile Val
                245                 250                 255
Ser Ala Leu Asp Tyr Leu His Ser Gly Lys Ile Val Tyr Arg Asp Leu
            260                 265                 270
Lys Leu Glu Asn Leu Met Leu Asp Lys Asp Gly His Ile Lys Ile Thr
        275                 280                 285
Asp Phe Gly Leu Cys Lys Glu Gly Ile Thr Asp Ala Ala Thr Met Lys
290                 295                 300
Thr Phe Cys Gly Thr Pro Glu Tyr Leu Ala Pro Glu Val Leu Glu Asp
305                 310                 315                 320
Asn Asp Tyr Gly Arg Ala Val Asp Trp Trp Gly Leu Gly Val Val Met
                325                 330                 335
Tyr Glu Met Met Cys Gly Arg Leu Pro Phe Tyr Asn Gln Asp His Glu
            340                 345                 350
Lys Leu Phe Glu Leu Ile Leu Met Glu Asp Ile Lys Phe Pro Arg Thr
        355                 360                 365
Leu Ser Ser Asp Ala Lys Ser Leu Leu Ser Gly Leu Leu Ile Lys Asp
370                 375                 380
Pro Asn Lys Arg Leu Gly Gly Gly Pro Asp Asp Ala Lys Glu Ile Met
385                 390                 395                 400
Arg His Ser Phe Phe Ser Gly Val Asn Trp Gln Asp Val Tyr Asp Lys
                405                 410                 415
```

```
Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
            435                 440                 445

Pro Glu Lys Cys Gln Gln Ser Asp Cys Gly Met Leu Gly Asn Trp Lys
            450                 455                 460

Lys
465

<210> SEQ ID NO 8
<211> LENGTH: 3608
<212> TYPE: DNA
<213> ORGANISM: Homo sapiens

<400> SEQUENCE: 8
```

| | | | | | |
|---|---|---|---|---|---|
| gcggccgctt | cccccggcc | gggccccgc | cgccccgcgg | tccccagagc | gccaggcccc | 60 |
| cgggggggagg | gagggagggc | gccggccgg | tgggagccag | cggcgcgcgg | tgggacccac | 120 |
| ggagccccgc | gacccgccga | gcctggagcc | gggccgggtc | ggggaagccg | gctccagccc | 180 |
| ggagcgaact | tcgcagcccg | tcgggggcg | gcggggaggg | ggcccggagc | cggaggaggg | 240 |
| ggcggccgcg | ggcacccccg | cctgtgcccc | ggcgtccccg | ggcaccatgc | tgtccaactc | 300 |
| ccagggccag | agcccgccgg | tgccgttccc | cgccccggcc | ccgccgccgc | agccccccac | 360 |
| ccctgccctg | ccgcaccccc | cggcgcagcc | gccgccgccg | ccccgcagc | agttcccgca | 420 |
| gttccacgtc | aagtccggcc | tgcagatcaa | gaagaacgcc | atcatcgatg | actacaaggt | 480 |
| caccagccag | gtcctggggc | tgggcatcaa | cggcaaagtt | ttgcagatct | caacaagag | 540 |
| gacccaggag | aaattcgccc | tcaaaatgct | tcaggactgc | ccaaggccc | gcagggaggt | 600 |
| ggagctgcac | tggcgggcct | cccagtgccc | gcacatcgta | cggatcgtgg | atgtgtacga | 660 |
| gaatctgtac | gcagggagga | agtgcctgct | gattgtcatg | gaatgtttgg | acggtggaga | 720 |
| actctttagc | cgaatccagg | atcgaggaga | ccaggcattc | acagaaagag | aagcatccga | 780 |
| aatcatgaag | agcatcggtg | aggccatcca | gtatctgcat | tcaatcaaca | ttgcccatcg | 840 |
| ggatgtcaag | cctgagaatc | tcttatacac | ctccaaaagg | cccaacgcca | tcctgaaact | 900 |
| cactgacttt | ggctttgcca | aggaaaccac | cagccacaac | tctttgacca | ctccttgtta | 960 |
| tacaccgtac | tatgtggctc | cagaagtgct | gggtccagag | aagtatgaca | agtcctgtga | 1020 |
| catgtggtcc | ctgggtgtca | tcatgtacat | cctgctgtgt | gggtatcccc | ccttctactc | 1080 |
| caaccacggc | cttgccatct | ctccgggcat | gaagactcgc | atccgaatgg | gccagtatga | 1140 |
| atttcccaac | ccagaatggt | cagaagtatc | agaggaagtg | aagatgctca | ttcggaatct | 1200 |
| gctgaaaaca | gagcccaccc | agagaatgac | catcaccgag | tttatgaacc | acccttggat | 1260 |
| catgcaatca | acaaaggtcc | ctcaaacccc | actgcacacc | agccgggtcc | tgaaggagga | 1320 |
| caaggagcgg | tggaggatg | tcaaggggtg | tcttcatgac | aagaacagcg | accaggccac | 1380 |
| ttggctgacc | aggttgtgag | cagaggattc | tgtgttcctg | tccaaactca | gtgctgtttc | 1440 |
| ttagaatcct | tttattccct | gggtctctaa | tgggaccta | agaccatct | ggtatcatct | 1500 |
| tctcattttg | cagaagagaa | actgaggccc | agaggcggag | ggcagtctgc | tcaaggtcac | 1560 |
| gcagctggtg | actggttggg | gcagaccgga | cccaggtttc | ctgactcctg | gcccaagtct | 1620 |
| cttcctccta | tcctgcggga | tcactggggg | gctctcaggg | aacagcagca | gtgccatagc | 1680 |
| caggctctct | gctgcccagc | gctggggtga | ggctgccgtt | gtcagcgtgg | accactaacc | 1740 |

```
agcccgtctt ctctctctgc tcccacccct gccgccctca ccctgcccctt gttgtctctg    1800 tctctcacgt ctctcttctg ctgtctctcc tacctgtctt ctggctctct ctgtaccctt    1860
cctggtgctg ccgtgccccc aggaggagat gaccagtgcc ttggccacaa tgcgcgttga    1920
ctacgagcag atcaagataa aaagattga agatgcatcc aaccctctgc tgctgaagag    1980
gcggaagaaa gctcgggccc tggaggctgc ggctctggcc cactgagcca ccgcgccctc    2040
ctgcccacgg gaggacaagc aataactctc tacaggaata tatttttaa acgaagagac    2100 agaactgtcc acatctgcct cctctcctcc tcagctgcat ggagcctgga actgcatcag    2160
tgactgaatt ctgccttggt tctgccacc ccagagtggg agaggctggg aggttgggag    2220
gctgtggaga gaagtgagca aggtgctctt gaacctgtgc tcattttgca attttatcag    2280
taatttgact tagagttttt acgaaacctc ttttgttgtc cttgcccccac tcctctccac    2340 cagacgcctt cctctctgga tactgcaaag gcttgtggtt tgttagaggg tatttgtgga    2400
aactgtcata gggattgtcc ctgtgttgtc ccatctgccc tccctgtttc tccacaacag    2460 cctgggggttg tccccgctgg ctcacgcgtt ctggagctc aaggccacct tggaggagga    2520
tgccacgcac ttcctctctc ggagccctca gacatctcca gtgtgccaga caaataggag    2580
tgagtgtatg tgtgtgtgtg tgtgtgtgtg tgtgcacacg tgtgtatgag tgcgcagatc    2640
tgtgcctggg atcgtgcatt tgaggggcca ggggcaggca gggctgcaga gggagacggc    2700
cctgctgggg cttaggaacc ttctcccttc ttgggtctgc cctgcccata ctgagcctgc    2760
caaagtgcct gggaagccca cccagattct gaaacaggcc ctctgtggcc tgtctctatt    2820
agctgggttc cgggaggcag agaggagtga ccgggcactg gcactgcgat caggaagact    2880 ggaccccag ccccagggc cccctcccc ccacttagtg ctggtcctag gtcctctgag    2940
gcactcatct actgaatgac ctctctactt cccctctctg ccattattaa cccatttttg    3000 tttatttttcc ttaaattttt agccatttct ccatgggcca ccgcccagct catgtaggtg    3060
agcctgggca gcttctgttg gcagagcttt tgcatttcct gtgtttgtcc tgggttctgg    3120
ggcatcagcc agctacccct tgtgggcaaa ggcagggcca cttttgaagt cttccctcag    3180
atttccattg tgtggcctgg tgggtcaggg ggagtctttg caccaaagat gtcctgactt    3240 tgccccccttg cccatcagcc atttgccatc accccaaaca actcagcttc ggggccggtg    3300 agggggggg cctccccag cacagatgag gagcagctgg ggtaggctgt ctgtgccatg    3360
gccccccact ccccctccc ttggaggag aggtggcagg aatacttcac ctttcctctc    3420 cctcagggc aggtggtgga ggggcgccca gggtcgtctt tgtgtatggg ggaaggcgct    3480
gggtgcctgc agcgcctccc ttgtctcaga tggtgtgtcc agcactcgat tgttgtaaac    3540
tgttgttttg tatgagcgaa attgtcttta ctaaacagat ttaatagtta aaaaaaaaaa    3600
aaaaaaaa                                                            3608
```

<210> SEQ ID NO 9
<211> LENGTH: 3071
<212> TYPE: DNA
<213> ORGANISM: Homo sapiens

<400> SEQUENCE: 9

```
gcggccgctt ccccccggcc gggccccgc cgcccgcgg tccccagagc gccaggcccc      60 cgggggagg gagggagggc gccggccggg tgggagccag cggcgcgcgg tgggacccac     120 ggagcccgc gacccgccga gcctggagcc gggccgggtc ggggaagccg gctccagccc     180
ggagcgaact tcgcagcccg tcgggggggcg gcggggaggg ggcccggagc cggaggaggg     240
```

```
ggcggccgcg ggcacccccg cctgtgcccc ggcgtcccg  ggcaccatgc tgtccaactc    300
ccagggccag agcccgccgg tgccgttccc cgccccggcc ccgccgccgc agcccccac     360 ccctgccctg ccgcaccccc cggcgcagcc gccgccgccg ccccgcagc  agttcccgca    420 gttccacgtc aagtccggcc tgcagatcaa gaagaacgcc atcatcgatg actacaaggt    480
caccagccag gtcctggggc tgggcatcaa cggcaaagtt ttgcagatct tcaacaagag    540
gacccaggag aaattcgccc tcaaaatgct tcaggactgc ccaaggccc  cagggaggt     600 ggagctgcac tggcgggcct cccagtgccc gcacatcgta cggatcgtgg atgtgtacga    660
gaatctgtac gcaggagga  agtgcctgct gattgtcatg gaatgtttgg acggtggaga    720
actctttagc cgaatccagg atcgaggaga ccaggcattc acagaaagag aagcatccga    780
aatcatgaag agcatcggtg aggccatcca gtatctgcat tcaatcaaca ttgcccatcg    840
ggatgtcaag cctgagaatc tcttatacac ctccaaaagg cccaacgcca tcctgaaact    900
cactgacttt ggctttgcca aggaaaccac cagccacaac tctttgacca ctccttgtta    960
tacaccgtac tatgtggctc cagaagtgct gggtccagag aagtatgaca gtcctgtga   1020 catgtggtcc ctgggtgtca tcatgtacat tctgctgtgt gggtatcccc ccttctactc   1080
caaccacggc cttgccatct ctccgggcat gaagactcgc atccgaatgg ccagtatga   1140 atttcccaac ccagaatggt cagaagtatc agaggaagtg aagatgctca ttcggaatct   1200
gctgaaaaca gagcccaccc agagaatgac catcaccgag tttatgaacc cccttggat    1260 catgcaatca acaaaggtcc ctcaaacccc actgcacacc agccgggtcc tgaaggagga   1320
caaggagcgg tgggaggatg tcaaggagga gatgaccagt gccttggcca caatgcgcgt   1380
tgactacgag cagatcaaga taaaaaagat tgaagatgca tccaaccctc tgctgctgaa   1440
gaggcggaag aaagctcggg ccctggaggc tgcggctctg gcccactgag ccaccgcgcc   1500
ctcctgccca cggaggaca  agcaataact ctctacagga atatatttt  taaacgaaga   1560 gacagaactg tccacatctg cctcctctcc tcctcagctg catggagcct ggaactgcat   1620
cagtgactga attctgcctt ggttctggcc accccagagt gggagaggct gggaggttgg   1680
gaggctgtgg agagaagtga gcaaggtgct cttgaacctg tgctcatttt gcaatttat    1740 cagtaatttg acttagagtt tttacgaaac ctcttttgtt gtccttgccc cactcctctc   1800
caccagacgc cttcctctct ggatactgca aaggcttgtg gtttgttaga gggtatttgt   1860
ggaaactgtc atagggattg tccctgtgtt gtcccatctg ccctccctgt ttctccacaa   1920
cagcctgggg ttgtccccgc tggctcacgc gttctgggag ctcaaggcca ccttggagga   1980
ggatgccacg cacttcctct ctcggagccc tcagacatct ccagtgtgcc agacaaatag   2040
gagtgagtgt atgtgtgtgt gtgtgtgtgt gtgtgtgcac acgtgtgtat gagtgcgcag   2100
atctgtgcct gggatcgtgc atttgagggg ccaggggcag gcagggctgc agaggagac    2160 ggccctgctg gggcttagga accttctccc ttcttgggtc tgccctgccc atactgagcc   2220
tgccaaagtg cctgggaagc ccacccagat tctgaaacag gccctctgtg gcctgtctct   2280
attagctggg ttccgggagg cagagaggag tgacccggca ctggcactgc gatcaggaag   2340
actggacccc cagcccccag ggccccctc  ccccactta  tgctggtcc  taggtcctct   2400 gaggcactca tctactgaat gacctctcta cttccccttc ttgccattat taacccattt   2460
ttgtttattt tccttaaatt tttagccatt tctccatggg ccaccgccca gctcatgtag   2520
gtgagcctgg gcagcttctg ttggcagagc ttttgcattt cctgtgtttg tcctgggttc   2580
```

```
tggggcatca gccagctacc ccttgtgggc aaaggcaggg ccactttga  agtcttccct    2640 cagatttcca ttgtgtggcc tggtgggtca gggggagtct ttgcaccaaa gatgtcctga    2700
ctttgccccc ttgcccatca gccatttgcc atcaccccaa acaactcagc ttcggggccg    2760
gtgaggggag gggcctcccc cagcacagat gaggagcagc tggggtaggc tgtctgtgcc    2820 atggccccc actccccctt cccttggagg gagaggtggc aggaatactt caccttcct      2880 ctccctcagg ggcaggtggt ggaggggcgc ccagggtcgt ctttgtgtat ggggaaggc     2940 gctgggtgcc tgcagcgcct cccttgtctc agatggtgtg tccagcactc gattgttgta    3000
aactgttgtt ttgtatgagc gaaattgtct ttactaaaca gatttaatag ttaaaaaaaa    3060
aaaaaaaaaa a                                                         3071
```

<210> SEQ ID NO 10
<211> LENGTH: 370
<212> TYPE: PRT
<213> ORGANISM: Homo sapiens

<400> SEQUENCE: 10

```
Met Leu Ser Asn Ser Gln Gly Gln Ser Pro Val Pro Phe Pro Ala
1               5                   10                  15

Pro Ala Pro Pro Gln Pro Pro Thr Pro Ala Leu Pro His Pro Pro
                20                  25                  30

Ala Gln Pro Pro Pro Pro Gln Gln Phe Pro Gln Phe His Val
            35                  40                  45

Lys Ser Gly Leu Gln Ile Lys Lys Asn Ala Ile Ile Asp Asp Tyr Lys
    50                  55                  60

Val Thr Ser Gln Val Leu Gly Leu Gly Ile Asn Gly Lys Val Leu Gln
65                  70                  75                  80

Ile Phe Asn Lys Arg Thr Gln Glu Lys Phe Ala Leu Lys Met Leu Gln
                85                  90                  95

Asp Cys Pro Lys Ala Arg Arg Glu Val Glu Leu His Trp Arg Ala Ser
                100                 105                 110

Gln Cys Pro His Ile Val Arg Ile Val Asp Val Tyr Glu Asn Leu Tyr
            115                 120                 125

Ala Gly Arg Lys Cys Leu Leu Ile Val Met Glu Cys Leu Asp Gly Gly
        130                 135                 140

Glu Leu Phe Ser Arg Ile Gln Asp Arg Gly Asp Gln Ala Phe Thr Glu
145                 150                 155                 160

Arg Glu Ala Ser Glu Ile Met Lys Ser Ile Gly Glu Ala Ile Gln Tyr
                165                 170                 175

Leu His Ser Ile Asn Ile Ala His Arg Asp Val Lys Pro Glu Asn Leu
            180                 185                 190

Leu Tyr Thr Ser Lys Arg Pro Asn Ala Ile Leu Lys Leu Thr Asp Phe
        195                 200                 205

Gly Phe Ala Lys Glu Thr Thr Ser His Asn Ser Leu Thr Thr Pro Cys
    210                 215                 220

Tyr Thr Pro Tyr Tyr Val Ala Pro Glu Val Leu Gly Pro Glu Lys Tyr
225                 230                 235                 240

Asp Lys Ser Cys Asp Met Trp Ser Leu Gly Val Ile Met Tyr Ile Leu
                245                 250                 255

Leu Cys Gly Tyr Pro Pro Phe Tyr Ser Asn His Gly Leu Ala Ile Ser
            260                 265                 270

Pro Gly Met Lys Thr Arg Ile Arg Met Gly Gln Tyr Glu Phe Pro Asn
        275                 280                 285
```

-continued

Pro Glu Trp Ser Glu Val Ser Glu Val Lys Met Leu Ile Arg Asn
    290                 295                 300

Leu Leu Lys Thr Glu Pro Thr Gln Arg Met Thr Ile Thr Glu Phe Met
305                 310                 315                 320

Asn His Pro Trp Ile Met Gln Ser Thr Lys Val Pro Gln Thr Pro Leu
                325                 330                 335

His Thr Ser Arg Val Leu Lys Glu Asp Lys Glu Arg Trp Glu Asp Val
            340                 345                 350

Lys Gly Cys Leu His Asp Lys Asn Ser Asp Gln Ala Thr Trp Leu Thr
        355                 360                 365

Arg Leu
    370

<210> SEQ ID NO 11
<211> LENGTH: 400
<212> TYPE: PRT
<213> ORGANISM: Homo sapiens

<400> SEQUENCE: 11

Met Leu Ser Asn Ser Gln Gly Gln Ser Pro Val Pro Phe Pro Ala
1               5                   10                  15

Pro Ala Pro Pro Gln Pro Thr Pro Ala Leu Pro His Pro Pro
                20                  25                  30

Ala Gln Pro Pro Pro Pro Gln Gln Phe Pro Gln Phe His Val
            35                  40                  45

Lys Ser Gly Leu Gln Ile Lys Lys Asn Ala Ile Ile Asp Asp Tyr Lys
50                  55                  60

Val Thr Ser Gln Val Leu Gly Leu Gly Ile Asn Gly Lys Val Leu Gln
65                  70                  75                  80

Ile Phe Asn Lys Arg Thr Gln Glu Lys Phe Ala Leu Lys Met Leu Gln
                85                  90                  95

Asp Cys Pro Lys Ala Arg Arg Glu Val Glu Leu His Trp Arg Ala Ser
                100                 105                 110

Gln Cys Pro His Ile Val Arg Ile Val Asp Val Tyr Glu Asn Leu Tyr
            115                 120                 125

Ala Gly Arg Lys Cys Leu Leu Ile Val Met Glu Cys Leu Asp Gly Gly
        130                 135                 140

Glu Leu Phe Ser Arg Ile Gln Asp Arg Gly Asp Gln Ala Phe Thr Glu
145                 150                 155                 160

Arg Glu Ala Ser Glu Ile Met Lys Ser Ile Gly Glu Ala Ile Gln Tyr
                165                 170                 175

Leu His Ser Ile Asn Ile Ala His Arg Asp Val Lys Pro Glu Asn Leu
            180                 185                 190

Leu Tyr Thr Ser Lys Arg Pro Asn Ala Ile Leu Lys Leu Thr Asp Phe
        195                 200                 205

Gly Phe Ala Lys Glu Thr Thr Ser His Asn Ser Leu Thr Thr Pro Cys
210                 215                 220

Tyr Thr Pro Tyr Tyr Val Ala Pro Glu Val Leu Gly Pro Glu Lys Tyr
225                 230                 235                 240

Asp Lys Ser Cys Asp Met Trp Ser Leu Gly Val Ile Met Tyr Ile Leu
                245                 250                 255

Leu Cys Gly Tyr Pro Pro Phe Tyr Ser Asn His Gly Leu Ala Ile Ser
            260                 265                 270

Pro Gly Met Lys Thr Arg Ile Arg Met Gly Gln Tyr Glu Phe Pro Asn

```
                275                 280                 285
Pro Glu Trp Ser Glu Val Ser Glu Glu Val Lys Met Leu Ile Arg Asn
    290                 295                 300

Leu Leu Lys Thr Glu Pro Thr Gln Arg Met Thr Ile Thr Glu Phe Met
305                 310                 315                 320

Asn His Pro Trp Ile Met Gln Ser Thr Lys Val Pro Gln Thr Pro Leu
                325                 330                 335

His Thr Ser Arg Val Leu Lys Glu Asp Lys Glu Arg Trp Glu Asp Val
                340                 345                 350

Lys Glu Glu Met Thr Ser Ala Leu Ala Thr Met Arg Val Asp Tyr Glu
                355                 360                 365

Gln Ile Lys Ile Lys Lys Ile Glu Asp Ala Ser Asn Pro Leu Leu Leu
    370                 375                 380

Lys Arg Arg Lys Lys Ala Arg Ala Leu Glu Ala Ala Leu Ala His
385                 390                 395                 400

<210> SEQ ID NO 12
<211> LENGTH: 2751
<212> TYPE: DNA
<213> ORGANISM: Homo sapiens

<400> SEQUENCE: 12
ccctttactc ctggctgcgg ggcgagccgg gcgtctgctg cagcggccgc ggtggctgag      60
gaggcccgag aggagtcggt ggcagcggcg gcggcgggac cggcagcagc agcagcagca     120
gcagcagcag caaccactag cctcctgccc cgcggcgctg ccgcacgagc ccacgagcc      180 gctcaccccg ccgttctcag cgctgcccga ccccgctggc gcgccctccc gccgccagtc     240
ccggcagcgc cctcagttgt cctccgactc gccctcggcc ttccgcgcca gccgcagcca     300
cagccgcaac gccacccgca gccacagcca cagccacagc ccaggcata gccttcggca     360 cagccccggc tccggctcct gcggcagctc ctctgggcac cgtccctgcg ccgacatcct     420
ggaggttggg atgctcttgt ccaaaatcaa ctcgcttgcc acctgcgcg ccgcgccctg     480 caacgacctg cacgccacca gctggcgcc cggcaaggag aaggagcccc tggagtcgca     540
gtaccaggtg ggcccgctac tgggcagcgg cggcttcggc tcggtctact caggcatccg     600
cgtctccgac aacttgccgg tggccatcaa acacgtggag aaggaccgga tttccgactg     660
gggagagctg cctaatggca ctcgagtgcc catggaagtg gtcctgctga agaaggtgag     720
ctcgggtttc tccggcgtca ttaggctcct ggactggttc gagaggcccg acagtttcgt     780
cctgatcctg gagaggcccg agccggtgca agatctcttc gacttcatca cggaaagggg     840
agccctgcaa gaggagctgg cccgcagctt cttctggcag gtgctggagg ccgtgcggca     900
ctgccacaac tgcggggtgc tccaccgcga catcaaggac gaaaacatcc ttatcgacct     960
caatcgcggc gagctcaagc tcatcgactt cgggtcgggg gcgctgctca aggacaccgt    1020
ctacacggac ttcgatggga cccgagtgta tagccctcca gagtggatcc gctaccatcg    1080
ctaccatggc aggtcggcgg cagtctggtc cctggggatc ctgctgtatg atatggtgtg    1140
tggagatatt cctttcgagc atgacgaaga gatcatcagg ggccaggttt cttcaggca    1200 gagggtctct tcagaatgtc agcatctcat tagatggtgc ttggccctga gaccatcaga    1260
taggccaacc ttcgaagaaa tccagaacca tccatggatg caagatgttc tcctgcccca    1320
ggaaactgct gagatccacc tccacagcct gtcgccgggg cccagcaaat agcagccttt    1380
ctggcaggtc ctcccctctc ttgtcagatg cccgagggag gggaagcttc tgtctccagc    1440
```

-continued

```
ttcccgagta ccagtgacac gtctcgccaa gcaggacagt gcttgataca ggaacaacat   1500
ttacaactca ttccagatcc caggcccctg gaggctgcct cccaacagtg gggaagagtg   1560
actctccagg ggtcctaggc ctcaactcct cccatagata ctctcttctt ctcataggtg   1620
tccagcattg ctggactctg aaatatcccg ggggtggggg gtgggggtgg gtcagaaccc   1680
tgccatggaa ctgtttcctt catcatgagt tctgctgaat gccgcgatgg gtcaggtagg   1740
ggggaaacag gttgggatgg gataggacta gcaccatttt aagtccctgt cacctcttcc   1800
gactctttct gagtgccttc tgtggggact ccggctgtgc tgggagaaat acttgaactt   1860
gcctctttta cctgctgctt ctccaaaaat ctgcctgggt tttgttccct attttctct    1920 cctgtcctcc ctcaccccct ccttcatatg aaaggtgcca tggaagaggc tacagggcca   1980
aacgctgagc cacctgccct ttttctgcc tcctttagta aaactccgag tgaactggtc    2040 ttccttttg gttttactt aactgtttca aagccaagac ctcacacaca caaaaaatgc    2100
acaaacaatg caatcaacag aaaagctgta aatgtgtgta cagttggcat ggtagtatac   2160
aaaaagattg tagtggatct aattttaag aaatttgcc tttaagttat ttacctgtt     2220 tttgtttctt gttttgaaag atgcgcattc taacctggag gtcaatgtta tgtatttatt   2280
tatttattta tttggttccc ttcctattcc aagcttccat agctgctgcc ctagttttct   2340
ttcctccttt cctcctctga cttggggacc ttttggggga gggctgcgac gcttgctctg   2400
tttgtggggt gacgggactc aggcgggaca gtgctgcagc tccctggctt ctgtggggcc   2460
cctcacctac ttaccaggt gggtcccggc tctgtgggtg atggggaggg gcattgctga    2520
ctgtgtatat aggataatta tgaaaagcag ttctggatgg tgtgccttcc agatcctctc   2580
tggggctgtg ttttgagcag caggtagcct gctggttta tctgagtgaa atactgtaca    2640
ggggaataaa agagatctta ttttttttt tatacttggc gttttttgaa taaaaccttt    2700
ttgtcttaaa aaaaaaaaaa aaaaaaaaa aaaaaaaaa aaaaaaaaa a               2751
```

<210> SEQ ID NO 13
<211> LENGTH: 313
<212> TYPE: PRT
<213> ORGANISM: Homo sapiens

<400> SEQUENCE: 13

```
Met Leu Leu Ser Lys Ile Asn Ser Leu Ala His Leu Arg Ala Ala Pro
1               5                   10                  15

Cys Asn Asp Leu His Ala Thr Lys Leu Ala Pro Gly Lys Glu Lys Glu
            20                  25                  30

Pro Leu Glu Ser Gln Tyr Gln Val Gly Pro Leu Leu Gly Ser Gly Gly
        35                  40                  45

Phe Gly Ser Val Tyr Ser Gly Ile Arg Val Ser Asp Asn Leu Pro Val
    50                  55                  60

Ala Ile Lys His Val Glu Lys Asp Arg Ile Ser Asp Trp Gly Glu Leu
65                  70                  75                  80

Pro Asn Gly Thr Arg Val Pro Met Glu Val Val Leu Leu Lys Lys Val
                85                  90                  95

Ser Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
        115                 120                 125

Leu Phe Asp Phe Ile Thr Glu Arg Gly Ala Leu Gln Glu Glu Leu Ala
    130                 135                 140
```

```
Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
    290                 295                 300

His Ser Leu Ser Pro Gly Pro Ser Lys
305                 310
```

<210> SEQ ID NO 14
<211> LENGTH: 6055
<212> TYPE: DNA
<213> ORGANISM: Homo sapiens

<400> SEQUENCE: 14

```
actgagtccc gggaccccgg gagagcggtc aatgtgtggt cgctgcgttt cctctgcctg    60
cgccgggcat cacttgcgcg ccgcagaaag tccgtctggc agcctggata tcctctccta   120
ccggcacccg cagacgcccc tgcagccgcg gtcggcgccc gggctcccta gccctgtgcg   180
ctcaactgtc ctgcgctgcg gggtgccgcg agttccacct ccgcgcctcc ttctctagac   240
aggcgctggg agaaagaacc ggctcccgag ttctgggcat ttcgcccggc tcgaggtgca   300
ggatgcagag caaggtgctg ctggccgtcg ccctgtggct ctgcgtggag acccgggccg   360
cctctgtggg tttgcctagt gtttctcttg atctgcccag gctcagcata caaaagaca    420
tacttacaat taaggctaat acaactcttc aaattacttg caggggacag agggacttgg   480
actggctttg gcccaataat cagagtggca gtgagcaaag ggtggaggtg actgagtgca   540
gcgatggcct cttctgtaag acactcacaa ttccaaaagt gatcggaaat gacactggag   600
cctacaagtg cttctaccgg gaaactgact tggcctcggt catttatgtc tatgttcaag   660
attacagatc tccatttatt gcttctgtta gtgaccaaca tggagtcgtg tacattactg   720
agaacaaaaa caaactgtg gtgattccat gtctcgggtc catttcaaat ctcaacgtgt   780
cactttgtgc aagatacca gaaagagat tgttcctga tggtaacaga atttcctggg   840
acagcaagaa gggctttact attcccagct acatgatcag ctatgctggc atggtcttct   900
gtgaagcaaa aattaatgat gaaagttacc agtctattat gtacatagtt gtcgttgtag   960
ggtataggat ttatgatgtg gttctgagtc cgtctcatgg aattgaacta tctgttggag  1020
aaaagcttgt cttaaattgt acagcaagaa ctgaactaaa tgtggggatt gacttcaact  1080
gggaataccc ttcttcgaag catcagcata agaaacttgt aaaccgagac ctaaaaaccc  1140
```

```
agtctgggag tgagatgaag aaattttga gcaccttaac tatagatggt gtaacccgga   1200
gtgaccaagg attgtacacc tgtgcagcat ccagtgggct gatgaccaag aagaacagca   1260
catttgtcag ggtccatgaa aaaccttttg ttgcttttgg aagtggcatg gaatctctgg   1320
tggaagccac ggtgggggag cgtgtcagaa tccctgcgaa gtaccttggt tacccacccc   1380
cagaaataaa atggtataaa aatggaatac cccttgagtc caatcacaca attaaagcgg   1440
ggcatgtact gacgattatg gaagtgagtg aaagagacac aggaaattac actgtcatcc   1500
ttaccaatcc catttcaaag gagaagcaga gccatgtggt ctctctggtt gtgtatgtcc   1560
caccccagat tggtgagaaa tctctaatct ctcctgtgga ttcctaccag tacggcacca   1620
ctcaaacgct gacatgtacg gtctatgcca ttcctccccc gcatcacatc cactggtatt   1680
ggcagttgga ggaagagtgc gccaacgagc ccagccaagc tgtctcagtg acaaacccat   1740
acccttgtga agaatggaga agtgtggagg acttccaggg aggaaataaa attgaagtta   1800
ataaaaatca atttgctcta attgaaggaa aaacaaaac tgtaagtacc cttgttatcc    1860
aagcggcaaa tgtgtcagct ttgtacaaat gtgaagcggt caacaaagtc gggagaggag   1920
agagggtgat ctccttccac gtgaccaggg gtcctgaaat tactttgcaa cctgacatgc   1980
agcccactga gcaggagagc gtgtcttgt ggtgcactgc agacagatct acgtttgaga    2040
acctcacatg gtacaagctt ggcccacagc ctctgccaat ccatgtggga gagttgccca   2100
cacctgtttg caagaacttg gatactcttt ggaaattgaa tgccaccatg ttctctaata   2160
gcacaaatga cattttgatc atggagctta agaatgcatc cttgcaggac caaggagact   2220
atgtctgcct tgctcaagac aggaagacca agaaaagaca ttgcgtggtc aggcagctca   2280
cagtcctaga gcgtgtggca cccacgatca caggaaacct ggagaatcag acgacaagta   2340
ttggggaaag catcgaagtc tcatgcacgg catctgggaa tcccccctcca cagatcatgt   2400 ggtttaaaga taatgagacc cttgtagaag actcaggcat tgtattgaag gatgggaacc   2460
ggaacctcac tatccgcaga gtgaggaagg aggacgaagg cctctacacc tgccaggcat   2520
gcagtgttct tggctgtgca aaagtggagg cattttttcat aatagaaggt gcccaggaaa   2580
agacgaactt ggaaatcatt attctagtag gcacggcgt gattgccatg ttcttctggc    2640
tacttcttgt catcatccta cggaccgtta agcgggccaa tggaggggaa ctgaagacag   2700
gctacttgtc catcgtcatg gatccagatg aactcccatt ggatgaacat tgtgaacgac   2760
tgccttatga tgccagcaaa tgggaattcc ccagagaccg gctgaagcta ggtaagcctc   2820
ttggccgtgg tgcctttggc caagtgattg aagcagatgc ctttggaatt gacaagacag   2880
caacttgcag gacagtagca gtcaaaatgt tgaaagaagg agcaacacac agtgagcatc   2940
gagctctcat gtctgaactc aagatcctca ttcatattgg tcaccatctc aatgtggtca   3000
accttctagg tgcctgtacc aagccaggag ggccactcat ggtgattgtg gaattctgca   3060
aatttggaaa cctgtccact tacctgagga gcaagagaaa tgaatttgtc ccctacaaga   3120 ccaaggggc acgattccgt caagggaaag actacgttgg agcaatccct gtggatctga   3180
aacggcgctt ggacagcatc accagtagcc agagctcagc cagctctgga tttgtggagg   3240
agaagtccct cagtgatgta gaagaagagg aagctcctga agatctgtat aaggacttcc   3300
tgaccttgga gcatctcatc tgttacagct tccaagtggc taagggcatg gagttcttgg   3360
catcgcgaaa gtgtatccac agggacctgg cggcacgaaa tatcctctta tcggagaaga   3420
acgtggttaa aatctgtgac tttggcttgg cccgggatat ttataaagat ccagattatg   3480
tcagaaaagg agatgctcgc ctcccctttga aatggatggc cccagaaaca attttttgaca   3540
```

```
gagtgtacac aatccagagt gacgtctggt cttttggtgt tttgctgtgg gaaatatttt    3600
ccttaggtgc ttctccatat cctggggtaa agattgatga agaattttgt aggcgattga    3660
aagaaggaac tagaatgagg gcccctgatt atactacacc agaaatgtac cagaccatgc    3720
tggactgctg gcacggggag cccagtcaga gacccacgtt ttcagagttg gtggaacatt    3780
tgggaaatct cttgcaagct aatgctcagc aggatggcaa agactacatt gttcttccga    3840
tatcagagac tttgagcatg gaagaggatt ctggactctc tctgcctacc tcacctgttt    3900
cctgtatgga ggaggaggaa gtatgtgacc ccaaattcca ttatgacaac acagcaggaa    3960
tcagtcagta tctgcagaac agtaagcgaa agagccggcc tgtgagtgta aaaacatttg    4020
aagatatccc gttagaagaa ccagaagtaa agtaatccc agatgacaac cagacggaca     4080
gtggtatggt tcttgcctca gaagagctga aaactttgga agacagaacc aaattatctc    4140
catcttttgg tggaatggtg cccagcaaaa gcagggagtc tgtggcatct gaaggctcaa    4200
accagacaag cggctaccag tccggatatc actccgatga cacagacacc accgtgtact    4260
ccagtgagga agcagaactt ttaaagctga tagagattgg agtgcaaacc ggtagcacag    4320
cccagattct ccagcctgac tcggggacca cactgagctc tcctcctgtt taaaaggaag    4380
catccacacc cccaactcct ggacatcaca tgagaggtgc tgctcagatt ttcaagtgtt    4440
gttctttcca ccagcaggaa gtagccgcat ttgattttca tttcgacaac agaaaaagga    4500
cctcggactg cagggagcca gtcttctagg catatcctgg aagaggcttg tgacccaaga    4560
atgtgtctgt gtcttctccc agtgttgacc tgatcctctt tttcattcat ttaaaaagca    4620
tttatcatgc cccctgctgc gggtctcacc atgggtttag aacaaagacg ttcaagaaat    4680
ggccccatcc tcaaagaagt agcagtacct ggggagctga cacttctgta aaactagaag    4740
ataaaccagg caatgtaagt gttcgaggtg ttgaagatgg gaaggatttg cagggctgag    4800
tctatccaag aggctttgtt taggacgtgg gtcccaagcc aagccttaag tgtggaattc    4860
ggattgatag aaaggaagac taacgttacc ttgctttgga gagtactgga gcctgcaaat    4920
gcattgtgtt tgctctggtg gaggtgggca tggggtctgt tctgaaatgt aaagggttca    4980
gacggggttt ctggttttag aaggttgcgt gttcttcgag ttgggctaaa gtagagttcg    5040
ttgtgctgtt tctgactcct aatgagagtt ccttccagac cgttacgtgt ctcctggcca    5100
agccccagga aggaaatgat gcagctctgg ctccttgtct cccaggctga tcctttattc    5160
agaataccac aaagaaagga cattcagctc aaggctccct gccgtgttga agagttctga    5220
ctgcacaaac cagcttctgg tttcttctgg aatgaatacc ctcatatctg tcctgatgtg    5280
atatgtctga gactgaatgc gggaggttca atgtgaagct gtgtgtggtg tcaaagtttc    5340
aggaaggatt ttacccttttt gttcttcccc ctgtccccaa cccactctca ccccgcaacc    5400
catcagtatt ttagttattt ggcctctact ccagtaaacc tgattgggtt tgttcactct    5460
ctgaatgatt attagccaga cttcaaaatt attttatagc ccaaattata acatctattg    5520
tattatttag acttttaaca tatagagcta tttctactga ttttgccct tgttctgtcc     5580
ttttttttcaa aaaagaaaat gtgttttttg tttggtacca tagtgtgaaa tgctgggaac    5640
aatgactata agacatgcta tggcacatat atttatagtc tgtttatgta gaaacaaatg    5700
taatatatta aagccttata tataatgaac tttgtactat tcacattttg tatcagtatt    5760
atgtagcata acaaaggtca taatgctttc agcaattgat gtcatttat taagaacat      5820
tgaaaaactt gaaggaatcc ctttgcaagg ttgcattact gtacccatca tttctaaaat    5880
```

```
ggaagagggg gtggctgggc acagtggccg acacctaaaa acccagcact ttggggggcc    5940
aaggtgggag gatcgcttga gcccaggagt tcaagaccag tctggccaac atggtcagat    6000
tccatctcaa agaaaaaagg taaaataaa ataaaatgga gaagaaggaa tcaga          6055
```

<210> SEQ ID NO 15
<211> LENGTH: 1356
<212> TYPE: PRT
<213> ORGANISM: Homo sapiens

<400> SEQUENCE: 15

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335
```

```
Glu Ser Leu Val Glu Ala Thr Val Gly Glu Arg Val Arg Ile Pro Ala
            340                 345                 350

Lys Tyr Leu Gly Tyr Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
            485                 490                 495

Ile Glu Val Asn Lys Asn Gln Phe Ala Leu Ile Glu Gly Lys Asn Lys
        500                 505                 510

Thr Val Ser Thr Leu Val Ile Gln Ala Ala Asn Val Ser Ala Leu Tyr
    515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
            565                 570                 575

Thr Phe Glu Asn Leu Thr Trp Tyr Lys Leu Gly Pro Gln Pro Leu Pro
        580                 585                 590

Ile His Val Gly Glu Leu Pro Thr Pro Val Cys Lys Asn Leu Asp Thr
    595                 600                 605

Leu Trp Lys Leu Asn Ala Thr Met Phe Ser Asn Ser Thr Asn Asp Ile
610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
            645                 650                 655

Arg Gln Leu Thr Val Leu Glu Arg Val Ala Pro Thr Ile Thr Gly Asn
        660                 665                 670

Leu Glu Asn Gln Thr Thr Ser Ile Gly Glu Ser Ile Glu Val Ser Cys
    675                 680                 685

Thr Ala Ser Gly Asn Pro Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
            725                 730                 735
```

```
Cys Gln Ala Cys Ser Val Leu Gly Cys Ala Lys Val Glu Ala Phe Phe
            740                 745                 750
Ile Ile Glu Gly Ala Gln Lys Thr Asn Leu Glu Ile Ile Ile Leu
            755                 760                 765
Val Gly Thr Ala Val Ile Ala Met Phe Phe Trp Leu Leu Val Ile
            770                 775                 780
Ile Leu Arg Thr Val Lys Arg Ala Asn Gly Gly Glu Leu Lys Thr Gly
785                 790                 795                 800
Tyr Leu Ser Ile Val Met Asp Pro Asp Glu Leu Pro Leu Asp Glu His
                    805                 810                 815
Cys Glu Arg Leu Pro Tyr Asp Ala Ser Lys Trp Glu Phe Pro Arg Asp
                    820                 825                 830
Arg Leu Lys Leu Gly Lys Pro Leu Gly Arg Gly Ala Phe Gly Gln Val
                    835                 840                 845
Ile Glu Ala Asp Ala Phe Gly Ile Asp Lys Thr Ala Thr Cys Arg Thr
850                 855                 860
Val Ala Val Lys Met Leu Lys Glu Gly Ala Thr His Ser Glu His Arg
865                 870                 875                 880
Ala Leu Met Ser Glu Leu Lys Ile Leu Ile His Ile Gly His His Leu
                    885                 890                 895
Asn Val Val Asn Leu Leu Gly Ala Cys Thr Lys Pro Gly Gly Pro Leu
                    900                 905                 910
Met Val Ile Val Glu Phe Cys Lys Phe Gly Asn Leu Ser Thr Tyr Leu
                    915                 920                 925
Arg Ser Lys Arg Asn Glu Phe Val Pro Tyr Lys Thr Lys Gly Ala Arg
                    930                 935                 940
Phe Arg Gln Gly Lys Asp Tyr Val Gly Ala Ile Pro Val Asp Leu Lys
945                 950                 955                 960
Arg Arg Leu Asp Ser Ile Thr Ser Ser Gln Ser Ser Ala Ser Ser Gly
                    965                 970                 975
Phe Val Glu Glu Lys Ser Leu Ser Asp Val Glu Glu Glu Ala Pro
                    980                 985                 990
Glu Asp Leu Tyr Lys Asp Phe Leu Thr Leu Glu His Leu Ile Cys Tyr
                    995                 1000                1005
Ser Phe Gln Val Ala Lys Gly Met Glu Phe Leu Ala Ser Arg Lys
    1010                1015                1020
Cys Ile His Arg Asp Leu Ala Ala Arg Asn Ile Leu Leu Ser Glu
    1025                1030                1035
Lys Asn Val Val Lys Ile Cys Asp Phe Gly Leu Ala Arg Asp Ile
    1040                1045                1050
Tyr Lys Asp Pro Asp Tyr Val Arg Lys Gly Asp Ala Arg Leu Pro
    1055                1060                1065
Leu Lys Trp Met Ala Pro Glu Thr Ile Phe Asp Arg Val Tyr Thr
    1070                1075                1080
Ile Gln Ser Asp Val Trp Ser Phe Gly Val Leu Leu Trp Glu Ile
    1085                1090                1095
Phe Ser Leu Gly Ala Ser Pro Tyr Pro Gly Val Lys Ile Asp Glu
    1100                1105                1110
Glu Phe Cys Arg Arg Leu Lys Glu Gly Thr Arg Met Arg Ala Pro
    1115                1120                1125
Asp Tyr Thr Thr Pro Glu Met Tyr Gln Thr Met Leu Asp Cys Trp
    1130                1135                1140
```

```
His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 16
<211> LENGTH: 13
<212> TYPE: PRT
<213> ORGANISM: Artificial sequence
<220> FEATURE:
<223> OTHER INFORMATION: Synthethic Polypeptide

<400> SEQUENCE: 16

Ala Glu Glu Glu Ile Tyr Gly Glu Phe Ala Lys Lys Lys
1               5                   10

<210> SEQ ID NO 17
<211> LENGTH: 12
<212> TYPE: PRT
<213> ORGANISM: Artificial sequence
<220> FEATURE:
<223> OTHER INFORMATION: Synthethic Polypeptide

<400> SEQUENCE: 17

Glu Ala Ile Tyr Ala Ala Pro Phe Ala Lys Lys Lys
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Synthethic Polypeptide
```

```
<400> SEQUENCE: 18

Glu Ala Ile Tyr Ala Ala Pro Phe
1               5
```